United States Patent
Belk et al.

(10) Patent No.: US 12,337,035 B2
(45) Date of Patent: Jun. 24, 2025

(54) TACI BINDING MOLECULES

(71) Applicant: Kite Pharma, Inc., Santa Monica, CA (US)

(72) Inventors: Jonathan Belk, Grantham, NH (US); Eugene Bolotin, Berkeley, CA (US); Raghavender Chivukula, Hayward, CA (US); Matthew Drever, Concord, CA (US); Edward Hai Dhow Liao, Petaluma, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 434 days.

(21) Appl. No.: 17/704,947

(22) Filed: Mar. 25, 2022

(65) Prior Publication Data

US 2022/0354892 A1    Nov. 10, 2022

Related U.S. Application Data

(60) Provisional application No. 63/310,492, filed on Feb. 15, 2022, provisional application No. 63/279,477, filed on Nov. 15, 2021, provisional application No. 63/209,869, filed on Jun. 11, 2021, provisional application No. 63/175,997, filed on Apr. 16, 2021.

(51) Int. Cl.
| | |
|---|---|
| *A61K 35/17* | (2025.01) |
| *A61K 40/11* | (2025.01) |
| *A61K 40/31* | (2025.01) |
| *A61K 40/42* | (2025.01) |
| *A61P 35/04* | (2006.01) |

(52) U.S. Cl.
CPC .......... *A61K 40/4215* (2025.01); *A61K 40/11* (2025.01); *A61K 40/31* (2025.01); *A61P 35/04* (2018.01); *A61K 2239/31* (2023.05); *A61K 2239/46* (2023.05)

(58) Field of Classification Search
CPC ................................ A61K 35/17; A61P 35/04
See application file for complete search history.

(56) References Cited

U.S. PATENT DOCUMENTS

2015/0344583 A1    12/2015 Armitage et al.

FOREIGN PATENT DOCUMENTS

WO    WO-02066516    8/2002

OTHER PUBLICATIONS

Rudikoff et al. Single amino acid substitution altering antigen-binding specificity. Proceedings of the National Academy of Sciences USA, vol. 79, p. 1979-1983. (Year: 1982).*
Panka et al. Variable region framework differences result in decreased or increased affinity of variant anti-digoxin antibodies. Proceedings of the National Academy of Sciences USA, vol. 85. (Year: 1988).*
Larson et al. Anti-TACI single and dual-targeting CAR T cells overcome BCMA antigen loss in multiple myeloma. Nature Comm 14: 1-15. (Year: 2023).*
National Cancer Institute (Car T Cells). https://www.cancer.gov/about-cancer/treatment/research/car-t-cells (Year: 2022).*
International Search Report and Written Opinion for International Application No. PCT/US2022/021997 dated Jul. 6, 2022. 11 pages.
Kulemzin et al., Engineering Chimeric Antigen Receptors, Acta Naturae 2017, vol. 9, No. 1(32), pp. 6-14.
Larson et al., Bispecific CAR T cells for multiple myeloma: natural ligand compared to tandem scFv design, J Immunol 2020, 204 (1 Supplement): 246.3.
Lee et al., An APRIL-based chimeric antigen receptor for dual targeting of BCMA and TACI in multiple myeloma, Blood 2018, vol. 131, No. 7, pp. 746-758.

* cited by examiner

*Primary Examiner* — Arthur S Leonard
*Assistant Examiner* — Keenan A Bates
(74) *Attorney, Agent, or Firm* — Sheppard Mullin Richter & Hampton LLP

(57) ABSTRACT

Provided are antibodies, fragments thereof, chimeric antigen receptors (CARs) and T cell receptors (TCRs) comprising one or more of the dual TACI-BCMA binding domains disclosed herein. Provided are compositions, cells and cell therapies comprising the same. Further provided are methods of treatment.

24 Claims, 15 Drawing Sheets

Specification includes a Sequence Listing.

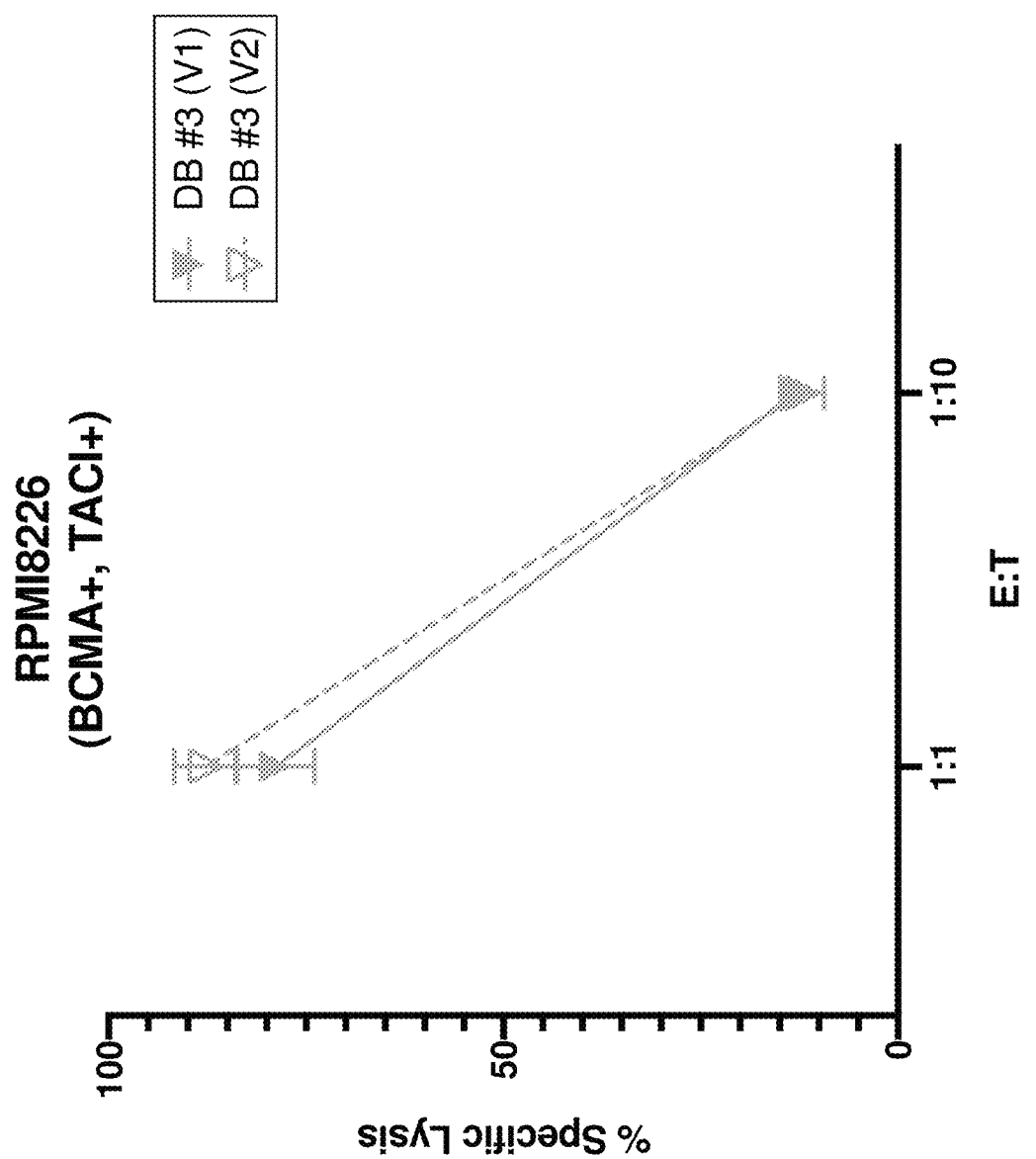

SEQUENCE LISTING

```
<160> NUMBER OF SEQ ID NOS: 304

<210> SEQ ID NO 1
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ala Asp Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Asp Ser Thr Ser Leu Pro Tyr Asn His Tyr Tyr Met
            100                 105                 110

Asp Val Trp Gly Lys Gly Thr Thr Val Thr Val Ser Ser
        115                 120                 125

<210> SEQ ID NO 2
<211> LENGTH: 375
<212> TYPE: DNA
<213> ORGANISM: Artificial Sequence
<220> FEATURE:
```

<223> OTHER INFORMATION: Description of Artificial Sequence: Synthetic
    polynucleotide

<400> SEQUENCE: 2
caggtgcagc tggtgcagtc tggggctgag gtgaagaagc ctgggtcctc ggtgaaggtc    60
tcctgcaagg cttctggagg caccttcgca gactatgcta tcagctgggt gcgacaggcc   120
cctggacaag ggcttgagtg gatgggaggg atcatccctaa tattgggcag agcaaactac   180
gcacagaagt tccagggcag agttacgatt accgcggacg aatccacgag cacagcctac   240
atggagctga gcagcctgag atctgaggac acggcggtgt actactgcgc cagagacaga   300
gacagcacaa gcctgccgta caaccactac tacatggacg tatggggcaa gggtacaact   360
gtcactgtct cctca                                                    375

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Thr Phe Ala Asp Tyr Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Ala Ile Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Thr Phe Ala Asp Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ile Pro Ile Leu Gly Arg Ala
1               5

<210> SEQ ID NO 7
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 7

Gly Ile Ile Pro Ile Leu Gly Arg Ala Asn Tyr Ala Gln Lys Phe Gln
1               5                   10                  15

Gly

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Pro Ile Leu Gly Arg
1               5

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Asp Arg Asp Ser Thr Ser Leu Pro Tyr Asn His Tyr Tyr Met
1               5                   10                  15

Asp Val

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Arg Asp Ser Thr Ser Leu Pro Tyr Asn His Tyr Tyr Met Asp Val
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Arg Asp Ser Thr Ser Leu Pro Tyr Asn His Tyr Tyr Met Asp Val
1               5                   10                  15

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ile Ala Pro Trp
                85                  90                  95

Thr Phe Gly Gly Gly Thr Lys Val Glu Ile Lys
            100                 105

<210> SEQ ID NO 13
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacatccaga tgacccagtc tccatcctcc ctgtctgcaa gcgttggaga tagagtcact      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc cgggacagat ttcactctca ccatcagcag tctgcaacct    240
gaagattttg caacttacta ctgtcagcaa agccacatcg ccccttggac ttttggcgga    300
gggaccaagg ttgagatcaa a                                              321

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ile Ser Ser Tyr
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Gln Ser Ile Ser Ser Tyr Leu Asn
1               5                   10

<210> SEQ ID NO 16
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 16

Arg Ala Ser Gln Ser Ile Ser Ser Tyr Leu Asn
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ser
1

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ser Ser Leu Gln Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ser Ser Leu Gln Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Ser His Ile Ala Pro Trp Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Ser His Ile Ala Pro Trp Thr
1               5
```

```
<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Ser His Ile Ala Pro Trp Thr
1               5

<210> SEQ ID NO 23
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Ala Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Asp Ser Thr Ser Leu Pro Tyr Asn His Tyr Tyr Met Asp Val Trp
225                 230                 235                 240

Gly Lys Gly Thr Thr Val Thr Val Ser Ser
                245                 250

<210> SEQ ID NO 24
<211> LENGTH: 750
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 24

```
gacatccaga tgacccagtc tccatcctcc ctgtctgcaa gcgttggaga tagagtcact      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc cgggacagat ttcactctca ccatcagcag tctgcaacct     240
gaagattttg caacttacta ctgtcagcaa agccacatcg ccccttggac ttttggcgga     300
gggaccaagg ttgagatcaa agggagcact agcggctctg caaacctgg atctggcgag      360
ggatctacca agggccaggt gcagctggtg cagtctgggg ctgaggtgaa gaagcctggg     420
tcctcggtga aggtctcctg caaggcttct ggaggcacct cgcagacta tgctatcagc      480
tgggtgcgac aggcccctgg acaagggctt gagtggatgg gagggatcat ccctatattg     540
ggcagagcaa actacgcaca gaagttccag ggcagagtta cgattaccgc ggacgaatcc     600
acgagcacag cctacatgga gctgagcagc ctgagatctg aggacacggc ggtgtactac     660
tgcgccagag acagagacag cacaagcctg ccgtacaacc actactacat ggacgtatgg     720
ggcaagggta caactgtcac tgtctcctca                                      750
```

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ala Asp Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Asp Arg Thr Ser Leu Pro Tyr Asn His Tyr Tyr Met
            100                 105                 110

Asp Val Trp Gly Lys Gly Thr Thr Val Thr Val Ser Ser
        115                 120                 125
```

<210> SEQ ID NO 26
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
caggtgcagc tggtgcagtc tggggctgag gtgaagaagc ctgggtcctc ggtgaaggtc      60
```

```
tcctgcaagg cttctggagg caccttcgca gactatgcta tcagctgggt gcgacaggcc    120
cctggacaag ggcttgagtg gatgggaggg atcatccc ta tattgggcag agcaaactac   180
gcacagaagt tccagggcag agttacgatt accgcggacg aatccacgag cacagcctac    240
atggagctga gcagcctgag atctgaggac acggcggtgt actactgcgc cagagacaga    300
gaccgtacaa gcctgccgta caaccactac tacatggacg tatggggcaa agggaccacg    360
gtcaccgttt cctca                                                     375
```

```
<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Thr Phe Ala Asp Tyr Ala
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Tyr Ala Ile Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Thr Phe Ala Asp Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ile Pro Ile Leu Gly Arg Ala
1               5

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

```
Gly Ile Ile Pro Ile Leu Gly Arg Ala Asn Tyr Ala Gln Lys Phe Gln
1               5                   10                  15

Gly

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Pro Ile Leu Gly Arg
1               5

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asp Arg Asp Arg Thr Ser Leu Pro Tyr Asn His Tyr Tyr Met
1               5                   10                  15

Asp Val

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Arg Asp Arg Thr Ser Leu Pro Tyr Asn His Tyr Tyr Met Asp Val
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Arg Asp Arg Thr Ser Leu Pro Tyr Asn His Tyr Tyr Met Asp Val
1               5                   10                  15

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Leu Ser Tyr
            20                  25                  30
```

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Ile Ala Pro Trp
                 85                  90                  95

Thr Phe Gly Gly Gly Thr Lys Val Glu Ile Lys
            100                 105

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacatccagt tgacccagtc tccatcctcc ctgtctgcaa gcgttggaga tagagtcact      60
atcacttgcc gggcaagtca gagcattctc agctatttaa attggtatca gcagaaacca     120
gggaaagccc ctaagctcct gatctatgct gcatccagtt tgcaaagtgg ggtcccatca     180
aggttcagtg gcagtggatc cgggacagat ttcactctca ccatcagcag tctgcaacct     240
gaagattttg caacttacta ctgtcagcaa agctcgatcg cccccttggac tttcggcgga     300 gggaccaagg ttgagatcaa a                                                321

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ser Ile Leu Ser Tyr
 1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ala Ser Gln Ser Ile Leu Ser Tyr Leu Asn
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ala Ser Gln Ser Ile Leu Ser Tyr Leu Asn

```
1               5                    10

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ala Ser
1

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ala Ser Ser Leu Gln Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ala Ser Ser Leu Gln Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Ser Ser Ile Ala Pro Trp Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Ser Ser Ile Ala Pro Trp Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 46

Gln Gln Ser Ser Ile Ala Pro Trp Thr
1               5

<210> SEQ ID NO 47
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Leu Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
130                 135                 140

Val Ser Cys Lys Ala Ser Gly Gly Thr Phe Ala Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Asp Arg Thr Ser Leu Pro Tyr Asn His Tyr Tyr Met Asp Val Trp
225                 230                 235                 240

Gly Lys Gly Thr Thr Val Thr Val Ser Ser
                245                 250

<210> SEQ ID NO 48
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gacatccagt tgacccagtc tccatcctcc ctgtctgcaa gcgttggaga tagagtcact     60

```
atcacttgcc gggcaagtca gagcattctc agctatttaa attggtatca gcagaaacca    120
gggaaagccc ctaagctcct gatctatgct gcatccagtt tgcaaagtgg ggtcccatca    180
aggttcagtg gcagtggatc cgggacagat ttcactctca ccatcagcag tctgcaacct    240
gaagattttg caacttacta ctgtcagcaa agctcgatcg ccccttggac tttcggcgga    300
gggaccaagg ttgagatcaa agggagcaca agcggctctg gcaaacctgg atctggcgag    360
ggatctacca agggccaggt gcagctggtg cagtctgggg ctgaggtgaa gaagcctggg    420
tcctcggtga aggtctcctg caaggcttct ggaggcacct tcgcagacta tgctatcagc    480
tgggtgcgac aggcccctgg acaagggctt gagtggatgg gagggatcat ccctatattg    540
gcagagcaa actacgcaca gaagttccag gcagagtta cgattaccgc ggacgaatcc      600
acgagcacag cctacatgga gctgagcagc ctgagatctg aggacacggc ggtgtactac    660
tgcgccagag acagagaccg tacaagcctg ccgtacaacc actactacat ggacgtatgg    720
ggcaaaggga ccacggtcac cgtttcctca                                     750
```

```
<210> SEQ ID NO 49
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Glu Asp Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Asp Leu Thr Ser Leu Pro Tyr Asn His Tyr Tyr Met
            100                 105                 110

Asp Val Trp Gly Lys Gly Thr Thr Val Thr Val Ser Ser
        115                 120                 125

```
<210> SEQ ID NO 50
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
caggtgcagc tggtgcagtc tggggctgag gtgaagaagc ctgggtcctc ggtgaaggtc     60
tcctgcaagg cttctggagg cacctt cgaa gactatgcta tcagctgggt gcgacaggcc   120
cctggacaag ggcttgagtg gatgggaggg atcatcccta tattgggccg agcaaactac    180
gcacagaagt tccagggcag agttacgatt accgcggacg aatccacgag cacagcctac    240
atggagctga gcagcctgag atctgaggac acggcggtgt actactgcgc cagagacaga    300
```

```
gacttgacaa gcctgccgta caaccactac tacatggacg tatggggcaa agggaccacg    360
gtcaccgttt cctca                                                     375
```

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Gly Gly Thr Phe Glu Asp Tyr Ala
1               5
```

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Asp Tyr Ala Ile Ser
1               5
```

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Gly Gly Thr Phe Glu Asp Tyr
1               5
```

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Ile Ile Pro Ile Leu Gly Arg Ala
1               5
```

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Gly Ile Ile Pro Ile Leu Gly Arg Ala Asn Tyr Ala Gln Lys Phe Gln
1               5                   10                  15

Gly
```

<210> SEQ ID NO 56

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Pro Ile Leu Gly Arg
1               5

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Arg Asp Arg Asp Leu Thr Ser Leu Pro Tyr Asn His Tyr Tyr Met
1               5                   10                  15

Asp Val

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Arg Asp Leu Thr Ser Leu Pro Tyr Asn His Tyr Tyr Met Asp Val
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Arg Asp Leu Thr Ser Leu Pro Tyr Asn His Tyr Tyr Met Asp Val
1               5                   10                  15

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Gln Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ala Ile Ala Pro Trp
                 85                  90                  95

Thr Phe Gly Gly Gly Thr Lys Val Glu Ile Lys
            100                 105
```

<210> SEQ ID NO 61
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gacatccagt tgacccagtc tccatcctcc ctgtctgcaa gcgttggaga tagagtcact    60
atcacttgcc gggcaagtca gagcattagc agctatttaa attggtatca gcagaaacca   120
gggaaagccc ctaagctcct gatctatgct gcatcccaat tgcaaagtgg ggtcccatca   180
aggttcagtg gcagtggatc cgggacagat tcactctcac catcagcagt ctgcaacct    240 gaagattttg caacttacta ctgtcagcaa agcgctatcg ccccttggac tttcggcgga   300
gggaccaagg ttgagatcaa a                                             321
```

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Gln Ser Ile Ser Ser Tyr
1               5
```

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Arg Ala Ser Gln Ser Ile Ser Ser Tyr Leu Asn
1               5                   10
```

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Arg Ala Ser Gln Ser Ile Ser Ser Tyr Leu Asn
1               5                   10
```

<210> SEQ ID NO 65
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 65

Ala Ala Ser
1

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ala Ser Gln Leu Gln Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Ala Ser Gln Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Ser Ala Ile Ala Pro Trp Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Ser Ala Ile Ala Pro Trp Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Ser Ala Ile Ala Pro Trp Thr
1               5
```

<210> SEQ ID NO 71
<211> LENGTH: 250
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Glu Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Asp Leu Thr Ser Leu Pro Tyr Asn His Tyr Tyr Met Asp Val Trp
225                 230                 235                 240

Gly Lys Gly Thr Thr Val Thr Val Ser Ser
                245                 250
```

<210> SEQ ID NO 72
<211> LENGTH: 750
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72

| | | | | | |
|---|---|---|---|---|---|
| gacatccagt | tgacccagtc | tccatcctcc | ctgtctgcaa gcgttggaga | tagagtcact | 60 |
| atcacttgcc | gggcaagtca | gagcattagc | agctatttaa | attggtatca gcagaaacca | 120 |
| gggaaagccc | ctaagctcct | gatctatgct | gcatcccaat | tgcaaagtgg | ggtcccatca | 180 |
| aggttcagtg | gcagtggatc | cgggacagat | ttcactctca | ccatcagcag | tctgcaacct | 240 |
| gaagattttg | caacttacta | ctgtcagcaa | agcgctatcg | ccccttggac | tttcggcgga | 300 |

```
gggaccaagg ttgagatcaa agggagcaca agcggctctg gcaaacctgg atctggcgag      360
ggatctacca agggccaggt gcagctggtg cagtctgggg ctgaggtgaa gaagcctggg      420
tcctcggtga aggtctcctg caaggcttct ggaggcacct tcgaagacta tgctatcagc      480
tgggtgcgac aggcccctgg acaagggctt gagtggatgg gagggatcat ccctatattg      540
ggccgagcaa actacgcaca gaagttccag ggcagagtta cgattaccgc ggacgaatcc      600
acgagcacag cctacatgga gctgagcagc ctgagatctg aggacacggc ggtgtactac      660
tgcgccagag acagagactt gacaagcctg ccgtacaacc actactacat ggacgtatgg      720
ggcaaaggga ccacggtcac cgtttcctca                                       750

<210> SEQ ID NO 73
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Thr Trp Glu Gly Ser Pro Tyr Tyr Tyr Gly Met
            100                 105                 110

Asp Val Trp Gly Gln Gly Thr Met Val Thr Val Ser Ser
        115                 120                 125

<210> SEQ ID NO 74
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtgcagc tggtgcagtc tggggctgaa gtgaagaagc ctgggtcctc ggtgaaggtc       60
tcctgcaagg cttctggagg cacctccagc cactatgcta tcagctgggt gcgacaggcc      120
cctggacaag gcttgagtg gatgggaggg atcatcccta tattgggccg agcaaactac      180
gcacagaagt tccagggcag agtcacgatt accgcggacg aatccacgag cacagcctac      240
atggagctga gcagcctgag atctgaggac acggcggtgt actactgcgc cagagacaga      300
acttgggaag gatctcccta ttattactac ggaatggacg tttggggcca agggacaatg      360
gtcaccgttt cctca                                                       375

<210> SEQ ID NO 75
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Gly Thr Phe Ser His Tyr Ala
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Tyr Ala Ile Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Thr Phe Ser His Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Ile Pro Ile Leu Gly Arg Ala
1               5

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ile Ile Pro Ile Leu Gly Arg Ala Asn Tyr Ala Gln Lys Phe Gln
1               5                   10                  15

Gly

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Ile Pro Ile Leu Gly Arg
1               5

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Arg Asp Arg Thr Trp Glu Gly Ser Pro Tyr Tyr Tyr Gly Met
1               5                   10                  15

Asp Val

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Arg Thr Trp Glu Gly Ser Pro Tyr Tyr Tyr Gly Met Asp Val
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Arg Thr Trp Glu Gly Ser Pro Tyr Tyr Tyr Gly Met Asp Val
1               5                   10                  15

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Leu Thr Gln Ser Pro Ser Ser Leu Ser Ala Ser Val Gly
1               5                   10                  15

Asp Arg Val Thr Ile Thr Cys Arg Ala Ser Thr Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Asp Ala Pro Trp
                85                  90                  95

Thr Phe Gly Gly Gly Thr Lys Val Glu Ile Lys
```

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gacatccagt tgacccagtc tccatcctcc ctgtctgcaa gcgttggaga cagggtcact      60
atcacttgcc gggcaagtac cagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agcgccgatg ccccttggac tttcggcgga     300
gggaccaagg ttgagatcaa a                                                321

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Ser Ile Ser Ser Tyr
1               5

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ala Ser Thr Ser Ile Ser Ser Tyr Leu Asn
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ala Ser Thr Ser Ile Ser Ser Tyr Leu Asn
1               5                   10

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Ala Ser

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Ala Ser Ser Leu Gln Ser
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Ala Ser Ser Leu Gln Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Ser Ala Asp Ala Pro Trp Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Ser Ala Asp Ala Pro Trp Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Ser Ala Asp Ala Pro Trp Thr
1               5

<210> SEQ ID NO 95
<211> LENGTH: 250
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 95

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Asp Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Ser His Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Thr Trp Glu Gly Ser Pro Tyr Tyr Tyr Gly Met Asp Val Trp
225                 230                 235                 240

Gly Gln Gly Thr Met Val Thr Val Ser Ser
                245                 250

<210> SEQ ID NO 96
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gacatccagt tgacccagtc tccatcctcc ctgtctgcaa gcgttggaga cagggtcact      60
atcacttgcc gggcaagtac cagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctcac catcagcagt ctgcaacct      240 gaagattttg caacttacta ctgtcagcaa agcgccgatg cccccttggac tttcggcgga    300 gggaccaagg ttgagatcaa agggagcaca agcggctctg gcaaacctgg atccggcgag    360
ggatctacca agggccaggt gcagctggtg cagtctgggg ctgaagtgaa gaagcctggg    420
tcctcggtga aggtctcctg caaggcttct ggaggcacct tcagccacta tgctatcagc    480

```
tgggtgcgac aggcccctgg acaagggctt gagtggatgg agggatcat ccctatattg    540 ggccgagcaa actacgcaca gaagttccag ggcagagtca cgattaccgc ggacgaatcc    600
acgagcacag cctacatgga gctgagcagc ctgagatctg aggacacggc ggtgtactac    660
tgcgccagag acagaacttg gaaggatct ccctattatt actacggaat ggacgtttgg    720
ggccaaggga caatggtcac cgtttcctca                                     750
```

```
<210> SEQ ID NO 97
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asp Asp Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Val Trp Glu Gly Ser Pro Tyr Tyr Tyr Gly Met
            100                 105                 110

Asp Val Trp Gly Gln Gly Thr Met Val Thr Val Ser Ser
        115                 120                 125

```
<210> SEQ ID NO 98
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caggtgcagc tggtgcagtc tggggctgag gtgaagaagc ctgggtcctc ggtgaaggtc     60
tcctgcaagg cttctggagg caccttcgac gactatgcta tcagctgggt tcgacaggcc    120
cctggacaag gcttgagtg gatgggaggg atcatcccta tattgggcag agcaaactac    180
gcacagaagt tccagggcag agtcacgatt accgcgacg aatccacgag cacagcctac    240
atggagctga gcagcctgag atctgaggac acggcggtgt actactgcgc cagagacaga    300
gtgtgggaag gatctcccta ttattactac ggaatggacg tttggggcca agggacaatg    360
gtcaccgttt cctca                                                     375
```

```
<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 99

Gly Gly Thr Phe Asp Asp Tyr Ala
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Tyr Ala Ile Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Thr Phe Asp Asp Tyr
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Ile Pro Ile Leu Gly Arg Ala
1               5

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ile Ile Pro Ile Leu Gly Arg Ala Asn Tyr Ala Gln Lys Phe Gln
1               5                   10                  15

Gly

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Pro Ile Leu Gly Arg
1               5

<210> SEQ ID NO 105
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Arg Asp Arg Val Trp Glu Gly Ser Pro Tyr Tyr Tyr Tyr Gly Met
1               5                   10                  15

Asp Val

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Arg Val Trp Glu Gly Ser Pro Tyr Tyr Tyr Tyr Gly Met Asp Val
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Arg Val Trp Glu Gly Ser Pro Tyr Tyr Tyr Tyr Gly Met Asp Val
1               5                   10                  15

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Gly Ala Pro Trp
                85                  90                  95

Thr Phe Gly Gly Gly Thr Lys Val Glu Ile Lys
            100                 105

<210> SEQ ID NO 109
<211> LENGTH: 321
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 109
gacatccagt tgacccagtc tccatcctcc ctgtctgcaa gcgttggaga tagagtcact      60
atcacttgcc gggcaagtca gagcattgcc agctatttaa attggtatca gcagaaacca     120
gggaaagccc ctaagctcct gatctatgct gcatccagtt tgcaaagtgg ggtcccatca     180
aggttcagtg gcagtggatc cgggacagat ttcactctca ccatcagcag tctgcaacct     240
gaagattttg caacttacta ctgtcagcaa agcgccggtg caccttggac tttcggcgga     300
gggaccaagg ttgagatcaa a                                               321

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ser Ile Ala Ser Tyr
1               5

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ala Ser Gln Ser Ile Ala Ser Tyr Leu Asn
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ala Ser Gln Ser Ile Ala Ser Tyr Leu Asn
1               5                   10

<210> SEQ ID NO 113
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ala Ser
1

<210> SEQ ID NO 114
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 114

Ala Ala Ser Ser Leu Gln Ser
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ala Ser Ser Leu Gln Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Ser Ala Gly Ala Pro Trp Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Ser Ala Gly Ala Pro Trp Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Gln Ser Ala Gly Ala Pro Trp Thr
1               5

<210> SEQ ID NO 119
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ala Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ala Gly Ala Pro Trp
             85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
130                 135                 140

Val Ser Cys Lys Ala Ser Gly Gly Thr Phe Asp Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
210                 215                 220

Arg Val Trp Glu Gly Ser Pro Tyr Tyr Tyr Gly Met Asp Val Trp
225                 230                 235                 240

Gly Gln Gly Thr Met Val Thr Val Ser Ser
                245                 250

<210> SEQ ID NO 120
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gacatccagt tgacccagtc tccatcctcc ctgtctgcaa gcgttggaga tagagtcact      60
atcacttgcc gggcaagtca gagcattgcc agctatttaa attggtatca gcagaaacca     120
gggaaagccc ctaagctcct gatctatgct gcatccagtt tgcaaagtgg ggtcccatca     180
aggttcagtg gcagtggatc cgggacagat ttcactctca ccatcagcag tctgcaacct     240
gaagattttg caacttacta ctgtcagcaa agcgccggtg caccttggac tttcggcgga     300
gggaccaagg ttgagatcaa agggagcaca agcggctctg gcaaacctgg atctggcgag     360
ggatctacca agggccaggt gcagctggtg cagtctgggg ctgaggtgaa gaagcctggg     420
tcctcggtga aggtctcctg caaggcttct ggaggcacct tcgacgacta tgctatcagc     480
tgggttcgac aggcccctgg acaagggctt gagtggatgg gagggatcat ccctatattg     540
ggcagagcaa actacgcaca gaagttccag ggcagagtca cgattaccgc ggacgaatcc     600
acgagcacag cctacatgga gctgagcagc ctgagatctg aggacacggc ggtgtactac     660
tgcgccagag acagagtgtg ggaaggatct ccctatatt actacggaat ggacgtttgg     720
```

```
ggccaaggga caatggtcac cgtttcctca                                       750
```

<210> SEQ ID NO 121
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Glu His Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Ser Trp Glu Gly Ser Pro Tyr Met Tyr Tyr Gly Met
            100                 105                 110

Asp Val Trp Gly Gln Gly Thr Met Val Thr Val Ser Ser
        115                 120                 125
```

<210> SEQ ID NO 122
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
caggtgcagc tggtgcagtc tggggctgag gtgaagaagc ctgggtcctc ggtgaaggtc    60
tcctgcaagg cttctggagg caccttcgaa cactatgcta tcagctgggt gcgacaggcc   120
cctggacagg gcttgagtg gatgggaggg atcatcccca tattgggccg agcaaactac   180
gcacagaagt tccagggcag agtcacgatt accgcggacg aatccacgag cacagcctac   240
atggagctga gcagcctgag atctgaggac acggcggtgt actactgcgc cagagacaga   300
agctgggaag gatctcccta tatgtactac ggaatggacg tttggggcca aggacaatg   360 gtcaccgttt cctca                                                    375
```

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Gly Gly Thr Phe Glu His Tyr Ala
1               5
```

<210> SEQ ID NO 124

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

His Tyr Ala Ile Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Thr Phe Glu His Tyr
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Ile Pro Ile Leu Gly Arg Ala
1               5

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Ile Ile Pro Ile Leu Gly Arg Ala Asn Tyr Ala Gln Lys Phe Gln
1               5                   10                  15

Gly

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Pro Ile Leu Gly Arg
1               5

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 129

Ala Arg Asp Arg Ser Trp Glu Gly Ser Pro Tyr Met Tyr Tyr Gly Met
1               5                   10                  15

Asp Val

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Arg Ser Trp Glu Gly Ser Pro Tyr Met Tyr Tyr Gly Met Asp Val
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Arg Ser Trp Glu Gly Ser Pro Tyr Met Tyr Tyr Gly Met Asp Val
1               5                   10                  15

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Leu Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Val Ala Pro Trp
                85                  90                  95

Thr Phe Gly Gly Gly Thr Lys Val Glu Ile Lys
            100                 105

<210> SEQ ID NO 133
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gacatccagt tgacccagtc tccatcctcc ctgtctgcaa gcgttggaga cagagttact      60
```

```
atcacttgcc gggcaagtca gagcattagc ctatatttaa attggtatca gcagaaacca    120
gggaaagccc ctaagctcct gatctatgct gcatccagtt tgcaaagtgg ggtcccatca    180
aggttcagtg gcagtggatc cgggacagat ttcactctca ccatcagcag tctgcaacct    240
gaagattttg caacttacta ctgtcagcaa gtggccgtcg ccccttggac tttcggcgga    300
gggaccaagg ttgagatcaa a                                              321
```

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Ser Ile Ser Leu Tyr
1               5

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Ala Ser Gln Ser Ile Ser Leu Tyr Leu Asn
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Ala Ser Gln Ser Ile Ser Leu Tyr Leu Asn
1               5                   10

<210> SEQ ID NO 137
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ala Ser
1

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ala Ser Ser Leu Gln Ser

```
1               5
```

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Ala Ala Ser Ser Leu Gln Ser
1               5
```

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gln Gln Val Ala Val Ala Pro Trp Thr
1               5
```

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Gln Gln Val Ala Val Ala Pro Trp Thr
1               5
```

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Gln Gln Val Ala Val Ala Pro Trp Thr
1               5
```

<210> SEQ ID NO 143
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Leu Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ala Val Ala Pro Trp
                 85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Ser Thr Lys Gly Gln Val Gln
            115                 120                 125

Leu Val Gln Ser Gly Ala Glu Val Lys Lys Pro Gly Ser Ser Val Lys
            130                 135                 140

Val Ser Cys Lys Ala Ser Gly Gly Thr Phe Glu His Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
            195                 200                 205

Ser Ser Leu Arg Ser Glu Asp Thr Ala Val Tyr Tyr Cys Ala Arg Asp
210                 215                 220

Arg Ser Trp Glu Gly Ser Pro Tyr Met Tyr Tyr Gly Met Asp Val Trp
225                 230                 235                 240

Gly Gln Gly Thr Met Val Thr Val Ser Ser
                245                 250
```

<210> SEQ ID NO 144
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
gacatccagt tgacccagtc tccatcctcc ctgtctgcaa gcgttggaga cagagttact    60
atcacttgcc gggcaagtca gagcattagc ctatatttaa attggtatca gcagaaacca   120
gggaaagccc ctaagctcct gatctatgct gcatccagtt tgcaaagtgg ggtcccatca   180
aggttcagtg gcagtggatc cgggacagat ttcactctca ccatcagcag tctgcaacct   240
gaagattttg caacttacta ctgtcagcaa gtggccgtcg cccttggac tttcggcgga   300
gggaccaagg ttgagatcaa agggagcaca agcggctctg gcaaacctgg atctggcgag   360
ggatctacca agggccaggt gcagctggtg cagtctgggg ctgaggtgaa gaagcctggg   420
tcctcggtga aggtctcctg caaggcttct ggaggcacct cgaacacta tgctatcagc   480
tgggtgcgac aggcccctgg acaggggctt gagtggatgg gagggatcat ccccatattg   540
ggccgagcaa actacgcaca gaagttccag ggcagagtca cgattaccgc ggacgaatcc   600
acgagcacag cctacatgga gctgagcagc ctgagatctg aggacacggc ggtgtactac   660
tgcgccagag acagaagctg ggaaggatct ccctatatgt actacggaat ggacgtttgg   720
ggccaaggga caatggtcac cgtttcctca                                   750
```

<210> SEQ ID NO 145
<211> LENGTH: 126
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Ser Glu
            20                  25                  30

Gly Met His Trp Val Arg Gln Ala Pro Gly Lys Gly Leu Glu Trp Val
        35                  40                  45

Ala Ser Ile Tyr Tyr Glu Gly Val Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Ser Tyr Tyr Asp Ser Ser Arg Leu Val Tyr His Gly
            100                 105                 110

Met Asp Val Trp Gly Gln Gly Thr Thr Val Thr Val Ser Ser
        115                 120                 125

<210> SEQ ID NO 146
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
caggtgcagc tggtggagtc tgggggaggc gtggtccagc ctggagggtc cctgagactc       60
tcctgcgctg catctggatt caccttcgcc agcgaaggca tgcactgggt ccgccaggct      120
ccaggcaagg ggctggagtg ggtggcatcc atatactatg agggagtcaa taaatactat      180
gcagactccg tgaagggccg attcaccatc tctagagaca attccaagaa cacgctgtat      240
ctgcaaatga atagcctgag agccgaggac acggcggtgt actactgcgc caaggacgtg      300
tcctactacg acagcagcag actagtttat cacggaatgg acgtatgggg gcaagggacc      360
acggtcaccg tttcctca                                                    378

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Phe Thr Phe Ala Ser Glu Gly
1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 148

Ser Glu Gly Met His
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Phe Thr Phe Ala Ser Glu
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Tyr Tyr Glu Gly Val Asn Lys
1               5

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Ile Tyr Tyr Glu Gly Val Asn Lys Tyr Tyr Ala Asp Ser Val Lys
1               5                   10                  15

Gly

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Tyr Glu Gly Val Asn
1               5

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Lys Asp Val Ser Tyr Tyr Asp Ser Ser Arg Leu Val Tyr His Gly
1               5                   10                  15

Met Asp Val
```

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Val Ser Tyr Tyr Asp Ser Ser Arg Leu Val Tyr His Gly Met Asp
1               5                   10                  15

Val

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Val Ser Tyr Tyr Asp Ser Ser Arg Leu Val Tyr His Gly Met Asp
1               5                   10                  15

Val

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Gly Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val His Asp Phe Pro Leu
                85                  90                  95

Thr Phe Gly Gly Gly Thr Lys Val Glu Ile Lys
            100                 105

<210> SEQ ID NO 157
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gacatccagt tgacccagtc tccatcctcc ctgtctgcaa gcgttggaga tagagtcact      60
atcacttgcc gggcaagtca gagcattagc agctatttaa attggtatca gcagaaacca     120

```
gggaaagccc ctaagctcct gatctatgca gccgggagtt tgcaaagtgg ggtcccatca      180
aggttcagtg gcagtggatc cgggacagat ttcactctca ccatcagcag tctgcaacct      240
gaagattttg caacttacta ctgtcagcaa gtgcacgact ccctctcac tttcggcgga       300 gggaccaagg ttgagatcaa a                                                321
```

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Ser Ile Ser Ser Tyr
1               5

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Ala Ser Gln Ser Ile Ser Ser Tyr Leu Asn
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ala Ser Gln Ser Ile Ser Ser Tyr Leu Asn
1               5                   10

<210> SEQ ID NO 161
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Ala Gly
1

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Ala Gly Ser Leu Gln Ser
1               5

```
<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Ala Gly Ser Leu Gln Ser
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Val His Asp Phe Pro Leu Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Gln Val His Asp Phe Pro Leu Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Gln Val His Asp Phe Pro Leu Thr
1               5

<210> SEQ ID NO 167
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
            65                  70                  75                  80
Glu Asp Phe Ala Thr Tyr Tyr Cys Gln Gln Val His Asp Phe Pro Leu
                    85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
                115                 120                 125

Leu Val Glu Ser Gly Gly Val Val Gln Pro Gly Arg Ser Leu Arg
        130                 135                 140

Leu Ser Cys Ala Ala Ser Gly Phe Thr Phe Ala Ser Glu Gly Met His
145                 150                 155                 160

Trp Val Arg Gln Ala Pro Gly Lys Gly Leu Glu Trp Val Ala Ser Ile
                165                 170                 175

Tyr Tyr Glu Gly Val Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
                195                 200                 205

Asn Ser Leu Arg Ala Glu Asp Thr Ala Val Tyr Tyr Cys Ala Lys Asp
        210                 215                 220

Val Ser Tyr Tyr Asp Ser Ser Arg Leu Val Tyr His Gly Met Asp Val
225                 230                 235                 240

Trp Gly Gln Gly Thr Thr Val Thr Val Ser Ser
                245                 250

<210> SEQ ID NO 168
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168
gacatccagt tgacccagtc tccatcctcc ctgtctgcaa gcgttggaga tagagtcact     60
atcacttgcc gggcaagtca gagcattagc agctatttaa attggtatca gcagaaacca    120
gggaaagccc ctaagctcct gatctatgca gccgggagtt tgcaaagtgg ggtcccatca    180
aggttcagtg gcagtggatc cgggacagat ttcactctca ccatcagcag tctgcaacct    240
gaagattttg caacttacta ctgtcagcaa gtgcacgact cccctctcac tttcggcgga    300
gggaccaagg ttgagatcaa agggagcaca agcggctctg gcaaacctgg atctggcgag    360
ggatctacca agggccaggt gcagctggtg gagtctgggg gaggcgtggt ccagcctggg    420
aggtccctga gactcctgcg ctgcatct ggattcacct cgccagcga aggcatgcac        480 tgggtccgcc aggctccagg caaggggctg gagtgggtgg catccatata ctatgaggga    540
gtcaataaat actatgcaga ctccgtgaag ggccgattca ccatctctag agacaattcc    600
aagaacacgc tgtatctgca aatgaatagc ctgagagccg aggacacggc ggtgtactac    660
tgcgccaagg acgtgtccta ctacgacagc agcagactag tttatcacgg aatggacgta    720
tgggggcaag ggaccacggt caccgtttcc tca                                  753

<210> SEQ ID NO 169
<211> LENGTH: 126
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 169

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Ser Glu
            20                  25                  30

Gly Met His Trp Val Arg Gln Ala Pro Gly Lys Gly Leu Glu Trp Val
        35                  40                  45

Ala Ser Ile Tyr Tyr Glu Gly Val Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser Tyr Tyr Asp Ser Ser Gly Leu Val Tyr His Gly
            100                 105                 110

Met Asp Val Trp Gly Gln Gly Thr Thr Val Thr Val Ser Ser
        115                 120                 125

<210> SEQ ID NO 170
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
caggtgcagc tggtggagtc tgggggaggc gtggtccagc ctgggaggtc cctgagactc      60
tcctgcgctg catctggatt caccttcgcc agcgaaggca tgcactgggt ccgccaggct     120
ccaggcaagg gctggagtg gtggcatcc atatactatg agggagtcaa taaatactat      180
gcagactccg tgaagggccg attcaccatc tccagagaca attccaagaa cacgctgtat     240
ctgcaaatga acagcctgag agccgaggac acggcggtgt actactgcgc caaggacaga     300
tcctactacg acagcagcgg gctagtttat cacggaatgg acgtatgggg gcaagggacc     360
acggtcaccg tttcctca                                                   378

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Phe Thr Phe Ala Ser Glu Gly
1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Glu Gly Met His

```
<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Phe Thr Phe Ala Ser Glu
1               5

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ile Tyr Tyr Glu Gly Val Asn Lys
1               5

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ile Tyr Tyr Glu Gly Val Asn Lys Tyr Tyr Ala Asp Ser Val Lys
1               5                   10                  15

Gly

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Tyr Tyr Glu Gly Val Asn
1               5

<210> SEQ ID NO 177
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Lys Asp Arg Ser Tyr Tyr Asp Ser Ser Gly Leu Val Tyr His Gly
1               5                   10                  15

Met Asp Val

<210> SEQ ID NO 178
<211> LENGTH: 17
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Arg Ser Tyr Tyr Asp Ser Ser Gly Leu Val Tyr His Gly Met Asp
1               5                   10                  15
Val

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Arg Ser Tyr Tyr Asp Ser Ser Gly Leu Val Tyr His Gly Met Asp
1               5                   10                  15
Val

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Gly Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val His Asp Phe Pro Leu
                85                  90                  95

Thr Phe Gly Gly Gly Thr Lys Val Glu Ile Lys
            100                 105

<210> SEQ ID NO 181
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
gacatccagt tgacccagtc tccatcctcc ctgtctgcaa gcgttggaga cagagtcact    60
atcacttgcc gggcaagtca gagcattagc agctatttaa attggtatca gcagaaacca   120
gggaaagccc ctaagctcct gatctatgct gcatccagtg acaaagtggg gtcccatca    180 aggttcagtg gcagtggatc cgggacagat ttcactctca ccatcagcag tctgcaacct   240

```
gaagattttg caacttacta ctgtcagcaa gtgcacgact tccctctcac tttcggcgga    300
gggaccaagg ttgagatcaa a                                              321
```

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Ser Ile Ser Ser Tyr
1               5

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ala Ser Gln Ser Ile Ser Ser Tyr Leu Asn
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ala Ser Gln Ser Ile Ser Ser Tyr Leu Asn
1               5                   10

<210> SEQ ID NO 185
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Ala Ser
1

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ala Ser Ser Gly Gln Ser
1               5

<210> SEQ ID NO 187
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 187

Ala Ala Ser Ser Gly Gln Ser
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Gln Val His Asp Phe Pro Leu Thr
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Gln Val His Asp Phe Pro Leu Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Gln Val His Asp Phe Pro Leu Thr
1               5

<210> SEQ ID NO 191
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Gly Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val His Asp Phe Pro Leu

```
                  85                  90                  95
Thr Phe Gly Gly Gly Thr Lys Val Glu Ile Lys Gly Ser Thr Ser Gly
                100                 105                 110

Ser Gly Lys Pro Gly Ser Gly Glu Gly Ser Thr Lys Gly Gln Val Gln
        115                 120                 125

Leu Val Glu Ser Gly Gly Gly Val Val Gln Pro Gly Arg Ser Leu Arg
    130                 135                 140

Leu Ser Cys Ala Ala Ser Gly Phe Thr Phe Ser Glu Gly Met His
145                 150                 155                 160

Trp Val Arg Gln Ala Pro Gly Lys Gly Leu Glu Trp Val Ala Ser Ile
                165                 170                 175

Tyr Tyr Glu Gly Val Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Asp
210                 215                 220

Arg Ser Tyr Tyr Asp Ser Ser Gly Leu Val Tyr His Gly Met Asp Val
225                 230                 235                 240

Trp Gly Gln Gly Thr Thr Val Thr Val Ser Ser
                245                 250
```

<210> SEQ ID NO 192
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
gacatccagt tgacccagtc tccatcctcc ctgtctgcaa gcgttggaga cagagtcact      60
atcacttgcc gggcaagtca gagcattagc agctatttaa attggtatca gcagaaacca    120
gggaaagccc ctaagctcct gatctatgct gcatccagtg acaaagtggg gtcccatca     180
aggttcagtg gcagtggatc cgggacagat ttcactctca ccatcagcag tctgcaacct    240
gaagattttg caacttacta ctgtcagcaa gtgcacgact ccctctcac tttcggcgga     300
gggaccaagg ttgagatcaa agggagcaca agcggctctg gcaaacctgg atctggcgag    360
ggatctacca agggccaggt gcagctggtg gagtctgggg gaggcgtggt ccagcctggg    420
aggtccctga ctctcctgc gctgcatct ggattcacct cgccagcga aggcatgcac       480
tgggtccgcc aggctccagg caaggggctg gagtgggtgg catccatata ctatgaggga    540
gtcaataaat actatgcaga ctccgtgaag ggccgattca ccatctccag agacaattcc    600
aagaacacgc tgtatctgca aatgaacagc ctgagagccg aggacacggc ggtgtactac    660
tgcgccaagg acagatccta ctacgacagc agcgggctag tttatcacgg aatggacgta    720
tgggggcaag ggaccacggt caccgtttcc tca                                 753
```

<210> SEQ ID NO 193
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Glu
            20                  25                  30

Gly Met Tyr Trp Val Arg Gln Ala Pro Gly Lys Gly Leu Glu Trp Val
        35                  40                  45

Ala Ala Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser Tyr Tyr Asp Ser Ser Gln Leu Val Tyr His Gly
            100                 105                 110

Met Asp Val Trp Gly Gln Gly Thr Thr Val Thr Val Ser Ser
        115                 120                 125
```

<210> SEQ ID NO 194
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 194

```
caagttcagc tggtggagtc tgggggaggc gtggtccagc ctggggaggtc cctgagactc    60
tcctgcgctg catctggatt caccttcagt agcgagggaa tgtactgggt ccgccaggct   120
ccaggcaagg gctggagtg gtggcagcc atatggtatg agggaagtaa taaatactat   180
gccgactccg tgaagggccg attcaccatc tctcgcgaca attccaaaaa tacgctgtat   240
ctgcaaatga atagccttag agccgaggac acggcggtgt actactgcgc caaggacaga   300
tcctactacg acagcagcca gctagtttat cacggaatgg acgtatgggg gcaagggacc   360
acggtcaccg tttcctca                                                 378
```

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

```
Gly Phe Thr Phe Ser Ser Glu Gly
1               5
```

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

```
Ser Glu Gly Met Tyr
1               5
```

```
<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Phe Thr Phe Ser Ser Glu
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Trp Tyr Glu Gly Ser Asn Lys
1               5

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Ile Trp Tyr Glu Gly Ser Asn Lys Tyr Tyr Ala Asp Ser Val Lys
1               5                   10                  15

Gly

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Trp Tyr Glu Gly Ser Asn
1               5

<210> SEQ ID NO 201
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Lys Asp Arg Ser Tyr Tyr Asp Ser Ser Gln Leu Val Tyr His Gly
1               5                   10                  15

Met Asp Val

<210> SEQ ID NO 202
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 202

Asp Arg Ser Tyr Tyr Asp Ser Ser Gln Leu Val Tyr His Gly Met Asp
1               5                   10                  15

Val

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asp Arg Ser Tyr Tyr Asp Ser Ser Gln Leu Val Tyr His Gly Met Asp
1               5                   10                  15

Val

<210> SEQ ID NO 204
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile His Asp Phe Pro Leu
                85                  90                  95

Thr Phe Gly Gly Gly Thr Lys Val Glu Ile Lys
            100                 105

<210> SEQ ID NO 205
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
gacatccagt tgacccagtc tccatcctcc ctgtctgcaa gcgttggaga cagagtcact      60
atcacttgcc gggcaagtca gagcattagc agctatttaa attggtatca gcagaaacca     120
gggaaagccc ctaagctcct gatctatgct gcatccagtt tgcaaggagg ggtcccatca     180
aggttcagtg gcagtggctc tgggacagat tcactctca ccatcagcag tctgcaacct      240
gaagattttg caacttacta ctgtcagcaa attcacgact ccctctcac tttcggcgga      300 gggaccaagg ttgagatcaa a          321

```
<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Ser Ile Ser Ser Tyr
1               5

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Ala Ser Gln Ser Ile Ser Ser Tyr Leu Asn
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Arg Ala Ser Gln Ser Ile Ser Ser Tyr Leu Asn
1               5                   10

<210> SEQ ID NO 209
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ala Ser
1

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Ala Ser Ser Leu Gln Gly
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                                  peptide

<400> SEQUENCE: 211

Ala Ala Ser Ser Leu Gln Gly
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Gln Ile His Asp Phe Pro Leu Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Gln Ile His Asp Phe Pro Leu Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Gln Ile His Asp Phe Pro Leu Thr
1               5

<210> SEQ ID NO 215
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Gly Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile His Asp Phe Pro Leu
                85                  90                  95

Thr Phe Gly Gly Gly Thr Lys Val Glu Ile Lys Gly Ser Thr Ser Gly
```

|   |   |   |   |   | 100 |   |   |   |   | 105 |   |   |   |   | 110 |   |
|---|---|---|---|---|---|---|---|---|---|---|---|---|---|---|---|---|

Ser Gly Lys Pro Gly Ser Gly Glu Gly Ser Thr Lys Gly Gln Val Gln
                 115                    120                125

Leu Val Glu Ser Gly Gly Gly Val Val Gln Pro Gly Arg Ser Leu Arg
130                     135                   140

Leu Ser Cys Ala Ala Ser Gly Phe Thr Phe Ser Ser Glu Gly Met Tyr
145               150                     155                 160

Trp Val Arg Gln Ala Pro Gly Lys Gly Leu Glu Trp Val Ala Ala Ile
                 165                   170                 175

Trp Tyr Glu Gly Ser Asn Lys Tyr Tyr Ala Asp Ser Val Lys Gly Arg
             180                    185                 190

Phe Thr Ile Ser Arg Asp Asn Ser Lys Asn Thr Leu Tyr Leu Gln Met
          195                  200                205

Asn Ser Leu Arg Ala Glu Asp Thr Ala Val Tyr Tyr Cys Ala Lys Asp
        210                 215                220

Arg Ser Tyr Tyr Asp Ser Ser Gln Leu Val Tyr His Gly Met Asp Val
225                     230                    235               240

Trp Gly Gln Gly Thr Thr Val Thr Val Ser Ser
             245                    250

<210> SEQ ID NO 216
<211> LENGTH: 753
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 216

| | |
|---|---|
| gacatccagt tgacccagtc tccatcctcc ctgtctgcaa gcgttggaga cagagtcact | 60 |
| atcacttgcc gggcaagtca gagcattagc agctatttaa attggtatca gcagaaacca | 120 |
| gggaaagccc ctaagctcct gatctatgct gcatccagtt tgcaaggagg ggtcccatca | 180 |
| aggttcagtg gcagtggctc tgggacagat ttcactctca ccatcagcag tctgcaacct | 240 |
| gaagattttg caacttacta ctgtcagcaa attcacgact ccctctcac tttcggcgga | 300 |
| gggaccaagg ttgagatcaa agggagcaca agcggctctg gcaaacctgg atctggcgag | 360 |
| ggatctacca agggccaagt tcagctggtg gagtctgggg gaggcgtggt ccagcctggg | 420 |
| aggtccctga gactctcctg cgctgcatct ggattcacct tcagtagcga gggaatgtac | 480 |
| tgggtccgcc aggctccagg caaggggctg gagtgggtgg cagccatatg gtatgaggga | 540 |
| agtaataaat actatgccga ctccgtgaag ggccgattca ccatctctcg cgacaattcc | 600 |
| aaaaatacgc tgtatctgca aatgaatagc cttagagccg aggacacggc ggtgtactac | 660 |
| tgcgccaagg acagatccta ctacgacagc agccagctag tttatcacgg aatggacgta | 720 |
| tgggggcaag ggaccacggt caccgtttcc tca | 753 |

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 217

Cys His Tyr Ser Glu Leu
1             5

```
<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V or I
<220> FEATURE:
<221> NAME/KEY: MOD_RES
<222> LOCATION: (4)..(4)
<223> OTHER INFORMATION: Any amino acid

<400> SEQUENCE: 218

Asp Xaa Glu Xaa Asn Pro Gly Pro
1               5

<210> SEQ ID NO 219
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Ser Thr Ser Gly Ser Gly Lys Pro Gly Ser Gly Glu Gly Ser Thr
1               5                   10                  15

Lys Gly

<210> SEQ ID NO 220
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gggagcacta gcggctctgg caaacctgga tctggcgagg gatctaccaa gggc        54

<210> SEQ ID NO 221
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 222
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
```

```
atgcttctcc tggtgacaag ccttctgctc tgtgagttac cacacccagc attcctcctg    60
attcct                                                               66
```

<210> SEQ ID NO 223
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Ser
1

<210> SEQ ID NO 224
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224

```
ggatcc                                                                6
```

<210> SEQ ID NO 225
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225

```
gggtcc                                                                6
```

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Gly Ser Gly Gly Gly Ser
1               5

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227

```
ggcggtggaa gcggaggagg ttcc                                           24
```

<210> SEQ ID NO 228
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
gggagcacaa gcggctctgg caaacctgga tctggcgagg gatctaccaa gggc    54

<210> SEQ ID NO 229
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gggagcacaa gcggctctgg caaacctgga tccggcgagg gatctaccaa gggc    54

<210> SEQ ID NO 230
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 231
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ctagacaatg agaagagcaa tggaaccatt atccatgtga aagggaaaca cctttgtcca    60
agtcccctat ttcccggacc ttctaagccc                                    90

<210> SEQ ID NO 232
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 233
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
accacgacgc cagcgccgcg accaccaaca ccggcgccca ccatcgcgtc gcaacccctg     60
tccctgcgcc ccgaggcgtg ccggccagcg gcggggggcg cagtgcacac gaggggctg    120 gacttcgcct gtgat                                                   135

<210> SEQ ID NO 234
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 235
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ttttgggtgc tggtggtggt tggtggagtc ctggcttgct atagcttgct agtaacagtg     60
gcctttatta ttttctgggt g                                              81

<210> SEQ ID NO 236
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 237
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
atctacatct gggcgcccct tggccgggact tgtggggtcc ttctcctgtc actggttatc     60 acccttt att gc                                                        72

<210> SEQ ID NO 238
<211> LENGTH: 113
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 238

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 239
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 239
ctgagagtga agttcagcag gagcgcagac gccccccgcgt accagcaggg ccagaaccag      60
ctctataacg agctcaatct aggacgaaga gaggagtacg atgttttgga caagaggcgt     120
ggccgggacc ctgagatggg gggaaagccg agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg ccccctcgc                            339

<210> SEQ ID NO 240
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 240

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 241
<211> LENGTH: 123
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 241
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 242
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
        35                  40

<210> SEQ ID NO 243
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
aaacggggca gaaagaaact cctgtatata ttcaaacaac catttatgag accagtacaa    60
actactcaag aggaagatgg ctgtagctgc cgatttccag aagaagaaga aggaggatgt   120
gaa                                                                 123

<210> SEQ ID NO 244
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Met Glu Trp Thr Trp Val Phe Leu Phe Leu Leu Ser Val Thr Ala Gly
1               5                   10                  15

Val His Ser

<210> SEQ ID NO 245
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Met Ala Leu Pro Val Thr Ala Leu Leu Leu Pro Leu Ala Leu Leu Leu
1               5                   10                  15

His Ala Ala Arg Pro
            20

<210> SEQ ID NO 246
<211> LENGTH: 463
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 246

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Ala Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Asp Ser Thr Ser Leu Pro Tyr Asn His Tyr Tyr Met Asp Val Trp
225                 230                 235                 240

Gly Lys Gly Thr Thr Val Thr Val Ser Ser Gly Ser Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365
```

```
Asn Gln Leu Tyr Asn Glu Leu Asn Leu Gly Arg Arg Glu Glu Tyr Asp
        370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
            435                 440                 445

Lys Asp Thr Tyr Asp Ala Leu His Met Gln Ala Leu Pro Pro Arg
        450                 455                 460

<210> SEQ ID NO 247
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
gacatccaga tgacccagtc tccatcctcc ctgtctgcaa gcgttggaga tagagtcact     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc cgggacagat ttcactctca ccatcagcag tctgcaacct    240
gaagattttg caacttacta ctgtcagcaa agccacatcg ccccttggac ttttggcgga    300
gggaccaagg ttgagatcaa agggagcact agcggctctg gcaaacctgg atctggcgag    360
ggatctacca agggccaggt gcagctggtg cagtctgggg ctgaggtgaa gaagcctggg    420
tcctcggtga aggtctcctg caaggcttct ggaggcacct cgcagactat gctatcagc    480
tgggtgcgac aggcccctgg acaagggctt gagtggatgg gagggatcat ccctatattg    540
gcagagcaa actacgcaca gaagttccag ggcagagtta cgattaccgc ggacgaatcc    600
acgagcacag cctacatgga gctgagcagc ctgagatctg aggacacggc ggtgtactac    660
tgcgccagag acagagacag cacaagcctg ccgtacaacc actactacat ggacgtatgg    720
ggcaagggta caactgtcac tgtctcctca gggtccctag acaatgagaa gagcaatgga    780
accattatcc atgtgaaagg gaaacacctt tgtccaagtc ccctatttcc cggaccttct    840
aagccctttt gggtgctggt ggtggttggt ggagtcctgg cttgctatag cttgctagta    900
acagtggcct ttattatttt ctgggtgagg agtaagagga gcaggctcct gcacagtgac    960
tacatgaaca tgactccccg ccgccccggg cccacccgca agcattacca gccctatgcc   1020
ccaccacgcg acttcgcagc ctatcgctcc ctgagagtga agttcagcag gagcgcagac   1080
gcccccgcgt accagcaggg ccagaaccag ctctataacg agctcaatct aggacgaaga   1140
gaggagtacg atgttttgga caagaggcgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg caaggggca cgatggcctt   1320
taccagggtc tcagtacagc caccaaggac acctacgacg cccttcacat gcaggccctg   1380
cccctcgc                                                             1389
```

<210> SEQ ID NO 248
<211> LENGTH: 463
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Leu Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Ala Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Asp Arg Thr Ser Leu Pro Tyr Asn His Tyr Tyr Met Asp Val Trp
225                 230                 235                 240

Gly Lys Gly Thr Thr Val Thr Val Ser Ser Gly Ser Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365
```

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 249
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gacatccagt tgacccagtc tccatcctcc ctgtctgcaa gcgttggaga tagagtcact      60
atcacttgcc gggcaagtca gagcattctc agctatttaa attggtatca gcagaaacca     120
gggaaagccc ctaagctcct gatctatgct gcatccagtt tgcaaagtgg ggtcccatca     180
aggttcagtg gcagtggatc cgggacagat ttcactctca ccatcagcag tctgcaacct     240
gaagattttg caacttacta ctgtcagcaa agctcgatcg cccccttggac tttcggcgga     300 gggaccaagg ttgagatcaa agggagcaca agcggctctg caaacctgg atctggcgag      360 ggatctacca agggccaggt gcagctggtg cagtctgggg ctgaggtgaa gaagcctggg     420
tcctcggtga aggtctcctg caaggcttct ggaggcacct tcgcagacta tgctatcagc     480
tgggtgcgac aggcccctgg acaagggctt gagtggatgg gagggatcat ccctatattg     540
ggcagagcaa actacgcaca agaagttccag gcagagtta cgattaccgc ggacgaatcc     600
acgagcacag cctacatgga gctgagcagc ctgagatctg aggacacggc ggtgtactac     660
tgcgccagag acagagaccg tacaagcctg ccgtacaacc actactacat ggacgtatgg     720
ggcaaaggga ccacggtcac cgtttcctca gggtccctag acaatgagaa gagcaatgga     780
accattatcc atgtgaaagg gaaacacctt tgtccaagtc ccctatttcc cggaccttct     840
aagccctttt gggtgctggt ggtggttggt ggagtcctgg cttgctatag cttgctagta     900
acagtggcct ttattatttt ctgggtgagg agtaagagga gcaggctcct gcacagtgac     960
tacatgaaca tgactccccg ccgcccgggg cccacccgca agcattacca gcctatgcc    1020 ccaccacgcg acttcgcagc ctatcgctcc ctgagagtga agttcagcag agcgcagac    1080 gccccgcgt accagcaggg ccagaaccag ctctataacg agctcaatct aggacgaaga    1140
gaggagtacg atgttttgga caagaggcgt ggccgggacc ctgagatggg gggaaagccg    1200
agaaggaaga accctcagga aggcctgtac aatgaactgc agaaagataa gatggcggag    1260
gcctacagtg agattgggat gaaggcgag cgccggaggg caaggggca cgatggcctt    1320 taccagggtc tcagtacagc caccaaggac acctacgacg cccttcacat gcaggccctg    1380
ccccctcgc                                                             1389

<210> SEQ ID NO 250

```
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Glu Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Asp Leu Thr Ser Leu Pro Tyr Asn His Tyr Tyr Met Asp Val Trp
225                 230                 235                 240

Gly Lys Gly Thr Thr Val Thr Val Ser Ser Gly Ser Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
```

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 251
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251

| gacatccagt | tgacccagtc | tccatcctcc | ctgtctgcaa | gcgttggaga | tagagtcact | 60 |
| atcacttgcc | gggcaagtca | gagcattagc | agctatttaa | attggtatca | gcagaaacca | 120 |
| gggaaagccc | ctaagctcct | gatctatgct | gcatcccaat | tgcaaagtgg | ggtcccatca | 180 |
| aggttcagtg | gcagtggatc | cgggacagat | ttcactctca | ccatcagcag | tctgcaacct | 240 |
| gaagattttg | caacttacta | ctgtcagcaa | agcgctatcg | ccccttggac | tttcggcgga | 300 |
| gggaccaagg | ttgagatcaa | agggagcaca | gcggctctg | caaacctgg | atctggcgag | 360 |
| ggatctacca | agggccaggt | gcagctggtg | cagtctgggg | ctgaggtgaa | gaagcctggg | 420 |
| tcctcggtga | aggtctcctg | caaggcttct | ggaggcacct | tcgaagacta | tgctatcagc | 480 |
| tgggtgcgac | aggcccctgg | acaagggctt | gagtggatgg | gagggatcat | ccctatattg | 540 |
| ggccgagcaa | actacgcaca | gaagttccag | ggcagagtta | cgattaccgc | ggacgaatcc | 600 |
| acgagcacag | cctacatgga | gctgagcagc | ctgagatctg | aggacacggc | ggtgtactac | 660 |
| tgcgccagag | acagagactt | gacaagcctg | ccgtacaacc | actactacat | ggacgtatgg | 720 |
| ggcaaaggga | ccacggtcac | cgtttcctca | gggtccctag | acaatgagaa | gagcaatgga | 780 |
| accattatcc | atgtgaaagg | gaaacacctt | tgtccaagtc | cctatttccc | ggaccttct | 840 |
| aagccctttt | gggtgctggt | ggtggttggt | ggagtcctgg | cttgctatag | cttgctagta | 900 |
| acagtggcct | ttattatttt | ctgggtgagg | agtaagagga | gcaggctcct | gcacagtgac | 960 |
| tacatgaaca | tgactccccg | ccgcccgggg | cccacccgca | agcattacca | gcccctatgcc | 1020 |
| ccaccacgcg | acttcgcagc | ctatcgctcc | ctgagagtga | agttcagcag | gagcgcagac | 1080 |
| gccccgcgt | accagcaggg | ccagaaccag | ctctataacg | agctcaatct | aggacgaaga | 1140 |
| gaggagtacg | atgttttgga | caagaggcgt | ggccgggacc | ctgagatggg | gggaaagccg | 1200 |
| agaaggaaga | accctcagga | aggcctgtac | aatgaactgc | agaaagataa | gatggcggag | 1260 |
| gcctacagtg | agattgggat | gaaaggcgag | cgccggaggg | gcaaggggca | cgatggcctt | 1320 |
| taccagggtc | tcagtacagc | caccaaggac | acctacgacg | cccttcacat | gcaggccctg | 1380 |
| ccccctcgc | | | | | | 1389 |

<210> SEQ ID NO 252
<211> LENGTH: 463

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ile Gln Leu Thr Gln Ser Pro Ser Ser Leu Ser Ala Ser Val Gly
1               5                   10                  15

Asp Arg Val Thr Ile Thr Cys Arg Ala Ser Thr Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Asp Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
130                 135                 140

Val Ser Cys Lys Ala Ser Gly Gly Thr Phe Ser His Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
210                 215                 220

Arg Thr Trp Glu Gly Ser Pro Tyr Tyr Tyr Gly Met Asp Val Trp
225                 230                 235                 240

Gly Gln Gly Thr Met Val Thr Val Ser Ser Gly Ser Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
370                 375                 380
```

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
            405                 410                 415

Lys Met Ala Glu Ala Tyr Ser Glu Ile Gly Met Lys Gly Glu Arg Arg
        420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
        450                 455                 460

<210> SEQ ID NO 253
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

| | |
|---|---|
| gacatccagt tgacccagtc tccatcctcc ctgtctgcaa gcgttggaga cagggtcact | 60 |
| atcacttgcc gggcaagtac cagcattagc agctatttaa attggtatca gcagaaacca | 120 |
| gggaaagccc ctaagctcct gatctatgct gcatccagtt tgcaaagtgg ggtcccatca | 180 |
| aggttcagtg gcagtggatc tgggacagat ttcactctca ccatcagcag tctgcaacct | 240 |
| gaagattttg caacttacta ctgtcagcaa agcgccgatg ccccttggac tttcggcgga | 300 |
| gggaccaagg ttgagatcaa agggagcaca agcggctctg gcaaacctgg atccggcgag | 360 |
| ggatctacca agggccaggt gcagctggtg cagtctgggg ctgaagtgaa gaagcctggg | 420 |
| tcctcggtga aggtctcctg caaggcttct ggaggcacct tcagccacta tgctatcagc | 480 |
| tgggtgcgac aggcccctgg acaagggctt gagtggatgg gagggatcat ccctatattg | 540 |
| gccgagcaa actacgcaca gaagttccag ggcagagtca cgattaccgc ggacgaatcc | 600 |
| acgagcacag cctacatgga gctgagcagc ctgagatctg aggacacggc ggtgtactac | 660 |
| tgcgccagag acagaacttg ggaaggatct ccctattatt actacggaat ggacgtttgg | 720 |
| ggccaaggga caatggtcac cgtttcctca gggtccctag acaatgagaa gagcaatgga | 780 |
| accattatcc atgtgaaagg gaaacacctt tgtccaagtc ccctatttcc cggaccttct | 840 |
| aagccctttt gggtgctggt ggtggttggt ggagtcctgg cttgctatag cttgctagta | 900 |
| acagtggcct ttattatttt ctgggtgagg agtaagagga gcaggctcct gcacagtgac | 960 |
| tacatgaaca tgactccccg ccgccccggg cccacccgca agcattacca gccctatgcc | 1020 |
| ccaccacgcg acttcgcagc ctatcgctcc ctgagagtga agttcagcag gagcgcagac | 1080 |
| gcccccgcgt accagcaggg ccagaaccag ctctataacg agctcaatct aggacgaaga | 1140 |
| gaggagtacg atgttttgga caagaggcgt ggccgggacc ctgagatggg ggaaagccg | 1200 |
| agaaggaaga accctcagga aggcctgtac aatgaactgc agaaagataa gatggcggag | 1260 |
| gcctacagtg agattgggat gaaaggcgag cgccggaggg caaggggca cgatggcctt | 1320 |
| taccagggtc tcagtacagc caccaaggac acctacgacg cccttcacat gcaggccctg | 1380 |
| ccccctcgc | 1389 |

<210> SEQ ID NO 254
<211> LENGTH: 463
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 254

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Gly Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Asp Asp Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Arg Val Trp Glu Gly Ser Pro Tyr Tyr Tyr Gly Met Asp Val Trp
225                 230                 235                 240

Gly Gln Gly Thr Met Val Thr Val Ser Ser Gly Ser Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 255
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
gacatccagt tgacccagtc tccatcctcc ctgtctgcaa gcgttggaga tagagtcact      60
atcacttgcc gggcaagtca gagcattgcc agctatttaa attggtatca gcagaaacca     120
gggaaagccc ctaagctcct gatctatgct gcatccagtt tgcaaagtgg ggtcccatca     180
aggttcagtg gcagtggatc cgggacagat ttcactctca ccatcagcag tctgcaacct     240
gaagattttg caacttacta ctgtcagcaa agcgccggtg caccttggac tttcggcgga     300
gggaccaagg ttgagatcaa agggagcaca agcggctctg caaacctgga tctggcgag     360 ggatctacca agggccaggt cagctggtg cagtctgggg ctgaggtgaa gaagcctggg     420
tcctcggtga aggtctcctg caaggcttct ggaggcacct tcgacgacta tgctatcagc     480
tgggttcgac aggcccctgg acaagggctt gagtggatgg gagggatcat ccctatattg     540
ggcagagcaa actacgcaca gaagttccag ggcagagtca cgattaccgc ggacgaatcc     600
acgagcacag cctacatgga gctgagcagc ctgagatctg aggacacggc ggtgtactac     660
tgcgccagag acagagtgtg gaaggatct cccctattatt actacggaat ggacgtttgg     720
ggccaaggga caatggtcac cgtttcctca gggtccctag acaatgagaa gagcaatgga     780
accattatcc atgtgaaagg gaaacacctt tgtccaagtc ccctatttcc cggaccttct     840 aagcccttt gggtgctggt ggtggttggt ggagtcctgg cttgctatag cttgctagta     900
acagtggcct ttattatttt ctgggtgagg agtaagagga gcaggctcct gcacagtgac     960
tacatgaaca tgactccccg ccgccccggg cccacccgca agcattacca gccctatgcc    1020
ccaccacgcg acttcgcagc ctatcgctcc ctgagagtga agttcagcag gagcgcagac    1080
gcccccgcgt accagcaggg ccagaaccag ctctataacg agctcaatct aggacgaaga    1140
gaggagtacg atgttttgga caagaggcgt ggccgggacc ctgagatggg gggaaagccg    1200
agaaggaaga accctcagga aggcctgtac aatgaactgc agaaagataa gatggcggag    1260
gcctacagtg agattgggat gaaaggcgag cgccggaggg caaggggca cgatggcctt    1320 taccagggtc tcagtacagc caccaaggac acctacgacg cccttcacat gcaggccctg    1380
ccccctcgc                                                            1389

<210> SEQ ID NO 256
<211> LENGTH: 463
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 256

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Ser Leu Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Val Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
130                 135                 140

Val Ser Cys Lys Ala Ser Gly Gly Thr Phe Glu His Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Tyr Cys Ala Arg Asp
210                 215                 220

Arg Ser Trp Glu Gly Ser Pro Tyr Met Tyr Tyr Gly Met Asp Val Trp
225                 230                 235                 240

Gly Gln Gly Thr Met Val Thr Val Ser Ser Gly Ser Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
370                 375                 380

Val Leu Asp Lys Arg Arg Gly Arg Asp Pro Glu Met Gly Gly Lys Pro
```

```
                385                 390                 395                 400
Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
                420                 425                 430

Arg Gly Lys Gly His Asp Gly Leu Tyr Gln Gly Leu Ser Thr Ala Thr
                435                 440                 445

Lys Asp Thr Tyr Asp Ala Leu His Met Gln Ala Leu Pro Pro Arg
                450                 455                 460

<210> SEQ ID NO 257
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
gacatccagt tgacccagtc tccatcctcc ctgtctgcaa gcgttggaga cagagttact      60
atcacttgcc gggcaagtca gagcattagc ctatatttaa attggtatca gcagaaacca     120
gggaaagccc ctaagctcct gatctatgct gcatccagtt tgcaaagtgg ggtcccatca     180
aggttcagtg gcagtggatc cgggacagat tcactctca ccatcagcag tctgcaacct     240
gaagattttg caacttacta ctgtcagcaa gtggccgtcg ccccttggac tttcggcgga     300
gggaccaagg ttgagatcaa agggagcaca agcggctctg caaacctgg atctggcgag     360 ggatctacca agggccaggt gcagctggtg cagtctgggg ctgaggtgaa gaagcctggg     420
tcctcggtga aggtctcctg caaggcttct ggaggcacct cgaacacta tgctatcagc     480 tgggtgcgac aggcccctgg acaggggctt gagtggatgg gagggatcat ccccatattg     540
ggccgagcaa actacgcaca gaagttccag ggcagagtca cgattaccgc ggacgaatcc     600
acgagcacag cctacatgga gctgagcagc ctgagatctg aggacacggc ggtgtactac     660
tgcgccagag acagaagctg ggaaggatct ccctatatgt actacggaat ggacgtttgg     720
ggccaaggga caatggtcac cgtttcctca gggtccctag acaatgagaa gagcaatgga     780
accattatcc atgtgaaagg aaacacctt tgtccaagtc cctatttcc cggaccttct     840 aagccctttt gggtgctggt ggtggttggt ggagtcctgg cttgctatag cttgctagta     900
acagtggcct ttattatttt ctgggtgagg agtaagagga gcaggctcct gcacagtgac     960
tacatgaaca tgactccccg ccgcccgggg cccacccgca agcattacca gccctatgcc    1020
ccaccacgcg acttcgcagc ctatcgctcc ctgagagtga agttcagcag agcgcagac    1080 gccccccgcgt accagcaggg ccagaaccag ctctataacg agctcaatct aggacgaaga    1140
gaggagtacg atgttttgga caagaggcgt ggccgggacc ctgagatggg gggaaagccg    1200
agaaggaaga accctcagga aggcctgtac aatgaactgc agaaagataa gatggcggag    1260
gcctacagtg agattgggat gaaaggcgag cgccggaggg caaggggca cgatggcctt    1320 taccagggtc tcagtacagc caccaaggac acctacgacg cccttcacat gcaggccctg    1380
ccccctcgc                                                            1389

<210> SEQ ID NO 258
<211> LENGTH: 464
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 258

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Gly Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val His Asp Phe Pro Leu
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Glu Ser Gly Gly Gly Val Val Gln Pro Gly Arg Ser Leu Arg
130                 135                 140

Leu Ser Cys Ala Ala Ser Gly Phe Thr Phe Ala Ser Glu Gly Met His
145                 150                 155                 160

Trp Val Arg Gln Ala Pro Gly Lys Gly Leu Glu Trp Val Ala Ser Ile
                165                 170                 175

Tyr Tyr Glu Gly Val Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Asp
210                 215                 220

Val Ser Tyr Tyr Asp Ser Ser Arg Leu Val Tyr His Gly Met Asp Val
225                 230                 235                 240

Trp Gly Gln Gly Thr Thr Val Thr Val Ser Ser Gly Ser Leu Asp Asn
                245                 250                 255

Glu Lys Ser Asn Gly Thr Ile Ile His Val Lys Gly Lys His Leu Cys
            260                 265                 270

Pro Ser Pro Leu Phe Pro Gly Pro Ser Lys Pro Phe Trp Val Leu Val
        275                 280                 285

Val Val Gly Gly Val Leu Ala Cys Tyr Ser Leu Leu Val Thr Val Ala
290                 295                 300

Phe Ile Ile Phe Trp Val Arg Ser Lys Arg Ser Arg Leu Leu His Ser
305                 310                 315                 320

Asp Tyr Met Asn Met Thr Pro Arg Arg Pro Gly Pro Thr Arg Lys His
                325                 330                 335

Tyr Gln Pro Tyr Ala Pro Pro Arg Asp Phe Ala Ala Tyr Arg Ser Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400
```

Pro Arg Arg Lys Asn Pro Gln Glu Gly Leu Tyr Asn Glu Leu Gln Lys
            405                 410                 415

Asp Lys Met Ala Glu Ala Tyr Ser Glu Ile Gly Met Lys Gly Glu Arg
        420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 259
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259

| | |
|---|---:|
| gacatccagt tgacccagtc tccatcctcc ctgtctgcaa gcgttggaga tagagtcact | 60 |
| atcacttgcc gggcaagtca gagcattagc agctatttaa attggtatca gcagaaacca | 120 |
| gggaaagccc ctaagctcct gatctatgca gccggagtt tgcaaagtgg ggtcccatca | 180 |
| aggttcagtg gcagtggatc cgggacagat ttcactctca ccatcagcag tctgcaacct | 240 |
| gaagattttg caacttacta ctgtcagcaa gtgcacgact ccctctcac tttcggcgga | 300 |
| gggaccaagg ttgagatcaa agggagcaca agcggctctg caaacctgg atctggcgag | 360 |
| ggatctacca agggccaggt gcagctggtg gagtctgggg gaggcgtggt ccagcctggg | 420 |
| aggtccctga gactcctg cgctgcatct ggattcacct tcgccagcga aggcatgcac | 480 |
| tgggtccgcc aggctccagg caaggggctg gagtgggtgg catccatata ctatgaggga | 540 |
| gtcaataaat actatgcaga ctccgtgaag ggccgattca ccatctctag agacaattcc | 600 |
| aagaacacgc tgtatctgca aatgaatagc ctgagagccg aggacacggc ggtgtactac | 660 |
| tgcgccaagg acgtgtccta ctacgacagc agcagactag tttatcacgg aatggacgta | 720 |
| tggggggcaag ggaccacggt caccgttttc tcagggtccc tagacaatga aagagcaat | 780 |
| ggaaccatta tccatgtgaa agggaaacac ctttgtccaa gtcccctatt tcccggacct | 840 |
| tctaagccct ttgggtgct ggtggtggtt ggtggagtcc tggcttgcta tagcttgcta | 900 |
| gtaacagtgg cctttattat tttctgggtg aggagtaaga ggagcaggct cctgcacagt | 960 |
| gactacatga acatgactcc ccgccgcccc gggcccaccc gcaagcatta ccagccctat | 1020 |
| gccccaccac gcgacttcgc agcctatcgc tccctgagag tgaagttcag caggagcgca | 1080 |
| gacgcccccg cgtaccagca gggccagaac cagctctata cgagctcaa tctaggacga | 1140 |
| agagaggagt acgatgtttt ggacaagagg cgtggccggg accctgagat ggggggaaag | 1200 |
| ccgagaagga agaaccctca ggaaggcctg tacaatgaac tgcagaaaga taagatggcg | 1260 |
| gaggcctaca gtgagattgg gatgaaaggc gagcgccgga ggggcaaggg gcacgatggc | 1320 |
| ctttaccagg gtctcagtac agccaccaag gacacctacg acgcccttca catgcaggcc | 1380 |
| ctgccccctc gc | 1392 |

<210> SEQ ID NO 260
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 260

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Gly Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val His Asp Phe Pro Leu
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Glu Ser Gly Gly Val Val Gln Pro Gly Arg Ser Leu Arg
130                 135                 140

Leu Ser Cys Ala Ala Ser Gly Phe Thr Phe Ala Ser Glu Gly Met His
145                 150                 155                 160

Trp Val Arg Gln Ala Pro Gly Lys Gly Leu Glu Trp Val Ala Ser Ile
                165                 170                 175

Tyr Tyr Glu Gly Val Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Asp
210                 215                 220

Arg Ser Tyr Tyr Asp Ser Ser Gly Leu Val Tyr His Gly Met Asp Val
225                 230                 235                 240

Trp Gly Gln Gly Thr Thr Val Thr Val Ser Ser Gly Ser Leu Asp Asn
                245                 250                 255

Glu Lys Ser Asn Gly Thr Ile Ile His Val Lys Gly Lys His Leu Cys
            260                 265                 270

Pro Ser Pro Leu Phe Pro Gly Pro Ser Lys Pro Phe Trp Val Leu Val
        275                 280                 285

Val Val Gly Gly Val Leu Ala Cys Tyr Ser Leu Leu Val Thr Val Ala
290                 295                 300

Phe Ile Ile Phe Trp Val Arg Ser Lys Arg Ser Arg Leu Leu His Ser
305                 310                 315                 320

Asp Tyr Met Asn Met Thr Pro Arg Arg Pro Gly Pro Thr Arg Lys His
                325                 330                 335

Tyr Gln Pro Tyr Ala Pro Pro Arg Asp Phe Ala Ala Tyr Arg Ser Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400
```

Pro Arg Arg Lys Asn Pro Gln Glu Gly Leu Tyr Asn Glu Leu Gln Lys
            405                 410                 415

Asp Lys Met Ala Glu Ala Tyr Ser Glu Ile Gly Met Lys Gly Glu Arg
        420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 261
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261

| | |
|---|---|
| gacatccagt tgacccagtc tccatcctcc ctgtctgcaa gcgttggaga cagagtcact | 60 |
| atcacttgcc gggcaagtca gagcattagc agctatttaa attggtatca gcagaaacca | 120 |
| gggaaagccc ctaagctcct gatctatgct gcatccagtg acaaagtgg ggtcccatca | 180 |
| aggttcagtg gcagtggatc cgggacagat ttcactctca ccatcagcag tctgcaacct | 240 |
| gaagattttg caacttacta ctgtcagcaa gtgcacgact ccctctcac tttcggcgga | 300 |
| gggaccaagg ttgagatcaa agggagcaca agcggctctg gcaaacctgg atctggcgag | 360 |
| ggatctacca agggccaggt gcagctggtg gagtctgggg gaggcgtggt ccagcctggg | 420 |
| aggtccctga gactctcctg cgctgcatct ggattcacct tcgccagcga aggcatgcac | 480 |
| tgggtccgcc aggctccagg caaggggctg gagtgggtgg catccatata ctatgaggga | 540 |
| gtcaataaat actatgcaga ctccgtgaag ggccgattca ccatctccag agacaattcc | 600 |
| aagaacacgc tgtatctgca aatgaacagc ctgagagccg aggacacggc ggtgtactac | 660 |
| tgcgccaagg acagatccta ctacgacagc agcgggctag tttatcacgg aatggacgta | 720 |
| tggggggcaag ggaccacggt caccgtcttcc tcagggtccc tagacaatga aagagcaat | 780 |
| ggaaccatta tccatgtgaa agggaaacac ctttgtccaa gtcccctatt tcccggacct | 840 |
| tctaagccct tttgggtgct ggtggtggtt ggtggagtcc tggcttgcta tagcttgcta | 900 |
| gtaacagtgg cctttattat tttctgggtg aggagtaaga ggagcaggct cctgcacagt | 960 |
| gactacatga acatgactcc ccgccgcccc gggcccaccc gcaagcatta ccagccctat | 1020 |
| gccccaccac gcgacttcgc agcctatcgc tccctgagag tgaagttcag caggagcgca | 1080 |
| gacgcccccg cgtaccagca gggccagaac cagctctata cgagctcaa tctaggacga | 1140 |
| agagaggagt acgatgtttt ggacaagagg cgtggccggg accctgagat ggggggaaag | 1200 |
| ccgagaagga gaacccctca ggaaggcctg tacaatgaac tgcagaaaga taagatggcg | 1260 |
| gaggcctaca gtgagattgg gatgaaaggc gagcgccgga ggggcaaggg gcacgatggc | 1320 |
| ctttaccagg gtctcagtac agccaccaag gacacctacg acgcccttca catgcaggcc | 1380 |
| ctgccccctc gc | 1392 |

<210> SEQ ID NO 262
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile His Asp Phe Pro Leu
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Glu Ser Gly Gly Gly Val Val Gln Pro Gly Arg Ser Leu Arg
    130                 135                 140

Leu Ser Cys Ala Ala Ser Gly Phe Thr Phe Ser Ser Glu Gly Met Tyr
145                 150                 155                 160

Trp Val Arg Gln Ala Pro Gly Lys Gly Leu Glu Trp Val Ala Ala Ile
                165                 170                 175

Trp Tyr Glu Gly Ser Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Asp
    210                 215                 220

Arg Ser Tyr Tyr Asp Ser Ser Gln Leu Val Tyr His Gly Met Asp Val
225                 230                 235                 240

Trp Gly Gln Gly Thr Thr Val Thr Val Ser Ser Gly Ser Leu Asp Asn
                245                 250                 255

Glu Lys Ser Asn Gly Thr Ile Ile His Val Lys Gly Lys His Leu Cys
            260                 265                 270

Pro Ser Pro Leu Phe Pro Gly Pro Ser Lys Pro Phe Trp Val Leu Val
        275                 280                 285

Val Val Gly Gly Val Leu Ala Cys Tyr Ser Leu Leu Val Thr Val Ala
    290                 295                 300

Phe Ile Ile Phe Trp Val Arg Ser Lys Arg Ser Arg Leu Leu His Ser
305                 310                 315                 320

Asp Tyr Met Asn Met Thr Pro Arg Arg Pro Gly Pro Thr Arg Lys His
                325                 330                 335

Tyr Gln Pro Tyr Ala Pro Pro Arg Asp Phe Ala Ala Tyr Arg Ser Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys 405                 410                 415
Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 263
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

| | |
|---|---:|
| gacatccagt tgacccagtc tccatcctcc ctgtctgcaa gcgttggaga cagagtcact | 60 |
| atcacttgcc gggcaagtca gagcattagc agctatttaa attggtatca gcagaaacca | 120 |
| gggaaagccc ctaagctcct gatctatgct gcatccagtt tgcaaggagg ggtcccatca | 180 |
| aggttcagtg gcagtggctc tgggacagat ttcactctca ccatcagcag tctgcaacct | 240 |
| gaagattttg caacttacta ctgtcagcaa attcacgact cccctctcac tttcggcgga | 300 |
| gggaccaagg ttgagatcaa aggagcaca agcggctctg caaacctgg atctggcgag | 360 |
| ggatctacca agggccaagt tcagctggtg agtctgggg gaggcgtggt ccagcctggg | 420 |
| aggtccctga ctctcctg cgctgcatct ggattcacct tcagtagcga gggaatgtac | 480 |
| tgggtccgcc aggctccagg caaggggctg gagtgggtgg cagccatatg gtatgaggga | 540 |
| agtaataaat actatgccga ctccgtgaag ggccgattca ccatctctcg cgacaattcc | 600 |
| aaaaatacgc tgtatctgca aatgaatagc cttagagccg aggacacggc ggtgtactac | 660 |
| tgcgccaagg acagatccta ctacgacagc agccagctag tttatcacgg aatggacgta | 720 |
| tggggcaag ggaccacggt caccgtttcc tcagggtccc tagacaatga agagcaat | 780 |
| ggaaccatta tccatgtgaa agggaaacac ctttgtccaa gtccctatt tcccggacct | 840 |
| tctaagccct ttgggtgct ggtggtggtt ggtggagtcc tggcttgcta tagcttgcta | 900 |
| gtaacagtgg cctttattat tttctgggtg aggagtaaga ggagcaggct cctgcacagt | 960 |
| gactacatga acatgactcc ccgccgcccc gggccacccc gcaagcatta ccagccctat | 1020 |
| gcccccaccac gcgacttcgc agcctatcgc tccctgagag tgaagttcag caggagcgca | 1080 |
| gacgccccg cgtaccagca gggccagaac cagctctata cgagctcaa tctaggacga | 1140 |
| agagaggagt acgatgtttt ggacaagagg cgtggccggg accctgagat gggggggaaag | 1200 |
| ccgagaagga agaaccctca ggaaggcctg tacaatgaac tgcagaaaga taagatggcg | 1260 |
| gaggcctaca gtgagattgg gatgaaaggc gagcgccgga ggggcaaggg gcacgatggc | 1320 |
| ctttaccagg gtctcagtac agccaccaag gacacctacg acgcccttca catgcaggcc | 1380 |
| ctgccccctc gc | 1392 |

<210> SEQ ID NO 264
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 264

Met Glu Ala Ala Val Ala Ala Pro Arg Pro Arg Leu Leu Leu Val
1               5                   10                  15

Leu Ala Ala Ala Ala Ala Ala Ala Ala Leu Leu Pro Gly Ala Thr
            20                  25                  30

Ala

<210> SEQ ID NO 265
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Met Glu Ala Ala Val Ala Ala Pro Arg Pro Arg Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu
        115                 120                 125

<210> SEQ ID NO 266
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 267
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

<210> SEQ ID NO 268
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268

```
atgcttctcc tggtgacaag ccttctgctc tgtgagttac cacacccagc attcctcctg    60
attcctgaac agaagctgat aagtgaggag gacttg                              96
```

<210> SEQ ID NO 269
<211> LENGTH: 152
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 269

```
Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Arg Val Asn Arg Gln
145                 150
```

<210> SEQ ID NO 270
<211> LENGTH: 194
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 270

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60
```

```
Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln

<210> SEQ ID NO 271
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
 50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 272
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
```

```
            20                  25                  30
Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Leu Leu Leu Val Ile Phe Gln
        130                 135                 140

Val Thr Gly Ile Ser Leu Leu Pro Pro Leu Gly Val Ala Ile Ser Val
145                 150                 155                 160

Ile Ile Ile Phe Tyr Cys Tyr
                165

<210> SEQ ID NO 273
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Ser Gly Pro Ile Leu Leu Thr
        130                 135                 140

Ile Ser Ile Leu Ser Phe Phe Ser Val Ala Leu Leu Val Ile Leu
145                 150                 155

<210> SEQ ID NO 274
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 274

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Ser Gly Pro Ile Leu Leu Thr
    130                 135                 140

Cys Pro Thr Ile Ser Ile Leu Ser Phe Phe Ser Val Ala Leu Leu Val
145                 150                 155                 160

Ile Leu

<210> SEQ ID NO 275
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Ala Cys Val Leu Trp Lys Lys Arg Ile Lys Pro Ile Val Trp Pro Ser
1               5                   10                  15

Leu Pro Asp His Lys Lys Thr Leu Glu His Leu Cys Lys Lys Pro Arg
            20                  25                  30

Lys Asn Leu Asn Val Ser Phe Asn Pro Glu Ser Phe Leu Asp Cys Gln
        35                  40                  45

Ile His Arg Val Asp Asp Ile Gln Ala Arg Asp Glu Val Glu Gly Phe
    50                  55                  60

Leu Gln Asp Thr Phe Pro Gln Gln Leu Glu Glu Ser Glu Lys Gln Arg
65                  70                  75                  80

Leu Gly Gly Asp Val Gln Ser Pro Asn Cys Pro Ser Glu Asp Val Val
                85                  90                  95

Ile Thr Pro Glu Ser Phe Gly Arg Asp Ser Ser Leu Thr Cys Leu Ala
            100                 105                 110

Gly Asn Val Ser Ala Cys Asp Ala Pro Ile Leu Ser Ser Ser Arg Ser
        115                 120                 125

Leu Asp Cys Arg Glu Ser Gly Lys Asn Gly Pro His Val Tyr Gln Asp
    130                 135                 140

Leu Leu Leu Ser Leu Gly Thr Thr Asn Ser Thr Leu Pro Pro Pro Phe
145                 150                 155                 160

Ser Leu Gln Ser Gly Ile Leu Thr Leu Asn Pro Val Ala Gln Gly Gln
                165                 170                 175

Pro Ile Leu Thr Ser Leu Gly Ser Asn Gln Glu Glu Ala Tyr Val Thr
```

```
                180                 185                 190
Met Ser Ser Phe Tyr Gln Asn Gln
        195                 200

<210> SEQ ID NO 276
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Ser Gly Pro Ile Leu Leu Thr
    130                 135                 140

Ile Ser Ile Leu Ser Phe Phe Ser Val Ala Leu Leu Val Ile Leu Ala
145                 150                 155                 160

Cys Val Leu Trp Lys Lys Arg Ile Lys Pro Ile Val Trp Pro Ser Leu
                165                 170                 175

Pro Asp His Lys Lys Thr Leu Glu His Leu Cys Lys Lys Pro Arg Lys
            180                 185                 190

Asn Leu Asn Val Ser Phe Asn Pro Glu Ser Phe Leu Asp Cys Gln Ile
        195                 200                 205

His Arg Val Asp Asp Ile Gln Ala Arg Asp Glu Val Glu Gly Phe Leu
    210                 215                 220

Gln Asp Thr Phe Pro Gln Gln Leu Glu Glu Ser Glu Lys Gln Arg Leu
225                 230                 235                 240

Gly Gly Asp Val Gln Ser Pro Asn Cys Pro Ser Glu Asp Val Val Ile
                245                 250                 255

Thr Pro Glu Ser Phe Gly Arg Asp Ser Ser Leu Thr Cys Leu Ala Gly
            260                 265                 270

Asn Val Ser Ala Cys Asp Ala Pro Ile Leu Ser Ser Ser Arg Ser Leu
        275                 280                 285

Asp Cys Arg Glu Ser Gly Lys Asn Gly Pro His Val Tyr Gln Asp Leu
    290                 295                 300

Leu Leu Ser Leu Gly Thr Thr Asn Ser Thr Leu Pro Pro Pro Phe Ser
305                 310                 315                 320

Leu Gln Ser Gly Ile Leu Thr Leu Asn Pro Val Ala Gln Gly Gln Pro
                325                 330                 335
```

```
Ile Leu Thr Ser Leu Gly Ser Asn Gln Glu Ala Tyr Val Thr Met
            340                 345                 350
Ser Ser Phe Tyr Gln Asn Gln
        355
```

<210> SEQ ID NO 277
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

```
Thr Ile Pro Pro His Val Gln Lys Ser Val Asn Asn Asp Met Ile Val
1               5                   10                  15
Thr Asp Asn Asn Gly Ala Val Lys Phe Pro Gln Leu Cys Lys Phe Cys
            20                  25                  30
Asp Val Arg Phe Ser Thr Cys Asp Asn Gln Lys Ser Cys Met Ser Asn
        35                  40                  45
Cys Ser Ile Thr Ser Ile Cys Glu Lys Pro Gln Glu Val Cys Val Ala
    50                  55                  60
Val Trp Arg Lys Asn Asp Glu Asn Ile Thr Leu Glu Thr Val Cys His
65                  70                  75                  80
Asp Pro Lys Leu Pro Tyr His Asp Phe Ile Leu Glu Asp Ala Ala Ser
                85                  90                  95
Pro Lys Cys Ile Met Lys Glu Lys Lys Pro Gly Glu Thr Phe Phe
            100                 105                 110
Met Cys Ser Cys Ser Ser Asp Glu Cys Asn Asp Asn Ile Ile Phe Ser
        115                 120                 125
Glu Glu Tyr Asn Thr Ser Asn Pro Asp Ser Gly Pro Ile Leu Leu Thr
    130                 135                 140
Cys Pro Thr Ile Ser Ile Leu Ser Phe Phe Ser Val Ala Leu Leu Val
145                 150                 155                 160
Ile Leu Ala Cys Val Leu Trp Lys Lys Arg Ile Lys Pro Ile Val Trp
                165                 170                 175
Pro Ser Leu Pro Asp His Lys Lys Thr Leu Glu His Leu Cys Lys Lys
            180                 185                 190
Pro Arg Lys Asn Leu Asn Val Ser Phe Asn Pro Glu Ser Phe Leu Asp
        195                 200                 205
Cys Gln Ile His Arg Val Asp Asp Ile Gln Ala Arg Asp Glu Val Glu
    210                 215                 220
Gly Phe Leu Gln Asp Thr Phe Pro Gln Gln Leu Glu Glu Ser Glu Lys
225                 230                 235                 240
Gln Arg Leu Gly Gly Asp Val Gln Ser Pro Asn Cys Pro Ser Glu Asp
                245                 250                 255
Val Val Ile Thr Pro Glu Ser Phe Gly Arg Asp Ser Ser Leu Thr Cys
            260                 265                 270
Leu Ala Gly Asn Val Ser Ala Cys Asp Ala Pro Ile Leu Ser Ser Ser
        275                 280                 285
Arg Ser Leu Asp Cys Arg Glu Ser Gly Lys Asn Gly Pro His Val Tyr
    290                 295                 300
Gln Asp Leu Leu Leu Ser Leu Gly Thr Thr Asn Ser Thr Leu Pro Pro
305                 310                 315                 320
Pro Phe Ser Leu Gln Ser Gly Ile Leu Thr Leu Asn Pro Val Ala Gln
                325                 330                 335
```

```
Gly Gln Pro Ile Leu Thr Ser Leu Gly Ser Asn Gln Glu Glu Ala Tyr
            340                 345                 350

Val Thr Met Ser Ser Phe Tyr Gln Asn Gln
        355                 360
```

<210> SEQ ID NO 278
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

```
Met Leu Leu Leu Val Thr Ser Leu Leu Cys Glu Leu Pro His Pro
1               5                   10                  15

Ala Phe Leu Leu Ile Pro Thr Ile Pro Pro His Val Gln Lys Ser Val
                20                  25                  30

Asn Asn Asp Met Ile Val Thr Asp Asn Gly Ala Val Lys Phe Pro
            35                  40                  45

Gln Leu Cys Lys Phe Cys Asp Val Arg Phe Ser Thr Cys Asp Asn Gln
50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp
145                 150                 155
```

<210> SEQ ID NO 279
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

```
Met Leu Leu Leu Val Thr Ser Leu Leu Cys Glu Leu Pro His Pro
1               5                   10                  15

Ala Phe Leu Leu Ile Pro Glu Gln Lys Leu Ile Ser Glu Glu Asp Leu
                20                  25                  30

Thr Ile Pro Pro His Val Gln Lys Ser Val Asn Asn Asp Met Ile Val
            35                  40                  45

Thr Asp Asn Asn Gly Ala Val Lys Phe Pro Gln Leu Cys Lys Phe Cys
50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
                100                 105                 110
```

Asp Pro Lys Leu Pro Tyr His Asp Phe Ile Leu Glu Asp Ala Ala Ser
            115                 120                 125

Pro Lys Cys Ile Met Lys Glu Lys Lys Lys Pro Gly Glu Thr Phe Phe
        130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp
                165

<210> SEQ ID NO 280
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Met Leu Leu Leu Val Thr Ser Leu Leu Cys Glu Leu Pro His Pro
1               5                   10                  15

Ala Phe Leu Leu Ile Pro Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Ser
145                 150                 155                 160

Gly Pro Ile Leu Leu Thr Ile Ser Ile Leu Ser Phe Phe Ser Val Ala
                165                 170                 175

Leu Leu Val Ile Leu Ala Cys Val Leu Trp Lys Lys Arg Ile Lys Pro
            180                 185                 190

Ile Val Trp Pro Ser Leu Pro Asp His Lys Lys Thr Leu Glu His Leu
        195                 200                 205

Cys Lys Lys Pro Arg Lys Asn Leu Asn Val Ser Phe Asn Pro Glu Ser
    210                 215                 220

Phe Leu Asp Cys Gln Ile His Arg Val Asp Asp Ile Gln Ala Arg Asp
225                 230                 235                 240

Glu Val Glu Gly Phe Leu Gln Asp Thr Phe Pro Gln Gln Leu Glu Glu
                245                 250                 255

Ser Glu Lys Gln Arg Leu Gly Gly Asp Val Gln Ser Pro Asn Cys Pro
            260                 265                 270

Ser Glu Asp Val Val Ile Thr Pro Glu Ser Phe Gly Arg Asp Ser Ser
        275                 280                 285

Leu Thr Cys Leu Ala Gly Asn Val Ser Ala Cys Asp Ala Pro Ile Leu

```
                290                 295                 300
Ser Ser Ser Arg Ser Leu Asp Cys Arg Glu Ser Gly Lys Asn Gly Pro
305                 310                 315                 320

His Val Tyr Gln Asp Leu Leu Ser Leu Gly Thr Thr Asn Ser Thr
                325                 330                 335

Leu Pro Pro Pro Phe Ser Leu Gln Ser Gly Ile Leu Thr Leu Asn Pro
                340                 345                 350

Val Ala Gln Gly Gln Pro Ile Leu Thr Ser Leu Gly Ser Asn Gln Glu
            355                 360                 365

Glu Ala Tyr Val Thr Met Ser Ser Phe Tyr Gln Asn Gln
370                 375                 380

<210> SEQ ID NO 281
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Met Leu Leu Val Thr Ser Leu Leu Cys Glu Leu Pro His Pro
1               5                   10                  15

Ala Phe Leu Leu Ile Pro Glu Gln Lys Leu Ile Ser Glu Glu Asp Leu
                20                  25                  30

Thr Ile Pro Pro His Val Gln Lys Ser Val Asn Asn Asp Met Ile Val
                35                  40                  45

Thr Asp Asn Asn Gly Ala Val Lys Phe Pro Gln Leu Cys Lys Phe Cys
50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
                100                 105                 110

Asp Pro Lys Leu Pro Tyr His Asp Phe Ile Leu Glu Asp Ala Ala Ser
                115                 120                 125

Pro Lys Cys Ile Met Lys Glu Lys Lys Pro Gly Glu Thr Phe Phe
130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp Ser Gly Pro Ile Leu Leu Thr
                165                 170                 175

Ile Ser Ile Leu Ser Phe Phe Ser Val Ala Leu Leu Val Ile Leu Ala
                180                 185                 190

Cys Val Leu Trp Lys Lys Arg Ile Lys Pro Ile Val Trp Pro Ser Leu
                195                 200                 205

Pro Asp His Lys Lys Thr Leu Glu His Leu Cys Lys Lys Pro Arg Lys
210                 215                 220

Asn Leu Asn Val Ser Phe Asn Pro Glu Ser Phe Leu Asp Cys Gln Ile
225                 230                 235                 240

His Arg Val Asp Asp Ile Gln Ala Arg Asp Glu Val Glu Gly Phe Leu
                245                 250                 255

Gln Asp Thr Phe Pro Gln Gln Leu Glu Glu Ser Glu Lys Gln Arg Leu
                260                 265                 270
```

Gly Gly Asp Val Gln Ser Pro Asn Cys Pro Ser Glu Asp Val Val Ile
            275                 280                 285

Thr Pro Glu Ser Phe Gly Arg Asp Ser Ser Leu Thr Cys Leu Ala Gly
        290                 295                 300

Asn Val Ser Ala Cys Asp Ala Pro Ile Leu Ser Ser Ser Arg Ser Leu
305                 310                 315                 320

Asp Cys Arg Glu Ser Gly Lys Asn Gly Pro His Val Tyr Gln Asp Leu
                325                 330                 335

Leu Leu Ser Leu Gly Thr Thr Asn Ser Thr Leu Pro Pro Pro Phe Ser
            340                 345                 350

Leu Gln Ser Gly Ile Leu Thr Leu Asn Pro Val Ala Gln Gly Gln Pro
        355                 360                 365

Ile Leu Thr Ser Leu Gly Ser Asn Gln Glu Glu Ala Tyr Val Thr Met
    370                 375                 380

Ser Ser Phe Tyr Gln Asn Gln
385                 390

<210> SEQ ID NO 282
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Met Leu Leu Leu Val Thr Ser Leu Leu Cys Glu Leu Pro His Pro
1               5                   10                  15

Ala Phe Leu Leu Ile Pro Thr Ile Pro Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Ser
145                 150                 155                 160

Gly Pro Ile Leu Leu Thr Ile Ser Ile Leu Ser Phe Phe Ser Val Ala
                165                 170                 175

Leu Leu Val Ile Leu Ala Cys Val Leu Trp Lys Lys Arg Ile Lys Pro
                180                 185                 190

Ile Val Trp Pro Ser Leu Pro Asp His Lys Lys Thr Leu Glu His Leu
            195                 200                 205

Cys Lys Lys Pro Arg Lys Asn Leu Asn Val Ser Phe Asn Pro Glu Ser
        210                 215                 220

Phe Leu Asp Cys Gln Ile His Arg Val Asp Asp Ile Gln Ala Arg Asp
225                 230                 235                 240

```
Glu Val Glu Gly Phe Leu Gln Asp Thr Phe Pro Gln Gln Leu Glu Glu
            245                 250                 255

Ser Glu Lys Gln Arg Leu Gly Gly Asp Val Gln Ser Pro Asn Cys Pro
        260                 265                 270

Ser Glu Asp Val Val Ile Thr Pro Glu Ser Phe Gly Arg Asp Ser Ser
    275                 280                 285

Leu Thr Cys Leu Ala Gly Asn Val Ser Ala Cys Asp Ala Pro Ile Leu
290                 295                 300

Ser Ser Ser Arg Ser Leu Asp Cys Arg Glu Ser Gly Lys Asn Gly Pro
305                 310                 315                 320

His Val Tyr Gln Asp Leu Leu Ser Leu Gly Thr Thr Asn Ser Thr
                325                 330                 335

Leu Pro Pro Pro Phe Ser Leu Gln Ser Gly Ile Leu Thr Leu Asn Pro
            340                 345                 350

Val Ala Gln Gly Gln Pro Ile Leu Thr Ser Leu Gly Ser Asn Gln Glu
                355                 360                 365

Glu Ala Tyr Val Thr Met Ser Ser Phe Tyr Gln Asn Gln
            370                 375                 380
```

<210> SEQ ID NO 283
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

```
Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
        35                  40                  45

Thr Asp Asn Asn Gly Ala Val Lys Phe Pro Gln Leu Cys Lys Phe Cys
50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
            100                 105                 110

Asp Pro Lys Leu Pro Tyr His Asp Phe Ile Leu Glu Asp Ala Ala Ser
        115                 120                 125

Pro Lys Cys Ile Met Lys Glu Lys Lys Lys Pro Gly Glu Thr Phe Phe
130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp Ser Gly Pro Ile Leu Leu Thr
                165                 170                 175

Cys Pro Thr Ile Ser Ile Leu Ser Phe Phe Ser Val Ala Leu Leu Val
            180                 185                 190

Ile Leu Ala Cys Val Leu Trp Lys Lys Arg Ile Lys Pro Ile Val Trp
        195                 200                 205

Pro Ser Leu Pro Asp His Lys Lys Thr Leu Glu His Leu Cys Lys Lys
```

210                 215                 220
Pro Arg Lys Asn Leu Asn Val Ser Phe Asn Pro Glu Ser Phe Leu Asp
225                 230                 235                 240

Cys Gln Ile His Arg Val Asp Asp Ile Gln Ala Arg Asp Glu Val Glu
                245                 250                 255

Gly Phe Leu Gln Asp Thr Phe Pro Gln Gln Leu Glu Glu Ser Glu Lys
                260                 265                 270

Gln Arg Leu Gly Gly Asp Val Gln Ser Pro Asn Cys Pro Ser Glu Asp
                275                 280                 285

Val Val Ile Thr Pro Glu Ser Phe Gly Arg Asp Ser Ser Leu Thr Cys
290                 295                 300

Leu Ala Gly Asn Val Ser Ala Cys Asp Ala Pro Ile Leu Ser Ser Ser
305                 310                 315                 320

Arg Ser Leu Asp Cys Arg Glu Ser Gly Lys Asn Gly Pro His Val Tyr
                325                 330                 335

Gln Asp Leu Leu Leu Ser Leu Gly Thr Thr Asn Ser Thr Leu Pro Pro
                340                 345                 350

Pro Phe Ser Leu Gln Ser Gly Ile Leu Thr Leu Asn Pro Val Ala Gln
                355                 360                 365

Gly Gln Pro Ile Leu Thr Ser Leu Gly Ser Asn Gln Glu Glu Ala Tyr
                370                 375                 380

Val Thr Met Ser Ser Phe Tyr Gln Asn Gln
385                 390

<210> SEQ ID NO 284
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Met Leu Leu Leu Val Thr Ser Leu Leu Leu Cys Glu Leu Pro His Pro
1               5                   10                  15

Ala Phe Leu Leu Ile Pro Thr Ile Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
                115                 120                 125

Pro Gly Glu Thr Phe Phe Met Cys Ser Cys Ser Ser Asp Glu Cys Asn
                130                 135                 140

Asp Asn Ile Ile Phe Ser Glu Glu Tyr Asn Thr Ser Asn Pro Asp Ser
145                 150                 155                 160

Gly Pro Ile Leu Leu Thr Cys Pro Thr Ile Ser Ile Leu Ser Phe Phe
                165                 170                 175

```
Ser Val Ala Leu Leu Val Ile Leu Ala Cys Val Leu Trp Lys Lys Arg
            180                 185                 190

Ile Lys Pro Ile Val Trp Pro Ser Leu Pro Asp His Lys Lys Thr Leu
        195                 200                 205

Glu His Leu Cys Lys Lys Pro Arg Lys Asn Leu Asn Val Ser Phe Asn
    210                 215                 220

Pro Glu Ser Phe Leu Asp Cys Gln Ile His Arg Val Asp Asp Ile Gln
225                 230                 235                 240

Ala Arg Asp Glu Val Glu Gly Phe Leu Gln Asp Thr Phe Pro Gln Gln
                245                 250                 255

Leu Glu Glu Ser Glu Lys Gln Arg Leu Gly Gly Asp Val Gln Ser Pro
            260                 265                 270

Asn Cys Pro Ser Glu Asp Val Val Ile Thr Pro Glu Ser Phe Gly Arg
        275                 280                 285

Asp Ser Ser Leu Thr Cys Leu Ala Gly Asn Val Ser Ala Cys Asp Ala
    290                 295                 300

Pro Ile Leu Ser Ser Ser Arg Ser Leu Asp Cys Arg Glu Ser Gly Lys
305                 310                 315                 320

Asn Gly Pro His Val Tyr Gln Asp Leu Leu Leu Ser Leu Gly Thr Thr
                325                 330                 335

Asn Ser Thr Leu Pro Pro Pro Phe Ser Leu Gln Ser Gly Ile Leu Thr
            340                 345                 350

Leu Asn Pro Val Ala Gln Gly Gln Pro Ile Leu Thr Ser Leu Gly Ser
        355                 360                 365

Asn Gln Glu Glu Ala Tyr Val Thr Met Ser Ser Phe Tyr Gln Asn Gln
    370                 375                 380

<210> SEQ ID NO 285
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ile Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Ala Asp Tyr Ala Ile Ser
145                 150                 155                 160
```

```
Trp Val Arg Gln Ala Pro Gly Gln Gly Leu Glu Trp Met Gly Gly Ile
                165                 170                 175
Ile Pro Ile Leu Gly Arg Ala Asn Tyr Ala Gln Lys Phe Gln Gly Arg
            180                 185                 190
Val Thr Ile Thr Ala Asp Glu Ser Thr Ser Thr Ala Tyr Met Glu Leu
        195                 200                 205
Ser Ser Leu Arg Ser Glu Asp Thr Ala Val Tyr Tyr Cys Ala Arg Asp
    210                 215                 220
Arg Asp Ser Thr Ser Leu Pro Tyr Asn His Tyr Tyr Met Asp Val Trp
225                 230                 235                 240
Gly Lys Gly Thr Thr Val Thr Val Ser Ser Gly Ser Leu Asp Asn Glu
                245                 250                 255
Lys Ser Asn Gly Thr Ile Ile His Val Lys Gly Lys His Leu Cys Pro
            260                 265                 270
Ser Pro Leu Phe Pro Gly Pro Ser Lys Pro Phe Trp Val Leu Val Val
        275                 280                 285
Val Gly Gly Val Leu Ala Cys Tyr Ser Leu Leu Val Thr Val Ala Phe
    290                 295                 300
Ile Ile Phe Trp Val Arg Ser Lys Arg Ser Arg Leu Leu His Ser Asp
305                 310                 315                 320
Tyr Met Asn Met Thr Pro Arg Arg Pro Gly Pro Thr Arg Lys His Tyr
                325                 330                 335
Gln Pro Tyr Ala Pro Pro Arg Asp Phe Ala Ala Tyr Arg Ser Leu Arg
            340                 345                 350
Val Lys Phe Ser Arg Ser Ala Asp Ala Pro Ala Tyr Gln Gln Gly Gln
        355                 360                 365
Asn Gln Leu Tyr Asn Glu Leu Asn Leu Gly Arg Arg Glu Glu Tyr Asp
    370                 375                 380
Val Leu Asp Lys Arg Arg Gly Arg Asp Pro Glu Met Gly Gly Lys Pro
385                 390                 395                 400
Arg Arg Lys Asn Pro Gln Glu Gly Leu Tyr Asn Glu Leu Gln Lys Asp
                405                 410                 415
Lys Met Ala Glu Ala Tyr Ser Glu Ile Gly Met Lys Gly Glu Arg Arg
            420                 425                 430
Arg Gly Lys Gly His Asp Gly Leu Tyr Gln Gly Leu Ser Thr Ala Thr
        435                 440                 445
Lys Asp Thr Tyr Asp Ala Leu His Met Gln Ala Leu Pro Pro Arg Gly
    450                 455                 460
Ser Gly Glu Gly Arg Gly Ser Leu Leu Thr Cys Gly Asp Val Glu Glu
465                 470                 475                 480
Asn Pro Gly Pro Met Gly Arg Gly Leu Leu Arg Gly Leu Trp Pro Leu
                485                 490                 495
His Ile Val Leu Trp Thr Arg Ile Ala Ser Thr Ile Pro Pro His Val
            500                 505                 510
Gln Lys Ser Val Asn Asn Asp Met Ile Val Thr Asp Asn Asn Gly Ala
        515                 520                 525
Val Lys Phe Pro Gln Leu Cys Lys Phe Cys Asp Val Arg Phe Ser Thr
    530                 535                 540
Cys Asp Asn Gln Lys Ser Cys Met Ser Asn Cys Ser Ile Thr Ser Ile
545                 550                 555                 560
Cys Glu Lys Pro Gln Glu Val Cys Val Ala Val Trp Arg Lys Asn Asp
                565                 570                 575
```

```
Glu Asn Ile Thr Leu Glu Thr Val Cys His Asp Pro Lys Leu Pro Tyr
            580                 585                 590

His Asp Phe Ile Leu Glu Asp Ala Ala Ser Pro Lys Cys Ile Met Lys
            595                 600                 605

Glu Lys Lys Lys Pro Gly Glu Thr Phe Phe Met Cys Ser Cys Ser Ser
        610                 615                 620

Asp Glu Cys Asn Asp Asn Ile Ile Phe Ser Glu Glu Tyr Asn Thr Ser
625                 630                 635                 640

Asn Pro Asp Leu Leu Leu Val Ile Phe Gln Val Thr Gly Ile Ser Leu
                645                 650                 655

Leu Pro Pro Leu Gly Val Ala Ile Ser Val Ile Ile Ile Phe Tyr Cys
            660                 665                 670

Tyr Arg Val Asn Arg Gln
            675

<210> SEQ ID NO 286
<211> LENGTH: 2035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286
```

| | | | | |---|
| gacatccaga | tgacccagtc | tccatcctcc | ctgtctgcaa | gcgttggaga | tagagtcact | 60 |
| atcacttgcc | gggcaagtca | gagcattagc | agctatttaa | attggtatca | gcagaaacca | 120 |
| gggaaagccc | ctaagctcct | catctatgct | gcatccagtt | tgcaaagtgg | ggtcccatca | 180 |
| aggtttagtg | gcagtggatc | cgggacagat | ttcactctca | ccatctcgag | cctgcaacct | 240 |
| gaagattttg | caacttacta | ctgtcagcaa | agccacatcg | ccccttggac | ttttggcgga | 300 |
| gggaccaagg | ttgagatcaa | agggagcact | agcggctctg | aaaaccggga | tctggcgag | 360 |
| ggatctacca | agggccaggt | gcagctggtg | cagtctgggg | ctgaagtcaa | aaagcctggg | 420 |
| tcctcggtga | aggtctcctg | caaggcttct | ggaggcacct | tcgcagacta | tgctatcagc | 480 |
| tgggtgcgac | aggcccccgg | acaagggctt | gagtggatgg | gaggaataat | ccctatattg | 540 |
| gcagagcaa | actacgcaca | gaagttccag | ggacgcgtta | cgattaccgc | ggacgaatct | 600 |
| acgagcacag | cctacatgga | gctgagcagc | ctgagatctg | aggacacggc | ggtgtattac | 660 |
| tgcgccagag | acagagacag | cacatctctg | ccgtacaacc | actattatat | ggacgtatgg | 720 |
| ggcaagggta | caactgtcac | tgtctcctct | gggagtctgg | acaacgagaa | gagcaacgga | 780 |
| actatcatcc | acgttaaggg | caagcattta | tgccctagcc | ctctgtttcc | cggacccagc | 840 |
| aagccgtttt | gggtactggt | ggtggtggga | ggagtgctgg | cttgttactc | tttactggtc | 900 |
| accgtggcct | tcatcatctt | ctgggttcga | agcaagaggt | ctagactgct | gcacagcgac | 960 |
| tacatgaaca | tgaccccag | aagacccggc | cccaccagaa | agcactacca | gccttacgcc | 1020 |
| cctcccgcg | acttcgccgc | ctatcgtagc | ctgcgcgtaa | agtttttcgag | gtctgctgat | 1080 |
| gccccagctt | accaacaagg | ccaaaatcag | ctttataatg | agttgaatct | aggcaggcgt | 1140 |
| gaagaatacg | acgtattaga | taagaggcgg | ggcagggacc | ctgaaatggg | cggcaaaccc | 1200 |
| agacggaaga | atccacaaga | gggattatat | aacgaacttc | agaaggacaa | aatggctgaa | 1260 |
| gcttacagcg | aaatcggaat | gaagggggag | aggcgcagag | aaaaggaca | tgatggacta | 1320 |
| tatcagggcc | tgtccaccgc | tacaaaagat | acctatgacg | cactgcatat | gcaggccttg | 1380 |
| cctccaagag | gttcaggaga | aggcagggc | tctctcctga | cctgcggcga | cgtggaagag | 1440 |

```
aaccctggcc ccatgggacg cggtttattg agaggactgt ggcccttaca catcgttctg   1500
tggactcgta tcgcctctac catcccccc catgtccaaa agagcgtaaa caacgatatg    1560
atcgtgaccg acaacaatgg cgctgtcaag ttcccacagc tgtgcaagtt ttgtgacgtg   1620
cgcttcagca cttgtgacaa tcagaaaagc tgcatgagca actgctccat cacctccatc   1680
tgtgagaaac cccaagaagt gtgcgtcgcc gtctggcgta agaacgacga gaacatcact   1740
ttagagactg tttgccacga tcccaaactg ccctaccatg acttcatatt ggaagatgca   1800
gcctctccca agtgtatcat gaaagaaaag aaaaaacctg gagagacctt cttcatgtgt   1860
tcttgttcgt ctgatgagtg caatgataat ataatcttca gcgaagagta caatacctcg   1920
aaccccgatc tgttgctcgt gatcttccaa gttaccggca tttctcttct gcctccgttg   1980
ggtgtggcaa tcagcgtgat catcattttc tactgctatc gtgttaaccg tcagt        2035
```

<210> SEQ ID NO 287
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Leu Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Val Ala Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ser Ser Val Lys
    130                 135                 140

Val Ser Cys Lys Ala Ser Gly Gly Thr Phe Glu His Tyr Ala Ile Ser
145                 150                 155                 160

Trp Val Arg Gln Ala Pro Gly Gln Gly Leu Glu Trp Met Gly Gly Ile
                165                 170                 175

Ile Pro Ile Leu Gly Arg Ala Asn Tyr Ala Gln Lys Phe Gln Gly Arg
            180                 185                 190

Val Thr Ile Thr Ala Asp Glu Ser Thr Ser Thr Ala Tyr Met Glu Leu
        195                 200                 205

Ser Ser Leu Arg Ser Glu Asp Thr Ala Val Tyr Cys Ala Arg Asp
    210                 215                 220

Arg Ser Trp Glu Gly Ser Pro Tyr Met Tyr Tyr Gly Met Asp Val Trp
225                 230                 235                 240

Gly Gln Gly Thr Met Val Thr Val Ser Ser Gly Ser Leu Asp Asn Glu
                245                 250                 255
```

```
Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg Gly
    450                 455                 460

Ser Gly Glu Gly Arg Gly Ser Leu Leu Thr Cys Gly Asp Val Glu Glu
465                 470                 475                 480

Asn Pro Gly Pro Met Gly Arg Gly Leu Leu Arg Gly Leu Trp Pro Leu
                485                 490                 495

His Ile Val Leu Trp Thr Arg Ile Ala Ser Thr Ile Pro Pro His Val
            500                 505                 510

Gln Lys Ser Val Asn Asn Asp Met Ile Val Thr Asp Asn Asn Gly Ala
        515                 520                 525

Val Lys Phe Pro Gln Leu Cys Lys Phe Cys Asp Val Arg Phe Ser Thr
    530                 535                 540

Cys Asp Asn Gln Lys Ser Cys Met Ser Asn Cys Ser Ile Thr Ser Ile
545                 550                 555                 560

Cys Glu Lys Pro Gln Glu Val Cys Val Ala Val Trp Arg Lys Asn Asp
                565                 570                 575

Glu Asn Ile Thr Leu Glu Thr Val Cys His Asp Pro Lys Leu Pro Tyr
            580                 585                 590

His Asp Phe Ile Leu Glu Asp Ala Ala Ser Pro Lys Cys Ile Met Lys
        595                 600                 605

Glu Lys Lys Lys Pro Gly Glu Thr Phe Phe Met Cys Ser Cys Ser Ser
    610                 615                 620

Asp Glu Cys Asn Asp Asn Ile Ile Phe Ser Glu Glu Tyr Asn Thr Ser
625                 630                 635                 640

Asn Pro Asp Leu Leu Leu Val Ile Phe Gln Val Thr Gly Ile Ser Leu
                645                 650                 655

Leu Pro Pro Leu Gly Val Ala Ile Ser Val Ile Ile Ile Phe Tyr Cys
            660                 665                 670
```

Tyr Arg Val Asn Arg Gln
    675

<210> SEQ ID NO 288
<211> LENGTH: 2035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288

| | | | | | |
|---|---|---|---|---|---|
| gacatccagt | tgacccagtc | tccatcctcc | ctgtctgcaa | gcgttggaga | cagagttact | 60 |
| atcacttgcc | gggcaagtca | gagcattagc | ctatatttaa | attggtatca | gcagaaacca | 120 |
| gggaaagccc | ctaagttgct | gatctatgct | gcatctagtt | tgcaaagtgg | ggtcccatca | 180 |
| cgattcagtg | gcagtggatc | cgggacagat | ttcactctca | ccatctcgag | tctacaacct | 240 |
| gaagattttg | caacttacta | ctgtcagcaa | gtggccgtcg | cccccttggac | tttcggcgga | 300 |
| gggaccaagg | ttgagatcaa | agggagcaca | agcggctctg | gaaaccggg | atctggcgag | 360 |
| ggatctacca | agggccaggt | gcagctggtg | cagtctgggg | ctgaggtgaa | aaagcctggg | 420 |
| tcctcggtga | aggtctcctg | caaggcttct | ggaggcacct | tcgaacacta | tgctatcagc | 480 |
| tgggtgcgac | aggcccctgg | acagggactt | gagtggatgg | gggggatcat | ccccatacta | 540 |
| ggccgagcaa | actacgcaca | gaagttccag | ggcagagtca | ctattaccgc | ggacgaatcg | 600 |
| acgagcacag | cctacatgga | gctgagcagc | ctgagatctg | aggacacggc | ggtgtattac | 660 |
| tgcgcccgtg | acagaagctg | gaaggatct | ccctatatgt | actacggaat | ggacgtttgg | 720 |
| ggccaaggga | caatggttac | cgttagcagt | gggagtctgg | acaacgagaa | gagcaacgga | 780 |
| actatcatcc | acgttaaggg | caagcattta | tgccctagcc | ctctgtttcc | cggacccagc | 840 |
| aagccgtttt | gggtactggt | ggtggtggga | ggagtgctgg | cttgttactc | tttactggtc | 900 |
| accgtggcct | tcatcatctt | ctgggttcga | agcaagaggt | ctagactgct | gcacagcgac | 960 |
| tacatgaaca | tgacccccag | aagacccggc | cccaccagaa | agcactacca | gccttacgcc | 1020 |
| cctcccccgcg | acttcgccgc | ctatcgtagc | ctgcgcgtaa | agttttcgag | gtctgctgat | 1080 |
| gccccagctt | accaacaagg | ccaaaatcag | ctttataatg | agttgaatct | aggcaggcgt | 1140 |
| gaagaatacg | acgtattaga | taagaggcgg | ggcagggacc | ctgaaatggg | cggcaaaccc | 1200 |
| agacggaaga | atccacaaga | gggattatat | aacgaacttc | agaaggacaa | aatggctgaa | 1260 |
| gcttacagcg | aaatcggaat | gaaggggggag | aggcgcagag | gaaaaggaca | tgatggacta | 1320 |
| tatcagggcc | tgtccaccgc | tacaaaagat | acctatgacg | cactgcatat | gcaggccttg | 1380 |
| cctccaagag | gttcaggaga | aggcaggggc | tctctcctga | cctgcggcga | cgtggaagag | 1440 |
| aaccctggcc | ccatgggacg | cggtttattg | agaggactgt | ggcccttaca | catcgttctg | 1500 |
| tggactcgta | tcgcctctac | catcccccccc | catgtccaaa | agagcgtaaa | caacgatatg | 1560 |
| atcgtgaccg | acaacaatgg | cgctgtcaag | ttcccacagc | tgtgcaagtt | ttgtgacgtg | 1620 |
| cgcttcagca | cttgtgacaa | tcagaaaagc | tgcatgagca | actgctccat | cacctccatc | 1680 |
| tgtgagaaac | cccaagaagt | gtgcgtcgcc | gtctggcgta | agaacgacga | gaacatcact | 1740 |
| ttagagactg | tttgccacga | tcccaaactg | ccctaccatg | acttcatatt | ggaagatgca | 1800 |
| gcctctccca | gtgtatcat | gaaagaaaag | aaaaaacctg | gagagacctt | cttcatgtgt | 1860 |
| tcttgttcgt | ctgatgagtg | caatgataat | ataatcttca | gcgaagagta | caatacctcg | 1920 |
| aaccccgatc | tgttgctcgt | gatcttccaa | gttaccggca | tttctcttct | gcctccgttg | 1980 | ggtgtggcaa tcagcgtgat catcattttc tactgctatc gtgttaaccg tcagt 2035

<210> SEQ ID NO 289
<211> LENGTH: 358
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Ile Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Thr Gly Ala Asn Ser Ser Leu Ala Asp Tyr Arg Gly
            100                 105                 110

Gln Gly Thr Leu Val Thr Val Ser Ser Phe Val Pro Val Phe Leu Pro
        115                 120                 125

Ala Lys Pro Thr Thr Thr Pro Ala Pro Arg Pro Pro Thr Pro Ala Pro
    130                 135                 140

Thr Ile Ala Ser Gln Pro Leu Ser Leu Arg Pro Glu Ala Cys Arg Pro
145                 150                 155                 160

Ala Ala Gly Gly Ala Val His Thr Arg Gly Leu Asp Phe Ala Cys Asp
                165                 170                 175

Ile Tyr Ile Trp Ala Pro Leu Ala Gly Thr Cys Gly Val Leu Leu Leu
            180                 185                 190

Ser Leu Val Ile Thr Leu Tyr Cys Asn His Arg Asn Lys Arg Gly Arg
        195                 200                 205

Lys Lys Leu Leu Tyr Ile Phe Lys Gln Pro Phe Met Arg Pro Val Gln
    210                 215                 220

Thr Thr Gln Glu Glu Asp Gly Cys Ser Cys Arg Phe Pro Glu Glu Glu
225                 230                 235                 240

Glu Gly Gly Cys Glu Leu Arg Val Lys Phe Ser Arg Ser Ala Asp Ala
                245                 250                 255

Pro Ala Tyr Gln Gln Gly Gln Asn Gln Leu Tyr Asn Glu Leu Asn Leu
            260                 265                 270

Gly Arg Arg Glu Glu Tyr Asp Val Leu Asp Lys Arg Arg Gly Arg Asp
        275                 280                 285

Pro Glu Met Gly Gly Lys Pro Arg Arg Lys Asn Pro Gln Glu Gly Leu
    290                 295                 300

Tyr Asn Glu Leu Gln Lys Asp Lys Met Ala Glu Ala Tyr Ser Glu Ile
305                 310                 315                 320

Gly Met Lys Gly Glu Arg Arg Arg Gly Lys Gly His Asp Gly Leu Tyr
                325                 330                 335

Gln Gly Leu Ser Thr Ala Thr Lys Asp Thr Tyr Asp Ala Leu His Met
            340                 345                 350

-continued

Gln Ala Leu Pro Pro Arg
        355

<210> SEQ ID NO 290
<211> LENGTH: 1074
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290
gaggtgcagc tgttggagtc cggggggaggc ttggtacagc ctgggggggtc cctgagactc      60 tcctgcgctg catctggatt cacctttttcg tcttatgcca tgagctgggt ccgccaggct     120
ccagggaagg ggctggagtg gtctctcatct attagtggta gtggtgatta catatattac     180
gcagactccg tgaagggccg gttcaccatc tccagagaca tatccaagaa cacgctgtat     240
ctgcaaatga acagtctgag agccgaggac acggccgtct attactgtgc gaaggaagga     300
acaggtgcca acagcagctt ggcagactac agaggccagg gcaccttggt aaccgtttcc     360
tcattcgtgc ccgtgttcct gccgccaag cctacaacaa ccctgctcc ccgtcctcct     420 acgcctgcac ctacaatcgc cagccagcct ctgtctctga ggccggaagc ttgtagacct     480
gcggctggcg gagccgtgca taccagagga ctggatttcg cctgcgacat ctacatttgg     540 gccccctttgg ctggaacatg tggcgttctg ctgctgagcc tcgtgatcac cctgtactgc     600
aaccaccgga caagcgggg ccgaaagaag ctgctgtaca tcttcaagca gcccttcatg     660 cggccccgtcc aaactaccca ggaagaggac ggctgctcct gtcgttttcc cgaggaagaa     720
gaaggcggct gcgagctgag agtgaagttc agcagaagcg ccgacgcgcc tgcctatcag     780
caagggcaga accagctgta taacgagtta aacctgggca gacgggaaga gtacgatgtg     840
ttggataaaa gacgtggccg ggatcctgag atgggggga agccgcgccg aaaaaaccct     900
caggaaggcc tgtacaatga actgcaaaag gataagatgg ccgaggccta cagtgagatt     960
gggatgaaag gcgagcgccg gaggggcaag gggcacgatg gcctttacca gggtttgagt    1020
accgccacca aggacaccta cgacgctctt cacatgcaag ccctgccccc tcgc          1074

<210> SEQ ID NO 291
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Ile Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
            85                  90                  95

```
Ala Lys Glu Gly Thr Gly Ala Asn Ser Ser Leu Ala Asp Tyr Arg Gly
            100                 105                 110

Gln Gly Thr Leu Val Thr Val Ser Ser Phe Val Pro Val Phe Leu Pro
            115                 120                 125

Ala Lys Pro Thr Thr Thr Pro Ala Pro Arg Pro Pro Thr Pro Ala Pro
            130                 135                 140

Thr Ile Ala Ser Gln Pro Leu Ser Leu Arg Pro Glu Ala Cys Arg Pro
145                 150                 155                 160

Ala Ala Gly Gly Ala Val His Thr Arg Gly Leu Asp Phe Ala Cys Asp
            165                 170                 175

Ile Tyr Ile Trp Ala Pro Leu Ala Gly Thr Cys Gly Val Leu Leu Leu
            180                 185                 190

Ser Leu Val Ile Thr Leu Tyr Cys Asn His Arg Asn Lys Arg Gly Arg
            195                 200                 205

Lys Lys Leu Leu Tyr Ile Phe Lys Gln Pro Phe Met Arg Pro Val Gln
            210                 215                 220

Thr Thr Gln Glu Glu Asp Gly Cys Ser Cys Arg Phe Pro Glu Glu Glu
225                 230                 235                 240

Glu Gly Gly Cys Glu Leu Arg Val Lys Phe Ser Arg Ser Ala Asp Ala
            245                 250                 255

Pro Ala Tyr Gln Gln Gly Gln Asn Gln Leu Tyr Asn Glu Leu Asn Leu
            260                 265                 270

Gly Arg Arg Glu Glu Tyr Asp Val Leu Asp Lys Arg Gly Arg Asp
            275                 280                 285

Pro Glu Met Gly Gly Lys Pro Arg Arg Lys Asn Pro Gln Glu Gly Leu
            290                 295                 300

Tyr Asn Glu Leu Gln Lys Asp Lys Met Ala Glu Ala Tyr Ser Glu Ile
305                 310                 315                 320

Gly Met Lys Gly Glu Arg Arg Arg Gly Lys Gly His Asp Gly Leu Tyr
            325                 330                 335

Gln Gly Leu Ser Thr Ala Thr Lys Asp Thr Tyr Asp Ala Leu His Met
            340                 345                 350

Gln Ala Leu Pro Pro Arg Gly Ser Gly Glu Gly Arg Gly Ser Leu Leu
            355                 360                 365

Thr Cys Gly Asp Val Glu Glu Asn Pro Gly Pro Met Gly Arg Gly Leu
370                 375                 380

Leu Arg Gly Leu Trp Pro Leu His Ile Val Leu Trp Thr Arg Ile Ala
385                 390                 395                 400

Ser Thr Ile Pro Pro His Val Gln Lys Ser Val Asn Asn Asp Met Ile
            405                 410                 415

Val Thr Asp Asn Asn Gly Ala Val Lys Phe Pro Gln Leu Cys Lys Phe
            420                 425                 430

Cys Asp Val Arg Phe Ser Thr Cys Asp Asn Gln Lys Ser Cys Met Ser
            435                 440                 445

Asn Cys Ser Ile Thr Ser Ile Cys Glu Lys Pro Gln Glu Val Cys Val
            450                 455                 460

Ala Val Trp Arg Lys Asn Asp Glu Asn Ile Thr Leu Glu Thr Val Cys
465                 470                 475                 480

His Asp Pro Lys Leu Pro Tyr His Asp Phe Ile Leu Glu Asp Ala Ala
            485                 490                 495

Ser Pro Lys Cys Ile Met Lys Glu Lys Lys Pro Gly Glu Thr Phe
            500                 505                 510
```

```
Phe Met Cys Ser Cys Ser Ser Asp Glu Cys Asn Asp Asn Ile Ile Phe
            515                 520                 525
Ser Glu Glu Tyr Asn Thr Ser Asn Pro Asp Leu Leu Leu Val Ile Phe
        530                 535                 540
Gln Val Thr Gly Ile Ser Leu Leu Pro Pro Leu Gly Val Ala Ile Ser
545                 550                 555                 560
Val Ile Ile Ile Phe Tyr Cys Tyr Arg Val Asn Arg Gln
                565                 570
```

<210> SEQ ID NO 292
<211> LENGTH: 1720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 292

| | | | | |
|---|---|---|---|---|
| gaggtgcagc | tgttggagtc | cggggggaggc | ttggtacagc | ctggggggtc cctgagactc | 60 |
| tcctgcgctg | catctggatt | cacctttcg | tcttatgcca | tgagctgggt ccgccaggct | 120 |
| ccagggaagg | ggctggagtg | ggtctcatct | attagtggta | gtggtgatta catatattac | 180 |
| gcagactccg | tgaagggccg | gttcaccatc | tccagagaca | tatccaagaa cacgctgtat | 240 |
| ctgcaaatga | acagtctgag | agccgaggac | acggccgtct | attactgtgc gaaggaagga | 300 |
| acaggtgcca | acagcagctt | ggcagactac | agaggccagg | gcaccttggt aaccgtttcc | 360 |
| tcattcgtgc | ccgtgttcct | gcccgccaag | cctacaacaa | ccctgctcc ccgtcctcct | 420 |
| acgcctgcac | ctacaatcgc | cagccagcct | ctgtctctga | ggccggaagc ttgtagacct | 480 |
| gcggctggcg | gagccgtgca | taccagagga | ctggatttcg | cctgcgacat ctacatttgg | 540 |
| gccccttttgg | ctggaacatg | tggcgttctg | ctgctgagcc | tcgtgatcac cctgtactgc | 600 |
| aaccaccgga | caagcggggg | ccgaaagaag | ctgctgtaca | tcttcaagca gcccttcatg | 660 |
| cggccgtcc | aaactaccca | ggaagaggac | ggctgctcct | gtcgttttcc cgaggaagaa | 720 |
| gaaggcggct | gcgagctgag | agtgaagttc | agcagaagcg | ccgacgcgcc tgcctatcag | 780 |
| caagggcaga | accagctgta | taacgagtta | aacctgggca | gacgggaaga gtacgatgtg | 840 |
| ttggataaaa | gacgtggccg | ggatcctgag | atgggggaa | agccgcgccg aaaaaacccct | 900 |
| caggaaggcc | tgtacaatga | actgcaaaag | gataagatgg | ccgaggccta cagtgagatt | 960 |
| gggatgaaag | gcgagcgccg | gaggggcaag | ggcacgatg | gcctttacca gggtttgagt | 1020 |
| accgccacca | aggacaccta | cgacgctctt | cacatgcaag | ccctgccccc tcgcggctct | 1080 |
| ggagaaggca | ggggctctct | gctgacctgc | ggcgacgtgg | aagagaaccc aggccccatg | 1140 |
| ggaagaggtt | tattgagagg | actgtggccc | ttacacatcg | ttctgtggac tcgtatcgcc | 1200 |
| tctaccatcc | cccccatgt | ccaaaagagc | gtaaacaacg | acatgatcgt gaccgacaac | 1260 |
| aatggcgctg | tcaagttccc | ccagctgtgc | aagttttgtg | acgtgcgctt cagcacttgt | 1320 |
| gacaatcaga | agagctgcat | gagcaactgc | tccatcacct | ccatctgtga aaaccccaa | 1380 |
| gaagtgtgcg | tcgccgtctg | gcgtaagaac | gacgagaaca | tcactttaga cacagtgtgc | 1440 |
| cacgatccca | aactgcccta | ccatgacttc | attttagaag | atgcagcctc tcccaagtgt | 1500 |
| atcatgaagg | aaaagaaaaa | gcctggcgag | accttcttca | tgtgttcttg ttcgtctgat | 1560 |
| gagtgcaacg | ataacatcat | cttcagcgaa | gagtacaata | cctcgaaccc cgatttatta | 1620 |
| ctggtgatct | tccaagttac | cggcatttct | cttctgcctc | cgttgggtgt ggctatcagc | 1680 |

```
gtgatcatca ttttctactg ctatcgtgtt aaccgtcagt                    1720
```

<210> SEQ ID NO 293
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293

```
gacatccaga tgacccagtc tccatcctcc ctgtctgcaa gcgttggaga tagagtcact    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc cgggacagat ttcactctca ccatcagcag tctgcaacct   240
gaagattttg caacttacta ctgtcagcaa agccacatcg cccctggac ttttggcgga   300
gggaccaagg ttgagatcaa agggagcact agcggctctg gcaaacctgg atctggcgag   360
ggatctacca agggccaggt gcagctggtg cagtctgggg ctgaggtgaa gaagcctggg   420
tcctcggtga aggtctcctg caaggcttct ggaggcacct cgcagactg tgctatcagc   480
tgggtgcgac aggcccctgg acaagggctt gagtggatgg gagggatcat ccctatattg   540
gcagagcaa actacgcaca gaagttccag gcagagtta cgattaccgc ggacgaatcc   600
acgagcacag cctacatgga gctgagcagc ctgagatctg aggacacggc ggtgtactac   660
tgcgccagag acagagacag cacaagcctg ccgtacaacc actactacat ggacgtatgg   720
ggcaagggta caactgtcac tgtctcctct gggtctctag acaatgagaa gagcaatgga   780
accattatcc atgtgaaagg gaaacacctt tgtccaagtc cctatttcc cggaccttct   840
aagccctttt gggtgctggt ggtggttggt ggagtcctgg cttgctatag cttgctagta   900
acagtggcct ttattatttt ctgggtgagg agtaagagga gcaggctcct gcacagtgac   960
tacatgaaca tgactccccg ccgcccggg cccacccgca agcattacca gccctatgcc  1020
ccaccacgcg acttcgcagc ctatcgctcc ctgagagtga agttcagcag gagcgcagac  1080
gcccccgcgt accagcaggg ccagaaccag ctctataacg agctcaatct aggacgaaga  1140
gaggagtacg atgttttgga caagaggcgt ggccgggacc ctgagatggg gggaaagccg  1200
agaaggaaga accctcagga aggcctgtac aatgaactgc agaaagataa gatggcggag  1260
gcctacagtg agattgggat gaaaggcgag cgccggaggg gcaaggggca cgatggcctt  1320
taccagggtc tcagtacagc caccaaggac acctacgacg cccttcacat gcaggccctg  1380
ccccctcgc                                                         1389
```

<210> SEQ ID NO 294
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 294

```
gacatccagt tgacccagtc tccatcctcc ctgtctgcaa gcgttggaga cagagttact    60
atcacttgcc gggcaagtca gagcattagc ctatatttaa attggtatca gcagaaacca   120
gggaaagccc ctaagctcct gatctatgct gcatccagtt tgcaaagtgg ggtcccatca   180
aggttcagtg gcagtggatc cgggacagat ttcactctca ccatcagcag tctgcaacct   240
```

| | |
|---|---|
| gaagattttg caacttacta ctgtcagcaa gtggccgtcg cccctggac tttcggcgga | 300 |
| gggaccaagg ttgagatcaa agggagcaca agcggctctg gcaaacctgg atctggcgag | 360 |
| ggatctacca agggccaggt gcagctggtg cagtctgggg ctgaggtgaa gaagcctggg | 420 |
| tcctcggtga aggtctcctg caaggcttct ggaggcacct tcgaacacta tgctatcagc | 480 |
| tgggtgcgac aggcccctgg acaggggctt gagtggatgg gagggatcat ccccatattg | 540 |
| ggccgagcaa actacgcaca gaagttccag ggcagagtca cgattaccgc ggacgaatcc | 600 |
| acgagcacag cctacatgga gctgagcagc ctgagatctg aggacacggc ggtgtactac | 660 |
| tgcgccagag acagaagctg ggaaggatct ccctatatgt actacggaat ggacgtttgg | 720 |
| ggccaaggga caatggtcac cgtttcctca gggtctctag acaatgagaa gagcaatgga | 780 |
| accattatcc atgtgaaagg gaaacacctt tgtccaagtc cctatttcc cggaccttct | 840 |
| aagccctttt gggtgctggt ggtggttggt ggagtcctgg cttgctatag cttgctagta | 900 |
| acagtggcct ttattatttt ctgggtgagg agtaagagga gcaggctcct gcacagtgac | 960 |
| tacatgaaca tgactccccg ccgccccggg cccacccgca agcattacca gccctatgcc | 1020 |
| ccaccacgcg acttcgcagc ctatcgctcc ctgagagtga agttcagcag gagcgcagac | 1080 |
| gccccgcgt accagcaggg ccagaaccag ctctataacg agctcaatct aggacgaaga | 1140 |
| gaggagtacg atgttttgga caagaggcgt ggccgggacc ctgagatggg gggaaagccg | 1200 |
| agaaggaaga accctcagga aggcctgtac aatgaactgc agaaagataa gatggcggag | 1260 |
| gcctacagtg agattgggat gaaaggcgag cgccggaggg gcaaggggca cgatggcctt | 1320 |
| taccagggtc tcagtacagc caccaaggac acctacgacg cccttcacat gcaggccctg | 1380 |
| ccccctcgc | 1389 |

<210> SEQ ID NO 295
<211> LENGTH: 2035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295

| | |
|---|---|
| gacatccaga tgacccagtc tccatcctcc ctgtctgcaa gcgttggaga tagagtcact | 60 |
| atcacttgcc gggcaagtca gagcattagc agctatttaa attggtatca gcagaaacca | 120 |
| gggaaagccc ctaagctcct gatctatgct gcatccagtt tgcaaagtgg ggtcccatca | 180 |
| aggttcagtg gcagtggatc cgggacagat ttcactctca ccatcagcag tctgcaacct | 240 |
| gaagattttg caacttacta ctgtcagcaa agccacatcg ccccttggac ttttggcgga | 300 |
| gggaccaagg ttgagatcaa agggagcact agcggctctg gcaaacctgg atctggcgag | 360 |
| ggatctacca agggccaggt gcagctggtg cagtctgggg ctgaggtgaa gaagcctggg | 420 |
| tcctcggtga aggtctcctg caaggcttct ggaggcacct tcgcagacta tgctatcagc | 480 |
| tgggtgcgac aggcccctgg acaagggctt gagtggatgg gagggatcat ccctatattg | 540 |
| ggcagagcaa actacgcaca gaagttccag ggcagagtta cgattaccgc ggacgaatcc | 600 |
| acgagcacag cctacatgga gctgagcagc ctgagatctg aggacacggc ggtgtactac | 660 |
| tgcgccagag acagagacag cacaagcctg ccgtacaacc actactacat ggacgtatgg | 720 |
| ggcaagggta caactgtcac tgtctcctct gggtctctag acaatgagaa gagcaatgga | 780 |
| accattatcc atgtgaaagg gaaacacctt tgtccaagtc cctatttcc cggaccttct | 840 |

```
aagcccttttt gggtgctggt ggtggttggt ggagtcctgg cttgctatag cttgctagta    900
acagtggcct ttattatttt ctgggtgagg agtaagagga gcaggctcct gcacagtgac    960
tacatgaaca tgactccccg ccgccccggg cccaccogca agcattacca gccctatgcc   1020
ccaccacgcg acttcgcagc ctatcgctcc ctgagagtga agttcagcag gagcgcagac   1080
gcccccgcgt accagcaggg ccagaaccag ctctataacg agctcaatct aggacgaaga   1140
gaggagtacg atgttttgga caagaggcgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg gcaaggggca cgatggcctt   1320
taccagggtc tcagtacagc caccaaggac acctacgacg cccttcacat gcaggccctg   1380
cccccctcgcg gctctggaga aggcaggggc tctctgctga cctgcggcga cgtggaagag   1440
aacccaggcc ccatgggaag aggtttattg agaggactgt ggcccttaca catcgttctg   1500
tggactcgta tcgcctctac catcccccccc catgtccaaa agagcgtaaa caacgacatg   1560
atcgtgaccg acaacaatgg cgctgtcaag ttcccccagc tgtgcaagtt ttgtgacgtg   1620
cgcttcagca cttgtgacaa tcagaagagc tgcatgagca actgctccat cacctccatc   1680
tgtgagaaac cccaagaagt gtgcgtcgcc gtctggcgta agaacgacga gaacatcact   1740
ttagagacag tgtgccacga tcccaaactg ccctaccatg acttcatttt agaagatgca   1800
gcctctccca agtgtatcat gaaggaaaag aaaaagcctg gcgagacctt cttcatgtgt   1860
tcttgttcgt ctgatgagtg caacgataac atcatcttca gcgaagagta caatacctcg   1920
aaccccgatt tattactggt gatcttccaa gttaccggca tttctcttct gcctccgttg   1980
ggtgtggcta tcagcgtgat catcatttttc tactgctatc gtgttaaccg tcagt         2035
```

<210> SEQ ID NO 296
<211> LENGTH: 2035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296

```
gacatccagt tgacccagtc tccatcctcc ctgtctgcaa gcgttggaga cagagttact     60
atcacttgcc gggcaagtca gagcattagc ctatatttaa attggtatca gcagaaacca    120
gggaaagccc ctaagctcct gatctatgct gcatccagtt tgcaaagtgg ggtcccatca    180
aggttcagtg gcagtggatc cgggacagat ttcactctca ccatcagcag tctgcaacct    240
gaagattttg caacttacta ctgtcagcaa gtggccgtcg ccccttggac tttcggcgga    300
gggaccaagg ttgagatcaa agggagcaca agcggctctg gcaaacctgg atctggcgag    360
ggatctacca agggccaggt gcagctggtg cagtctgggg ctgaggtgaa gaagcctggg    420
tcctcggtga aggtctcctg caaggcttct ggaggcacct cgaacactta tgctatcagc    480
tgggtgcgac aggcccctgg acaggggctt gagtggatgg gagggatcat ccccatattg    540
ggccgagcaa actacgcaca gaagttccag ggcagagtca cgattaccgc ggacgaatcc    600
acgagcacag cctacatgga gctgagcagc ctgagatctg aggacacggc ggtgtactac    660
tgcgccagag acagaagctg ggaaggatct ccctatatgt actacggaat ggacgtttgg    720
ggccaaggga caatggtcac cgtttcctca gggtctctag acaatgagaa gagcaatgga    780
accattatcc atgtgaaagg gaaacacctt tgtccaagtc ccctatttcc cggaccttct    840
```

```
aagcccttt  gggtgctggt  ggtggttggt  ggagtcctgg  cttgctatag  cttgctagta      900
acagtggcct  ttattatttt  ctgggtgagg  agtaagagga  gcaggctcct  gcacagtgac      960
tacatgaaca  tgactccccg  ccgccccggg  cccacccgca  agcattacca  gccctatgcc     1020
ccaccacgcg  acttcgcagc  ctatcgctcc  ctgagagtga  agttcagcag  gagcgcagac     1080
gcccccgcgt  accagcaggg  ccagaaccag  ctctataacg  agctcaatct  aggacgaaga     1140
gaggagtacg  atgttttgga  caagaggcgt  ggccgggacc  ctgagatggg  gggaaagccg     1200
agaaggaaga  accctcagga  aggcctgtac  aatgaactgc  agaaagataa  gatggcggag     1260
gcctacagtg  agattgggat  gaaaggcgag  cgccggaggg  gcaaggggca  cgatggcctt     1320
taccagggtc  tcagtacagc  caccaaggac  acctacgacg  cccttcacat  gcaggccctg     1380 cccccctcgcg  gctctggaga  aggcaggggc  tctctgctga  cctgcggcga  cgtggaagag     1440
aacccaggcc  ccatgggaag  aggtttattg  agaggactgt  ggcccttaca  catcgttctg     1500
tggactcgta  tcgcctctac  catcccccccc  catgtccaaa  agagcgtaaa  caacgacatg     1560
atcgtgaccg  acaacaatgg  cgctgtcaag  ttcccccagc  tgtgcaagtt  ttgtgacgtg     1620
cgcttcagca  cttgtgacaa  tcagaagagc  tgcatgagca  actgctccat  cacctccatc     1680
tgtgagaaac  cccaagaagt  gtgcgtcgcc  gtctggcgta  agaacgacga  gaacatcact     1740
ttagagacag  tgtgccacga  tcccaaactg  ccctaccatg  acttcatttt  agaagatgca     1800
gcctctccca  agtgtatcat  gaaggaaaag  aaaaagcctg  gcgagacctt  cttcatgtgt     1860
tcttgttcgt  ctgatgagtg  caacgataac  atcatcttca  gcgaagagta  caatacctcg     1920
aaccccgatt  tattactggt  gatcttccaa  gttaccggca  tttctcttct  gcctccgttg     1980
ggtgtggcta  tcagcgtgat  catcattttc  tactgctatc  gtgttaaccg  tcagt         2035
```

<210> SEQ ID NO 297
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser Glu Glu
            100

<210> SEQ ID NO 298
<211> LENGTH: 134
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 298

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser Glu Glu Leu Leu Val Ile Phe Gln Val
            100                 105                 110

Thr Gly Ile Ser Leu Leu Pro Pro Leu Gly Val Ala Ile Ser Val Ile
        115                 120                 125

Ile Ile Phe Tyr Cys Tyr
    130

<210> SEQ ID NO 299
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Gly Arg Gly Leu Leu Arg Gly Leu Trp Pro Leu His Ile Val Leu
1               5                   10                  15

Trp Thr Arg Ile Ala Ser Gln Leu Cys Lys Phe Cys Asp Val Arg Phe
            20                  25                  30

Ser Thr Cys Asp Asn Gln Lys Ser Cys Met Ser Asn Cys Ser Ile Thr
        35                  40                  45

Ser Ile Cys Glu Lys Pro Gln Glu Val Cys Val Ala Val Trp Arg Lys
    50                  55                  60

Asn Asp Glu Asn Ile Thr Leu Glu Thr Val Cys His Asp Pro Lys Leu
65                  70                  75                  80

Pro Tyr His Asp Phe Ile Leu Glu Asp Ala Ala Ser Pro Lys Cys Ile
                85                  90                  95

Met Lys Glu Lys Lys Lys Pro Gly Glu Thr Phe Phe Met Cys Ser Cys
            100                 105                 110

Ser Ser Asp Glu Cys Asn Asp Asn Ile Ile Phe Ser Glu Glu Leu Leu
        115                 120                 125

Leu Val Ile Phe Gln Val Thr Gly Ile Ser Leu Leu Pro Pro Leu Gly
    130                 135                 140

Val Ala Ile Ser Val Ile Ile Ile Phe Tyr Cys Tyr
145                 150                 155

<210> SEQ ID NO 300
<211> LENGTH: 2103
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 300

| | | | | | |
|---|---|---|---|---|---|
| atgcttctcc | tggtgacaag | ccttctgctc | tgtgaattac | cacacccagc | attcctcctg | 60 |
| attcctgaca | tccagatgac | ccagtctcca | tcctccctgt | ctgcaagcgt | tggagataga | 120 |
| gtcactatca | cttgccgggc | aagtcagagc | attagcagct | atttaaattg | gtatcagcag | 180 |
| aaaccaggga | aagcccctaa | gctcctgatc | tatgctgcat | ccagtttgca | aagtggggtc | 240 |
| ccatcaaggt | tcagtggcag | tggatccggg | acagatttca | ctctcaccat | cagcagtctg | 300 |
| caacctgaag | attttgcaac | ttactactgt | cagcaaagcc | acatcgcccc | ttggactttt | 360 |
| ggcggaggga | ccaaggttga | gatcaaaggg | agcactagcg | gctctggcaa | acctggatct | 420 |
| ggcgagggat | ctaccaaggg | ccaggtgcag | ctggtgcagt | ctggggctga | ggtgaagaag | 480 |
| cctgggtcct | cggtgaaggt | ctcctgcaag | gcttctggag | gcaccttcgc | agactatgct | 540 |
| atcagctggg | tgcgacaggc | ccctggacaa | gggcttgagt | ggatgggagg | gatcatccct | 600 |
| atattgggca | gagcaaacta | cgcacagaag | ttccagggca | gagttacgat | taccgcggac | 660 |
| gaatccacga | gcacagccta | catggagctg | agcagcctga | gatctgagga | cacggcggtg | 720 |
| tactactgcg | ccagagacag | agacagcaca | agcctgccgt | acaaccacta | ctacatggac | 780 |
| gtatgggca | agggtacaac | tgtcactgtc | tcctctgggt | ctctagacaa | tgagaagagc | 840 |
| aatggaacca | ttatccatgt | gaaagggaaa | cacctttgtc | caagtcccct | atttcccgga | 900 |
| ccttctaagc | ccttttgggt | gctggtggtg | gttggtggag | tcctggcttg | ctatagcttg | 960 |
| ctagtaacag | tggcctttat | tattttctgg | gtgaggagta | agaggagcag | gctcctgcac | 1020 |
| agtgactaca | tgaacatgac | tccccgccgc | cccgggccca | cccgcaagca | ttaccagccc | 1080 |
| tatgccccac | cacgcgactt | cgcagcctat | cgctccctga | gagtgaagtt | cagcaggagc | 1140 |
| gcagacgccc | ccgcgtacca | gcagggccag | aaccagctct | ataacgagct | caatctagga | 1200 |
| cgaagagagg | agtacgatgt | tttggacaag | aggcgtggcc | gggaccctga | gatggggga | 1260 |
| aagccgagaa | ggaagaaccc | tcaggaaggc | ctgtacaatg | aactgcagaa | agataagatg | 1320 |
| gcggaggcct | acagtgagat | tgggatgaaa | ggcgagcgcc | ggaggggcaa | ggggcacgat | 1380 |
| ggcctttacc | agggtctcag | tacagccacc | aaggacacct | acgacgccct | tcacatgcag | 1440 |
| gccctgcccc | ctcgcggctc | tggagaaggc | aggggctctc | tgctgacctg | cggcgacgtg | 1500 |
| gaagagaacc | caggccccat | gggaagaggt | ttattgagag | gactgtggcc | cttacacatc | 1560 |
| gttctgtgga | ctcgtatcgc | ctctaccatc | ccccccatg | tccaaaagag | cgtaaacaac | 1620 |
| gacatgatcg | tgaccgacaa | caatggcgct | gtcaagttcc | cccagctgtg | caagttttgt | 1680 |
| gacgtgcgct | tcagcacttg | tgacaatcag | aagagctgca | tgagcaactg | ctccatcacc | 1740 |
| tccatctgtg | agaaacccca | agaagtgtgc | gtcgccgtct | ggcgtaagaa | cgacgagaac | 1800 |
| atcactttag | agacagtgtg | ccacgatccc | aaactgccct | accatgactt | catttagaa | 1860 |
| gatgcagcct | ctcccaagtg | tatcatgaag | gaaaagaaaa | agcctggcga | gaccttcttc | 1920 |
| atgtgttctt | gttcgtctga | tgagtgcaac | gataacatca | tcttcagcga | agagtacaat | 1980 |
| acctcgaacc | ccgatttatt | actggtgatc | ttccaagtta | ccggcatttc | tcttctgcct | 2040 |
| ccgttgggtg | tggctatcag | cgtgatcatc | attttctact | gctatcgtgt | taaccgtcag | 2100 |
| tga | | | | | 2103 |

<210> SEQ ID NO 301

<211> LENGTH: 2102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 301

```
atgcttctcc tggtgacaag ccttctgctc tgtgaattac cacacccagc attcctcctg      60
attcctgaca tccagttgac ccagtctcca tcctccctgt ctgcaagcgt tggagacaga     120
gttactatca cttgccgggc aagtcagagc attagctat atttaaattg gtatcagcag      180
aaaccaggga aagcccctaa gctcctgatc tatgctgcat ccagtttgca aagtggggtc     240
ccatcaaggt tcagtggcag tggatccggg acagatttca ctctcaccat cagcagtctg     300
caacctgaag attttgcaac ttactactgt cagcaagtgg ccgtcgcccc ttggactttc     360
ggcggaggga ccaaggttga tcaaaggg agcacaagcg ctctggcaa acctggatct        420
ggcgagggat ctaccaaggg ccaggtgcag ctggtgcagt ctggggctga ggtgaagaag     480
cctgggtcct cggtgaaggt ctcctgcaag gcttctggag gcaccttcga acactatgct     540
atcagctggg tgcgacaggc ccctggacag gggcttgagt ggatggggag gatcatcccc     600
atattgggcc gagcaaacta cgcacagaag ttccagggca gagtcacgat taccgcggac     660
gaatccacga gcacagccta catggagctg agcagcctga tctgagga cacggcggtg       720
tactactgcg ccagagacag aagctgggaa ggatctccct atatgtacta cggaatggac     780
gtttggggcc aagggacaat ggtcaccgtt cctcagggt ctctagacaa tgagaagagc      840
aatggaacca ttatccatgt gaagggaaa cacctttgtc caagtcccct atttcccgga      900
ccttctaagc cttttgggt gctggtggtg gttggtggag tcctggcttg ctatagcttg      960
ctagtaacag tggcctttat tatttctgg gtgaggagta agaggagcag gctcctgcac     1020
agtgactaca tgaacatgac tccccgccgc cccgggccca cccgcaagca ttaccagccc    1080
tatgccccac cacgcgactt cgcagcctat cgctccctga gagtgaagtt cagcaggagc    1140
gcagacgccc ccgcgtacca gcagggccag aaccagctct ataacgagct caatctagga    1200
cgaagagagg agtacgatgt tttggacaag aggcgtggcc gggaccctga gatgggggga    1260
aagccgagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gcc ctgccc ctcgcggctc tggagaaggc aggggctctc tgctgacctg cggcgacgtg    1500
gaagagaacc caggccccat gggaagaggt ttattgagag actgtggcc cttacacatc    1560
gttctgtgga ctcgtatcgc ctctaccatc ccccccatg tccaaaagag cgtaaacaac    1620
gacatgatcg tgaccgacaa caatggcgct gtcaagttcc cccagctgtg caagttttgt    1680
gacgtgcgct tcagcacttg tgacaatcag aagagctgca tgagcaactg ctccatcacc    1740
tccatctgtg agaaacccca agaagtgtgc gtcgccgtct ggcgtaagaa cgacgagaac    1800
atcactttag agacagtgtg ccacgatccc aaactgccct accatgactt cattttagaa    1860
gatgcagcct ctcccaagtg tatcatgaag gaaagaaaa agcctggcga gaccttcttc    1920
atgtgttctt gttcgtctga tgagtgcaac gataacatca tcttcagcga agagtacaat    1980
acctcgaacc ccgatttatt actggtgatc ttccaagtta ccggcatttc tcttctgcct    2040
ccgttgggtg tggctatcag cgtgatcatc attttctact gctatcgtgt taaccgtcag    2100
```

| | | |
|---|---|---|
| tg | | 2102 |

<210> SEQ ID NO 302
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302

| | | |
|---|---|---|
| atgcttctcc tggtgacaag ccttctgctc tgtgaattac cacacccagc attcctcctg | | 60 |
| attcctgaca tccagatgac ccagtctcca tcctccctgt ctgcaagcgt tggagataga | | 120 |
| gtcactatca cttgccgggc aagtcagagc attagcagct atttaaattg gtatcagcag | | 180 |
| aaaccaggga aagcccctaa gctcctgatc tatgctgcat ccagtttgca aagtggggtc | | 240 |
| ccatcaaggt tcagtggcag tggatccggg acagatttca ctctcaccat cagcagtctg | | 300 |
| caacctgaag attttgcaac ttactactgt cagcaaagcc acatcgcccc ttggactttt | | 360 |
| ggcggaggga ccaaggttga gatcaaaggg agcactagcg gctctggcaa acctggatct | | 420 |
| ggcgagggat ctaccaaggg ccaggtgcag ctggtgcagt ctggggctga ggtgaagaag | | 480 |
| cctgggtcct cggtgaaggt ctcctgcaag gcttctggag gcaccttcgc agactatgct | | 540 |
| atcagctggg tgcgacaggc ccctggacaa gggcttgagt ggatgggagg gatcatccct | | 600 |
| atattgggca gagcaaacta cgcacagaag ttccagggca gagttacgat taccgcggac | | 660 |
| gaatccacga gcacagccta catggagctg agcagcctga gatctgagga cacggcggtg | | 720 |
| tactactgcg ccagagacag agacagcaca agcctgccgt acaaccacta ctacatggac | | 780 |
| gtatggggca agggtacaac tgtcactgtc tcctctgggt ctctagacaa tgagaagagc | | 840 |
| aatggaacca ttatccatgt gaaagggaaa cacctttgtc caagtcccct atttcccgga | | 900 |
| ccttctaagc ccttttgggt gctggtggtg gttggtggag tcctggcttg ctatagcttg | | 960 |
| ctagtaacag tggcctttat tattttctgg gtgaggagta gaggagcag gctcctgcac | | 1020 |
| agtgactaca tgaacatgac tccccgccgc cccgggccca cccgcaagca ttaccagccc | | 1080 |
| tatgccccac cacgcgactt cgcagcctat cgctccctga gagtgaagtt cagcaggagc | | 1140 |
| gcagacgccc ccgcgtacca gcagggccag aaccagctct ataacgagct caatctagga | | 1200 |
| cgaagagagg agtacgatgt tttggacaag aggcgtggcc gggaccctga gatgggggga | | 1260 |
| aagccgagaa ggaagaaccc tcaggaaggc ctgtacaatg aactgcagaa agataagatg | | 1320 |
| gcggaggcct acagtgagat tgggatgaaa ggcgagcgcc ggaggggcaa ggggcacgat | | 1380 |
| ggcctttacc agggtctcag tacagccacc aaggacacct acgacgccct tcacatgcag | | 1440 |
| gccctgcccc ctcgctga | | 1458 |

<210> SEQ ID NO 303
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303

| | | |
|---|---|---|
| atgcttctcc tggtgacaag ccttctgctc tgtgaattac cacacccagc attcctcctg | | 60 |
| attcctgaca tccagttgac ccagtctcca tcctccctgt ctgcaagcgt tggagacaga | | 120 |
| gttactatca cttgccgggc aagtcagagc attagcctat atttaaattg gtatcagcag | | 180 |

```
aaaccaggga aagcccctaa gctcctgatc tatgctgcat ccagtttgca aagtggggtc    240
ccatcaaggt tcagtggcag tggatccggg acagatttca ctctcaccat cagcagtctg    300
caacctgaag attttgcaac ttactactgt cagcaagtgg ccgtcgcccc ttggactttc    360
ggcggaggga ccaaggttga gatcaaaggg agcacaagcg gctctggcaa acctggatct    420
ggcgagggat ctaccaaggg ccaggtgcag ctggtgcagt ctggggctga ggtgaagaag    480
cctgggtcct cggtgaaggt ctcctgcaag gcttctggag gcaccttcga acactatgct    540
atcagctggg tgcgacaggc ccctggacag gggcttgagt ggatgggagg gatcatcccc    600
atattgggcc gagcaaacta cgcacagaag ttccagggca gagtcacgat taccgcggac    660
gaatccacga gcacagccta catggagctg agcagcctga gatctgagga cacggcggtg    720
tactactgcg ccagagacag aagctgggaa ggatctccct atatgtacta cggaatggac    780
gtttggggcc aagggacaat ggtcaccgtt tcctcagggt ctctagacaa tgagaagagc    840
aatggaacca ttatccatgt gaaagggaaa cacctttgtc caagtcccct atttcccgga    900
ccttctaagc ccttttgggt gctggtggtg gttggtggag tcctggcttg ctatagcttg    960
ctagtaacag tggcctttat tattttctgg gtgaggagta agaggagcag gctcctgcac   1020
agtgactaca tgaacatgac tccccgccgc cccgggccca cccgcaagca ttaccagccc   1080
tatgccccac cacgcgactt cgcagcctat cgctccctga gagtgaagtt cagcaggagc   1140
gcagacgccc ccgcgtacca gcagggccag aaccagctct ataacgagct caatctagga   1200
cgaagagagg agtacgatgt tttggacaag aggcgtggcc gggaccctga tgggggga    1260 aagccgagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgctga                                                 1458

<210> SEQ ID NO 304
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
```

```
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues
<220> FEATURE:
<221> NAME/KEY: SITE
<222> LOCATION: (1)..(50)
<223> OTHER INFORMATION: This sequence may encompass 1-5 "(G)n(S)n"
      repeating units wherein n = 1-5

<400> SEQUENCE: 304

Gly Gly Gly Gly Gly Ser Ser Ser Ser Gly Gly Gly Gly Gly Ser
1               5                   10                  15

Ser Ser Ser Ser Gly Gly Gly Gly Gly Ser Ser Ser Ser Gly Gly
            20                  25                  30

Gly Gly Gly Ser Ser Ser Ser Ser Gly Gly Gly Gly Gly Ser Ser Ser
        35                  40                  45

Ser Ser
    50
```

TACI BINDING MOLECULES

CROSS REFERENCE TO RELATED APPLICATIONS

This application claims priority to U.S. Provisional Application No. 63/175,997, filed Apr. 16, 2021, U.S. Provisional Application No. 63/209,869, filed Jun. 11, 2021, U.S. Provisional Application No. 63/279,477 filed Nov. 15, 2021 and U.S. Provisional Application No. 63/310,492 filed Feb. 15, 2022, which are incorporated herein in their entireties for all purposes.

SEQUENCE LISTING

The instant application contains a Sequence Listing which has been submitted electronically in ASCII format and is hereby incorporated by reference in its entirety. Said ASCII copy, created on Jun. 3, 2022, is named K-1111-US-NP_SL.txt and is 263,001 bytes in size.

TECHNICAL FIELD

The present disclosure relates to the field of cell therapy, and more specifically, to antibodies, CARs and/or TCRs that target antigens present on multiple myeloma cells.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen. A need exists for CARs and TCRs for targeting and killing cancer cells and, in particular, cells expressing transmembrane activator and CAML interactor (TACI) and/or B-cell maturation antigen (BCMA), such as multiple myeloma cells.

SUMMARY

Disclosed are antibodies, antigen binding fragments thereof, and nucleic acids encoding the same, comprising a dual TACI-BCMA binding domain. In embodiments, the dual TACI-BCMA binding domain comprises sequences of three heavy chain complementarity determining regions (HCDRs) of any one of the heavy chain variable region (HCVR) from SEQ ID NOs: 1, 25, 49, 73, 97, 121, 145, 169, and 193 and sequences of three light chain CDRs (LCDRs) of any one of the light chain variable region (LCVR) from SEQ ID NOs: 12, 36, 60, 84, 108, 132, 156, 180, and 204.

In embodiments, the dual TACI-BCMA binding domain comprises a first domain comprising three heavy chain complementarity determining regions (HCDR1, HCDR2 and HCDR3) and a second domain comprising three light chain complementarity determining regions (LCDR1, LCDR2 and LCDR3), wherein (i) the HCDR1 has a sequence according to any one of SEQ ID NOs: 3-5, 27-29, 51-53, 75-77, 99-101, 123-125, 147-149, 171-173, and 195-197; (ii) the HCDR2 has a sequence according to any one of SEQ ID NOs: 6-8, 30-32, 54-56, 78-80, 102-104, 126-128, 150-152, 174-176, and 198-200; (iii) the HCDR3 has a sequence according to any one of SEQ ID NOs: 9-11, 33-35, 57-59, 81-83, 105-107, 129-131, 153-155, 177-179, and 201-203; (iv) the LCDR1 has a sequence according to any one of SEQ ID NOs: 14-16, 38-40, 62-64, 86-88, 110-112, 134-136, 158-160, 182-184, and 206-208; (v) the LCDR2 has a sequence according to any one of SEQ ID NOs: 17-19, 41-43, 65-67, 89-91, 113-115, 137-139, 161-163, 185-187, and 209-211; and (vi) the LCDR3 has a sequence according to any one of SEQ ID NOs: 20-22, 44-46, 68-70, 92-94, 116-118, 140-142, 164-166, 188-190, and 212-214. In embodiments, the HCDRs comprise: (i) an HCDR1 according to any one of SEQ ID NOs: 3-5; an HCDR2 according to any one of SEQ ID NOs: 6-8; an HCDR3 according to any one of SEQ ID NOs: 9-11; (ii) an HCDR1 according to any one of SEQ ID NOs: 27-29; an HCDR2 according to any one of SEQ ID NOs: 30-32; an HCDR3 according to any one of SEQ ID NOs: 33-35; (iii) an HCDR1 according to any one of SEQ ID NOs: 51-53; an HCDR2 according to any one of SEQ ID NOs: 54-56; an HCDR3 according to any one of SEQ ID NOs: 57-59; (iv) an HCDR1 according to any one of SEQ ID NOs: 75-77; an HCDR2 according to any one of SEQ ID NOs: 78-80; an HCDR3 according to any one of SEQ ID NOs: 81-83; (v) an HCDR1 according to any one of SEQ ID NOs: 99-101; an HCDR2 according to any one of SEQ ID NOs: 102-104; an HCDR3 according to any one of SEQ ID NOs: 105-107; (vi) an HCDR1 according to any one of SEQ ID NOs: 123-125; an HCDR2 according to any one of SEQ ID NOs: 126-128; an HCDR3 according to any one of SEQ ID NOs: 129-131; (vii) an HCDR1 according to any one of SEQ ID NOs: 147-149; an HCDR2 according to any one of SEQ ID NOs: 150-152; an HCDR3 according to any one of SEQ ID NOs: 153-155; (viii) an HCDR1 according to any one of SEQ ID NOs: 171-173; an HCDR2 according to any one of SEQ ID NOs: 174-176; an HCDR3 according to any one of SEQ ID NOs: 177-179; or (ix) an HCDR1 according to any one of SEQ ID NOs: 195-197; an HCDR2 according to any one of SEQ ID NOs: 198-200; an HCDR3 according to any one of SEQ ID NOs: 201-203; and the LCDRs comprise: (i) an LCDR1 according to any one of SEQ ID NOs: 14-16; an LCDR2 according to any one of SEQ ID NOs: 17-19; an LCDR3 according to any one of SEQ ID NOs: 20-22; (ii) an LCDR1 according to any one of SEQ ID NOs: 38-40; an LCDR2 according to any one of SEQ ID NOs: 41-43; an LCDR3 according to any one of SEQ ID NOs: 44-46; (iii) an LCDR1 according to any one of SEQ ID NOs: 62-64; an LCDR2 according to any one of SEQ ID NOs: 65-67; an LCDR3 according to any one of SEQ ID NOs: 68-70; (iv) an LCDR1 according to any one of SEQ ID NOs: 86-88; an LCDR2 according to any one of SEQ ID NOs: 89-91; an LCDR3 according to any one of SEQ ID NOs: 92-94; (v) an LCDR1 according to any one of SEQ ID NOs: 110-112; an LCDR2 according to any one of SEQ ID NOs: 113-115; an LCDR3 according to any one of SEQ ID NOs: 116-118; (vi) an LCDR1 according to any one of SEQ ID NOs: 134-136; an LCDR2 according to any one of SEQ ID NOs: 137-139; an LCDR3 according to any one of SEQ ID NOs: 140-142; (vii) an LCDR1 according to any one of SEQ ID NOs: 158-160; an LCDR2 according to any one of SEQ ID NOs: 161-163; an LCDR3 according to any one of SEQ ID NOs: 164-166; (viii) an LCDR1 according to any one of SEQ ID NOs: 182-184; an LCDR2 according to any one of SEQ ID NOs: 185-187; an LCDR3 according to any one of SEQ ID NOs: 188-190; or (ix) an LCDR1 according to any one of SEQ ID NOs: 206-208; an LCDR2 according to any one of SEQ ID NOs: 209-211; an LCDR3 according to any one of SEQ ID NOs: 212-214.

In embodiment, the antibody, or antigen binding fragment thereof, comprises a first domain comprising three heavy chain complementarity determining regions (HCDRs) and a second domain comprising three light chain complementarity determining regions (LCDRs), wherein: the HCDRs and LCDRs comprise: (i) an HCDR1 according to any one of SEQ ID NOs: 3-5; an HCDR2 according to any one of SEQ ID NOs: 6-8; an HCDR3 according to any one of SEQ ID NOs: 9-11; an LCDR1 according to any one of SEQ ID NOs: 14-16; an LCDR2 according to any one of SEQ ID NOs: 17-19; an LCDR3 according to any one of SEQ ID NOs: 20-22; (ii) an HCDR1 according to any one of SEQ ID NOs: 27-29; an HCDR2 according to any one of SEQ ID NOs: 30-32; an HCDR3 according to any one of SEQ ID NOs: 33-35; an LCDR1 according to any one of SEQ ID NOs: 38-40; an LCDR2 according to any one of SEQ ID NOs: 41-43; an LCDR3 according to any one of SEQ ID NOs: 44-46; (iii) an HCDR1 according to any one of SEQ ID NOs: 51-53; an HCDR2 according to any one of SEQ ID NOs: 54-56; an HCDR3 according to any one of SEQ ID NOs: 57-59; an LCDR1 according to any one of SEQ ID NOs: 62-64; an LCDR2 according to any one of SEQ ID NOs: 65-67; an LCDR3 according to any one of SEQ ID NOs: 68-70; (iv) an HCDR1 according to any one of SEQ ID NOs: 75-77; an HCDR2 according to any one of SEQ ID NOs: 78-80; an HCDR3 according to any one of SEQ ID NOs: 81-83; an LCDR1 according to any one of SEQ ID NOs: 86-88; an LCDR2 according to any one of SEQ ID NOs: 89-91; an LCDR3 according to any one of SEQ ID NOs: 92-94; (v) an HCDR1 according to any one of SEQ ID NOs: 99-101; an HCDR2 according to any one of SEQ ID NOs: 102-104; an HCDR3 according to any one of SEQ ID NOs: 105-107; an LCDR1 according to any one of SEQ ID NOs: 110-112; an LCDR2 according to any one of SEQ ID NOs: 113-115; an LCDR3 according to any one of SEQ ID NOs: 116-118; (vi) an HCDR1 according to any one of SEQ ID NOs: 123-125; an HCDR2 according to any one of SEQ ID NOs: 126-128; an HCDR3 according to any one of SEQ ID NOs: 129-131; an LCDR1 according to any one of SEQ ID NOs: 134-136; an LCDR2 according to any one of SEQ ID NOs: 137-139; an LCDR3 according to any one of SEQ ID NOs: 140-142; (vii) an HCDR1 according to any one of SEQ ID NOs: 147-149; an HCDR2 according to any one of SEQ ID NOs: 150-152; an HCDR3 according to any one of SEQ ID NOs: 153-155; an LCDR1 according to any one of SEQ ID NOs: 158-160; an LCDR2 according to any one of SEQ ID NOs: 161-163; an LCDR3 according to any one of SEQ ID NOs: 164-166; (viii) an HCDR1 according to any one of SEQ ID NOs: 171-173; an HCDR2 according to any one of SEQ ID NOs: 174-176; an HCDR3 according to any one of SEQ ID NOs: 177-179; an LCDR1 according to any one of SEQ ID NOs: 182-184; an LCDR2 according to any one of SEQ ID NOs: 185-187; an LCDR3 according to any one of SEQ ID NOs: 188-190; or (ix) an HCDR1 according to any one of SEQ ID NOs: 195-197; an HCDR2 according to any one of SEQ ID NOs: 198-200; an HCDR3 according to any one of SEQ ID NOs: 201-203; an LCDR1 according to any one of SEQ ID NOs: 206-208; an LCDR2 according to any one of SEQ ID NOs: 209-211; an LCDR3 according to any one of SEQ ID NOs: 212-214.

In embodiments, the antibody, or antigen binding fragment thereof comprises a first heavy chain variable domain comprising the three HCDRs and a light chain variable domain comprising the three LCDRs, wherein: (i) the heavy chain variable domain is at least 80% identical to SEQ ID NO: 1, SEQ ID NO: 25, SEQ ID NO: 49, SEQ ID NO: 73, SEQ ID NO: 97, SEQ ID NO: 121, SEQ ID NO: 145, SEQ ID NO: 169, or SEQ ID NO: 193; and (ii) the light chain variable domain is at least 80% identical to SEQ ID NO: 12, SEQ ID NO: 36, SEQ ID NO: 60, SEQ ID NO: 84, SEQ ID NO: 108, SEQ ID NO: 132, SEQ ID NO: 156, SEQ ID NO: 180, or SEQ ID NO: 204. In embodiments, the antibody, or antigen binding fragment thereof comprises a first heavy chain variable domain comprising the three HCDRs and a light chain variable domain comprising the three LCDRs, wherein: (i) the heavy chain variable domain is at least 80% identical to SEQ ID NO: 1 and the light chain variable domain is at least 80% identical to SEQ ID NO: 12; (ii) the heavy chain variable domain is at least 80% identical to SEQ ID NO: 25 and the light chain variable domain is at least 80% identical to SEQ ID NO: 36; (iii) the heavy chain variable domain is at least 80% identical to SEQ ID NO: 49 and the light chain variable domain is at least 80% identical to SEQ ID NO: 60; (iv) the heavy chain variable domain is at least 80% identical to SEQ ID NO: 73 and the light chain variable domain is at least 80% identical to SEQ ID NO: 84; (v) the heavy chain variable domain is at least 80% identical to SEQ ID NO: 97 and the light chain variable domain is at least 80% identical to SEQ ID NO: 108; (vi) the heavy chain variable domain is at least 80% identical to SEQ ID NO: 121 and the light chain variable domain is at least 80% identical to SEQ ID NO: 132; (vii) the heavy chain variable domain is at least 80% identical to SEQ ID NO: 145 and the light chain variable domain is at least 80% identical to SEQ ID NO: 156; (viii) the heavy chain variable domain is at least 80% identical to SEQ ID NO: 169 and the light chain variable domain is at least 80% identical to SEQ ID NO: 180; or (ix) the heavy chain variable domain is at least 80% identical to SEQ ID NO: 193 and the light chain variable domain is at least 80% identical to SEQ ID NO: 204. In certain embodiments, the three HCDRs and the three LCDRs are comprised by a single polypeptide. In certain embodiments, the antigen binding fragment thereof comprises an scFv.

Disclosed are chimeric antigen receptors and nucleic acids encoding the same, comprised by the antibody, or antigen binding fragment thereof of any of the antibodies, or an antigen binding fragments thereof, disclosed herein. In embodiments, the chimeric antigen receptor comprises a transmembrane domain of 4-1BB/CD137, an alpha chain of a T cell receptor, a beta chain of a T cell receptor, 2B4, CD3 epsilon, CD4, CD5, CD8 alpha, CD9, CD16, CD19, CD22, CD28, CD33, CD37, CD45, CD64, CD80, CD86, CD134, CD137, CD154, NKG2D, or a zeta chain of a T cell receptor, or any combination thereof.

Disclosed is a recombinant vector comprising the nucleic acids encoding a disclosed antibody, antigen binding fragment thereof, CAR or TCR. In embodiments, a recombinant vector or nucleic acid further comprises a nucleic acid encoding a dominant negative TGFβ receptor (DN TGFβR) In embodiments, a DN TGFβR comprises an extracellular domain (ECD) from a TGF-β receptor and a transmembrane domain (TMD), wherein the recombinant polypeptide lacks amino acid residues responsible for signaling and phosphorylation present in a wild-type TGF-β receptor. In embodiments, the ECD is from TGF-βRI or TGF-βRII. In embodiments, the TMD is the transmembrane domain from TGF-βRI, TGF-βRII, PDGFR, CD4, CD8, CD28, CD127, CD132, CD3ζ, 4-IBB, OX40, ICOS, CTLA-4, PD-1, LAG-3, 2B4, IL-5, IL-7, IL-7Rα, BTLA or mutants of any of the foregoing. In embodiments, the DN TGFβR further comprises a heterologous intracellular domain (ICD) which lacks amino acid residues responsible for signaling and phosphorylation present in wild-type TGF-β receptor.

Disclosed are host cells transformed with a disclosed nucleic acid or disclosed recombinant vector and pharmaceutical compositions comprising the same. In embodiments, a host cell is transformed with a nucleic acid encoding a disclosed CAR or TCR. In embodiments, a host cell is transformed with a nucleic acid encoding a disclosed CAR or TCR, and a nucleic acid encoding a dominant negative TGFβ receptor (DN TGFβR). In certain embodiments, the host cell is transformed with a nucleic acid encoding a membrane bound IL-15-IL-15Rα sushi domain chimeric receptor. In embodiment, the host cell comprises an iPSC, a T cell or a NK cell.

Disclosed is a method of treating disease in a patient in need of thereof, comprising administering a T cell and/or an NK cell or a pharmaceutical composition comprising the same, wherein the T cell and/or an NK cell comprises disclose CAR or TCR. In embodiments, the disease is multiple myeloma. Disclosed is a method of inducing an immune response in a subject or immunizing a subject against a multiple myeloma, the method comprising administering to the subject a T cell and/or an NK cell or a pharmaceutical composition comprising the same, wherein the T cell and/or an NK cell comprises disclose CAR or TCR. In embodiments, the T cell and/or an NK cell s allogeneic to the patient.

BRIEF DESCRIPTION OF THE DRAWINGS

FIGS. 4A-4D show results of 24-hour in vitro cytotoxicity assays of codon-optimized and noncodon-optimized CARs linked to TGFβII DNR.

DETAILED DESCRIPTION

Terms

Figure 1:
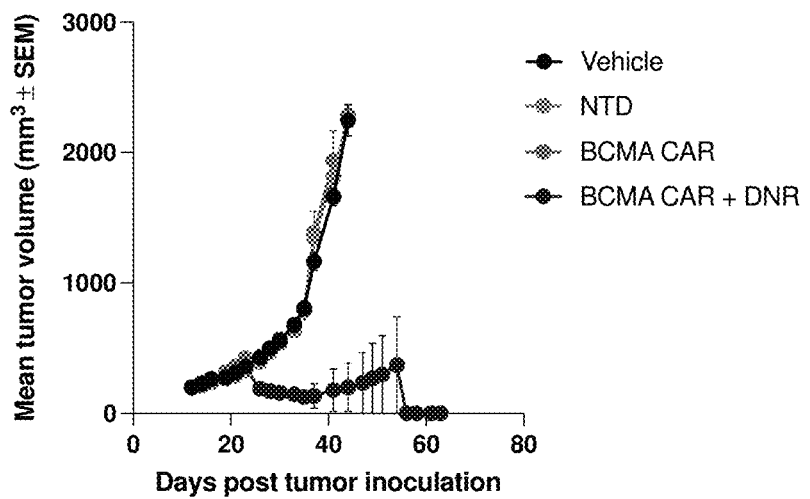
FIG. 1 shows enhanced efficacy with TGFβRII dominant-negative receptors (DNRs) observed with low dose CAR-T cell treatment in RPMI8226 myeloma model. (A) CAR targeted BCMA; (B) CAR targeted both TACI and BCMA (binder #1); and (C) CAR targeted both TACI and BCMA (binder #3).
Figure 1:
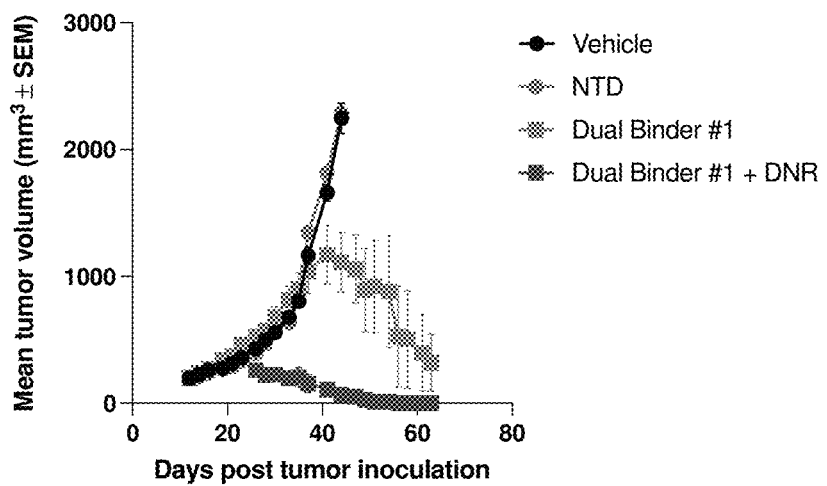
Figure 1:
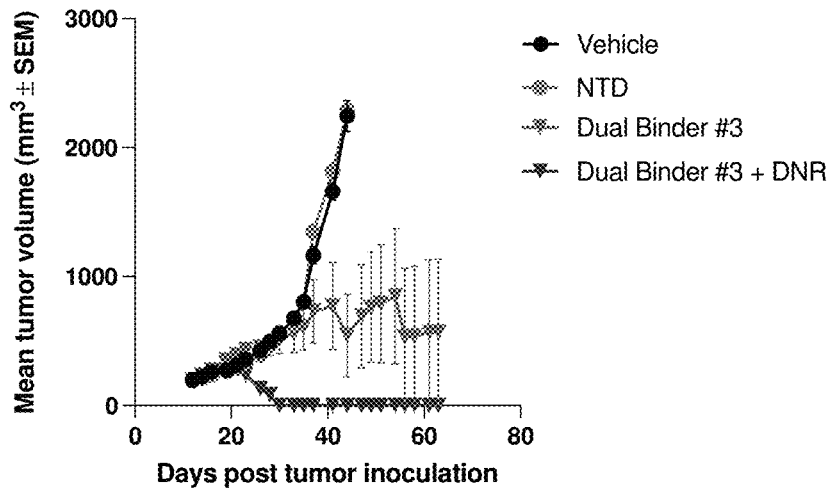

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; and B and C; A (alone); B (alone); and C (alone).

The term "e.g.," as used herein, is used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2$^{nd}$ ed., (2001), CRC Press; "The Dictionary of Cell & Molecular Biology", 5$^{th}$ ed., (2013), Academic Press; and "The Oxford Dictionary Of Biochemistry And Molecular Biology", Cammack et al. eds., 2$^{nd}$ ed, (2006), Oxford University Press, provide those of skill in the art with a general dictionary for many of the terms used in this disclosure.

"Administering" refers to the physical introduction of an agent to a subject, such as a modified T cell disclosed herein, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms, "activated" and "activation" refer to the state of a T cell that has been sufficiently stimulated to induce detectable cellular proliferation. In one embodiment, activation may also be associated with induced cytokine production, and detectable effector functions. The term "activated T cells" refers to, among other things, T cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

The term "agent" may refer to a molecule or entity of any class comprising, or a plurality of molecules or entities, any of which may be, for example, a polypeptide, nucleic acid, saccharide, lipid, small molecule, metal, cell (such as a T cell or NK cell or progenitor of such cells, for example an iPSC), or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

The term "allogeneic" refers to any material derived from one individual which is then introduced to another individual of the same species, e.g., allogeneic T cell or NK cell transplantation.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, human heavy-chain antibodies (e.g. UniAbs) single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Trans-Bodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," "antigen binding fragment," or "antibody fragment" or "antigen binding domain" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, an antigen binding molecule is a chimeric antigen receptor (CAR) or an engineered T cell receptor (TCR). In certain embodiments, the antigen binding molecule or domain binds to transmembrane activator and CAML interactor (TACI) and/or B-cell maturation antigen (BCMA). In certain embodiments, the antigen binding molecule or domain is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule or domain comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR (e.g., a CDR provided in the present disclosure) in that it is either identical in sequence or contains between 1, 2, 3, 4, or 5 (e.g., 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g., 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody. In various embodiments, an antigen binding fragment cross-competes with the reference antibody, for example, binding to substantially the same or identical epitope as the reference antibody An antigen binding fragment may be produced by any means. For example, in some embodiments, an antigen binding fragment may be enzymatically or chemically produced by fragmentation of an intact antibody. In some embodiments, an antigen binding fragment may be recombinantly produced (such as by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| CDR Numbering | | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |

TABLE 1-continued

| CDR Numbering | | | | |
|---|---|---|---|---|
| Loop | Kabat | AbM | Chothia | Contact |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha ($\alpha$), delta ($\delta$), epsilon ($\epsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

An "antigen" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a TCR or CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of transmembrane activator and CAML interactor (TACI) and/or B-cell maturation antigen (BCMA). A "target" is any molecule bound by a binding domain, antigen binding system, CAR or antigen binding agent, e.g., an antibody.

"Antigen-specific targeting region" (ASTR) refers to the region of the CAR, antibody or TCR, which targets specific antigens. The targeting regions on a CAR or TCR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of this disclosure. In fact, almost any molecule that binds a given antigen with high affinity can be used as an antigen-specific targeting region, as will be appreciated by those of skill in the art.

"Antigen presenting cell" or "APC" refers to cells that process and present antigens to T cells. Exemplary APCs comprise dendritic cells, macrophages, B cells, certain activated epithelial cells, and other cell types capable of TCR stimulation and appropriate T cell costimulation.

An "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

"Binding affinity" generally refers to the strength of the sum total of non-covalent interactions between a single binding site of a molecule (e.g., an antibody) and its binding partner (e.g., an antigen). Unless indicated otherwise "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

The term "KD" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec −1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M−1×sec-1 or 1/M) refers to the association rate constant of a particular antibody-antigen interaction, or the association rate constant of an antibody or antibody-binding fragment.

The term "$K_A$" (M−1 or 1/M) refers to the association equilibrium constant of a particular antibody-antigen interaction, or the association equilibrium constant of an antibody or antibody binding fragment. The association equilibrium constant is obtained by dividing the $k_a$ by the $k_d$.

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding domain, antibody, or antigen binding system with a target of the binding domain, antibody, or antigen binding system as compared to association of the binding domain, antibody, or antigen binding system with an entity that is not the target (i.e. non-target). In some embodiments, the binding domain, antibody, or antigen binding system can bind two different but related targets, such as both TACI and BCMA. In some embodiments, a binding domain, antibody, or antigen binding system selectively binds a target if binding between the binding domain, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding domain, antibody, or antigen binding system and a non-target. In some embodiments, a binding domain, antibody, or antigen binding system selectively binds a target if the binding affinity is less than about $10^{-5}$ M, less than about $10^{-6}$ M, less than about $10^{-7}$ M, less than about $10^{-8}$ M, or less than about $10^{-9}$ M.

In another embodiment, molecules that specifically bind to an antigen bind with a dissociation constant ($K_d$) of about $1 \times 10^{-7}$ M. In some embodiments, the antigen binding molecule specifically binds an antigen with "high affinity" when the $K_d$ is about $1 \times 10^{-9}$ M to about $5 \times 10^{-9}$ M. In some embodiments, the antigen binding molecule specifically binds an antigen with "very high affinity" when the $K_d$ is $1 \times 10^{-10}$ M to about $5 \times 10^{-10}$ M. In one embodiment, the antigen binding molecule has a $K_d$ of $10^{-9}$ M. In one embodiment, the off-rate is less than about $1 \times 10^{-5}$. In embodiments, the antigen binding molecule binds TACI and BCMA with a $K_d$ of about $1 \times 10^{-10}$ M to about $5 \times 10^{-10}$ M.

In certain embodiments, provided herein is an antibody or an antigen binding molecule thereof that binds to the target human antigen, e.g., In certain embodiments, the antigen binding molecule binds to TACI and BCMA with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. In some embodiments, the methods of the present disclosure can be used to reduce the tumor size of a tumor derived from, for example, prostate cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, multiple myeloma, and combinations of said cancers. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1α), MIP-1β (MIP-1b), gamma-induced protein 10 (IP-10), and thymus and activation regulated chemokine (TARC or CCL17).

"Chimeric antigen receptor" or "CAR" refers to a molecule engineered to comprise a binding domain and a means of activating immune cells (for example T cells such as naive T cells, central memory T cells, effector memory T cells, NK cells or combination thereof) upon antigen binding. CARs are also known as artificial T cell receptors, chimeric T cell receptors or chimeric immunoreceptors. In some embodiments, a CAR comprises a binding domain, an extracellular domain, a transmembrane domain, one or more co-stimulatory domains, and an intracellular signaling domain. A T cell that has been genetically engineered to express a chimeric antigen receptor may be referred to as a CAR T cell. Similarly, an NK cell that has been genetically engineered to express a chimeric antigen receptor may be referred to as a CAR NK cell.

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include an decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7.1.8, etc.) the response (reference response) produced by vehicle, a control composition.

"Extracellular domain" (or "ECD") refers to a portion of a polypeptide that, when the polypeptide is present in a cell membrane, is understood to reside outside of the cell membrane, in the extracellular space.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, NKG2D, 2B4 and CD154. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRγ chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling domains which are known as immunoreceptor tyrosine-based activation domain or ITAMs.

Examples of ITAM containing primary cytoplasmic signaling sequences that are of particular use in the disclosure include those derived from DAP10, DAP12, TCRzeta, FcRgamma, FcRbeta, CD3zeta, CD3gamma, CD3delta, CD3epsilon, CD5, CD22, CD79a, CD79b and CD66d.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1 BB (CD137), OX40 (CD134), CD30, CD40, PD-1, ICOS (CD278), LFA-1, CD2, CD7, LIGHT, NKD2C, 2B4, CD137, DAP12, B7-H2 and a ligand that specifically binds CD83. Accordingly, while the present disclosure provides exemplary costimulatory domains derived from CD28, other costimulatory domains are contemplated for use with the CARs described herein. The inclusion of one or more co stimulatory signaling domains may enhance the efficacy and expansion of T cells and NK cells expressing CAR receptors. The intracellular signaling and costimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from 4-1BB, CD28, CD134 and CD278) may more effectively direct antitumor activity as well as increased cytokine secretion, lytic activity, survival and proliferation in CAR expressing T cells in vitro, and in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

A "costimulatory signal" refers to a signal, which in combination with a primary signal, such as TCR/CD3 ligation, leads to a T cell response, such as, but not limited to, proliferation and/or upregulation or down regulation of key molecules.

A "costimulatory ligand" includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

Exemplary amino acid categorization

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |

TABLE 2-continued

Exemplary amino acid categorization

| Amino Acid | 3-Letter | 1-Letter | Property | Property | Hydropathy Index |
|---|---|---|---|---|---|
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

Exemplary amino acid categorization

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

An antigen binding molecule, such as an antibody, an antigen binding fragment thereof, CAR or TCR, "cross-competes" with a reference binding molecule, such as an antibody or an antigen binding fragment thereof, if the interaction between an antigen and the first antigen binding molecule blocks, limits, inhibits, or otherwise reduces the ability of the reference binding molecule to interact with the antigen. Cross competition can be complete, e.g., binding of the antigen binding molecule to the antigen completely blocks the ability of the reference binding molecule to bind the antigen, or it can be partial, e.g., binding of the antigen binding molecule to the antigen reduces the ability of the reference antigen binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137: 3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

A "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence domain, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, TACI and BCMA, which are transmembrane proteins expressed on multiple myeloma cells.

In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, which are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

An "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

"Endogenous" with reference to a gene, protein, and/or nucleic acid refers to the natural presence of that gene, protein, and/or nucleic acid in a cell, such as an immune cell.

"Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g. without introduction of the exogenous nucleic acid.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man. In embodiments, a CAR is a fusion protein. In embodiments, a TCR is a fusion protein.

The term "gene product" or "expression product" generally refers to an RNA transcribed from the gene (pre- and/or post-processing) or a polypeptide (pre- and/or post-modification) encoded by an RNA transcribed from the gene.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or NK cell, which can either be obtained from a patient or a donor. In some embodiments, the cell that is modified is an induced pluripotent stem cell (iPSC) which can be differentiated to a lymphocyte, such as a T cell or NK cell. The cell can be modified to express an exogenous construct, such as, e.g., a chimeric antigen receptor (CAR) or a T cell receptor (TCR), which is incorporated into the cell's genome. Other gene edits can also be done, for example to reduce rejection and/or enhance cell fitness. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell or NK cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents.

A "T cell receptor" or "TCR" refers to antigen-recognition molecules present on the surface of T cells. During normal T cell development, each of the four TCR genes, $\alpha$, $\beta$, $\gamma$, and $\delta$, may rearrange leading to highly diverse TCR proteins.

The term "heterologous" means from any source other than naturally occurring sequences. For example, a heterologous sequence included as a part of a costimulatory protein is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, NK cells and T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells or NK cells of the immunotherapy can come from any source known in the art. For example, T cells and NK cells can be differentiated in vitro from a hematopoietic stem cell population (for example iPSCs) or can be obtained from a subject. T cells and NK cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell or an NK cell. The term "in vivo" refers to events that occur within a multi-cellular organism, such as a human or a non-human animal.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Linker" (L) or "linker domain" or "linker region" refers to an oligo- or polypeptide region from about 1 to 100 amino acids in length, for example linking together any of the domains/regions of a CAR, TCR, a Dominant Negative TGFβ receptor and/or scFv, or ever one of more of those polypeptides together. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL (SEQ ID NO: 217) sequences of porcine teschovirus (P2A), virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ domain (SEQ ID NO: 218), which results in cleavage between the 2A glycine and the 2B proline. In some examples, a cleavable linker is used to connect a CAR or TCR with a Dominant Negative TGFβ receptor. Other linkers will be apparent to those of skill in the art and may be used in connection with this disclosure. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a CAR or TCR. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide. In another example it may be used to connect to or more polypeptides to be expressed, such as a CAR or TCR and a TGFβ-DNR. In some examples, the CAR, or and the TGFβ-DNR are connected by a cleavable linker.

Other linkers include non-cleavable linkers. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues.

The term "lymphocyte" includes natural killer (NK) cells, T cells, or B cells. NK cells are a type of cytotoxic (cell toxic) lymphocyte that represent a component of the inherent immune system. NK cells reject tumors and cells infected by viruses. It works through the process of apoptosis or programmed cell death. They were termed "natural killers" because they do not require activation in order to kill cells. T cells play a role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element. In embodiments, a promotor is operably linked to nucleic a A "patient" includes any human who is afflicted with a cancer (e.g., multiple myeloma). The terms "subject" and "patient" are used interchangeably herein.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "proliferation" refers to an increase in cell division, either symmetric or asymmetric division of cells. In some embodiments, "proliferation" refers to the symmetric or asymmetric division of T cells. "Increased proliferation" occurs when there is an increase in the number of cells in a treated sample compared to cells in a non-treated sample.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+ T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+ T lymphocytes. However, Treg cells within a tumor microenvironment (i.e. tumor-infiltrating Treg cells), Treg cells may make up as much as 20-30% of the total CD4+ T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

"Single chain variable fragment", "single-chain antibody variable fragments" or "scFv" antibodies refer to forms of antibodies comprising the variable regions of only the heavy and light chains, connected by a linker peptide.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

"Stimulation," refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

A "therapeutically effective amount," "effective dose," "effective amount," or "therapeutically effective dosage" of a therapeutic agent, e.g., engineered CAR T cells or NK cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "transmembrane domain" is a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. A transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

The disclosure may employ, unless indicated specifically to the contrary, methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); *Harlow and Lane, Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

TACI and BCMA Binding Agents

The present disclosure provides antigen binding agents, such as antibodies, chimeric antigen receptors (CARs) and T cell receptors (TCRs) comprising at least a single antigen binding domain that binds to both transmembrane activator and CAML interactor (TACI) and B-cell maturation antigen (BCMA), referred to herein as a dual TACI-BCMA binding domain. Among other things, the present disclosure provides methods and compositions useful for treatment of cancer and/or for initiating or modulating immune responses. In various embodiments, the dual TACI-BCMA binding domain is an scFv. Exemplary dual TACI-BCMA binding domain amino acid sequences, and nucleic acid sequences encoding the same, are provided herein, for example in Tables 4-12. In some embodiments, the dual TACI-BCMA binding domain of the present disclosure is comprised by a chimeric antigen receptor (CAR). In some embodiments, the dual TACI-BCMA binding domain of the present disclosure is comprised by a T cell receptor (TCR). In some embodiments, an antigen binding agent of the present disclosure is an engineered T cell receptor (TCR). In some embodiments, the CARs and/or TCRs are expressed with a dominant negative TFGβ Receptor (DN TFGβ R). In some embodiments, the CARs and/or TCRs are expressed with a membrane bound interleukin 15 (IL-15), IL-15Rα sushi-domain chimeric receptor. Disclosed are antibodies and fragments thereof that include a dual TACI-BCMA binding domain, such as disclosed in Tables 4-12.

Various embodiments of the present disclosure provide a vector encoding a dual TACI-BCMA binding domain or dual TACI-BCMA binding agent provided herein, e.g., a vector encoding a dual TACI-BCMA binding CAR or TCR. Various embodiments of the present disclosure provide a vector encoding a DN TFGβ R, e.g., a vector encoding a dual TACI-BCMA binding CAR and a DN TFGβ R. In some embodiments the DN TFGβ R is encoded in a separate vector from the vector encoding the a dual TACI-BCMA binding CAR or TCR. In some embodiments the DN TFGβ R is encoded in the same vector encoding the dual TACI-BCMA binding CAR or TCR. Various embodiments of the present disclosure provide a vector encoding an IL-15-IL-15Rα sushi-domain chimeric receptor, e.g., a vector encoding a dual TACI-BCMA binding CAR and an IL-15-IL-15Rα sushi-domain chimeric receptor. In some embodiments the IL-15-IL-15Rα sushi-domain chimeric receptor is encoded in a separate vector from the vector encoding the a dual TACI-BCMA binding CAR or TCR. In some embodiments the IL-15-IL-15Rα sushi-domain chimeric receptor is encoded in the same vector encoding the dual TACI-BCMA binding CAR or TCR.

Various embodiments of the present disclosure provide a dual TACI-BCMA binding agent that is a cell encoding or expressing a dual TACI-BCMA binding CAR or TCR, e.g., a T cell or NK cell engineered to encode or express a dual TACI-BCMA binding CAR or TCR. The present disclosure provides immune cells genetically modified with an integrated gene, e.g., a nucleotide sequence of interest (e.g., a constitutive expression construct and/or an inducible expression construct that comprises such nucleotide sequence. In embodiments, the immune cells are further engineered to express a DN TFGβ R. In embodiments, the immune cells are further engineered to express an L-15-IL-15Rα sushi-domain chimeric receptor. In some embodiments, the present disclosure provides methods of treating a subject having a tumor, such as a multiple myeloma, comprising administering to the subject a dual TACI-BCMA binding agent therapy described herein and/or a protein therapeutic described herein. In some embodiments, methods further comprise administration of one or more additional therapies (e.g., a second binding agent (e.g., CAR T cell, CAR-NK cell, TCR-T cell, TIL cell, allogeneic NK cell, and autologous NK cell), an antibody-drug conjugate, an antibody, a bispecific antibody, a T cell-engaging bispecific antibody, an engineered antibody, and/or a polypeptide described herein).

A dual TACI-BCMA binding domain of the present disclosure may comprise antigen-binding sequences as found in an antibody described herein. In some instances, a dual TACI-BCMA binding domain of the present disclosure comprises a dual TACI-BCMA binding domain described herein, such as an scFv. Unless otherwise indicated, it is to be appreciated the references to TACI and BCMA in the present disclosure relate to human TACI and human BCMA. In various embodiments, a dual TACI-BCMA binding domain of the present disclosure comprises at least one heavy chain CDR (HCDR) provided herein, e.g., at least one HCDR disclosed in any one of Tables 4-12. In various embodiments, a dual TACI-BCMA binding domain of the present disclosure comprises two HCDRs provided herein, e.g., at least two HCDRs disclosed in any one of Tables 4-12. In various embodiments, a dual TACI-BCMA binding domain of the present disclosure comprises three HCDRs provided herein, e.g., three HCDRs disclosed in any one of Tables 4-12. In various embodiments, a dual TACI-BCMA binding domain of the present disclosure comprises at least one light chain CDR (LCDR) provided herein, e.g., at least one LCDR disclosed in any one of Tables 4-12. In various embodiments, a dual TACI-BCMA binding domain of the present disclosure comprises two LCDRs provided herein, e.g., at least two LCDRs disclosed in any one of Tables 4-12. In various embodiments, a dual TACI-BCMA binding domain of the present disclosure comprises three LCDRs provided herein, e.g., three LCDRs disclosed in any one of Tables 4-12.

In various embodiments, a dual TACI-BCMA binding domain of the present disclosure comprises at least one HCDR provided herein, e.g., at least one HCDR disclosed in any one of Tables 4-12, and at least one LCDR provided herein, e.g., at least one LCDR disclosed in any one of Tables 4-12. In various embodiments, a dual TACI-BCMA binding domain of the present disclosure comprises one HCDR provided herein, e.g., at least one HCDR disclosed in any one of Tables 4-12, and one LCDR provided herein, e.g., derived from the same Table of Tables 4-12 as the HCDR(s). In various embodiments, a dual TACI-BCMA binding domain of the present disclosure comprises two HCDRs provided herein, e.g., at least two HCDRs disclosed in any one of Tables 4-12, and two LCDRs provided herein, e.g., at least two LCDRs disclosed in any one of Tables 4-12. In various embodiments, a dual TACI-BCMA binding domain of the present disclosure comprises two HCDRs provided herein, e.g., at least two HCDRs disclosed in any one of Tables 4-12, and two LCDRs provided herein, e.g., derived from the same Table of Tables 4-12 as the HCDR(s). In various embodiments, a dual TACI-BCMA binding domain of the present disclosure comprises three HCDRs provided herein, e.g., three HCDRs disclosed in any one of Tables 4-15, and three LCDRs provided herein, e.g., three LCDRs disclosed in any one of Tables 4-15. In various embodiments, a dual TACI-BCMA binding domain of the present disclosure comprises three HCDRs provided herein, e.g., three HCDRs disclosed in any one of Tables 4-15, and three LCDRs derived from the same Table of Tables 4-15 as the HCDR(s).

In various embodiments, a dual TACI-BCMA binding domain of the present disclosure comprises at least one heavy chain framework region (heavy chain FR) of a heavy chain variable domain disclosed herein, e.g., at least one heavy chain FR of a heavy chain variable domain disclosed in any one of Tables 4-12. In various embodiments, a dual TACI-BCMA binding domain of the present disclosure comprises two heavy chain FRs of a heavy chain variable domain disclosed herein, e.g., at least two heavy chain FRs of a heavy chain variable domain disclosed in any one of Tables 4-12. In various embodiments, a dual TACI-BCMA binding domain of the present disclosure comprises three heavy chain FRs of a heavy chain variable domain disclosed herein, e.g., three heavy chain FRs of a heavy chain variable domain disclosed in any one of Tables 4-12.

In various embodiments, a dual TACI-BCMA binding domain of the present disclosure comprises at least one light chain FR of a light chain variable domain disclosed herein, e.g., at least one light chain FR of a light chain variable domain disclosed in any one of Tables 4-12. In various embodiments, a dual TACI-BCMA binding domain of the present disclosure comprises two light chain FRs of a light chain variable domain disclosed herein, e.g., at least two light chain FRs of a light chain variable domain disclosed in any one of Tables 4-12. In various embodiments, a dual TACI-BCMA binding domain of the present disclosure comprises three light chain FRs of a light chain variable domain disclosed herein, e.g., three light chain FRs of a light chain variable domain disclosed in any one of Tables 4-12.

In various embodiments, a dual TACI-BCMA binding domain of the present disclosure comprises at least one heavy chain FR of a heavy chain variable domain disclosed herein, e.g., at least one heavy chain FR of a heavy chain variable domain disclosed in any one of Tables 4-12, and at least one light chain FR of a light chain variable domain disclosed herein, e.g., at least one light chain FR of a light chain variable domain disclosed in any one of Tables 4-12. In various embodiments, a dual TACI-BCMA binding domain of the present disclosure comprises one heavy chain FR of a heavy chain variable domain disclosed herein, e.g., at least one heavy chain FR of a heavy chain variable domain disclosed in any one of Tables 4-12, and one light chain FR of a light chain variable domain disclosed herein, e.g., derived from the same Table of Tables 4-12 as the heavy chain FR(s). In various embodiments, a dual TACI-BCMA binding domain of the present disclosure comprises two heavy chain FRs of a heavy chain variable domain disclosed herein, e.g., at least two heavy chain FRs of a heavy chain variable domain disclosed in any one of Tables 4-12, and two light chain FRs of a light chain variable domain disclosed herein, e.g., at least two light chain FRs of a light chain variable domain disclosed in any one of Tables 4-12. In various embodiments, a dual TACI-BCMA binding domain of the present disclosure comprises two heavy chain FRs of a heavy chain variable domain disclosed herein, e.g., at least two heavy chain FRs of a heavy chain variable domain disclosed in any one of Tables 4-12, and two light chain FRs of a light chain variable domain disclosed herein, e.g., derived from the same Table of Tables 4-12 as the heavy chain FR(s). In various embodiments, a dual TACI-BCMA binding domain of the present disclosure comprises three heavy chain FRs of a heavy chain variable domain disclosed herein, e.g., three heavy chain FRs of a heavy chain variable domain disclosed in any one of Tables 4-12, and three light chain FRs of a light chain variable domain disclosed herein, e.g., three light chain FRs of a light chain variable domain disclosed in any one of Tables 4-12. In various embodiments, a dual TACI-BCMA binding domain of the present disclosure comprises three heavy chain FRs of a heavy chain variable domain disclosed herein, e.g., three light chain FRs of a light chain variable domain disclosed in any one of Tables 4-12, and three light chain FRs derived from the same Table of Tables 4-12 as the heavy chain FR(s).

Exemplary antibody sequences provided in Tables 4-12 are suitable for use in any antibody format, comprising, e.g., a tetrameric antibody, a monospecific antibody, a bispecific antibody, an antigen binding fragment, or a binding domain. Heavy chain variable domains and light chain variable domains and portions thereof provided in Tables 4-12 may be comprised in a dual TACI-BCMA binding domain.

In various embodiments, a dual TACI-BCMA binding domain of the present disclosure comprises one, two, or three FRs that together or each individually have at least 75% identity (e.g., at least 75%, at least 80%, at least 90%, at least 95%, or 100%, e.g., 85-90%, 85-95%, 85-100%, 90-95%, 90-100%, or 95-100%) to corresponding FR(s) of a heavy chain variable domain of a heavy chain variable domain disclosed in in any one of Tables 4-12. In various embodiments, a dual TACI-BCMA binding domain of the present disclosure comprises one, two, or three FRs that together or each individually have at least 75% identity (e.g., at least 75%, at least 80%, at least 90%, at least 95%, or 100%) to corresponding FR(s) of a light chain variable domain of a light chain variable domain disclosed in any one of Tables 4-12.

In various embodiments, a dual TACI-BCMA binding domain of the present disclosure comprises at least one heavy chain variable domain having at least 75% sequence identity to a heavy chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%). In various embodiments, a dual TACI-BCMA binding domain of the present disclosure comprises two heavy chain variable domains each having at least 75% sequence identity to a heavy chain variable domain disclosed in Tables 4-12 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, a dual TACI-BCMA binding domain of the present disclosure comprises at least one light chain variable domain having at least 75% sequence identity to a light chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%). In various embodiments, a dual TACI-BCMA binding domain of the present disclosure comprises two light chain variable domains each having at least 75% sequence identity to a light chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, a dual TACI-BCMA binding domain of the present disclosure comprises at least one heavy chain variable domain having at least 75% sequence identity to a heavy chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%). In certain embodiments, a dual TACI-BCMA binding domain of the present disclosure comprises one heavy chain variable domain having at least 75% sequence identity to a heavy chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%) and one light chain variable domain having at least 75% sequence identity to a light chain variable domain disclosed in any one of Tables 4-12 (e.g., at least 75%, at least 80%, at least 90%, at least 95%, or 100% identity; e.g., 85-90%, 85-95%, 85-100%, 90-95%, 90-100%, or 95-100%), where the heavy chain variable domain and light chain variable domain are optionally derived from the same Table of Tables 4-12.

In various embodiments, a dual TACI-BCMA binding domain of the present disclosure comprises two heavy chain variable domains each having at least 75% sequence identity to a heavy chain variable domain disclosed in Tables 4-12 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Tables 4-12 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; (ii) each of the light chain variable domains may be same or different; (iii) at least one heavy chain variable domain and at least one light chain variable domain may be derived from the same Table of Tables 4-12; or (iv) the two heavy chain variable domains and the two light chain variable domains are all derived from the same Table of Tables 4-12.

Each of Tables 4-12 represents the heavy chain variable domain and light chain variable domain sequences of an exemplary antibody, comprising (i) the heavy chain variable domain of the exemplary antibody; (ii) a DNA sequence encoding the heavy chain variable domain (iii) three heavy chain variable domain CDRs of the heavy chain variable domain, according to IMGT, Kabat, and Chothia numbering; (iv) the light chain variable domain of the exemplary antibody; (v) a DNA sequence encoding the light chain variable domain; and (vi) three light chain variable domain CDRs of the light chain variable domain, according to IMGT, Kabat, and Chothia numbering. Information provided in each table provides framework amino acid sequences, as well as nucleotide sequences encoding each CDR amino acid sequence and nucleotide sequences encoding corresponding FR amino acid sequence.

In various embodiments, a dual TACI-BCMA binding domain may comprise a heavy chain variable domain of the present disclosure (e.g., having at least 75% sequence identity to a heavy chain variable domain of any one of Tables 4-12, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-12, e.g., at least 80%, 85%, 90%, 95%, or 100% identity; e.g., 85-90%, 85-95%, 85-100%, 90-95%, 90-100%, or 95-100%), and a linker (e.g., a linker according to SEQ ID NO: 219). In various embodiments a dual TACI-BCMA binding domain may comprise a leader sequence, a heavy chain variable domain of the present disclosure (e.g., having at least 75% sequence identity to a heavy chain variable domain of any one of Tables 4-12, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-12, e.g., at least 80%, 85%, 90%, 95%, or 100% identity; e.g., 85-90%, 85-95%, 85-100%, 90-95%, 90-100%, or 95-100%), and a linker. If provided with an amino acid or nucleotide sequence of a dual TACI-BCMA binding domain comprising a heavy chain variable domain of the present disclosure and a light chain variable domain of the present disclosure, the linker joining the two variable domains will be apparent from the sequence in view of the present disclosure. If provided with an amino acid or nucleotide sequence of a dual TACI-BCMA binding domain comprising a heavy chain variable domain of the present disclosure and a light chain variable domain of the present disclosure, the leader sequence will be apparent in view of the present disclosure. For the avoidance of doubt, a heavy chain variable domain and a light chain variable domain of the present disclosure may be present in any orientation, e.g., an orientation in which the heavy chain variable domain is C terminal of the light chain variable domain or in which the heavy chain variable domain is N terminal of the light chain variable domain. In various embodiments a dual TACI-BCMA binding domain may comprise a linker according to SEQ ID NO: 219.

In certain embodiments, a dual TACI-BCMA binding domain of the present disclosure comprises an a dual TACI-BCMA binding domain that comprises a heavy chain variable domain of the present disclosure, a light chain variable domain of the present disclosure, and a linker having at least 75% sequence identity to SEQ ID NO: 219 (e.g., at least 75%, at least 80%, at least 90%, at least 95%, or 100% identity; e.g., 85-90%, 85-95%, 85-100%, 90-95%, 90-100%, or 95-100%). In certain embodiments, an TACI-BCMA binding domain of the present disclosure comprises a dual TACI-BCMA binding domain that comprises a linker according to SEQ ID NO: 219. In certain embodiments, a dual TACI-BCMA binding domain of the present disclosure comprises a dual TACI-BCMA binding domain that comprises a heavy chain variable domain of the present disclosure, a light chain variable domain of the present disclosure, and a leader sequence having at least 75% sequence identity to SEQ ID NO: 221 (e.g., at least 75%, at least 80%, at least 90%, at least 95%, or 100% identity; e.g., 85-90%, 85-95%, 85-100%, 90-95%, 90-100%, or 95-100%). In certain embodiments, a dual TACI-BCMA binding domain of the present disclosure comprises a dual TACI-BCMA binding domain that comprises a CSF2RA leader sequence according to SEQ ID NO: 221 (MLLLVTSLLLCELPHPAFLLIP; SEQ ID NO: 221). In embodiments, a leader sequence may be encoded by nucleic acid sequence at least 75% sequence identity to: ATGCTTCTCCTGGTGACAAGCCTTCTGCTCTGTGAGTTACCACACCCAGCATTCCTC CTGATTCCT (SEQ ID NO: 222) (e.g., at least 75%, at least 80%, at least 90%, at least 95%, or 100% identity; e.g., 85-90%, 85-95%, 85-100%, 90-95%, 90-100%, or 95-100%). In certain embodiments, a dual TACI-BCMA binding domain of the present disclosure comprises a dual TACI-BCMA binding domain that comprises a heavy chain variable domain of the present disclosure, a light chain variable domain of the present disclosure, a linker of the present disclosure, and a leader sequence of the present disclosure.

A binding agent of the present disclosure that is based on an exemplary antibody provided herein, such as for example Abs 1-9, may be provided in any fragment or format, comprising a heavy chain variable domain according to the indicated exemplary antibody and a light chain variable domain according to the indicated exemplary antibody.

TABLE 4

Exemplary Antibody Sequences 1 (Ab1)

| SEQ ID NO: | Description | Sequence |
|---|---|---|
| 1 | Heavy Chain Variable Domain | QVQLVQSGAEVKKPGSSVKVSCKASGGTFADYAISWVRQAPGQGLEWMG GIIPILGRANYAQKFQGRVTITADESTSTAYMELSSLRSEDTAVYYCAR DRDSTSLPYNHYYMDVWGKGTTVTVSS |
| 2 | VH (DNA) | caggtgcagctggtgcagtctggggctgaggtgaagaagcctgggtcct cggtgaaggtctcctgcaaggcttctggaggccaccttcgcagactatgc tatcagctgggtgcgacaggcccctggacaagggcttgagtggatggga gggatcatccctatattgggcagagcaaactacgcacagaagttccagg gcagagttacgattaccgcggacgaatccacgagcacagcctacatgga gctgagcagcctgagatctgaggacacggcggtgtactactgcgccaga gacagagacagcacaagcctgccgtacaaccactactacatggacgtat ggggcaagggtacaactgtcactgtctcctca |
| 3 | CDRH1 IMGT (Prot) | GGTFADYA |
| 4 | CDRH1 Kabat (Prot) | DYAIS |
| 5 | CDRH1 Chothia (Prot) | GGTFADY |

TABLE 4-continued

Exemplary Antibody Sequences 1 (Ab1)

| SEQ ID NO: | Description | Sequence |
|---|---|---|
| 6 | CDRH2 IMGT (Prot) | IIPILGRA |
| 7 | CDRH2 Kabat (Prot) | GIIPILGRANYAQKFQG |
| 8 | CDRH2 Chothia (Prot) | IPILGR |
| 9 | CDRH3 IMGT (Prot) | ARDRDSTSLPYNHYYMDV |
| 10 | CDRH3 Kabat (Prot) | DRDSTSLPYNHYYMDV |
| 11 | CDRH3 Chothia (Prot) | DRDSTSLPYNHYYMDV |
| 12 | Light Chain Variable Domain | DIQMTQSPSSLSASVGDRVTITCRASQSISSYLNWYQQKPGKAPKLLIY AASSLQSGVPSRFSGSGSGTDFTLTISSLQPEDFATYYCQQSHIAPWTF GGGTKVEIK |
| 13 | VL (DNA) | gacatccagatgacccagtctccatcctccctgtctgcaagcgttggag atagagtcactatcacttgccgggcaagtcagagcattagcagctattt aaaattggtatcagcagaaaccagggaaagcccctaagctcctgatctat gctgcatccagtttgcaaagtggggtcccatcaaggttcagtggcagtg gatccgggacagatttcactctcaccatcagcagtctgcaacctgaaga ttttgcaacttactactgtcagcaaagccacatcgccccttggactttt ggcggagggaccaaggttgagatcaaa |
| 14 | CDRL1 IMGT (Prot) | QSISSY |
| 15 | CDRL1 Kabat (Prot) | RASQSISSYLN |
| 16 | CDRL1 Chothia (Prot) | RASQSISSYLN |
| 17 | CDRL2 IMGT (Prot) | AAS |
| 18 | CDRL2 Kabat (Prot) | AASSLQS |
| 19 | CDRL2 Chothia (Prot) | AASSLQS |
| 20 | CDRL3 IMGT (Prot) | QQSHIAPWT |
| 21 | CDRL3 Kabat (Prot) | QQSHIAPWT |
| 22 | CDRL3 Chothia (Prot) | QQSHIAPWT |
| 23 | ScFv | DIQMTQSPSSLSASVGDRVTITCRASQSISSYLNWYQQKPGKAPKLLIY AASSLQSGVPSRFSGSGSGTDFTLTISSLQPEDFATYYCQQSHIAPWTF GGGTKVEIKGSTSGSGKPGSGEGSTKGVQLVQSGAEVKKPGSSVKVSC KASGGTFADYAISWVRQAPGQGLEWMGGIIPILGRANYAQKFQGRVTIT ADESTSTAYMELSSLRSEDTAVYYCARDRDSTSLPYNHYYMDVWGKGTT VTVSS |
| 24 | ScFv | gacatccagatgacccagtctccatcctccctgtctgcaagcgttggag atagagtcactatcacttgccgggcaagtcagagcattagcagctattt aaaattggtatcagcagaaaccagggaaagcccctaagctcctgatctat gctgcatccagtttgcaaagtggggtcccatcaaggttcagtggcagtg gatccgggacagatttcactctcaccatcagcagtctgcaacctgaaga ttttgcaacttactactgtcagcaaagccacatcgccccttggactttt ggcggagggaccaaggttgagatcaaagggagcactagcggctctgga aacctggatctggcgagggatctaccaagggccaggtgcagctggtgca gtctggggctgaggtgaagaagcctgggtcctcggtgaaggtctcctgc |

TABLE 4-continued

Exemplary Antibody Sequences 1 (Ab1)

| SEQ ID NO: | Description | Sequence |
|---|---|---|
| | | aaggcttctggaggcaccttcgcagactatgctatcagctgggtgcgac aggcccctggacaagggcttgagtggatgggagggatcatccctatatt gggcagagcaaactacgcacagaagttccagggcagagttacgattacc gcggacgaatccacgagcacagcctacatggagctgagcagcctgagat ctgaggacacggcggtgtactactgcgccagagacagagacagcacaag cctgccgtacaaccactactacatggacgtatggggcaagggtacaact gtcactgtctcctca |

TABLE 5

Exemplary Antibody Sequences 2 (Ab2)

| SEQ ID NO: | Description | Sequence |
|---|---|---|
| 25 | Heavy Chain Variable Domain | QVQLVQSGAEVKKPGSSVKVSCKASGGTFADYAISWVRQAPGQGLEWM GGIIPILGRANYAQKFQGRVTITADESTSTAYMELSSLRSEDTAVYYC ARDRDRTSLPYNHYYMDVWGKGTTVTVSS |
| 26 | VH (DNA) | caggtgcagctggtgcagtctggggctgaggtgaagaagcctgggtcc tcggtgaaggtctcctgcaaggcttctggaggcaccttcgcagactat gctatcagctgggtgcgacaggcccctggacaagggcttgagtggatg ggagggatcatccctatattgggcagagcaaactacgcacagaagttc cagggcagagttacgattaccgcggacgaatccacgagcacagcctac atggagctgagcagcctgagatctgaggacacggcggtgtactactgc gccagagacagagaccgtacaagcctgccgtacaaccactactacatg gacgtatgggcaaagggaccacggtcaccgtttcctca |
| 27 | CDRH1 IMGT (Prot) | GGTFADYA |
| 28 | CDRH1 Kabat (Prot) | DYAIS |
| 29 | CDRH1 Chothia (Prot) | GGTFADY |
| 30 | CDRH2 IMGT (Prot) | IIPILGRA |
| 31 | CDRH2 Kabat (Prot) | GIIPILGRANYAQKFQG |
| 32 | CDRH2 Chothia (Prot) | IPILGR |
| 33 | CDRH3 IMGT (Prot) | ARDRDRTSLPYNHYYMDV |
| 34 | CDRH3 Kabat (Prot) | DRDRTSLPYNHYYMDV |
| 35 | CDRH3 Chothia (Prot) | DRDRTSLPYNHYYMDV |
| 36 | Light Chain Variable Domain | DIQLTQSPSSLSASVGDRVTITCRASQSILSYLNWYQQKPGKAPKLLI YAASSLQSGVPSRFSGSGSGTDFTLTISSLQPEDFATYYCQQSSIAPW TFGGGTKVEIK |
| 37 | VL (DNA) | gacatccagttgacccagtctccatcctccctgtctgcaagcgttgga gatagagtcactatcacttgccgggcaagtcagagcattctcagctat ttaaattggtatcagcagaaaccagggaaagcccctaagctcctgatc tatgctgcatccagttttgcaaagtggggtcccatcaaggttcagtggc agtggatccgggacagatttcactctcaccatcagcagtctgcaacct gaagattttgcaacttactactgtcagcaaagctcgatcgcccttgg actttcggcggagggaccaaggttgagatcaaa |
| 38 | CDRL1 IMGT (Prot) | QSILSY |

TABLE 5-continued

Exemplary Antibody Sequences 2 (Ab2)

| SEQ ID NO: | Description | Sequence |
|---|---|---|
| 39 | CDRL1 Kabat (Prot) | RASQSILSYLN |
| 40 | CDRL1 Chothia (Prot) | RASQSILSYLN |
| 41 | CDRL2 IMGT (Prot) | AAS |
| 42 | CDRL2 Kabat (Prot) | AASSLQS |
| 43 | CDRL2 Chothia (Prot) | AASSLQS |
| 44 | CDRL3 IMGT (Prot) | QQSSIAPWT |
| 45 | CDRL3 Kabat (Prot) | QQSSIAPWT |
| 46 | CDRL3 Chothia (Prot) | QQSSIAPWT |
| 47 | ScFv | DIQLTQSPSSLSASVGDRVTITCRASQSILSYLNWYQQKPGKAPKLLI YAASSLQSGVPSRFSGSGSGTDFTLTISSLQPEDFATYYCQQSSIAPW TFGGGTKVEIKGSTSGSGKPGSGEGSTKGQVQLVQSGAEVKKPGSSVK VSCKASGGTFADYAISWVRQAPGQGLEWMGGIIPILGRANYAQKFQGR VTITADESTSTAYMELSSLRSEDTAVYYCARDRDRTSLPYNHYYMDVW GKGTTVTVSS |
| 48 | ScFv | gacatccagttgacccagtctccatcctccctgtctgcaagcgttgga gatagagtcactatcacttgccgggcaagtcagagcattctcagctat ttaaattggtatcagcagaaaccagggaaagcccctaagctcctgatc tatgctgcatccagtttgcaaagtggggtcccatcaaggttcagtggc agtggatccgggacagatttcactctcaccatcagcagtctgcaacct gaagattttgcaacttactactgtcagcaaagctcgatcgcccccttgg actttcggcggagggaccaaggttgagatcaaagggagcacaagcggc tctggcaaacctggatctggcgagggatctaccaagggccaggtgcag ctggtgcagtctggggctgaggtgaagaagcctgggtcctcggtgaag gtctcctgcaaggcttctggaggcaccttcgcagactatgctatcagc tgggtgcgacaggcccctggacaagggcttgagtggatgggagggatc atccctatattgggcagagcaaactacgcacagaagttccagggcaga gttacgattaccgcggacgaatccacgagcacagcctacatggagctg agcagcctgagatctgaggacacggcggtgtactactgcgccagagac agagaccgtacaagcctgccgtacaaccactactacatggacgtatgg ggcaaagggaccacggtcaccgtttcctca |

TABLE 6

Exemplary Antibody Sequences 3 (Ab3)

| SEQ ID NO: | Description | Sequence |
|---|---|---|
| 49 | Heavy Chain Variable Domain | QVQLVQSGAEVKKPGSSVKVSCKASGGTFEDYAISWVRQAPGQGLEWM GGIIPILGRANYAQKFQGRVTITADESTSTAYMELSSLRSEDTAVYYC ARDRDLTSLPYNHYYMDVWGKGTTVTVSS |
| 50 | VH (DNA) | caggtgcagctggtgcagtctggggctgaggtgaagaagcctgggtcc tcggtgaaggtctcctgcaaggcttctggaggcaccttcgaagactat gctatcagctgggtgcgacaggcccctggacaagggcttgagtggatg ggagggatcatccctatattgggccgagcaaactacgcacagaagttc cagggcagagttacgattaccgcggacgaatccacgagcacagcctac atggagctgagcagcctgagatctgaggacacggcggtgtactactgc gccagagacagagacttgacaagcctgccgtacaaccactactacatg gacgtatggggcaaagggaccacggtcaccgtttcctca |
| 51 | CDRH1 IMGT (Prot) | GGTFEDYA |

TABLE 6-continued

Exemplary Antibody Sequences 3 (Ab3)

| SEQ ID NO: | Description | Sequence |
|---|---|---|
| 52 | CDRH1 Kabat (Prot) | DYAIS |
| 53 | CDRH1 Chothia (Prot) | GGTFEDY |
| 54 | CDRH2 IMGT (Prot) | IIPILGRA |
| 55 | CDRH2 Kabat (Prot) | GIIPILGRANYAQKFQG |
| 56 | CDRH2 Chothia (Prot) | IPILGR |
| 57 | CDRH3 IMGT (Prot) | ARDRDLTSLPYNHYYMDV |
| 58 | CDRH3 Kabat (Prot) | DRDLTSLPYNHYYMDV |
| 59 | CDRH3 Chothia (Prot) | DRDLTSLPYNHYYMDV |
| 60 | Light Chain Variable Domain | DIQLTQSPSSLSASVGDRVTITCRASQSISSYLNWYQQKPGKAPKLLI YAASQLQSGVPSRFSGSGSGTDFTLTISSLQPEDFATYYCQQSAIAPW TFGGGTKVEIK |
| 61 | VL (DNA) | gacatccagttgacccagtctccatcctccctgtctgcaagcgttgga gatagagtcactatcacttgccgggcaagtcagagcattagcagctat ttaaattggtatcagcagaaaccagggaaagcccctaagctcctgatc tatgctgcatcccaattgcaaagtggggtcccatcaaggttcagtggc agtggatccgggacagatttcactctcaccatcagcagtctgcaacct gaagattttgcaacttactactgtcagcaaagcgctatcgccccttgg actttcggcggagggaccaaggttgagatcaaa |
| 62 | CDRL1 IMGT (Prot) | QSISSY |
| 63 | CDRL1 Kabat (Prot) | RASQSISSYLN |
| 64 | CDRL1 Chothia (Prot) | RASQSISSYLN |
| 65 | CDRL2 IMGT (Prot) | AAS |
| 66 | CDRL2 Kabat (Prot) | AASQLQS |
| 67 | CDRL2 Chothia (Prot) | AASQLQS |
| 68 | CDRL3 IMGT (Prot) | QQSAIAPWT |
| 69 | CDRL3 Kabat (Prot) | QQSAIAPWT |
| 70 | CDRL3 Chothia (Prot) | QQSAIAPWT |
| 71 | ScFv | DIQLTQSPSSLSASVGDRVTITCRASQSISSYLNWYQQKPGKAPKLLI YAASQLQSGVPSRFSGSGSGTDFTLTISSLQPEDFATYYCQQSAIAPW TFGGGTKVEIKGSTSGSGKPGSGEGSTKGQVQLVQSGAEVKKPGSSVK VSCKASGGTFEDYAISWVRQAPGQGLEWMGGIIPILGRANYAQKFQGR VTITADESTSTAYMELSSLRSEDTAVYYCARDRDLTSLPYNHYYMDVW GKGTTVTVSS |
| 72 | ScFv | gacatccagttgacccagtctccatcctccctgtctgcaagcgttgga gatagagtcactatcacttgccgggcaagtcagagcattagcagctat ttaaattggtatcagcagaaaccagggaaagcccctaagctcctgatc tatgctgcatcccaattgcaaagtggggtcccatcaaggttcagtggc agtggatccgggacagatttcactctcaccatcagcagtctgcaacct |

TABLE 6-continued

Exemplary Antibody Sequences 3 (Ab3)

| SEQ ID NO: | Description | Sequence |
|---|---|---|
| | | gaagattttgcaacttactactgtcagcaaagcgctatcgccccttgg<br>actttcggcggagggaccaaggttgagatcaaagggagcacaagcggc<br>tctggcaaacctggatctggcgagggatctaccaagggccaggtgcag<br>ctggtgcagtctggggctgaggtgaagaagcctgggtcctcggtgaag<br>gtctcctgcaaggcttctggaggcaccttcgaagactatgctatcagc<br>tgggtgcgacaggcccctggacaagggcttgagtggatgggagggatc<br>atccctatattgggccgagcaaactacgcacagaagttccagggcaga<br>gttacgattaccgcggacgaatccacgagcacagcctacatggagctg<br>agcagcctgagatctgaggacacggcggtgtactactgcgccagagac<br>agagacttgacaagcctgccgtacaaccactactacatggacgtatgg<br>ggcaaagggaccacggtcaccgtttcctca |

TABLE 7

Exemplary Antibody Sequences 4 (Ab4)

| SEQ ID NO: | Description | Sequence |
|---|---|---|
| 73 | Heavy Chain Variable Domain | QVQLVQSGAEVKKPGSSVKVSCKASGGTFSHYAISWVRQAPGQGLEWM<br>GGIIPILGRANYAQKFQGRVTITADESTSTAYMELSSLRSEDTAVYYC<br>ARDRTWEGSPYYYYGMDVWGQGTMVTVSS |
| 74 | VH (DNA) | caggtgcagctggtgcagtctggggctgaagtgaagaagcctgggtcc<br>tcggtgaaggtctcctgcaaggcttctggaggcaccttcagccactat<br>gctatcagctgggtgcgacaggcccctggacaagggcttgagtggatg<br>ggagggatcatccctatattgggccgagcaaactacgcacagaagttc<br>cagggcagagtcacgattaccgcggacgaatccacgagcacagcctac<br>atggagctgagcagcctgagatctgaggacacggcggtgtactactgc<br>gccagagacagaacttgggaaggatctcctattattactacggaatg<br>gacgtttggggccaagggacaatggtcaccgtttcctca |
| 75 | CDRH1 IMGT (Prot) | GGTFSHYA |
| 76 | CDRH1 Kabat (Prot) | HYAIS |
| 77 | CDRH1 Chothia (Prot) | GGTFSHY |
| 78 | CDRH2 IMGT (Prot) | IIPILGRA |
| 79 | CDRH2 Kabat (Prot) | GIIPILGRANYAQKFQG |
| 80 | CDRH2 Chothia (Prot) | IPILGR |
| 81 | CDRH3 IMGT (Prot) | ARDRTWEGSPYYYYGMDV |
| 82 | CDRH3 Kabat (Prot) | DRTWEGSPYYYYGMDV |
| 83 | CDRH3 Chothia (Prot) | DRTWEGSPYYYYGMDV |
| 84 | Light Chain Variable Domain | DIQLTQSPSSLSASVGDRVTITCRASTSISSYLNWYQQKPGKAPKLLI<br>YAASSLQSGVPSRFSGSGSGTDFTLTISSLQPEDFATYYCQQSADAPW<br>TFGGGTKVEIK |
| 85 | VL (DNA) | gacatccagttgacccagtctccatcctccctgtctgcaagcgttgga<br>gacagggtcactatcacttgccgggcaagtaccagcattagcagctat<br>ttaaattggtatcagcagaaaccagggaaagcccctaagctcctgatc<br>tatgctgcatccagtttgcaaagtggggtcccatcaaggttcagtggc<br>agtggatctgggacagatttcactctcaccatcagcagtctgcaacct<br>gaagattttgcaacttactactgtcagcaaagcgccgatgcccccttgg<br>actttcggcggagggaccaaggttgagatcaaa |

TABLE 7-continued

Exemplary Antibody Sequences 4 (Ab4)

| SEQ ID NO: | Description | Sequence |
|---|---|---|
| 86 | CDRL1 IMGT (Prot) | TSISSY |
| 87 | CDRL1 Kabat (Prot) | RASTSISSYLN |
| 88 | CDRL1 Chothia (Prot) | RASTSISSYLN |
| 89 | CDRL2 IMGT (Prot) | AAS |
| 90 | CDRL2 Kabat (Prot) | AASSLQS |
| 91 | CDRL2 Chothia (Prot) | AASSLQS |
| 92 | CDRL3 IMGT (Prot) | QQSADAPWT |
| 93 | CDRL3 Kabat (Prot) | QQSADAPWT |
| 94 | CDRL3 Chothia (Prot) | QQSADAPWT |
| 95 | ScFv | DIQLTQSPSSLSASVGDRVTITCRASTSISSYLNWYQQKPGKAPKLLI YAASSLQSGVPSRFSGSGSGTDFTLTISSLQPEDFATYYCQQSADAPW TFGGGTKVEIKGSTSGSGKPGSGEGSTKGVQLVQSGAEVKKPGSSVK VSCKASGGTFSHYAISWVRQAPGQGLEWMGGIIPILGRANYAQKFQGR VTITADESTSTAYMELSSLRSEDTAVYYCARDRTWEGSPYYYYGMDVW GQGTMVTVSS |
| 96 | ScFv | gacatccagttgacccagtctccatcctccctgtctgcaagcgttgga gacagggtcactatcacttgccgggcaagtaccagcattagcagctat ttaaattggtatcagcagaaaccagggaaagcccctaagctcctgatc tatgctgcatccagtttgcaaagtggggtcccatcaaggttcagtggc agtggatctgggacagatttcactctcaccatcagcagtctgcaacct gaagattttgcaacttactactgtcagcaaagcgccgatgccccttgg actttcggcggagggaccaaggttgagatcaaagggagcacaagcggc tctggcaaacctggatccggcgagggatctaccaagggccaggtgcag ctggtgcagtctggggctgaagtgaagaagcctgggtcctcggtgaag gtctcctgcaaggcttctggaggcaccttcagccactatgctatcagc tgggtgcgacaggcccctggacaagggcttgagtggatgggagggatc atccctatattgggccgagcaaactacgcacagaagttccagggcaga gtcacgattaccgcggacgaatccacgagcacagcctacatggagctg agcagcctgagatctgaggacacggcggtgtactactgcgccagagac agaactgggaaggatctccctattattactacggaatggacgtttgg ggccaagggacaatggtcaccgtttcctca |

TABLE 8

Exemplary Antibody Sequences 5 (Ab5)

| SEQ ID NO: | Description | Sequence |
|---|---|---|
| 97 | Heavy Chain Variable Domain | QVQLVQSGAEVKKPGSSVKVSCKASGGTFDDYAISWVRQAPGQGLEWM GGIIPILGRANYAQKFQGRVTITADESTSTAYMELSSLRSEDTAVYYC ARDRVWEGSPYYYYGMDVWGQGTMVTVSS |
| 98 | VH (DNA) | caggtgcagctggtgcagtctggggctgaggtgaagaagcctgggtcc tcggtgaaggtctcctgcaaggcttctggaggcaccttcgacgactat gctatcagctgggttcgacaggcccctggacaagggcttgagtggatg ggagggatcatccctatattgggcagagcaaactacgcacagaagttc cagggcagagtcacgattaccgcggacgaatccacgagcacagcctac atggagctgagcagcctgagatctgaggacacggcggtgtactactgc gccagagacagagtgtgggaaggatctccctattattactacggaatg gacgtttggggccaagggacaatggtcaccgtttcctca |

TABLE 8-continued

Exemplary Antibody Sequences 5 (Ab5)

| SEQ ID NO: | Description | Sequence |
|---|---|---|
| 99 | CDRH1 IMGT (Prot) | GGTFDDYA |
| 100 | CDRH1 Kabat (Prot) | DYAIS |
| 101 | CDRH1 Chothia (Prot) | GGTFDDY |
| 102 | CDRH2 IMGT (Prot) | IIPILGRA |
| 103 | CDRH2 Kabat (Prot) | GIIPILGRANYAQKFQG |
| 104 | CDRH2 Chothia (Prot) | IPILGR |
| 105 | CDRH3 IMGT (Prot) | ARDRVWEGSPYYYYGMDV |
| 106 | CDRH3 Kabat (Prot) | DRVWEGSPYYYYGMDV |
| 107 | CDRH3 Chothia (Prot) | DRVWEGSPYYYYGMDV |
| 108 | Light Chain Variable Domain | DIQLTQSPSSLSASVGDRVTITCRASQSIASYLNWYQQKPGKAPKLLI YAASSLQSGVPSRFSGSGSGTDFTLTISSLQPEDFATYYCQQSAGAPW TFGGGTKVEIK |
| 109 | VL (DNA) | gacatccagttgacccagtctccatcctccctgtctgcaagcgttgga gatagagtcactatcacttgccgggcaagtcagagcattgccagctat ttaaattggtatcagcagaaaccagggaaagcccctaagctcctgatc tatgctgcatccagtttgcaaagtggggtcccatcaaggttcagtggc agtggatccgggacagatttcactctcaccatcagcagtctgcaacct gaagattttgcaacttactactgtcagcaaagcgccggtgcaccttgg actttcggcggagggaccaaggttgagatcaaa |
| 110 | CDRL1 IMGT (Prot) | QSIASY |
| 111 | CDRL1 Kabat (Prot) | RASQSIASYLN |
| 112 | CDRL1 Chothia (Prot) | RASQSIASYLN |
| 113 | CDRL2 IMGT (Prot) | AAS |
| 114 | CDRL2 Kabat (Prot) | AASSLQS |
| 115 | CDRL2 Chothia (Prot) | AASSLQS |
| 116 | CDRL3 IMGT (Prot) | QQSAGAPWT |
| 117 | CDRL3 Kabat (Prot) | QQSAGAPWT |
| 118 | CDRL3 Chothia (Prot) | QQSAGAPWT |
| 119 | ScFv | DIQLTQSPSSLSASVGDRVTITCRASQSIASYLNWYQQKPGKAPKLLI YAASSLQSGVPSRFSGSGSGTDFTLTISSLQPEDFATYYCQQSAGAPW TFGGGTKVEIKGSTSGSGKPGSGEGSTKGQVQLVQSGAEVKKPGSSVK VSCKASGGTFDDYAISWVRQAPGQGLEWMGGIIPILGRANYAQKFQGR VTITADESTSTAYMELSSLRSEDTAVYYCARDRVWEGSPYYYYGMDVW GQGTMVTVSS |

TABLE 8-continued

Exemplary Antibody Sequences 5 (Ab5)

| SEQ ID NO: | Description | Sequence |
|---|---|---|
| 120 | ScFv | gacatccagttgacccagtctccatcctccctgtctgcaagcgttgga gatagagtcactatcacttgccgggcaagtcagagcattgccagctat ttaaattggtatcagcagaaaccagggaaagcccctaagctcctgatc tatgctgcatccagtttgcaaagtggggtcccatcaaggttcagtggc agtggatccgggacagatttcactctcaccatcagcagtctgcaacct gaagattttgcaacttactactgtcagaaagcgccggtgcaccttgg acttcggcggagggaccaaggttgagatcaaagggagcacaagcggc tctggcaaacctggatctggcgagggatctaccaagggccaggtgcag ctggtgcagtctggggctgaggtgaagaagcctgggtcctcggtgaag gtctcctgcaaggcttctggaggcaccttcgacgactatgctatcagc tgggttcgacaggcccctggacaagggcttgagtggatgggagggatc atccctatattgggcagagcaaactacgcacagaagttccagggcaga gtcacgattaccgcggacgaatccacgagcacagcctacatggagctg agcagcctgagatctgaggacacggcggtgtactactgcgccagagac agagtgtgggaaggatctccctattattactacggaatggacgtttgg ggccaagggacaatggtcaccgtttcctca |

TABLE 9

Exemplary Antibody Sequences 6 (Ab6)

| SEQ ID NO: | Description | Sequence |
|---|---|---|
| 121 | Heavy Chain Variable Domain | QVQLVQSGAEVKKPGSSVKVSCKASGGTFEHYAISWVRQAPGQGLEWM GGIIPILGRANYAQKFQGRVTITADESTSTAYMELSSLRSEDTAVYYC ARDRSWEGSPYMYYGMDVWGQGTMVTVSS |
| 122 | VH (DNA) | caggtgcagctggtgcagtctggggctgaggtgaagaagcctgggtcc tcggtgaaggtctcctgcaaggcttctggaggcaccttcgaacactat gctatcagctgggtgcgacaggcccctggacaggggcttgagtggatg ggagggatcatccccatattgggccgagcaaactacgcacagaagttc cagggcagagtcacgattaccgcggacgaatccacgagcacagcctac atggagctgagcagcctgagatctgaggacacgcggtgtactactgc gccagagacagaagctgggaaggatctccctatatgtactacggaatg gacgtttggggccaagggacaatggtcaccgtttcctca |
| 123 | CDRH1 IMGT (Prot) | GGTFEHYA |
| 124 | CDRH1 Kabat (Prot) | HYAIS |
| 125 | CDRH1 Chothia (Prot) | GGTFEHY |
| 126 | CDRH2 IMGT (Prot) | IIPILGRA |
| 127 | CDRH2 Kabat (Prot) | GIIPILGRANYAQKFQG |
| 128 | CDRH2 Chothia (Prot) | IPILGR |
| 129 | CDRH3 IMGT (Prot) | ARDRSWEGSPYMYYGMDV |
| 130 | CDRH3 Kabat (Prot) | DRSWEGSPYMYYGMDV |
| 131 | CDRH3 Chothia (Prot) | DRSWEGSPYMYYGMDV |
| 132 | Light Chain Variable Domain | DIQLTQSPSSLSASVGDRVTITCRASQSISLYLNWYQQKPGKAPKLLI YAASSLQSGVPSRFSGSGSGTDFTLTISSLQPEDFATYYCQQVAVAPW TFGGGTKVEIK |
| 133 | VL (DNA) | gacatccagttgacccagtctccatcctccctgtctgcaagcgttgga gacagagttactatcacttgccgggcaagtcagagcattagcctatat ttaaattggtatcagcagaaaccagggaaagcccctaagctcctgatc tatgctgcatccagtttgcaaagtggggtcccatcaaggttcagtggc |

TABLE 9-continued

Exemplary Antibody Sequences 6 (Ab6)

| SEQ ID NO: | Description | Sequence |
|---|---|---|
|  |  | agtggatccgggacagatttcactctcaccatcagcagtctgcaacct gaagattttgcaacttactactgtcagcaagtggccgtcgccccttgg actttcggcggagggaccaaggttgagatcaaa |
| 134 | CDRL1 IMGT (Prot) | QSISLY |
| 135 | CDRL1 Kabat (Prot) | RASQSISLYLN |
| 136 | CDRL1 Chothia (Prot) | RASQSISLYLN |
| 137 | CDRL2 IMGT (Prot) | AAS |
| 138 | CDRL2 Kabat (Prot) | AASSLQS |
| 139 | CDRL2 Chothia (Prot) | AASSLQS |
| 140 | CDRL3 IMGT (Prot) | QQVAVAPWT |
| 141 | CDRL3 Kabat (Prot) | QQVAVAPWT |
| 142 | CDRL3 Chothia (Prot) | QQVAVAPWT |
| 143 | ScFv | DIQLTQSPSSLSASVGDRVTITCRASQSISLYLNWYQQKPGKAPKLLI YAASSLQSGVPSRFSGSGSGTDFTLTISSLQPEDFATYYCQQVAVAPW TFGGGTKVEIKGSTSGSGKPGSGEGSTKGQVQLVQSGAEVKKPGSSVK VSCKASGGTFEHYAISWVRQAPGQGLEWMGGIIPILGRANYAQKFQGR VTITADESTSTAYMELSSLRSEDTAVYYCARDRSWEGSPYMYYGMDVW GQGTMVTVSS |
| 144 | ScFv | gacatccagttgacccagtctccatcctccctgtctgcaagcgttgga gacagagttactatcacttgccgggcaagtcagagcattagcctatat ttaaaattggtatcagcagaaaccagggaaagccccctaagctcctgatc tatgctgcatccagtttgcaaagtggggtcccatcaaggttcagtggc agtggatccgggacagatttcactctcaccatcagcagtctgcaacct gaagattttgcaacttactactgtcagcaagtggccgtcgccccttgg actttcggcggagggaccaaggttgagatcaaagggagcacaagcggc tctggcaaacctggatctggcgagggatctaccaagggccaggtgcag ctggtgcagtctggggctgaggtgaagaagcctgggtcctcggtgaag gtctcctgcaaggcttctggaggcaccttcgaacactatgctatcagc tgggtgcgacaggcccctggacaggggcttgagtggatgggagggatc atccccatattgggccgagcaaactacgcacagaagttccagggcaga gtcacgattaccgcggacgaatccacgagcacagcctacatggagctg agcagcctgagatctgaggacacggcggtgtactactgcgccagagac agaagctgggaaggatctccctatatgtactacggaatggacgtttgg ggccaagggacaatggtcaccgttcctca |

TABLE 10

Exemplary Antibody Sequences 7 (Ab7)

| SEQ ID NO: | Description | Sequence |
|---|---|---|
| 145 | Heavy Chain Variable Domain | QVQLVESGGGVVQPGRSLRLSCAASGFTFASEGMHWVRQAPGKGLEWV ASIYYEGVNKYYADSVKGRFTISRDNSKNTLYLQMNSLRAEDTAVYYC AKDVSYYDSSRLVYHGMDVWGQGTTVTVSS |
| 146 | VH (DNA) | caggtgcagctggtggagtctgggggaggcgtggtccagcctggggagg tccctgagactctcctgcgctgcatctggattcaccttcgccagcgaa ggcatgcactgggtccgccaggctccaggcaaggggctggagtgggtg gcatccatatactatgagggagtcaataaatactatgcagactccgtg aagggccgattcaccatctctagagacaattccaagaacacgctgtat ctgcaaatgaatagcctgagagccgaggacacggcggtgtactactgc |

TABLE 10-continued

Exemplary Antibody Sequences 7 (Ab7)

| SEQ ID NO: | Description | Sequence |
|---|---|---|
| | | gccaaggacgtgtcctactacgacagcagcagactagtttatcacgga atggacgtatgggggcaagggaccacggtcaccgtttcctca |
| 147 | CDRH1 IMGT (Prot) | GFTFASEG |
| 148 | CDRH1 Kabat (Prot) | SEGMH |
| 149 | CDRH1 Chothia (Prot) | GFTFASE |
| 150 | CDRH2 IMGT (Prot) | IYYEGVNK |
| 151 | CDRH2 Kabat (Prot) | SIYYEGVNKYYADSVKG |
| 152 | CDRH2 Chothia (Prot) | YYEGVN |
| 153 | CDRH3 IMGT (Prot) | AKDVSYYDSSRLVYHGMDV |
| 154 | CDRH3 Kabat (Prot) | DVSYYDSSRLVYHGMDV |
| 155 | CDRH3 Chothia (Prot) | DVSYYDSSRLVYHGMDV |
| 156 | Light Chain Variable Domain | DIQLTQSPSSLSASVGDRVTITCRASQSISSYLNWYQQKPGKAPKLLI YAAGSLQSGVPSRFSGSGSGTDFTLTISSLQPEDFATYYCQQVHDFPL TFGGGTKVEIK |
| 157 | VL (DNA) | gacatccagttgacccagtctccatcctccctgtctgcaagcgttgga gatagagtcactatcacttgccgggcaagtcagagcattagcagctat ttaaaattggtatcagcagaaaccagggaaagcccctaagctcctgatc tatgcagccgggagtttgcaaagtggggtcccatcaaggttcagtggc agtggatccgggacagatttcactctcaccatcagcagtctgcaacct gaagattttgcaacttactactgtcagcaagtgcacgacttccctctc actttcggcggagggaccaaggttgagatcaaa |
| 158 | CDRL1 IMGT (Prot) | QSISSY |
| 159 | CDRL1 Kabat (Prot) | RASQSISSYLN |
| 160 | CDRL1 Chothia (Prot) | RASQSISSYLN |
| 161 | CDRL2 IMGT (Prot) | AAG |
| 162 | CDRL2 Kabat (Prot) | AAGSLQS |
| 163 | CDRL2 Chothia (Prot) | AAGSLQS |
| 164 | CDRL3 IMGT (Prot) | QQVHDFPLT |
| 165 | CDRL3 Kabat (Prot) | QQVHDFPLT |
| 166 | CDRL3 Chothia (Prot) | QQVHDFPLT |
| 167 | ScFv | DIQLTQSPSSLSASVGDRVTITCRASQSISSYLNWYQQKPGKAPKLLI YAAGSLQSGVPSRFSGSGSGTDFTLTISSLQPEDFATYYCQQVHDFPL TFGGGTKVEIKGSTSGSGKPGSGEGSTKGVQLVESGGGVVQPGRSLR LSCAASGFTFASEGMHWVRQAPGKGLEWVASIYYEGVNKYYADSVKGR FTISRDNSKNTLYLQMNSLRAEDTAVYYCAKDVSYYDSSRLVYHGMDV WGQGTTVTVSS |

TABLE 10-continued

Exemplary Antibody Sequences 7 (Ab7)

| SEQ ID NO: | Description | Sequence |
|---|---|---|
| 168 | ScFv | gacatccagttgacccagtctccatcctccctgtctgcaagcgttgga
gatagagtcactatcacttgccgggcaagtcagagcattagcagctat
ttaaaattggtatcagcagaaaccagggaaagcccctaagctcctgatc
tatgcagccgggagtttgcaaagtggggtcccatcaaggttcagtggc
agtggatccgggacagatttcactctcaccatcagcagtctgcaacct
gaagattttgcaacttactactgtcagcaagtgcacgacttccctctc
actttcggcggagggaccaaggttgagatcaaagggagcacaagcggc
tctggcaaacctggatctggcgagggatctaccaagggccaggtgcag
ctggtggagtctggggggaggcgtggtccagcctggggaggtccctgaga
ctctcctgcgctgcatctggattcaccttcgccagcgaaggcatgcac
tgggtccgccaggctccaggcaaggggctggagtgggtggcatccata
tactatgagggagtcaataaatactatgcagactccgtgaagggccga
ttcaccatctctagagacaattccaagaacacgctgtatctgcaaatg
aatagcctgagagccgaggacacggcggtgtactactgcgccaaggac
gtgtcctactacgacagcagcagactagtttatcacggaatggacgta
tgggggcaagggaccacggtcaccgtttcctca |

TABLE 11

Exemplary Antibody Sequences 8 (Ab8)

| SEQ ID NO: | Description | Sequence |
|---|---|---|
| 169 | Heavy Chain Variable Domain | QVQLVESGGGWQPGRSLRLSCAASGFTFASEGMHWVRQAPGKGLEWV
ASIYYEGVNKYYADSVKGRFTISRDNSKNTLYLQMNSLRAEDTAVYYC
AKDRSYYDSSGLVYHGMDVWGQGTTVTVSS |
| 170 | VH (DNA) | caggtgcagctggtggagtctggggggaggcgtggtccagcctggggagg
tccctgagactctcctgcgctgcatctggattcaccttcgccagcgaa
ggcatgcactgggtccgccaggctccaggcaaggggctggagtgggtg
gcatccatatactatgagggagtcaataaatactatgcagactccgtg
aagggccgattcaccatctccagagacaattccaagaacacgctgtat
ctgcaaatgaacagcctgagagccgaggacacggcggtgtactactgc
gccaaggacagatcctactacgacagcagcgggctagtttatcacgga
atggacgtatgggggcaagggaccacggtcaccgtttcctca |
| 171 | CDRH1 IMGT (Prot) | GFTFASEG |
| 172 | CDRH1 Kabat (Prot) | SEGMH |
| 173 | CDRH1 Chothia (Prot) | GFTFASE |
| 174 | CDRH2 IMGT (Prot) | IYYEGVNK |
| 175 | CDRH2 Kabat (Prot) | SIYYEGVNKYYADSVKG |
| 176 | CDRH2 Chothia (Prot) | YYEGVN |
| 177 | CDRH3 IMGT (Prot) | AKDRSYYDSSGLVYHGMDV |
| 178 | CDRH3 Kabat (Prot) | DRSYYDSSGLVYHGMDV |
| 179 | CDRH3 Chothia (Prot) | DRSYYDSSGLVYHGMDV |
| 180 | Light Chain Variable Domain | DIQLTQSPSSLSASVGDRVTITCRASQSISSYLNWYQQKPGKAPKLLI
YAASSGQSGVPSRFSGSGSGTDFTLTISSLQPEDFATYYCQQVHDFPL
TFGGGTKVEIK |
| 181 | VL (DNA) | gacatccagttgacccagtctccatcctccctgtctgcaagcgttgga
gacagagtcactatcacttgccgggcaagtcagagcattagcagctat
ttaaattggtatcagcagaaaccagggaaagcccctaagctcctgatc |

TABLE 11-continued

Exemplary Antibody Sequences 8 (Ab8)

| SEQ ID NO: | Description | Sequence |
|---|---|---|
|  |  | tatgctgcatccagtggacaaagtggggtcccatcaaggttcagtggc agtggatccgggacagatttcactctcaccatcagcagtctgcaacct gaagattttgcaacttactactgtcagcaagtgcacgacttccctctc actttcggcggagggaccaaggttgagatcaaa |
| 182 | CDRL1 IMGT (Prot) | QSISSY |
| 183 | CDRL1 Kabat (Prot) | RASQSISSYLN |
| 184 | CDRL1 Chothia (Prot) | RASQSISSYLN |
| 185 | CDRL2 IMGT (Prot) | AAS |
| 186 | CDRL2 Kabat (Prot) | AASSGQS |
| 187 | CDRL2 Chothia (Prot) | AASSGQS |
| 188 | CDRL3 IMGT (Prot) | QQVHDFPLT |
| 189 | CDRL3 Kabat (Prot) | QQVHDFPLT |
| 190 | CDRL3 Chothia (Prot) | QQVHDFPLT |
| 191 | ScFv | DIQLTQSPSSLSASVGDRVTITCRASQSISSYLNWYQQKPGKAPKLLI YAASSGQSGVPSRFSGSGSGTDFTLTISSLQPEDFATYYCQQVHDFPL TFGGGTKVEIKGSTSGSGKPGSGEGSTKGQVQLVESGGGVVQPGRSLR LSCAASGFTFASEGMHWVRQAPGKGLEWVASIYYEGVNKYYADSVKGR FTISRDNSKNTLYLQMNSLRAEDTAVYYCAKDRSYYDSSGLVYHGMDV WGQGTTVTVSS |
| 192 | ScFv | gacatccagttgacccagtctccatcctccctgtctgcaagcgttgga gacagagtcactatcacttgccgggcaagtcagagcattagcagctat ttaaattggtatcagcagaaaccagggaaagcccctaagctcctgatc tatgctgcatccagtggacaaagtggggtcccatcaaggttcagtggc agtggatccgggacagatttcactctcaccatcagcagtctgcaacct gaagattttgcaacttactactgtcagcaagtgcacgacttccctctc actttcggcggagggaccaaggttgagatcaaagggagcacaagcggc tctggcaaacctggatctggcgagggatctaccaagggccaggtgcag ctggtggagtctgggggaggcgtggtccagcctggggaggtccctgaga ctctcctgcgctgcatctggattcaccttcgccagcgaaggcatgcac tgggtccgccaggctccaggcaaggggctggagtgggtggcatccata tactatgagggagtcaataaatactatgcagactccgtgaagggccga ttcaccatctccagagacaattccaagaacacgctgtatctgcaaatg aacagcctgagagccgaggacacggcggtgtactactgcgccaaggac agatcctactacgacagcagcgggctagtttatcacggaatggacgta tgggggcaagggaccacggtcaccgtttcctca |

TABLE 12

Exemplary Antibody Sequences 9 (Ab9)

| SEQ ID NO: | Description | Sequence |
|---|---|---|
| 193 | Heavy Chain Variable Domain | QVQLVESGGGVVQPGRSLRLSCAASGFTFSSEGMYWVRQAPGKGLEWV AAIWYEGSNKYYADSVKGRFTISRDNSKNTLYLQMNSLRAEDTAVYYC AKDRSYYDSSQLVYHGMDVWGQGTTVTVSS |
| 194 | VH (DNA) | caagttcagctggtggagtctggggaggcgtggtccagcctggggagg tccctgagactctcctgcgctgcatctggattcaccttcagtagegag ggaatgtactgggtccgccaggctccaggcaaggggctggagtgggtg gcagccatatggtatgagggaagtaataaatactatgccgactccgtg aaggggccgattcaccatctctcgcgacaattccaaaaatacgctgtat |

TABLE 12-continued

Exemplary Antibody Sequences 9 (Ab9)

| SEQ ID NO: | Description | Sequence |
|---|---|---|
| | | ctgcaaatgaatagccttagagccgaggacacggcggtgtactactgc gccaaggacagatcctactacgacagcagccagctagtttatcacgga atggacgtatgggggcaagggaccacggtcaccgtttcctca |
| 195 | CDRH1 IMGT (Prot) | GFTFSSEG |
| 196 | CDRH1 Kabat (Prot) | SEGMY |
| 197 | CDRH1 Chothia (Prot) | GFTFSSE |
| 198 | CDRH2 IMGT (Prot) | IWYEGSNK |
| 199 | CDRH2 Kabat (Prot) | AIWYEGSNKYYADSVKG |
| 200 | CDRH2 Chothia (Prot) | WYEGSN |
| 201 | CDRH3 IMGT (Prot) | AKDRSYYDSSQLVYHGMDV |
| 202 | CDRH3 Kabat (Prot) | DRSYYDSSQLVYHGMDV |
| 203 | CDRH3 Chothia (Prot) | DRSYYDSSQLVYHGMDV |
| 204 | Light Chain Variable Domain | DIQLTQSPSSLSASVGDRVTITCRASQSISSYLNWYQQKPGKAPKLLI YAASSLQGGVPSRFSGSGSGTDFTLTISSLQPEDFATYYCQQIHDFPL TFGGGTKVEIK |
| 205 | VL (DNA) | gacatccagttgacccagtctccatcctccctgtctgcaagcgttgga gacagagtcactatcacttgccgggcaagtcagagcattagcagctat ttaaattggtatcagcagaaaccagggaaagcccctaagctcctgatc tatgctgcatccagtttgcaaggaggggtcccatcaaggttcagtggc agtggctctgggacagatttcactctcaccatcagcagtctgcaacct gaagattttgcaacttactactgtcagcaaattcacgacttccctctc actttcggcggagggaccaaggttgagatcaaa |
| 206 | CDRL1 IMGT (Prot) | QSISSY |
| 207 | CDRL1 Kabat (Prot) | RASQSISSYLN |
| 208 | CDRL1 Chothia (Prot) | RASQSISSYLN |
| 209 | CDRL2 IMGT (Prot) | AAS |
| 210 | CDRL2 Kabat (Prot) | AASSLQG |
| 211 | CDRL2 Chothia (Prot) | AASSLQG |
| 212 | CDRL3 IMGT (Prot) | QQIHDFPLT |
| 213 | CDRL3 Kabat (Prot) | QQIHDFPLT |
| 214 | CDRL3 Chothia (Prot) | QQIHDFPLT |

TABLE 12-continued

Exemplary Antibody Sequences 9 (Ab9)

| SEQ ID NO: | Description | Sequence |
|---|---|---|
| 215 | ScFv | DIQLTQSPSSLSASVGDRVTITCRASQSISSYLNWYQQKPGKAPKLLI<br>YAASSLQGGVPSRFSGSGSGTDFTLTISSLQPEDFATYYCQQIHDFPL<br>TFGGGTKVEIKGSTSGSGKPGSGEGSTKGQVQLVESGGGVVQPGRSLR<br>LSCAASGFTFSSEGMYWVRQAPGKGLEWVAAIWYEGSNKYYADSVKGR<br>FTISRDNSKNTLYLQMNSLRAEDTAVYYCAKDRSYYDSSQLVYHGMDV<br>WGQGTTVTVSS |
| 216 | ScFv | gacatccagttgacccagtctccatcctccctgtctgcaagcgttgga<br>gacagagtcactatcacttgccgggcaagtcagagcattagcagctat<br>ttaaattggtatcagcagaaaccagggaaagcccctaagctcctgatc<br>tatgctgcatccagtttgcaaggaggggtcccatcaaggttcagtggc<br>agtggctctgggacagatttcactctcaccatcagcagtctgcaacct<br>gaagattttgcaacttactactgtcagcaaattcacgacttccctctc<br>actttcggcggagggaccaaggttgagatcaaagggagcacaagcggc<br>tctggcaaacctggatctggcgagggatctaccaagggccaagttcag<br>ctggtggagtctggggggaggcgtggtccagcctgggaggtccctgaga<br>ctctcctgcgctgcatctggattccacttcagtagcgagggaatgtac<br>tgggtccgccaggctccaggcaaggggctggagtgggtggcagccata<br>tggtatgagggaagtaataaatactatgccgactccgtgaagggccga<br>ttcaccatctctcgcgacaattccaaaaatacgctgtatctgcaaatg<br>aatagccttagagccgaggacacggcggtgtactactgcgccaaggac<br>agatcctactacgacagcagccagctagtttatcacggaatggacgta<br>tgggggcaagggaccacggtcaccgtttcctca |

Chimeric antigen receptors (CARs) are engineered receptors that may direct or redirect T cells or NK cells (e.g., patient or donor T or NK cells) to target a selected antigen. A CAR may be engineered to recognize an antigen and, when bound to that antigen, activate the immune cell to attack and destroy the cell bearing that antigen. When these antigens exist on tumor cells, an immune cell that expresses the CAR may target and kill the tumor cell. CARs generally comprise an extracellular binding domain that mediates antigen binding (e.g., a dual TACI-BCMA binding domain), a transmembrane domain that spans, or is understood to span, the cell membrane when the CAR is present at a cell surface or cell membrane, and an intracellular (or cytoplasmic) signaling domain.

According to at least one non-limiting view, there have been at least three "generations" of CAR compositions. In a first generation of CARs, a binding domain (e.g., a single chain fragment variable, binding domain) is linked or connected to a signaling domain (e.g., CD3ζ) via a transmembrane domain, optionally comprising a hinge domain and one or more spacers. In a second generation of CARs, a costimulatory domain (CM1, such as CD28, 4-1BB, or OX-40) is introduced with the signaling domain (e.g., CD3ζ). In a third generation of CARs, a second costimulatory domain (CM2) is comprised.

TCRs are heterodimers composed of an α-chain and a β-chain. TCR signaling requires recruitment of signaling proteins that generate an immune synapse. In addition, TCR localization at the plasma membrane depends on CD3 complex, which is expressed in T cells. Engineered single chain TCRs may be generated, e.g., using transmembrane and signaling domains of CAR constructs, methods and constructs for which are known (e.g., sTCR and TCR-CAR molecules, e.g., fusion of a TCRβ chain with CD28 TM and CD28 and CD3ζ signaling modules).

A dual TACI-BCMA binding system of the present disclosure may comprise one or more antigen binding domains that bind TACI and BCMA. In some embodiments, an antigen binding system further comprises a costimulatory domain, and/or an extracellular domain (e.g., a "hinge" or "spacer" region), and/or a transmembrane domain, and/or an intracellular (signaling) domain, and/or a CD3-zeta or CD3-epsilon activation domain. In some embodiments, a dual TACI-BCMA binding system of the present disclosure comprises at least a binding domain that binds human TACI and BCMA, a costimulatory domain, an extracellular domain, a transmembrane domain, and a CD3-zeta or CD3-epsilon activating domain.

In some embodiments, a dual TACI-BCMA binding CAR of the present disclosure may comprise an antigen binding system that comprises one or more, or all, of a leader peptide (P), dual TACI-BCMA binding (B), a costimulatory protein's extracellular domain (E), a transmembrane domain (T), a costimulatory domain (C), a second costimulatory domain (C'), and an activation domain (A). In some instances, a dual TACI-BCMA binding CAR is configured according to the following: B E T A. In some instances, a dual TACI-BCMA binding CAR is configured according to the following: PB ET A. In some instances, a dual TACI-BCMA binding CAR is configured according to the following: B E T C A. In some instances a dual TACI-BCMA binding CAR is configured according to the following: PB ETC A. In some instances, a dual TACI-BCMA binding CAR is configured according to the following: B ETC C' A. In some instances, a dual TACI-BCMA binding CAR is configured according to the following: PB ETC C' A. In some embodiments, a dual TACI-BCMA binding CAR comprises a VH and a VL, optionally wherein the CAR is configured according to the following: P-VH-VL-E-T-C-A or P-VL-VH-E-T-C-A. In some embodiments, the VH and the VL are connected by a linker (L), optionally wherein the CAR is configured according to the following, from N-terminus to C-terminus: P-VH-L-VL-E-T-C-A or P-VH-L-VL-E-T-C-A.

One or more antigen binding domains determine the target(s) of an antigen binding system. A binding domain of an antigen binding system may comprise any dual TACI-BCMA binding domain, e.g., an antibody provided by the present disclosure, e.g., a binding domain of the present disclosure. Binding domain are used in chimeric antigen receptors at least in part because they may be engineered to be expressed as part of a single chain along with the other CAR components. See, for example, U.S. Pat. Nos. 7,741, 465, and 6,319,494 as well as Eshhar et al., Cancer Immunol Immunotherapy (1997) 45: 131-136, Krause et al., J. Exp. Med., Volume 188, No. 4, 1998 (619-626); Finney et al., Journal of Immunology, 1998, 161: 2791-2797, each of which is incorporated herein by reference with respect to binding domains in CARs. A binding domain or scFv, is a single chain antigen binding fragment comprising a heavy chain variable domain and a light chain variable domain, which heavy chain variable domain and light chain variable domain are linked or connected together. See, for example, U.S. Pat. Nos. 7,741,465, and 6,319,494 as well as Eshhar et al., Cancer Immunol Immunotherapy (1997) 45: 131-136, each of which is incorporated herein by reference with respect to binding domain domains. When derived from a parent antibody, a binding domain may retain some of, retain all of, or essentially retain the parent antibody's binding of a target antigen. In some embodiments, a CAR contemplated herein comprises antigen-specific binding domain that may be a scFv (a murine, human or humanized scFv) that binds an antigen expressed on a cancer cell. In a certain embodiment, the scFv binds TACI and BCMA.

In certain embodiments, the CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers $(G_{1-5}S_{1-5})$n (SEQ ID NO: 304), where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, *Rev. Computational Chem.* 11173-142 (1992)). Other linkers contemplated herein include Whitlow linkers (see Whitlow, *Protein Eng.* 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker (SEQ ID NO: 223). In another embodiment, any of the constructs described herein comprise a "GSG" linker. In an example a glycine-serine linker comprises or consists of the amino acid sequence GS (SEQ ID NO: 223), which may be encoded by the nucleic acid sequence according to ggatcc (SEQ ID NO: 224) or gggtcc (SEQ ID NO: 225). In an example a glycine-serine linker comprises or consists of the amino acid sequence GGGSGGGS (SEQ ID NO: 226), which may be encoded by the nucleic acid sequence according to ggcggtggaagcggaggaggttcc (SEQ ID NO: 227). In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 219 (GST-SGSGKPGSGEGSTKG (SEQ ID NO: 219). In an embodiment, a linker is encoded by a nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid sequence according to (SEQ ID NO: 220)
gggagcactagcggctctggcaaacctggatctggcgagggatctacca agggc, (SEQ ID NO: 228)
gggagcacaagcggctctggcaaacctggatctggcgagggatctaccaa gggc,
or (SEQ ID NO: 229)
gggagcacaagcggctctggcaaacctggatccggcgagggatctaccaa gggc.

In embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy,* 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

In some embodiments, an Antigen binding system of the present disclosure may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof. A hinge may be derived from a natural source or from a synthetic source. Hinge domains suitable for use in the CARs described herein include the hinge region derived from the extracellular regions of type 1 membrane proteins such as CD8a, CD4, CD28 and CD7, which may be wild-type hinge regions from these molecules or may be altered, for example a truncated CD28 hinge domain. A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8a, CD80, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof.

In embodiments, the hinge domain comprises a truncated CD28 hinge region (CD28T) hinge region, such as disclosed in International Patent Application No: PCT/US2017/025351, filed Mar. 31, 2017, which is incorporated herein by reference in its entirety. In embodiments the CARs described herein comprise a CD28T hinge domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 230 (LD-NEKSNGTIIHVKGKHLCPSPLFPGPSKP (SEQ ID NO: 230)). In embodiments, a CD28T hinge domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 231)
ctagacaatgagaagagcaatggaaccattatccatgtgaaagggaaaca cctttgtccaagtcccctatttcccggaccttctaagccc.

In embodiments, the hinge domain comprises a CD8a hinge region. In embodiments the CARs described herein comprise a hinge domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 232 (TTTPAPRPPT-PAPTIASQPLSLRPEACRPAAGGAVHTRGLDFACD (SEQ ID NO: 232)). In embodiments, hinge domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 233)
accacgacgccagcgccgcgaccaccaacaccggcgccaccatcgcgtc gcaaccctgtccctgcgccccgaggcgtgccggccagcggcgggggcg cagtgcacacgaggggctggacttcgcctgtgat.

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort (PSORT.org) and Prosite (prosite.expasy.org) are exemplary of such programs.

The type of transmembrane domain comprised in an antigen binding system described herein is not limited to any type. In some embodiments, a transmembrane domain is selected that is naturally associated with a binding domain and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, 2B4, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRT AM, cytokine receptor, DAP-10, DAP-12, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

In embodiments, the CARs described herein comprise a TM domain from CD28 having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 234 (FWVLVVVGGV-LACYSLLVTVAFIIFWV (SEQ ID NO: 234)). In embodiments, a TM domain from CD28 is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 235)
ttttgggtgctggtggtggttggtggagtcctggcttgctatagcttgct agtaacagtggcctttattattttctgggtg.

In embodiments, the CARs described herein comprise a TM domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 236 (IYI-WAPLAGTCGVLLLSLVITLYC (SEQ ID NO: 236)). In embodiments, the TM domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 237)
atctacatctgggcgcccttggccgggacttgtggggtccttctcctgtca ctggttatcacccttattgc.

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a polypeptide sequence known. Optionally, short spacers may form linkages between any or some of the extracellular, transmembrane, and intracellular domains of the CAR.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises an immunoreceptor tyrosine-based activation domain (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CDiia, CDiib, CDiic, CDiid, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

Illustrative examples of ITAM containing primary signaling domains that are useful in the present disclosure include those derived from TCRζ, FcRγ, FcRβ, DAP12, CD3γ, CD3δ, CD3ε, CD3ζ, CD22, CD79a, CD79b, and CD66d. In some embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain. In one embodiment, the CARs have a CD3ζ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 238. LRVKFSRSADAPAYQQGQNQLYNELNLGR-REEYDVLDKRRGRDPEMGGKPRRKNPQE GLY-NELQKDKMAEAYSEIGMKGERRRGKGHDGLYQGL-STATKDTYDALHMQALPPR (SEQ ID NO: 238). In embodiments, a CD3ζ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 239)
ctgagagtgaagttcagcaggagcgcagacgccccgcgtaccagcagggc cagaaccagctctataacgagctcaatctaggacgaagagaggagtacgat gttttggacaagaggcgtggccgggaccctgagatgggggggaaagccgaga aggaagaaccctcaggaaggcctgtacaatgaactgcagaaagataagatg gcggaggcctacagtgagattgggatgaaaggcgagcgccggaggggcaag gggcacgatggcctttaccagggtctcagtacagccaccaaggacacctac gacgcccttcacatgcaggccctgccccctcgc.

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. In some embodiments, costimulatory molecules may include DAP-10, DAP-12, CD27, CD28, CD137(4-IBB), OX40 (CD134), CD30, CD40, PD-I, ICOS (CD278), CTLA4, LFA-1, CD2, CD7, LIGHT, TRIM, LCK3, SLAM, DAPIO, LAGS, HVEM, B7-H3, NKD2C, GITR, CD5, ICAM-1, CD11a, Lck, TNFR-I, TNFR-II, FasR, NKG2C, and B7-H3, and CD83.

In embodiments, the CARs comprise a CD28 costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 240. RSKRSRLLHSDYMNMT-PRRPGPTRKHYQPYAPPRDFAAYRS (SEQ ID NO: 240). In embodiments, a CD28 costimulatory domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 241)
aggagtaagaggagcaggctcctgcacagtgactacatgaacatgactcc ccgccgccccgggcccacccgcaagcattaccagccctatgccccaccac gcgacttcgcagcctatcgctcc.

In embodiments, the CARs comprise a 4-IBB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 242. KRGRKKLLY-IFKQPFMRPVQTTQEEDGCSCRFPEEEEGGCE (SEQ ID NO: 242). In embodiments, a 4-IBB costimulatory domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to

```
                                        (SEQ ID NO: 243)
aaacggggcagaaagaaactcctgtatatattcaaacaaccatttatgag accagtacaaactactcaagaggaagatggctgtagctgccgatttccag aagaagaagaaggaggatgtgaa.
```

The engineered CARs described herein may also comprise an N-terminal signal peptide or tag at the N-terminus of the scFv or antigen binding domain. In one embodiment, a heterologous signal peptide may be used. The antigen binding domain or scFV may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly any known tag sequence known in the art may also be used. In one embodiment a signal sequence is a CSF2RA signal sequence. In embodiments, the CARs described herein comprise a CSF2RA signal sequence having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 221;

```
                                        (SEQ ID NO: 221)
        MLLLVTSLLLCELPHPAFLLIP (SEQ ID NO: 244)
        SEQ ID MEWTWVFLFLLSVTAGVHS,
        or (SEQ ID NO: 245)
        MALPVTALLLPLALLLHAARP.
```

Components of a CAR may be exchanged or "swapped" using routine techniques of biotechnology for equivalent components. To provide just a few non-limiting and partial examples, a CAR of the present disclosure may comprise a binding domain as provided herein in combination with a hinge provided herein and a costimulatory domain provided herein. In certain examples, a CAR of the present disclosure may comprise a leader sequence as provided herein together with a binding domain as provided herein in combination with a hinge provided herein and s costimulatory domain provided herein.

The present disclosure comprises conjugates in which an antibody of the present disclosure is associated with a therapeutic agent or a detectable moiety. In various embodiments, the therapeutic agent is an anti-cancer agent as provided herein. In certain embodiments, provided conjugate comprises one or more detectable moieties, i.e., is "labeled" with one or more such moieties. In some such embodiments, a conjugate of the present disclosure is useful in diagnostic or imaging applications, e.g., diagnosing or imaging cancer. Any of a wide variety of detectable moieties may be used in labeled antibody conjugates described herein. Suitable detectable moieties comprise, without limitation: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

The present disclosure comprises nucleic acids encoding dual TACI-BCMA binding domains provided herein. The present disclosure comprises nucleic acids encoding antibodies of the provided herein, comprising, without limitation, nucleic acids encoding dual TACI-BCMA binding domains. The present disclosure comprises nucleic acids encoding antigen binding systems provided herein, comprising without limitation nucleic acids encoding dual TACI-BCMA binding chimeric antigen receptors. The nucleic acid sequence of SEQ ID NO: 2 comprises and provides exemplary nucleic acid sequences corresponding to and encoding each of SEQ ID NOs: 1 and 3-11. The nucleic acid sequence of SEQ ID NO: 13 comprises and provides exemplary nucleic acid sequences corresponding to and encoding each of SEQ ID NOs: 12 and 14-22. The nucleic acid sequence of SEQ ID NO: 24 comprises and provides exemplary nucleic acid sequence corresponding to and encoding SEQ ID NO: 23.

The nucleic acid sequence of SEQ ID NO: 26 comprises and provides exemplary nucleic acid sequences corresponding to and encoding each of SEQ ID NOs: 25 and 27-35. The nucleic acid sequence of SEQ ID NO: 37 comprises and provides exemplary nucleic acid sequences corresponding to and encoding each of SEQ ID NOs: 36 and 38-46. The nucleic acid sequence of SEQ ID NO: 48 comprises and provides an exemplary nucleic acid sequence corresponding to and encoding SEQ ID NO: 47.

The nucleic acid sequence of SEQ ID NO: 50 comprises and provides exemplary nucleic acid sequences corresponding to and encoding each of SEQ ID NOs: 49 and 51-59. The nucleic acid sequence of SEQ ID NO: 61 comprises and provides exemplary nucleic acid sequences corresponding to and encoding each of SEQ ID NOs: 60 and 62-70. The nucleic acid sequence of SEQ ID NO: 72 comprises and provides an exemplary nucleic acid sequence corresponding to and encoding SEQ ID NO: 71.

The nucleic acid sequence of SEQ ID NO: 74 comprises and provides exemplary nucleic acid sequences corresponding to and encoding each of SEQ ID NOs: 73 and 75-83. The nucleic acid sequence of SEQ ID NO: 85 comprises and provides exemplary nucleic acid sequences corresponding to and encoding each of SEQ ID NOs: 84 and 86-94. The nucleic acid sequence of SEQ ID NO: 76 comprises and provides an exemplary nucleic acid sequence corresponding to and encoding SEQ ID NO: 95.

The nucleic acid sequence of SEQ ID NO: 98 comprises and provides exemplary nucleic acid sequences corresponding to and encoding each of SEQ ID NOs: 97 and 99-107. The nucleic acid sequence of SEQ ID NO: 109 comprises and provides exemplary nucleic acid sequences corresponding to and encoding each of SEQ ID NOs: 108 and 110-118. The nucleic acid sequence of SEQ ID NO: 120 comprises and provides an exemplary nucleic acid sequence corresponding to and encoding SEQ ID NO: 119.

The nucleic acid sequence of SEQ ID NO: 122 comprises and provides exemplary nucleic acid sequences corresponding to and encoding each of SEQ ID NOs: 121 and 123-131. The nucleic acid sequence of SEQ ID NO: 133 comprises and provides exemplary nucleic acid sequences corresponding to and encoding each of SEQ ID NOs: 132 and 134-142. The nucleic acid sequence of SEQ ID NO: 144 comprises and provides an exemplary nucleic acid sequence corresponding to and encoding SEQ ID NO: 143.

The nucleic acid sequence of SEQ ID NO: 146 comprises and provides exemplary nucleic acid sequences corresponding to and encoding each of SEQ ID NOs: 145 and 147-155. The nucleic acid sequence of SEQ ID NO: 157 comprises and provides exemplary nucleic acid sequences corresponding to and encoding each of SEQ ID NOs: 156 and 158-166. The nucleic acid sequence of SEQ ID NO: 168 comprises and provides an exemplary nucleic acid sequence corresponding to and encoding SEQ ID NO: 167.

The nucleic acid sequence of SEQ ID NO: 170 comprises and provides exemplary nucleic acid sequences corresponding to and encoding each of SEQ ID NOs: 169 and 171-179. The nucleic acid sequence of SEQ ID NO: 181 comprises and provides exemplary nucleic acid sequences corresponding to and encoding each of SEQ ID NOs: 180 and 182-190. The nucleic acid sequence of SEQ ID NO: 192 comprises and provides an exemplary nucleic acid sequence corresponding to and encoding SEQ ID NO: 191.

The nucleic acid sequence of SEQ ID NO: 194 comprises and provides exemplary nucleic acid sequences corresponding to and encoding each of SEQ ID NOs: 193 and 195-203. The nucleic acid sequence of SEQ ID NO: 205 comprises and provides exemplary nucleic acid sequences corresponding to and encoding each of SEQ ID NOs: 204 and 206-214. The nucleic acid sequence of SEQ ID NO: 216 comprises and provides an exemplary nucleic acid sequence corresponding to and encoding SEQ ID NO: 215.

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 246. DIQMTQSPSSLSASVGDRVTITCRASQSIS-SYLNWYQQKPGKAPKLLIYAASSLQSGVPS RFSGSGSGTDFTLTISSLQPEDFA-TYYCQQSHIAPWTFGGGTKVEIKGSTSGSGKPGSGE GSTKGQVQLVQSGAEVKKPGSSVKVSCK-ASGGTFADYAISWVRQAPGQGLEWMGGIIP ILGRAN-YAQKFQGRVTITADESTSTAYMELSSLRSEDTAVYY-CARDRDSTSLPYNHYY MDVWGKGTTVTVSSGSLD-NEKSNGTIIHVKGKHLCPSPLFPGPSKPFWVLVVV-GGVLA CYSLLVTVAFIIFWVRSKRSRLLHSDYMNMT-PRRPGPTRKHYQPYAPPRDFAAYRSLRV KFSRSADA-PAYQQGQNQLYNELNLGRREEYDVLDKRR-GRDPEMGGKPRRKNPQEGLY NELQKDKMAEAYSEIGMKGERRRGKGHDGLYQGL-STATKDTYDALHMQALPPR (SEQ ID NO: 246). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 247)
gacatccagatgacccagtctccatcctccctgtctgcaagcgttgga gatagagtcactatcacttgccgggcaagtcagagcattagcagctattt aaattggtatcagcagaaaccagggaaagcccctaagctcctgatctatg ctgcatccagtttgcaaagtggggtcccatcaaggttcagtggcagtgga tccgggacagatttcactctcaccatcagcagtctgcaacctgaagattt tgcaacttactactgtcagcaaagccacatcgcccttggacttttggcg gagggaccaaggttgagatcaaagggagcactagcggctctggcaaacct ggatctggcgagggatctaccaagggccaggtgcagctggtgcagtctgg ggctgaggtgaagaagcctgggtcctcggtgaaggtctcctgcaaggctt ctggaggcaccttcgcagactatgctatcagctgggtgcgacaggcccct ggacaagggcttgagtggatgggagggatcatccctatattgggcagagc aaactacgcacagaagttccagggcagagttacgattaccgcggacgaat ccacgagcacagcctacatggagctgagcagcctgagatctgaggacacg gcggtgtactactgcgccagagacagagacagcacaagcctgccgtacaa ccactactacatggacgtatggggcaagggtacaactgtcactgtctcct cagggtccctagacaatgagaagagcaatggaaccattatccatgtgaaa gggaaacacctttgtccaagtcccctatttcccggaccttctaagcccctt ttgggtgctggtggtggttggtggagtcctggcttgctatagcttgctag taacagtggcctttattattttctgggtgaggagtaagaggagcaggctc ctgcacagtgactacatgaacatgactccccgccgccccgggcccacccg caagcattaccagccctatgccccaccacgcgacttcgcagcctatcgct ccctgagagtgaagttcagcaggagcgcagacgcccccgcgtaccagcag ggccagaaccagctctataacgagctcaatctaggacgaagagaggagta cgatgttttggacaagaggcgtggccgggaccctgagatgggggaaagc cgagaaggaagaaccctcaggaaggcctgtacaatgaactgcagaaagat aagatggcggaggcctacagtgagattgggatgaaaggcgagcgccggag gggcaaggggcacgatggcctttaccagggtctcagtacagccaccaagg acacctacgacgcccttcacatgcaggccctgccccctcgc.

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 248. DIQLTQSPSSLSASVGDRVTITCRASQSIL-SYLNWYQQKPGKAPKLLIYAASSLQSGVPSR FSGSGSGTDFTLTISSLQPEDFATYYCQQS-SIAPWTFGGGTKVEIKGSTSGSGKPGSGEGS TKGQVQLVQSGAEVKKPGSSVKVSCK-ASGGTFADYAISWVRQAPGQGLEWMGGIIPIL GRAN-YAQKFQGRVTITADESTSTAYMELSSLRSEDTAVYY-CARDRDRTSLPYNHYYMD VWGKGTTVTVSSGSLD-NEKSNGTIIHVKGKHLCPSPLFPGPSKPFWVLV-VVGGVLACYS LLVTVAFIIFWVR-SKRSRLLHSDYMNMTPRRPGPTRKHYQPYAPPRD-FAAYRSLRVKFS RSADAPAYQQGQNQLYNELNLGR-REEYDVLDKRRGRDPEMGGKPRRKNPQEGLYNEL QKDKMAEAYSEIGMKGERRRGKGHDGLYQGL- STATKDTYDALHMQALPPR (SEQ ID NO: 248). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 249)
gacatccagttgacccagtctccatcctccctgtctgcaagcgttggaga tagagtcactatcacttgccgggcaagtcagagcattctcagctatttaa attggtatcagcagaaaccagggaaagcccctaagctcctgatctatgct gcatccagtttgcaaagtggggtcccatcaaggttcagtggcagtggatc cgggacagatttcactctcaccatcagcagtctgcaacctgaagattttg caacttactactgtcagcaaagctcgatcgcccttggactttcggcgga gggaccaaggttgagatcaaagggagcacaagcggctctggcaaacctgg atctggcgagggatctaccaagggccaggtgcagctggtgcagtctgggg ctgaggtgaagaagcctgggtcctcggtgaaggtctcctgcaaggcttct ggaggcaccttcgcagactatgctatcagctgggtgcgacaggcccctgg acaagggcttgagtggatgggagggatcatccctatattgggcagagcaa actacgcacagaagttccagggcagagttacgattaccgcggacgaatcc acgagcacagcctacatggagctgagcagcctgagatctgaggacacggc ggtgtactactgcgccagagacagagaccgtacaagcctgccgtacaacc actactacatggacgtatggggcaaagggaccacggtcaccgtttcctca gggtccctagacaatgagaagagcaatggaaccattatccatgtgaaagg gaaacacctttgtccaagtccctatttcccggaccttctaagccctttt gggtgctggtggtggttggtggagtcctggcttgctatagcttgctagta acagtggcctttattattttctgggtgaggagtaagaggagcaggctcct gcacagtgactacatgaacatgactccccgccgcccccgggcccacccgca agcattaccagccctatgccccaccacgcgacttcgcagcctatcgctcc ctgagagtgaagttcagcaggagcgcagacgccccgcgtaccagcaggg ccagaaccagctctataacgagctcaatctaggacgaagagaggagtacg atgttttggacaagaggcgtggccgggaccctgagatgggggaaagccg agaaggaagaaccctcaggaaggcctgtacaatgaactgcagaaagataa gatggcggaggcctacagtgagattgggatgaaaggcgagcgccggaggg gcaaggggcacgatggcctttaccagggtctcagtacagccaccaaggac acctacgacgccttcacatgcaggccctgccccctcgc.

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 250. DIQLTQSPSSLSASVGDRVTITCRASQSIS-SYLNWYQQKPGKAPKLLIYAASQLQSGVPS RFSGSGSGTDFTLTISSLQPEDFATYYCQQSA-IAPWTFGGGTKVEIKGSTSGSGKPGSGE GSTKGQVQLVQSGAEVKKPGSSVKVSCKASGGT-FEDYAISWVRQAPGQGLEWMGGIIP ILGRAN-YAQKFQGRVTITADESTSTAYMELSSLRSEDTAVYY-CARDRDLTSLPYNHYY MDVWGKGTTVTVSSGSLD-NEKSNGTIIHVKGKHLCPSPLFPGPSKPFWVLVVV-GGVLA CYSLLVTVAFIIFWVRSKRSRLLHSDYMNMT-PRRPGPTRKHYQPYAPPRDFAAYRSLRV KFSRSADA-PAYQQGGQNQLYNELNLGRREEYDVLDKRR-GRDPEMGGKPRRKNPQEGLY NELQKDKMAEAYSEIGMKGERRRGKGHDGLYQGL-STATKDTYDALHMQALPPR (SEQ ID NO: 250). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 251)
gacatccagttgacccagtctccatcctccctgtctgcaagcgttggag atagagtcactatcacttgccgggcaagtcagagcattagcagctattt aaattggtatcagcagaaaccagggaaagcccctaagctcctgatctat gctgcatcccaattgcaaagtggggtcccatcaaggttcagtggcagtg gatccgggacagatttcactctcaccatcagcagtctgcaacctgaaga ttttgcaacttactactgtcagcaaagctatcgcccttggactttc ggcggagggaccaaggttgagatcaaagggagcacaagcggctctggca aacctggatctggcgagggatctaccaagggccaggtgcagctggtgca gtctggggctgaggtgaagaagcctgggtcctcggtgaaggtctcctgc aaggcttctggaggcaccttcgaagactatgctatcagctgggtgcgac aggcccctggacaagggcttgagtggatgggagggatcatccctatatt gggccgagcaaactacgcacagaagttccagggcagagttacgattacc gcggacgaatccacgagcacagcctacatggagctgagcagcctgagat ctgaggacacggcggtgtactactgcgccagagacagagacttgacaag cctgccgtacaaccactacatggacgtatggggcaaagggaccacg gtcaccgtttcctcagggtccctagacaatgagaagagcaatggaacca ttatccatgtgaaagggaaacacctttgtccaagtccctatttcccgg accttctaagccctttgggtgctggtggtggttggtggagtcctggct tgctatagcttgctagtaacagtggcctttattattttctgggtgagga gtaagaggagcaggctcctgcacagtgactacatgaacatgactccccg ccgcccgggcccaccccgcaagcattaccagccctatgccccaccacgc gacttcgcagcctatcgctccctgagagtgaagttcagcaggagcgcag acgccccgcgtaccagcagggccagaaccagctctataacgagctcaa tctaggacgaagagaggagtacgatgttttggacaagaggcgtggccgg gaccctgagatgggggaaagccgagaaggaagaaccctcaggaaggcc tgtacaatgaactgcagaaagataagatggcggaggcctacagtgagat tgggatgaaaggcgagcgccggaggggcaaggggcacgatggcctttac cagggtctcagtacagccaccaaggacacctacgacgccttcacatgc aggccctgccccctcgc.

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 252. DIQLTQSPSSLSASVGDRVTITCRASTSIS-SYLNWYQQKPGKAPKLLIYAASSLQSGVPSR FSGSGSGTDFTLTISSLQPEDFATYYCQQS-ADAPWTFGGGTKVEIKGSTSGSGKPGSGEG STKGQVQLVQSGAEVKKPGSSVKVSCK-ASGGTFSHYAISWVRQAPGQGLEWMGGIIPIL GRAN-YAQKFQGRVTITADESTSTAYMELSSLRSEDTAVYY-CARDRTWEGSPYYYYGM DVWGQGTMVTVSSGSLD-NEKSNGTIIHVKGKHLCPSPLFPGPSKPFWVLVV-VGGVLAC YSLLVTVAFIIFWVR-SKRSRLLHSDYMNMTPRRPGPTRKHYQPYAPPRD-FAAYRSLRVK FSRSADAPAYQQGQNQLYNELNLGR-REEYDVLDKRRGRDPEMGGKPRRKNPQEGLYN ELQKDKMAEAYSEIGMKGERRRGKGHDGLYQGL-STATKDTYDALHMQALPPR (SEQ ID NO: 252). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 253)
gacatccagttgacccagtctccatcctccctgtctgcaagcgttgga gacagggtcactatcacttgccgggcaagtaccagcattagcagctat ttaaattggtatcagcagaaaccagggaaagcccctaagctcctgatc tatgctgcatccagtttgcaaagtggggtcccatcaaggttcagtggc agtggatctgggacagatttcactctcaccatcagcagtctgcaacct gaagattttgcaacttactactgtcagcaaagcgccgatgcccttgg actttcggcggagggaccaaggttgagatcaaagggagcacaagcggc tctggcaaacctggatccggcgagggatctaccaagggccaggtgcag ctggtgcagtctggggctgaagtgaagaagcctgggtcctcggtgaag gtctcctgcaaggcttctggaggcaccttcagccactatgctatcagc tgggtgcgacaggcccctggacaagggcttgagtggatgggagggatc atccctatattgggccgagcaaactacgcacagaagttccagggcaga gtcacgattaccgcggacgaatccacgagcacagcctacatggagctg agcagcctgagatctgaggacacggcggtgtactactgcgccagagac agaacttgggaaggatctccctattattactacggaatggacgtttgg ggccaagggacaatggtcaccgtttcctcagggtccctagacaatgag aagagcaatggaaccattatccatgtgaaagggaaacacctttgtcca agtccctatttcccgaccttctaagccctttgggtgctggtggtg gttggtggagtcctggcttgctatagcttgctagtaacagtggcctt attattttctgggtgaggagtaagaggagcaggctcctgcacagtgac tacatgaacatgactccccgccgccccgggcccacccgcaagcattac cagccctatgcccaccacgcgacttcgcagcctatcgctccctgaga gtgaagttcagcaggagcgcagacgccccccgcgtaccagcagggccag aaccagctctataacgagctcaatctaggacgaagagaggagtacgat gttttggacaagaggcgtggccgggaccctgagatggggggaaagccg In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 254. DIQLTQSPSSLSASVGDRVTITCRASQSIA-SYLNWYQQKPGKAPKLLIYAASSLQSGVPS RFSGSGSGTDFTLTISSLQPEDFA-TYYCQQSAGAPWTFGGGTKVEIKGSTSGSGKPGSGE GSTKGQVQLVQSGAEVKKPGSSVKVSCKASGGTFD-DYAISWVRQAPGQGLEWMGGIIP ILGRAN-YAQKFQGRVTITADESTSTAYMELSSLRSEDTAVYY-CARDRVWEGSPYYYYG MDVWGQGTMVTVSSGSLD-NEKSNGTIIHVKGKHLCPSPLFPGPSKPFWVLVVV-GGVLA CYSLLVTVAFIIFWVRSKRSRLLHSDYMNMT-PRRPGPTRKHYQPYAPPRDFAAYRSLRV KFSRSADA-PAYQQGQNQLYNELNLGRREEYDVLDKRR-GRDPEMGGKPRRKNPQEGLY NELQKDKMAEAYSEIGMKGERRRGKGHDGLYQGL-STATKDTYDALHMQALPPR (SEQ ID NO: 254). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 255)
gacatccagttgacccagtctccatcctccctgtctgcaagcgttggag atagagtcactatcacttgccgggcaagtcagagcattgccagctattt aaattggtatcagcagaaaccagggaaagcccctaagctcctgatctat gctgcatccagtttgcaaagtggggtcccatcaaggttcagtggcagtg gatccgggacagatttcactctcaccatcagcagtctgcaacctgaaga ttttgcaacttactactgtcagcaaagcgccggtgccttggacttc ggcggagggaccaaggttgagatcaaaggagcacaagcggctctggca aacctggatctggcgagggatctaccaagggccaggtgcagctggtgca gtctggggctgaggtgaagaagcctgggtcctcggtgaaggtctcctgc aaggcttctggaggcaccttcgacgactatgctatcagctgggttcgac aggcccctggacaagggcttgagtggatgggagggatcatccctatatt gggcagagcaaactacgcacagaagttccagggcagagtcacgattacc gcggacgaatccacgagcacagcctacatggagctgagcagcctgagat ctgaggacacggcggtgtactactgcgccagagacagagtgtgggaagg atctccctattattactacggaatggacgtttggggccaagggacaatg gtcaccgtttcctcagggtccctagacaatgagaagagcaatggaacca ttatccatgtgaaagggaaacacctttgtccaagtcccctatttccgg accttctaagcccttttgggtgctggtggtggttggtggagtcctggct

```
tgctatagcttgctagtaacagtggcctttattattttctgggtgagga gtaagaggagcaggctcctgcacagtgactacatgaacatgactcccg ccgcccgggcccaccgcaagcattaccagccctatgcccaccacgc gacttcgcagcctatcgctccctgagagtgaagttcagcaggagcgcag acgccccgcgtaccagcagggccagaaccagctctataacgagctcaa tctaggacgaagagaggagtacgatgttttggacaagaggcgtggccgg gaccctgagatgggggaaagccgagaaggaagaaccctcaggaaggcc tgtacaatgaactgcagaaagataagatggcggaggcctacagtgagat tgggatgaaaggcgagcgccggaggggcaaggggcacgatggcctttac cagggtctcagtacagccaccaaggacacctacgacgccttcacatgc aggccctgcccctcgc.
```

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 256. DIQLTQSPSSLSASVGDRVTITCRASQSIS-LYLNWYQQKPGKAPKLLIYAASSLQSGVPSR FSGSGSGTDFTLTISSLQPEDFATYYCQQVA-VAPWTFGGGTKVEIKGSTSGSGKPGSGEG STKGQVQLVQSGAEVKKPGSSVKVSCKASGGTFE-HYAISWVRQAPGQGLEWMGGIIPI LGRAN-YAQKFQGRVTITADESTSTAYMELSSLRSEDTAVYY-CARDRSWEGSPYMYYG MDVWGQGTMVTVSSGSLD-NEKSNGTIIHVKGKHLCPSPLFPGPSKPFWVLVVV-GGVLA CYSLLVTVAFIIFWVRSKRSRLLHSDYMNMT-PRRPGPTRKHYQPYAPPRDFAAYRSLRV KFSRSADA-PAYQQGGQNQLYNELNLGRREEYDVLDKRR-GRDPEMGGKPRRKNPQEGLY NELQKDKMAEAYSEIGMKGERRRGKGHDGLYQGL-STATKDTYDALHMQALPPR (SEQ ID NO: 256). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

```
                                    (SEQ ID NO: 257)
gacatccagttgacccagtctccatcctccctgtctgcaagcgttggag acagagttactatcacttgccgggcaagtcagagcattagcctatattt aaattggtatcagcagaaaccagggaaagcccctaagctcctgatctat gctgcatccagtttgcaaagtggggtcccatcaaggttcagtggcagtg gatccgggacagatttcactctcaccatcagcagtctgcaacctgaaga ttttgcaacttactactgtcagcaagtggccgtcgcccttggactttc ggcggagggaccaaggttgagatcaaagggagcacaagcggctctggca aacctggatctggcgagggatctaccaagggccaggtgcagctggtgca gtctggggctgaggtgaagaagcctggtcctcggtgaaggtctcctgc aaggcttctggaggcaccttcgaacactatgctatcagctgggtgcgac aggcccctggacaggggcttgagtggatgggagggatcatcccatatt
```

```
gggccgagcaaactacgcacagaagttccagggcagagtcacgattacc gcggacgaatccacgagcacagcctacatggagctgagcagcctgagat ctgaggacacggcggtgtactactgcgccagagacagaagctgggaagg atctccctatatgtactacggaatggacgtttggggccaagggacaatg gtcaccgtttcctcagggtccctagacaatgagaagagcaatggaacca ttatccatgtgaaagggaaacacctttgtccaagtccctattcccgg accttctaagccctttgggtgctggtggtggttggtggagtcctggct tgctatagcttgctagtaacagtggcctttattatttctgggtgagga gtaagaggagcaggctcctgcacagtgactacatgaacatgactcccg ccgcccgggcccaccgcaagcattaccagccctatgcccaccacgc gacttcgcagcctatcgctccctgagagtgaagttcagcaggagcgcag acgccccgcgtaccagcagggccagaaccagctctataacgagctcaa tctaggacgaagagaggagtacgatgttttggacaagaggcgtggccgg gaccctgagatgggggaaagccgagaaggaagaaccctcaggaaggcc tgtacaatgaactgcagaaagataagatggcggaggcctacagtgagat tgggatgaaaggcgagcgccggaggggcaaggggcacgatggcctttac cagggtctcagtacagccaccaaggacacctacgacgccttcacatgc aggccctgcccctcgc.
```

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 258. DIQLTQSPSSLSASVGDRVTITCRASQSIS-SYLNWYQQKPGKAPKLLIYAAGSLQSGVPS RFSGSGSGTDFTLTISSLQPEDFA-TYYCQQVHDFPLTFGGGTKVEIKGSTSGSGKPGSGE GSTKGQVQLVESGGGVVQPGRSLRLS-CAASGFTFASEGMHWVRQAPGKGLEWVASIY YEGVNKYYADSVKGRFTISRDNSKNTLYLQMNSL-RAEDTAVYYCAKDVSYYDSSRLV YHGMDVWGQGTTVTVSSGSLD-NEKSNGTIIHVKGKHLCPSPLFPGPSKPFWVLVVVGG VLACYSLLVTVAFIIFWVRSKRSRLLHSDYMNMT-PRRPGPTRKHYQPYAPPRDFAAYRS LRVKFSRSADA-PAYQQGGQNQLYNELNLGRREEYDVLDKRR-GRDPEMGGKPRRKNPQE GLYNELQKDKMAEAYS EIGMKGERRRGKGHDGLYQGLS TATKDTY-DALHMQALPPR (SEQ ID NO: 258). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

```
                                    (SEQ ID NO: 259)
gacatccagttgacccagtctccatcctccctgtctgcaagcgttggag atagagtcactatcacttgccgggcaagtcagagcattagcagctattt aaattggtatcagcagaaaccagggaaagcccctaagctcctgatctat gcagccgggagtttgcaaagtggggtcccatcaaggttcagtggcagtg
```

-continued

```
gatccgggacagatttcactctcaccatcagcagtctgcaacctgaaga ttttgcaacttactactgtcagcaagtgcacgacttccctctcactttc ggcggagggaccaaggttgagatcaaagggagcacaagcggctctggca aacctggatctggcgagggatctaccaagggccaggtgcagctggtgga gtctggggggaggcgtggtccagcctggggaggtccctgagactctcctgc gctgcatctggattccacttcgccagcgaaggcatgcactgggtccgcc aggctccaggcaaggggctggagtgggtggcatccatatactatgaggg agtcaataaatactatgcagactccgtgaagggccgattcaccatctct agagacaattccaagaacacgctgtatctgcaaatgaatagcctgagag ccgaggacacggcggtgtactactgcgccaaggacgtgtcctactacga cagcagcagactagtttatcacggaatggacgtatggggcaagggacc acggtcaccgtttcctcagggtccctagacaatgagaagagcaatggaa ccattatccatgtgaaagggaaacacctttgtccaagtccctatttcc cggaccttctaagccctttgggtgctggtggtggttggtggagtcctg gcttgctatagcttgctagtaacagtggcctttattattttctgggtga ggagtaagaggagcaggctcctgcacagtgactacatgaacatgactcc ccgccgccccgggcccacccgcaagcattaccagccctatgcccacca cgcgacttcgcagcctatcgctccctgagagtgaagttcagcaggagcg cagacgccccgcgtaccagcagggccagaaccagctctataacgagct caatctaggacgaagagaggagtacgatgttttggacaagaggcgtggc cgggaccctgagatggggggaaagccgagaaggaagaaccctcaggaag gcctgtacaatgaactgcagaaagataagatggcggaggcctacagtga gattgggatgaaaggcgagcgccggaggggcaaggggcacgatggcctt taccagggtctcagtacagccaccaaggacacctacgacgcccttcaca tgcaggccctgccccctcgc.
```

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 260. DIQLTQSPSSLSASVGDRVTITCRASQSISSYLNWYQQKPGKAPKLLIYAASSGQSGVPSRFSGSGSGTDFTLTISSLQPEDFATYYCQQVHDFPLTFGGGTKVEIKGSTSGSGKPGSGEGS TKGQVQLVESGGGVVQPGRSLRLSCAASGFTFASEGMHWVRQAPGKGLEWVASIYYE GVNKYYADSVKGRFTISRDNSKNTLYLQMNSLRAEDTAVYYCAKDRSYYDSSGLVYH GMDVWGQGTTVTVSSGSLDNEKSNGTIIHVKGKHLCPSPLFPGPSKPFWVLVVVGGVL ACYSLLVTVAFIIFWVRSKRSRLLHSDYMNMTPRRPGPTRKHYQPYAPPRDFAAYRSLR VKFSRSADAPAYQQGQNQLYNELNLGRREEYDVLDKRRGRDPEMGGKPRRKNPQEGLYNELQKDKMAEAYS EIGMKGERRRGKGHDGLYQGLSTATKDTYDALHMQALPPR (SEQ ID NO: 260). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 261)
```
gacatccagttgacccagtctccatcctccctgtctgcaagcgttggag acagagtcactatcacttgccgggcaagtcagagcattagcagctattt aaattggtatcagcagaaaccagggaaagcccctaagctcctgatctat gctgcatccagtggacaaagtggggtcccatcaaggttcagtggcagtg gatccgggacagatttcactctcaccatcagcagtctgcaacctgaaga ttttgcaacttactactgtcagcaagtgcacgacttccctctcactttc ggcggagggaccaaggttgagatcaaagggagcacaagcggctctggca aacctggatctggcgagggatctaccaagggccaggtgcagctggtgga gtctggggggaggcgtggtccagcctggggaggtccctgagactctcctgc gctgcatctggattccacttcgccagcgaaggcatgcactgggtccgcc aggctccaggcaaggggctggagtgggtggcatccatatactatgaggg agtcaataaatactatgcagactccgtgaagggccgattcaccatctcc agagacaattccaagaacacgctgtatctgcaaatgaacagcctgagag ccgaggacacggcggtgtactactgcgccaaggacagatcctactacga cagcagcgggctagtttatcacggaatggacgtatggggcaagggacc acggtcaccgtttcctcagggtccctagacaatgagaagagcaatggaa ccattatccatgtgaaagggaaacacctttgtccaagtccctatttcc cggaccttctaagccctttgggtgctggtggtggttggtggagtcctg gcttgctatagcttgctagtaacagtggcctttattattttctgggtga ggagtaagaggagcaggctcctgcacagtgactacatgaacatgactcc ccgccgccccgggcccacccgcaagcattaccagccctatgcccacca cgcgacttcgcagcctatcgctccctgagagtgaagttcagcaggagcg cagacgccccgcgtaccagcagggccagaaccagctctataacgagct caatctaggacgaagagaggagtacgatgttttggacaagaggcgtggc cgggaccctgagatggggggaaagccgagaaggaagaaccctcaggaag gcctgtacaatgaactgcagaaagataagatggcggaggcctacagtga gattgggatgaaaggcgagcgccggaggggcaaggggcacgatggcctt taccagggtctcagtacagccaccaaggacacctacgacgcccttcaca tgcaggccctgccccctcgc.
```

In an embodiment, a dual TACI-BCMA binding CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 262. DIQLTQSPSSLSASVGDRVTITCRASQSISSYLNWYQQKPGKAPKLLIYAASSLQGGVPS RFSGSGSGTDFTLTISSLQPEDFATYYCQQIHDFPLTFGGGTKVEIKGSTSGSGKPGSGEG STKGQVQLVESGGGVVQPGRSLRLSCAASGFTFSSEGMYWVRQAPGKGLEWVAAIWY EGSNKYYADSVKGRFTISRDNSKNTLYLQMNSLRAEDTAVYYCAKDRSYYDSSQLVY HGMDVWGQGTTVTVSSGSLDNEKSNGTIIHVKGKHLCPSPLFPGPSKPFWVLV- VVGGV LACYSLLVTVAFIIFWVR-SKRSRLLHSDYMNMTPRRPGPTRKHYQPYAPPRD-FAAYRSL RVKFSRSADAPAYQQGQNQLYNELNLGR-REEYDVLDKRRGRDPEMGGKPRRKNPQEG LYNELQKDKMAEAYSEIGMKGERRRGKGHDG-LYQGLSTATKDTYDALHMQALPPR (SEQ ID NO: 262). In embodiments, a dual TACI-BCMA binding CAR is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 263)
gacatccagttgacccagtctccatcctccctgtctgcaagcgttggag acagagtcactatcacttgccgggcaagtcagagcattagcagctattt aaattggtatcagcagaaaccagggaaagcccctaagctcctgatctat gctgcatccagtttgcaaggagggtcccatcaaggttcagtggcagtg gctctgggacagatttcactctcaccatcagcagtctgcaacctgaaga ttttgcaacttactactgtcagcaaattcacgacttccctctcactttc ggcggagggaccaaggttgagatcaaagggagcacaagcggctctggca aacctggatctggcgagggatctaccaagggccaagttcagctggtgga gtctggggaggcgtggtccagcctggggaggtccctgagactctcctgc gctgcatctggattccacttcagtagcgagggaatgtactgggtccgcc aggctccaggcaaggggctggagtgggtggcagccatatggtatgaggg aagtaataaatactatgccgactccgtgaagggccgattcaccatctct cgcgacaattccaaaaatacgctgtatctgcaaatgaatagccttagag ccgaggacacggcggtgtactactgcgccaaggacagatcctactacga cagcagccagctagtttatcacggaatggacgtatggggcaagggacc acggtcaccgtttcctcagggtccctagacaatgagaagagcaatggaa ccattatccatgtgaaagggaaacacctttgtccaagtcccctatttcc cggaccttctaagccttttgggtgctggtggtggttggtggagtcctg gcttgctatagcttgctagtaacagtggcctttattattttctgggtga ggagtaagaggagcaggctcctgcacagtgactacatgaacatgactcc ccgccgccccgggcccaccgcaagcattaccagccctatgccccacca cgcgacttcgcagcctatcgctccctgagagtgaagttcagcaggagcg cagacgccccgcgtaccagcagggccagaaccagctctataacgagct caatctaggacgaagagaggagtacgatgttttggacaagaggcgtggc cgggaccctgagatggggggaaagccgagaaggaagaaccctcaggaag gcctgtacaatgaactgcagaaagataagatggcggaggcctacagtga gattgggatgaaaggcgagcgccggaggggcaaggggcacgatggcctt taccagggtctcagtacagccaccaaggacacctacgacgcccttcaca tgcaggccctgccccctcgc.

In embodiments, a dual TACI-BCMA binding CAR is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 293)
GACATCCAGATGACCCAGTCTCCATCCTCCCTGTCTGCAAGCGTTGGAG

AtAGAGTCACtATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCcGGGACAGATTTCACTCTCACCATCAGCAGTCTGCAACCTGAAGA

TTTTGCAACTTACTACTGTCAGCAAAGCCACATCGCCCCTTGGACTTTT

GGCGGAGGGACCAAGGTTGAGATCAAAGGGAGCACtAGCGGCTCTGGCA

AACCTGGATCTGGCGAGGGATCTACCAAGGGCCAGGTGCAGCTGGTGCA

GTCTGGGGCTGAGGTGAAGAAGCCTGGGTCCTCGGTGAAGGTCTCCTGC

AAGGCTTCTGGAGGCACCTTCGCAGACTATGCTATCAGCTGGGTGCGAC

AGGCCCCTGGACAAGGGCTTGAGTGGATGGGAGGGATCATCCCTATATT

GGGCAGAGCAAACTACGCACAGAAGTTCCAGGGCAGAGTtACGATTACC

GCGGACGAATCCACGAGCACAGCCTACATGGAGCTGAGCAGCCTGAGAT

CTGAGGACACGGCGGTGTACTACTGCGCCAGAGACAGAGACAGCACAAG

CCTGCCGTACAACCACTACTACATGGACGTATGGGGCAAGGGTACAACT

GTCACtGTCTCCTCtggGtctCTAGACAATGAGAAGAGCAATGGAACCA

TTATCCATGTGAAAGGGAAACACCTTTGTCCAAGTCCCCTATTTCCCGG

ACCTTCTAAGCCCTTTTGGGTGCTGGTGGTGGTTGGTGGAGTCCTGGCT

TGCTATAGCTTGCTAGTAACAGTGGCCTTTATTATTTTCTGGGTGAGGA

GTAAGAGGAGCAGGCTCCTGCACAGTGACTACATGAACATGACTCCCCG

CCGCCCCGGGCCCACCCGCAAGCATTACCAGCCCTATGCCCCACCACGC

GACTTCGCAGCCTATCGCTCCCTGAGAGTGAAGTTCAGCAGGAGCGCAG

ACGCCCCCGCGTACCAGCAGGGCCAGAACCAGCTCTATAACGAGCTCAA

TCTAGGACGAAGAGAGGAGTACGATGTTTTGGACAAGAGgCGTGGCCGG

GACCCTGAGATGGGGGGAAAGCCGAGAAGGAAGAACCCTCAGGAAGGCC

TGTACAATGAACTGCAGAAAGATAAGATGGCGGAGGCCTACAGTGAGAT

TGGGATGAAAGGCGAGCGCCGGAGGGGCAAGGGGCACGATGGCCTTTAC

CAGGGTCTCAGTACAGCCACCAAGGACACCTACGACGCCCTTCACATGC

AGGCCCTGCCCCCTCGC.

In embodiments, a dual TACI-BCMA binding CAR is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

(SEQ ID NO: 294)
GACATCCAGTTGACCCAGTCTCCATCCTCCCTGTCTGCAAGCGTTGGAG

ACAGAGTtACtATCACTTGCCGGGCAAGTCAGAGCATTAGCCTATATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCcGGGACAGATTTCACTCTCACCATCAGCAGTCTGCAACCTGAAGA

TTTTGCAACTTACTACTGTCAGCAAGTGGCCGTCGCCCCTTGGACTTTC

```
GGCGGAGGGACCAAGGTTGAGATCAAAGGGAGCACAAGCGGCTCTGGCA

AACCTGGATCTGGCGAGGGATCTACCAAGGGCCAGGTGCAGCTGGTGCA

GTCTGGGGCTGAGGTGAAGAAGCCTGGGTCCTCGGTGAAGGTCTCCTGC

AAGGCTTCTGGAGGCACCTTCGAACACTATGCTATCAGCTGGGTGCGAC

AGGCCCCTGGACAGGGGCTTGAGTGGATGGGAGGGATCATCCCcATATT

GGGCCGAGCAAACTACGCACAGAAGTTCCAGGGCAGAGTCACGATTACC

GCGGACGAATCCACGAGCACAGCCTACATGGAGCTGAGCAGCCTGAGAT

CTGAGGACACGGCGGTGTACTACTGCGCCAGAGACAGAAGCTGGGAAGG

ATCTCCCTATATGTACTACGGAATGGACGTTTGGGGCCAAGGGACAATG

GTCACCGTtTCCTCAggGtctCTAGACAATGAGAAGAGCAATGGAACCA

TTATCCATGTGAAAGGGAAACACCTTTGTCCAAGTCCCCTATTTCCCGG

ACCTTCTAAGCCCTTTTGGGTGCTGGTGGTGGTTGGTGGAGTCCTGGCT

TGCTATAGCTTGCTAGTAACAGTGGCCTTTATTATTTTCTGGGTGAGGA

GTAAGAGGAGCAGGCTCCTGCACAGTGACTACATGAACATGACTCCCCG

CCGCCCCGGGCCCACCCGCAAGCATTACCAGCCCTATGCCCCACCACGC

GACTTCGCAGCCTATCGCTCCCTGAGAGTGAAGTTCAGCAGGAGCGCAG

ACGCCCCGCGTACCAGCAGGGCCAGAACCAGCTCTATAACGAGCTCAA

TCTAGGACGAAGAGAGGAGTACGATGTTTTGGACAAGAGgCGTGGCCGG

GACCCTGAGATGGGGGAAAGCCGAGAAGGAAGAACCCTCAGGAAGGCC

TGTACAATGAACTGCAGAAAGATAAGATGGCGGAGGCCTACAGTGAGAT

TGGGATGAAAGGCGAGCGCCGGAGGGGCAAGGGGCACGATGGCCTTTAC

CAGGGTCTCAGTACAGCCACCAAGGACACCTACGACGCCCTTCACATGC

AGGCCCTGCCCCCTCGC.
```

In embodiments, a codon optimized dual TACI-BCMA binding CAR (e.g. Dual binder #1 (CAR only) Version 2) is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

```
                                              (SEQ ID NO: 302)
ATGCTTCTCCTGGTGACAAGCCTTCTGCTCTGTGAATTACCACACCCAG

CATTCCTCCTGATTCCTGACATCCAGATGACCCAGTCTCCATCCTCCCT

GTCTGCAAGCGTTGGAGATAGAGTCACTATCACTTGCCGGGCAAGTCAG

AGCATTAGCAGCTATTTAAATTGGTATCAGCAGAAACCAGGGAAAGCCC

CTAAGCTCCTGATCTATGCTGCATCCAGTTTGCAAAGTGGGGTCCCATC

AAGGTTCAGTGGCAGTGGATCCGGGACAGATTTCACTCTCACCATCAGC

AGTCTGCAACCTGAAGATTTTGCAACTTACTACTGTCAGCAAAGCCACA

TCGCCCCTTGGACTTTTGGCGGAGGGACCAAGGTTGAGATCAAAGGGAG

CACTAGCGGCTCTGGCAAACCTGGATCTGGCGAGGGATCTACCAAGGGC

CAGGTGCAGCTGGTGCAGTCTGGGGCTGAGGTGAAGAAGCCTGGGTCCT

CGGTGAAGGTCTCCTGCAAGGCTTCTGGAGGCACCTTCGCAGACTATGC
```

```
                                              (SEQ ID NO: 303)
ATGCTTCTCCTGGTGACAAGCCTTCTGCTCTGTGAATTACCACACCCAG

CATTCCTCCTGATTCCTGACATCCAGTTGACCCAGTCTCCATCCTCCCT

GTCTGCAAGCGTTGGAGACAGAGTTACTATCACTTGCCGGGCAAGTCAG

AGCATTAGCCTATATTTAAATTGGTATCAGCAGAAACCAGGGAAAGCCC

CTAAGCTCCTGATCTATGCTGCATCCAGTTTGCAAAGTGGGGTCCCATC

AAGGTTCAGTGGCAGTGGATCCGGGACAGATTTCACTCTCACCATCAGC

AGTCTGCAACCTGAAGATTTTGCAACTTACTACTGTCAGCAAGTGGCCG

TCGCCCCTTGGACTTTCGGCGGAGGGACCAAGGTTGAGATCAAAGGGAG

CACAAGCGGCTCTGGCAAACCTGGATCTGGCGAGGGATCTACCAAGGGC

CAGGTGCAGCTGGTGCAGTCTGGGGCTGAGGTGAAGAAGCCTGGGTCCT

CGGTGAAGGTCTCCTGCAAGGCTTCTGGAGGCACCTTCGAACACTATGC

TATCAGCTGGGTGCGACAGGCCCCTGGACAGGGGCTTGAGTGGATGGGA

GGGATCATCCCATATTGGGCCGAGCAAACTACGCACAGAAGTTCCAGG

GCAGAGTCACGATTACCGCGGACGAATCCACGAGCACAGCCTACATGGA

GCTGAGCAGCCTGAGATCTGAGGACACGGCGGTGTACTACTGCGCCAGA

GACAGAAGCTGGGAAGGATCTCCCTATATGTACTACGGAATGGACGTTT
```

```
GGGGCCAAGGGACAATGGTCACCGTTTCCTCAGGGTCTCTAGACAATGA

GAAGAGCAATGGAACCATTATCCATGTGAAAGGGAAACACCTTTGTCCA

AGTCCCTATTTCCCGGACCTTCTAAGCCCTTTTGGGTGCTGGTGGTGG

TTGGTGGAGTCCTGGCTTGCTATAGCTTGCTAGTAACAGTGGCCTTTAT

TATTTTCTGGGTGAGGAGTAAGAGGAGCAGGCTCCTGCACAGTGACTAC

ATGAACATGACTCCCCGCCGCCCCGGGCCCACCCGCAAGCATTACCAGC

CCTATGCCCCACCACGCGACTTCGCAGCCTATCGCTCCCTGAGAGTGAA

GTTCAGCAGGAGCGCAGACGCCCCCGCGTACCAGCAGGGCCAGAACCAG

CTCTATAACGAGCTCAATCTAGGACGAAGAGAGGAGTACGATGTTTTGG

ACAAGAGGCGTGGCCGGGACCCTGAGATGGGGGGAAAGCCGAGAAGGAA

GAACCCTCAGGAAGGCCTGTACAATGAACTGCAGAAAGATAAGATGGCG

GAGGCCTACAGTGAGATTGGGATGAAAGGCGAGCGCCGGAGGGGCAAGG

GGCACGATGGCCTTTACCAGGGTCTCAGTACAGCCACCAAGGACACCTA

CGACGCCCTTCACATGCAGGCCCTGCCCCCTCGCTGA.
```

Both engineered T cell receptors (TCR) and chimeric antigen receptor (CAR) therapies harness the specificity and immunotherapeutic effect of T cells for the treatment of a wide variety of malignancies. Some studies suggest that these therapies may be susceptible to the suppressive factors in the TME that result from T cell suppression by TGF-β (Bendle et al., J Immunol, 191:3232-3239 (2013) and Vong et al., Blood, 130:1791 (2017)). The present disclosure contemplates the use of the dominant negative (DN) TGF-β Receptors described herein in combination with either TCR or CAR therapies as a way to maintain, or in some cases, restore TCR and/or CAR expansion in the presence of TGF-β suppression.

Chimeric antigen receptor (CAR) T cell therapy provides another therapeutic approach against tumor progression. Clinically, investigators have demonstrated that CAR expansion and persistence is correlated with therapeutic efficacy. Without being bound by any theory, it is believed that TGF-β repressed T cell populations found in the TME may be limiting CAR T cell expansion and persistence in patients who do not respond to CAR therapy. The resulting inhibitory cytokines in the TME are believed to limit CAR cell function and expansion. Thus, TGF-β could limit the efficacy of therapeutic engineered T cells or NK cells.

Combining any CAR constructs or TCRs as described herein with a DN TGF-β receptors may restore, maintain or enhance the therapeutic effect of CAR T therapy challenged by TGF-β suppression. Thus, in embodiments, the DN TGF-β receptors, for example DN TGF-βRI or RII, are co-expressed in a T cell or an NK cell with a dual TACI-BCMA binding CAR, as described herein. In some embodiments, the DN TGF-β receptors, for example DN TGF-βRI or RII, are co-expressed in a T cell or NK cell with a dual TACI-BCMA binding CAR, such as described herein. In some embodiments the DN TGF-β receptors, for example DN TGF-βRI or RII, are co-expressed in a T cell or NK cell with a dual TACI-BCMA binding TCR. Exemplary DN TGF-β receptors are described in International Patent Application No. PCT/US2020/070157, which is hereby incorporated herein by reference in its entirety.

The engineered TGF-β receptors may comprise an N-terminal signal peptide at the N-terminus, for example at the N-terminus of the extracellular ligand binding domain of DN TGF-βRI. In one embodiment, a heterologous signal peptide may be used. The extracellular domain of a DN TGF-βRI may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as a DN TGF-βRI is generally expressed at the cell surface as a mature protein lacking the signal peptide, whereas the precursor form of the polypeptide includes the signal peptide. Any suitable signal sequence may be used. In one embodiment described herein, the DN TGF-βRI comprises the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 264 or a portion thereof.

```
                                         (SEQ ID NO: 264)
MEAAVAAPRPRLLLLVLAAAAAAAAALLPGATA.
```

In the present disclosure, the signal peptide is joined to the N-terminus of the extracellular antigen-binding domain of the DN TGF-βRI as a fusion protein. In one embodiment, the DN TGF-βRI comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRI and a signal peptide at the N-terminus of the extracellular domain TGF-βRI, having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 265.

```
                                         (SEQ ID NO: 265)
MEAAVAAPRPRLLLLVLAAAAAAAAALLPGATALQCFCHLCTKDNFTCV

TDGLCFVSVTETTDKVIHNSMCIAEIDLIPRDRPFVCAPSSKTGSVTTT

YCCNQDHCNKIELPTTVKSSPGLGPVEL.
```

The engineered DN TGF-βRII constructs may also comprise an N-terminal signal peptide at the N-terminus of the extracellular ligand binding domain of TGF-βRII. In one embodiment, a heterologous signal peptide may be used. The extracellular domain of a DN TGF-βRII may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as a DN TGF-βRII is generally found at the cell surface as a mature protein lacking the signal peptide, whereas the precursor form of the polypeptide includes the signal peptide. Any suitable signal sequence may be used. In one embodiment described herein, the DN TGF-βRII constructs described herein comprise a signal sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 266 or a portion thereof. MGRGLLRGLWPLHIVLWTRIAS (SEQ ID NO: 266). In another embodiment, the signal sequence is derived from Colony Stimulating Factor 2 Receptor Alpha subunit (CSF2Rα) comprising the amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 221 or a portion thereof. MLLLVTSLLLCELPHPAFLLIP (SEQ ID NO: 221). The signal sequences described herein may also be optionally used with any suitable protein tag, including but not limited to: V5-tag, myc-tag, HA-tag, Spot-tag, NE-tag. In one embodiment described herein, the signal sequence and tag comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 267. MLLLVTSLLLCELPHPAFLLIPEQKLISEEDL (SEQ ID NO: 267). In embodiments, the signal sequence and tag may be encoded by nucleic acid sequence at least 75% sequence identity to atgcttctcctggtgacaagccttctgctctgtgagttaccacacccagcattcctcctgattcctgaacagaagctgataagtgaggaggact tg (SEQ ID NO: 268) (e.g., at least 75%, at least 80%, at least 90%, at least 95%, or 100% identity; e.g., 85-90%, 85-95%, 85-100%, 90-95%, 90-100%, or 95-100%).

It is understood that use of this signal peptide is exemplary. Any suitable signal peptide, as are well known in the art, may be applied to the DN TGF-βRI or RII to provide cell surface expression in an immune cell. Useful signal peptides may be derived from cell surface proteins naturally expressed in the T cell NK cell or precursor cell thereof, including any of the signal peptides of the polypeptides disclosed herein. Thus, any suitable signal peptide may be utilized to direct the DN TGF-βRI RII to be expressed at the cell surface of a T cell or NK cell.

In embodiments, a DN TGF-βRI comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 269.

(SEQ ID NO: 269)
MEAAVAAPRPRLLLLVLAAAAAAAAALLPGATALQCFCHLCTKDNFTCV

TDGLCFVSVTETTDKVIHNSMCIAEIDLIPRDRPFVCAPSSKTGSVTTT

YCCNQDHCNKIELPTTVKSSPGLGPVELAAVIAGPVCFVCISLMLMVYI

RVNRQ.

In one embodiment a DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 270:

(SEQ ID NO: 270)
MGRGLLRGLWPLHIVLWTRIASTIPPHVQKSVNNDMIVTDNNGAVKFPQ

LCKFCDVRFSTCDNQKSCMSNCSITSICEKPQEVCVAVWRKNDENITLE

TVCHDPKLPYHDFILEDAASPKCIMKEKKKPGETFFMCSCSSDECNDNI

IFSEEYNTSNPDLLLVIFQVTGISLLPPLGVAISVIIIFYCYRVNRQ.

In an embodiment a DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 271.

(SEQ ID NO: 271)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPD.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRII as shown in the amino acid sequence of SEQ ID NO: 272.

(SEQ ID NO: 272)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPDLLLVIFQVTG

ISLLPPLGVAISVIIIFYCY.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 273.

(SEQ ID NO: 273)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPDSGPILLTISI

LSFFSVALLVIL.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) as shown in the amino acid sequence of SEQ ID NO: 274.

(SEQ ID NO: 274)
TIPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPDSGPILLTCPT

ISILSFFSVALLVIL.

T In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 275.

(SEQ ID NO: 275)
ACVLWKKRIKPIVWPSLPDHKKTLEHLCKKPRKNLNVSFNPESFLDCQIH

RVDDIQARDEVEGFLQDTFPQQLEESEKQRLGGDVQSPNCPSEDVVITPE

SFGRDSSLTCLAGNVSACDAPILSSSRSLDCRESGKNGPHVYQDLLLSLG

TTNSTLPPPFSLQSGILTLNPVAQGQPILTSLGSNQEEAYVTMSSFYQNQ.

In one embodiment described herein, the DN TGF-βRII comprises an amino acid sequence at least 75% sequence identity to (such as, at least 75%, at least 80%, at least 90%, at least 95%, or 100% identity e.g., 85-90%, 85-95%, 85-100%, 90-95%, 90-100%, or 95-100%) the amino acid sequence of SEQ ID NO: 276.

(SEQ ID NO: 276)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGPILLTISILSF

FSVALLVILACVLWKKRIKPIVWPSLPDHKKTLEHLCKKPRKNLNVSFNP

ESFLDCQIHRVDDIQARDEVEGFLQDTFPQQLEESEKQRLGGDVQSPNCP

SEDVVITPESFGRDSSLTCLAGNVSACDAPILSSSRSLDCRESGKNGPHV

YQDLLLSLGTTNSTLPPPFSLQSGILTLNPVAQGQPILTSLGSNQEEAYV

TMSSFYQNQ.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) to the amino acid sequence of SEQ ID NO: 277.

(SEQ ID NO: 277)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGPILLTCPTISI

LSFFSVALLVILACVLWKKRIKPIVWPSLPDHKKTLEHLCKKPRKNLNVS

FNPESFLDCQIHRVDDIQARDEVEGFLQDTFPQQLEESEKQRLGGDVQSP

NCPSEDVVITPESFGRDSSLTCLAGNVSACDAPILSSSRSLDCRESGKNG

PHVYQDLLLSLGTTNSTLPPPFSLQSGILTLNPVAQGQPILTSLGSNQEE

AYVTMSSFYQNQ.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 278.

(SEQ ID NO: 278)
MLLLVTSLLLCELPHPAFLLIPTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPD.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 279.

(SEQ ID NO: 279)
MLLLVTSLLLCELPHPAFLLIPEQKLISEEDLTIPPHVQKSVNNDMIVTD

NNGAVKFPQLCKFCDVRFSTCDNQKSCMSNCSITSICEKPQEVCVAVWRK

NDENITLETVCHDPKLPYHDFILEDAASPKCIMKEKKKPGETFFMCSCSS

DECNDNIIFSEEYNTSNPD.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 280.

(SEQ ID NO: 280)
MLLLVTSLLLCELPHPAFLLIPTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDSGPILLTISILSFFSVALLVILACVLWKKRIKPIVWPSLPD

HKKTLEHLCKKPRKNLNVSFNPESFLDCQIHRVDDIQARDEVEGFLQDTF

PQQLEESEKQRLGGDVQSPNCPSEDVVITPESFGRDSSLTCLAGNVSACD

APILSSSRSLDCRESGKNGPHVYQDLLLSLGTTNSTLPPPFSLQSGILTL

NPVAQGQPILTSLGSNQEEAYVTMSSFYQNQ.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 281.

(SEQ ID NO: 281)
MLLLVTSLLLCELPHPAFLLIPEQKLISEEDLTIPPHVQKSVNNDMIVTD

NNGAVKFPQLCKFCDVRFSTCDNQKSCMSNCSITSICEKPQEVCVAVWRK

NDENITLETVCHDPKLPYHDFILEDAASPKCIMKEKKKPGETFFMCSCSS

DECNDNIIFSEEYNTSNPDSGPILLTISILSFFSVALLVILACVLWKKRI

KPIVWPSLPDHKKTLEHLCKKPRKNLNVSFNPESFLDCQIHRVDDIQARD

EVEGFLQDTFPQQLEESEKQRLGGDVQSPNCPSEDVVITPESFGRDSSLT

CLAGNVSACDAPILSSSRSLDCRESGKNGPHVYQDLLLSLGTTNSTLPPP

FSLQSGILTLNPVAQGQPILTSLGSNQEEAYVTMSSFYQNQ.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 282.

(SEQ ID NO: 282)
MLLLVTSLLLCELPHPAFLLIPTIPPHVQKSVNNDMIVTDNNGAVKFPQL

CKFCDVRFSTCDNQKSCMSNCSITSICEKPQEVCVAVWRKNDENITLETV

-continued

CHDPKLPYHDFILEDAASPKCIMKEKKKPGETFFMCSCSSDECNDNIIFS

EEYNTSNPDSGPILLTISILSFFSVALLVILACVLWKKRIKPIVWPSLPD

HKKTLEHLCKKPRKNLNVSFNPESFLDCQIHRVDDIQARDEVEGFLQDTF

PQQLEESEKQRLGGDVQSPNCPSEDVVITPESFGRDSSLTCLAGNVSACD

APILSSSRSLDCRESGKNGPHVYQDLLLSLGTTNSTLPPPFSLQSGILTL

NPVAQGQPILTSLGSNQEEAYVTMSSFYQNQ.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 283.

(SEQ ID NO: 283)
MLLLVTSLLLCELPHPAFLLIPEQKLISEEDLTIPPHVQKSVNNDMIVTD

NNGAVKFPQLCKFCDVRFSTCDNQKSCMSNCSITSICEKPQEVCVAVWRK

NDENITLETVCHDPKLPYHDFILEDAASPKCIMKEKKKPGETFFMCSCSS

DECNDNIIFSEEYNTSNPDSGPILLTCPTISILSFFSVALLVILACVLWK

KRIKPIVWPSLPDHKKTLEHLCKKPRKNLNVSFNPESFLDCQIHRVDDIQ

ARDEVEGFLQDTFPQQLEESEKQRLGGDVQSPNCPSEDVVITPESFGRDS

SLTCLAGNVSACDAPILSSSRSLDCRESGKNGPHVYQDLLLSLGTTNSTL

PPPFSLQSGILTLNPVAQGQPILTSLGSNQEEAYVTMSSFYQNQ.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 284.

(SEQ ID NO: 284)
MLLLVTSLLLCELPHPAFLLIPTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDSGPILLTCPTISILSFFSVALLVILACVLWKKRIKPIVWPS

LPDHKKTLEHLCKKPRKNLNVSFNPESFLDCQIHRVDDIQARDEVEGFLQ

DTFPQQLEESEKQRLGGDVQSPNCPSEDVVITPESFGRDSSLTCLAGNVS

ACDAPILSSSRSLDCRESGKNGPHVYQDLLLSLGTTNSTLPPPFSLQSGI

LTLNPVAQGQPILTSLGSNQEEAYVTMSSFYQNQ.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 297.

(SEQ ID NO: 297)
QLCKFCDVRFSTCDNQKSCMSNCSITSICEKPQEVCVAVWRKNDENITLE

TVCHDPKLPYHDFILEDAASPKCIMKEKKKPGETFFMCSCSSDECNDNII

FSEE.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 298.

(SEQ ID NO: 298)
QLCKFCDVRFSTCDNQKSCMSNCSITSICEKPQEVCVAVWRKNDENITLE

TVCHDPKLPYHDFILEDAASPKCIMKEKKKPGETFFMCSCSSDECNDNII

FSEELLLVIFQVTGISLLPPLGVAISVIIIFYCY.

In an embodiment, an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 299.

(SEQ ID NO: 299)
MGRGLLRGLWPLHIVLWTRIASQLCKFCDVRFSTCDNQKSCMSNCSITSI

CEKPQEVCVAVWRKNDENITLETVCHDPKLPYHDFILEDAASPKCIMKEK

KKPGETFFMCSCSSDECNDNIIFSEELLLVIFQVTGISLLPPLGVAISVI

IIFYCY.

The present disclosure contemplates, the expression of polynucleotides encoding the a dual TACI-BCMA CARs, and TCRs disclosed herein and the co-expression of polynucleotides comprising the engineered DN TGF-β Receptors with a dual TACI-BCMA binding CARs, TCRs and fragments thereof, cells and compositions comprising the same, and vectors that express polypeptides.

In one embodiment described herein, a dual TACI-BCMA binding CAR linked to a DN TGF-β Receptor has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 285. DIQMTQSPSSL-SASVGDRVTITCRASQSISSYLNWYQQKPGKAPKLLI-YAASSLQSGVPS RFSGSGSGTDFTLTISSLQPEDFA-TYYCQQSHIAPWTFGGGTKVEIKGSTSGSGKPGSGE GSTKGQVQLVQSGAEVKKPGSSVKVSCK-ASGGTFADYAISWVRQAPGQGLEWMGGIIP ILGRAN-YAQKFQGRVTITADESTSTAYMELSSLRSEDTAVYY-CARDRDSTSLPYNHYY MDVWGKGTTVTVSSGSLD-NEKSNGTIIHVKGKHLCPSPLFPGPSKPFWVLV-VVGGVLA CYSLLVTVAFIIFWVR-SKRSRLLHSDYMNMTPRRPGPTRKHYQPYAPPRD-FAAYRSLRV KFSRSADAPAYQQGQNQLYNELNLGR-REEYDVLDKRRGRDPEMGGKPRRKNPQEGLY NELQKDKMAEAYSEIGMKGERRRGKGHDGLYQGL-STATKDTYDALHMQALPPRGSGE GRGSLLTCGD-VEENPGPMGRGLLRGLWPLHIVLWTRIASTIP-PHVQKSVNNDMIVTDNN GAVKFPQLCKFCDVRFSTCDNQKSCMSNC-SITSICEKPQEVCVAVWRKNDENITLETVC HDPKLPYHDFILEDAASPKCI-MKEKKKPGETFFMCSCSSDECNDNIIF-SEEYNTSNPDLLL VIFQVTGISLLPPLGVAISVIII-FYCYRVNRQ (SEQ ID NO: 285). In embodiments, a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 286)
GACATCCAGATGACCCAGTCTCCATCCTCCCTGTCTGCAAGCGTTGGAGA
TAGAGTCACTATCACTTGCCGGGCAAGTCAGAGCATTAGCAGCTATTTAA
ATTGGTATCAGCAGAAACCAGGGAAAGCCCCTAAGCTCCTCATCTATGCT
GCATCCAGTTTGCAAAGTGGGGTCCCATCAAGGTTTAGTGGCAGTGGATC
CGGGACAGATTTCACTCTCACCATCTCGAGCCTGCAACCTGAAGATTTTG
CAACTTACTACTGTCAGCAAAGCCACATCGCCCCTTGGACTTTTGGCGGA
GGGACCAAGGTTGAGATCAAAGGGAGCACTAGCGGCTCTGGAAAACCGGG
ATCTGGCGAGGGATCTACCAAGGGCCAGGTGCAGCTGGTGCAGTCTGGGG
CTGAAGTCAAAAAGCCTGGGTCCTCGGTGAAGGTCTCCTGCAAGGCTTCT
GGAGGCACCTTCGCAGACTATGCTATCAGCTGGGTGCGACAGGCCCCCGG
ACAAGGGCTTGAGTGGATGGGAGGAATAATCCCTATATTGGGCAGAGCAA
ACTACGCACAGAAGTTCCAGGGACGCGTTACGATTACCGCGGACGAATCT
ACGAGCACAGCCTACATGGAGCTGAGCAGCCTGAGATCTGAGGACACGGC
GGTGTATTACTGCGCCAGAGACAGAGACAGCACaTCTCTGCCGTACAACC
ACTATTATATGGACGTATGGGGCAAGGGTACAACTGTCACTGTCTCCTCT
GGGAGTCTGGACAACGAGAAGAGCAACGGAACTATCATCCACGTTAAGGG
CAAGCATTTATGCCCTAGCCCTCTGTTTCCCGGACCCAGCAAGCCGTTTT
GGGTACTGGTGGTGGTGGGAGGAGTGCTGGCTTGTTACTCTTTACTGGTC
ACCGTGGCCTTCATCATCTTCTGGGTTCGAAGCAAGAGGTCTAGACTGCT
GCACAGCGACTACATGAACATGACCCCCAGAAGACCCGGCCCCACCGAAA
AGCACTACCAGCCTTACGCCCCTCCCCGCGACTTCGCCGCCTATCGTAGC
CTGCGCGTAAAGTTTTCGAGGTCTGCTGATGCCCCAGCTTACCAACAAGG
CCAAAATCAGCTTTATAATGAGTTGAATCTAGGCAGGCGTGAAGAATACG
ACGTATTAGATAAGAGGCGGGGCAGGGACCCTGAAATGGGCGGCAAACCC
AGACGGAAGAATCCACAAGAGGGATTATATAACGAACTTCAGAAGGACAA
AATGGCTGAAGCTTACAGCGAAATCGGAATGAAGGGGGAGAGGCGCAGAG
GAAAAGGACATGATGGACTATATCAGGGCCTGTCCACCGCTACAAAAGAT
ACCTATGACGCACTGCATATGCAGGCCTTGCCTCCAAGAGGTTCAGGAGA
AGGCAGGGGCTCTCTCCTGACCTGCGGCGACTGGAAGAGAACCCTGGCC
CCATGGGACGCGGTTTATTGAGAGGACTGTGGCCCTTACACATCGTTCTG
TGGACTCGTATCGCCTCTACCATCCCCCCCCATGTCCAAAAGAGCGTAAA
CAACGATATGATCGTGACCGACAACAATGGCGCTGTCAAGTTCCCACAGC
TGTGCAAGTTTTGTGACGTGCGCTTCAGCACTTGTGACAATCAGAAAGC
TGCATGAGCAACTGCTCCATCACCTCCATCTGTGAGAAACCCCAAGAAGT
GTGCGTCGCCGTCTGGCGTAAGAACGACGAGAACATCACTTTAGAGACTG
TTTGCCACGATCCCAAACTGCCCTACCATGACTTCATATTGGAAGATGCA
GCCTCTCCCAAGTGTATCATGAAAGAAAAGAAAAAACCTGGAGAGACCTT
CTTCATGTGTTCTTGTTCGTCTGATGAGTGCAATGATAATATAATCTTCA

GCGAAGAGTACAATACCTCGAACCCCGATCTGTTGCTCGTGATCTTCCAA
GTTACCGGCATTTCTCTTCTGCCTCCGTTGGGTGTGGCAATCAGCGTGAT
CATCATTTTCTACTGCTATCGTGTTAACCGTCAGT.

In one embodiment described herein, a dual TACI-BCMA binding CAR linked to a DN TGF-β Receptor has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 287. DIQLTQSPSSL-SASVGDRVTITCRASQSISLYLNWYQQKPGKAPKLLI-YAASSLQSGVPSR FSGSGSGTDFTLTISSLQPEDFA-TYYCQQVAVAPWTFGGGTKVEIKGSTSGSGKPG-SGEG STKGQVQLVQSGAEVKKPGSSVKVSCK-ASGGTFEHYAISWVRQAPGQGLEWMGGIIPI LGRAN-YAQKFQGRVTITADESTSTAYMELSSLRSEDTAVYY-CARDRSWEGSPYMYYG MDVWGQGTMVTVSSGSLD-NEKSNGTIIHVKGKHLCPSPLFPGPSKPFWVLVVV-GGVLA CYSLLVTVAFIIFWVRSKRSRLLHSDYMNMT-PRRPGPTRKHYQPYAPPRDFAAYRSLRV KFSRSADA-PAYQQGGQNQLYNELNLGRREEYDVLDKRR-GRDPEMGGKPRRKNPQEGLY NELQKDKMAEAYSEIGMKGERRRGKGHDGLYQGL-STATKDTYDALHMQALPPRGSGE GRGSLLTCGD-VEENPGPMGRGLLRGLWPLHIVLWTRIASTIP-PHVQKSVNNDMIVTDNN GAVKFPQLCKFCDVRFSTCDNQKSCMSNC-SITSICEKPQEVCVAVWRKNDENITLETVC HDPKLPYHDFILEDAASPKCI-MKEKKKPGETFFMCSCSSDECNDNIIF-SEEYNTSNPDLLL VIFQVTGISLLPPLGVAISVIII-FYCYRVNRQ (SEQ ID NO: 287). In embodiments a dual TACI-BCMA binding CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 288)
GACATCCAGTTGACCCAGTCTCCATCCTCCCTGTCTGCAAGCGTTGGAGA
CAGAGTTACTATCACTTGCCGGGCAAGTCAGAGCATTAGCCTATATTTAA
ATTGGTATCAGCAGAAACCAGGGAAAGCCCCTAAGTTGCTGATCTATGCT
GCATCTAGTTTGCAAAGTGGGGTCCCATCACGATTCAGTGGCAGTGGATC
CGGGACAGATTTCACTCTCACCATCTCgAGTCTACAACCTGAAGATTTTG
CAACTTACTACTGTCAGCAAGTGGCCGTCGCCCCTTGGACTTTCGGCGGA
GGGACCAAGGTTGAGATCAAAGGGAGCACAAGCGGCTCTGGAAAACCGGG
ATCTGGCGAGGGATCTACCAAGGGCCAGGTGCAGCTGGTGCAGTCTGGGG
CTGAGGTGAAAAAGCCTGGGTCCTCGGTGAAGGTCTCCTGCAAGGCTTCT
GGAGGCACCTTCGAACACTATGCTATCAGCTGGGTGCGACAGGCCCCTGG
ACAGGGACTTGAGTGGATGGGGGGATCATCCCCATACTAGGCCGAGCAA
ACTACGCACAGAAGTTCCAGGGCAGAGTCACTATTACCGCGGACGAATCG

```
ACGAGCACAGCCTACATGGAGCTGAGCAGCCTGAGATCTGAGGACACGGC
GGTGTATTACTGCGCCCGTGACAGAAGCTGGGAAGGATCTCCCTATATGT
ACTACGGAATGGACGTTTGGGGCCAAGGGACAATGGTTACCGTTAGCAGT
GGGAGTCTGGACAACGAGAAGAGCAACGGAACTATCATCCACGTTAAGGG
CAAGCATTTATGCCCTAGCCCTCTGTTTCCCGGACCCAGCAAGCCGTTTT
GGGTACTGGTGGTGGTGGGAGGAGTGCTGGCTTGTTACTCTTTACTGGTC
ACCGTGGCCTTCATCATCTTCTGGGTTCGAAGCAAGAGGTCTAGACTGCT
GCACAGCGACTACATGAACATGACCCCCAGAAGACCCGGCCCCACCAGAA
AGCACTACCAGCCTTACGCCCCTCCCCGCGACTTCGCCGCCTATCGTAGC
CTGCGCGTAAAGTTTTCGAGGTCTGCTGATGCCCCAGCTTACCAACAAGG
CCAAAATCAGCTTTATAATGAGTTGAATCTAGGCAGGCGTGAAGAATACG
ACGTATTAGATAAGAGGCGGGGCAGGGACCCTGAAATGGGCGGCAAACCC
AGACGGAAGAATCCACAAGAGGGATTATATAACGAACTTCAGAAGGACAA
AATGGCTGAAGCTTACAGCGAAATCGGAATGAAGGGGAGAGGCGCAGAG
GAAAAGGACATGATGGACTATATCAGGGCCTGTCCACCGCTACAAAAGAT
ACCTATGACGCACTGCATATGCAGGCCTTGCCTCCAAGAGGTTCAGGAGA
AGGCAGGGGCTCTCTCCTGACCTGCGGCGACTGGAAGAGAACCCTGGCC
CCATGGGACGCGGTTTATTGAGAGGACTGTGGCCCTTACACATCGTTCTG
TGGACTCGTATCGCCTCTACCATCCCCCCCATGTCCAAAAGAGCGTAAA
CAACGATATGATCGTGACCGACAACAATGGCGCTGTCAAGTTCCCACAGC
TGTGCAAGTTTTGTGACGTGCGCTTCAGCACTTGTGACAATCAGAAAAGC
TGCATGAGCAACTGCTCCATCACCTCCATCTGTGAGAAACCCCAAGAAGT
GTGCGTCGCCGTCTGGCGTAAGAACGACGAGAACATCACTTTAGAGACTG
TTTGCCACGATCCCAAACTGCCCTACCATGACTTCATATTGGAAGATGCA
GCCTCTCCCAAGTGTATCATGAAAGAAAAGAAAAAACCTGGAGAGACCTT
CTTCATGTGTTCTTGTTCGTCTGATGAGTGCAATGATAATATAATCTTCA
GCGAAGAGTACAATACCTCGAACCCCGATCTGTTGCTCGTGATCTTCCAA
GTTACCGGCATTTCTCTTCTGCCTCCGTTGGGTGTGGCAATCAGCGTGAT
CATCATTTTCTACTGCTATCGTGTTAACCGTCAGT.
```

In embodiments a codon optimized dual TACI-BCMA binding CAR linked to a DN TGF-β Receptor (e.g. Dual binder #1+DNR Version 2) is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                           (SEQ ID NO: 300)
ATGCTTCTCCTGGTGACAAGCCTTCTGCTCTGTGAATTACCACACCCAG
CATTCCTCCTGATTCCTGACATCCAGATGACCCAGTCTCCATCCTCCCT
GTCTGCAAGCGTTGGAGATAGAGTCACTATCACTTGCCGGGCAAGTCAG
AGCATTAGCAGCTATTTAAATTGGTATCAGCAGAAACCAGGGAAAGCCC
CTAAGCTCCTGATCTATGCTGCATCCAGTTTGCAAAGTGGGGTCCCATC
AAGGTTCAGTGGCAGTGGATCCGGGACAGATTTCACTCTCACCATCAGC
AGTCTGCAACCTGAAGATTTTGCAACTTACTACTGTCAGCAAAGCCACA
TCGCCCCTTGGACTTTTGGCGGAGGGACCAAGGTTGAGATCAAAGGGAG
CACTAGCGGCTCTGGCAAACCTGGATCTGGCGAGGGATCTACCAAGGGC
CAGGTGCAGCTGGTGCAGTCTGGGGCTGAGGTGAAGAAGCCTGGGTCCT
CGGTGAAGGTCTCCTGCAAGGCTTCTGGAGGCACCTTCGCAGACTATGC
TATCAGCTGGGTGCGACAGGCCCCTGGACAAGGGCTTGAGTGGATGGGA
GGGATCATCCCTATATTGGGCAGAGCAAACTACGCACAGAAGTTCCAGG
GCAGAGTTACGATTACCGCGGACGAATCCACGAGCACAGCCTACATGGA
GCTGAGCAGCCTGAGATCTGAGGACACGGCGGTGTACTACTGCGCCAGA
GACAGAGACAGCACAAGCCTGCCGTACAACCACTACTACATGGACGTAT
GGGGCAAGGGTACAACTGTCACTGTCTCCTCTGGGTCTCTAGACAATGA
GAAGAGCAATGGAACCATTATCCATGTGAAAGGGAAACACCTTTGTCCA
AGTCCCCTATTTCCCGGACCTTCTAAGCCCTTTTGGGTGCTGGTGGTGG
TTGGTGGAGTCCTGGCTTGCTATAGCTTGCTAGTAACAGTGGCCTTTAT
TATTTTCTGGGTGAGGAGTAAGAGGAGCAGGCTCCTGCACAGTGACTAC
ATGAACATGACTCCCCGCCGCCCCGGGCCCACCCGCAAGCATTACCAGC
CCTATGCCCCACCACGCGACTTCGCAGCCTATCGCTCCCTGAGAGTGAA
GTTCAGCAGGAGCGCAGACGCCCCCGCGTACCAGCAGGGCCAGAACCAG
CTCTATAACGAGCTCAATCTAGGACGAAGAGAGGAGTACGATGTTTTGG
ACAAGAGGCGTGGCCGGGACCCTGAGATGGGGGGAAAGCCGAGAAGGAA
GAACCCTCAGGAAGGCCTGTACAATGAACTGCAGAAAGATAAGATGGCG
GAGGCCTACAGTGAGATTGGGATGAAAGGCGAGCGCCGGAGGGGCAAGG
GGCACGATGGCCTTTACCAGGGTCTCAGTACAGCCACCAAGGACACCTA
CGACGCCCTTCACATGCAGGCCCTGCCCCCTCGCGGCTCTGGAGAAGGC
AGGGGCTCTCTGCTGACCTGCGGCGACGTGGAAGAGAACCCAGGCCCCA
TGGGAAGAGGTTTATTGAGAGGACTGTGGCCCTTACACATCGTTCTGTG
GACTCGTATCGCCTCTACCATCCCCCCCATGTCCAAAAGAGCGTAAAC
AACGACATGATCGTGACCGACAACAATGGCGCTGTCAAGTTCCCCCAGC
TGTGCAAGTTTTGTGACGTGCGCTTCAGCACTTGTGACAATCAGAAGAG
CTGCATGAGCAACTGCTCCATCACCTCCATCTGTGAGAAACCCCAAGAA
GTGTGCGTCGCCGTCTGGCGTAAGAACGACGAGAACATCACTTTAGAGA
CAGTGTGCCACGATCCCAAACTGCCCTACCATGACTTCATTTTAGAAGA
TGCAGCCTCTCCCAAGTGTATCATGAAGGAAAGAAAAAGCCTGGCGAG
ACCTTCTTCATGTGTTCTTGTTCGTCTGATGAGTGCAACGATAACATCA
TCTTCAGCGAAGAGTACAATACCTCGAACCCCGATTTATTACTGGTGAT
CTTCCAAGTTACCGGCATTTCTCTTCTGCCTCCGTTGGGTGTGGCTATC
AGCGTGATCATCATTTTCTACTGCTATCGTGTTAACCGTCAGTGA.
```

In embodiments a codon optimized dual TACI-BCMA binding CAR linked to a DN TGF-β Receptor (e.g. Dual binder #3+DNR Version 2) is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 301)
ATGCTTCTCCTGGTGACAAGCCTTCTGCTCTGTGAATTACCACACCCAG

CATTCCTCCTGATTCCTGACATCCAGTTGACCCAGTCTCCATCCTCCCT

GTCTGCAAGCGTTGGAGACAGAGTTACTATCACTTGCCGGGCAAGTCAG

AGCATTAGCCTATATTTAAATTGGTATCAGCAGAAACCAGGGAAAGCCC

CTAAGCTCCTGATCTATGCTGCATCCAGTTTGCAAAGTGGGGTCCCATC

AAGGTTCAGTGGCAGTGGATCCGGGACAGATTTCACTCTCACCATCAGC

AGTCTGCAACCTGAAGATTTTGCAACTTACTACTGTCAGCAAGTGGCCG

TCGCCCCTTGGACTTTCGGCGGAGGGACCAAGGTTGAGATCAAAGGGAG

CACAAGCGGCTCTGGCAAACCTGGATCTGGCGAGGGATCTACCAAGGGC

CAGGTGCAGCTGGTGCAGTCTGGGGCTGAGGTGAAGAAGCCTGGGTCCT

CGGTGAAGGTCTCCTGCAAGGCTTCTGGAGGCACCTTCGAACACTATGC

TATCAGCTGGGTGCGACAGGCCCCTGGACAGGGGCTTGAGTGGATGGGA

GGGATCATCCCCATATTGGGCCGAGCAAACTACGCACAGAAGTTCCAGG

GCAGAGTCACGATTACCGCGGACGAATCCACGAGCACAGCCTACATGGA

GCTGAGCAGCCTGAGATCTGAGGACACGGCGGTGTACTACTGCGCCAGA

GACAGAAGCTGGGAAGGATCTCCCTATATGTACTACGGAATGGACGTTT

GGGGCCAAGGGACAATGGTCACCGTTTCCTCAGGGTCTCTAGACAATGA

GAAGAGCAATGGAACCATTATCCATGTGAAAGGGAAACACCTTTGTCCA

AGTCCCTATTTCCCGGACCTTCTAAGCCCTTTTGGGTGCTGGTGGTGG

TTGGTGGAGTCCTGGCTTGCTATAGCTTGCTAGTAACAGTGGCCTTTAT

TATTTTCTGGGTGAGGAGTAAGAGGAGCAGGCTCCTGCACAGTGACTAC

ATGAACATGACTCCCCGCCGCCCCGGGCCCACCCGCAAGCATTACCAGC

CCTATGCCCACCACGCGACTTCGCAGCCTATCGCTCCCTGAGAGTGAA

GTTCAGCAGGAGCGCAGACGCCCCGCGTACCAGCAGGGCCAGAACCAG

CTCTATAACGAGCTCAATCTAGGACGAAGAGAGGAGTACGATGTTTTGG

ACAAGAGGCGTGGCCGGGACCCTGAGATGGGGGGAAAGCCGAGAAGGAA

GAACCCTCAGGAAGGCCTGTACAATGAACTGCAGAAAGATAAGATGGCG

GAGGCCTACAGTGAGATTGGGATGAAAGGCGAGCGCCGGAGGGCAAGG

GGCACGATGGCCTTTACCAGGGTCTCAGTACAGCCACCAAGGACACCTA

CGACGCCCTTCACATGCAGGCCCTGCCCCCTCGCGGCTCTGGAGAAGGC

AGGGGCTCTCTGCTGACCTGCGGCGACGTGGAAGAGAACCCAGGCCCCA

TGGGAAGAGGTTTATTGAGAGGACTGTGGCCCTTACACATCGTTCTGTG

GACTCGTATCGCCTCTACCATCCCCCCCCATGTCCAAAAGAGCGTAAAC

AACGACATGATCGTGACCGACAACAATGGCGCTGTCAAGTTCCCCCAGC

TGTGCAAGTTTTGTGACGTGCGCTTCAGCACTTGTGACAATCAGAAGAG

CTGCATGAGCAACTGCTCCATCACCTCCATCTGTGAGAAACCCCAAGAA

GTGTGCGTCGCCGTCTGGCGTAAGAACGACGAGAACATCACTTTAGAGA

CAGTGTGCCACGATCCCAAACTGCCCTACCATGACTTCATTTTAGAAGA

TGCAGCCTCTCCCAAGTGTATCATGAAGGAAAAGAAAAAGCCTGGCGAG

ACCTTCTTCATGTGTTCTTGTTCGTCTGATGAGTGCAACGATAACATCA

TCTTCAGCGAAGAGTACAATACCTCGAACCCCGATTTATTACTGGTGAT

CTTCCAAGTTACCGGCATTTCTCTTCTGCCTCCGTTGGGTGTGGCTATC

AGCGTGATCATCATTTTCTACTGCTATCGTGTTAACCGTCAGTG.

"Polypeptide," "polypeptide fragment," "peptide" and "protein" are, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in some embodiments, it may be desirable to improve the binding affinity and/or other biological properties of the engineered DN TGF-β Receptors and engineered dual TACI-BCMA binding CAR and TCRs. Receptors by introducing one or more substitutions, deletions, additions and/or insertions. Preferably, polypeptides of the disclosure include polypeptides having at least about 50%, 60%, 65%, 70%, 75%, 85%, 90%, 95%, 98%, or 99% amino acid identity thereto. Polypeptides of the disclosure include variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. Polypeptides include "polypeptide fragments." Polypeptide fragments refer to a polypeptide, which may be monomeric or multi-meric that has an amino-terminal deletion, a carboxyl-terminal deletion, and/or an internal deletion or substitution of a naturally-occurring or recombinantly-produced polypeptide. In certain embodiments, a polypeptide fragment may comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support. As noted above, polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol*, 154: 367-382), U.S. Pat. No. 4,873, 192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants may be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Where expression of two or more polypeptides is desired, the polynucleotide sequences encoding them may be separated by an IRES sequence. In another embodiment, two or more polypeptides may be expressed as a fusion protein that comprises one or more self-cleaving polypeptide sequences, such as a T2A polypeptide. In other embodiments, they are expressed from different promotors and can be in two or more vectors. In some embodiments, a dual TACI-BCMA binding CAR or TCR is encoded in the same vector as an engineered DN TGF-β Receptor and is operably linked to the same promotor as the engineered DN TGF-β Receptor where the sequences are separated by an IRES sequence. In some embodiments, a dual TACI-BCMA binding CAR or TCR is encoded in the same vector as an engineered DN TGF-β Receptor is operably linked to a different promotor than the promotor the engineered DN TGF-β Receptor. In an embodiment, a DN TGF-β Receptor is expressed with an anti-BCMA CAR, such as described in International Patent Application Nos: PCT/US2018/039917 and PCT/2018/038549, both of which are specifically incorporated herein by reference in their entirety. In certain embodiments, the dual TACI-BCMA binding CAR or TCR is expressed on a cell that has also been engineered to express an engineered membrane bound IL-15-IL-15Rα sushi domain chimeric receptor, such as disclosed in U.S. Provisional Patent No. 63/159,610, filed on Mar. 11, 2021 which is specifically incorporated herein by reference in its entirety. In some embodiments, a dual TACI-BCMA binding CAR or TCR is encoded in the same vector as an engineered membrane bound IL-15-IL-15Rα sushi domain chimeric receptor and is operably linked to the same promoter as the an engineered membrane bound IL-15-IL-15Rα sushi domain chimeric receptor where the sequences are separated by an IRES sequence or a cleavable linker. In some embodiments, a dual TACI-BCMA binding CAR or TCR is encoded in the same vector as an engineered membrane bound IL-15-IL-15Rα sushi domain chimeric receptor is operably linked to a different promotor than the promotor the an engineered membrane bound IL-15-IL-15Rα sushi domain chimeric receptor. In some embodiments, a dual TACI-BCMA binding CAR is encoded in a different vector as an engineered membrane bound IL-15-IL-15Rα sushi domain chimeric receptor.

In an embodiment an anti-BCMA CAR has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 289. EVQLLESGG-GLVQPGGSLRLSCAASGFTFSSYAMSWVRQAPGK-GLEWVSSISGSGDYIY YADSVKGRFTISRDISKNT-LYLQMNSLRAEDTAVYYCAKEGTGANSSLADY-RGQGTLV TVSSFVPVFLPAKPTTTPAPRPPTPAPTIA-SQPLSLRPEACRPAAGGAVHTRGLDFACDIYI WAPLAGTCGVLLLSLVITLYCNHRNKRGRKKLLY-IFKQPFMRPVQTTQEEDGCSCRFPE EEEGGCELRVKFSRSADAPAYQQGQNQLYNELNL-GRREEYDVLDKRRGRDPEMGGKP RRKNPQEGLY-NELQKDKMAEAYSEIGMKGERRRGKGHDGLYQGL-STATKDTYDALH MQALPPR (SEQ ID NO: 289). In embodiments, an anti-BCMA CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                        (SEQ ID NO: 290)
GAGGTGCAGCTGTTGGAGTCCGGGGGAGGCTTGGTACAGCCTGGGGGGT

CCCTGAGACTCTCCTGCGCTGCATCTGGATTCACCTTTTCGTCTTATGC

CATGAGCTGGGTCCGCCAGGCTCCAGGGAAGGGGCTGGAGTGGGTCTCA

TCTATTAGTGGTAGTGGTGATTACATATATTACGCAGACTCCGTGAAGG

GCCGGTTCACCATCTCCAGAGACATATCCAAGAACACGCTGTATCTGCA

AATGAACAGTCTGAGAGCCGAGGACACGGCCGTCTATTACTGTGCGAAG

GAAGGAACAGGTGCCAACAGCAGCTTGGCAGACTACAGAGGCCAGGGCA

CCTTGGTAACCGTtTCCTCATTCGTGCCCGTGTTCCTGCCCGCCAAGCC

TACAACAACCCCTGCTCCCCGTCCTCCTACGCCTGCACCTACAATCGCC

AGCCAGCCTCTGTCTCTGAGGCCGGAAGCTTGTAGACCTGCGGCTGGCG

GAGCCGTGCATACCAGAGGACTGGATTTCGCCTGCGACATCTACATTTG

GGCCCCTTTGGCTGGAACATGTGGCGTTCTGCTGCTGAGCCTCGTGATC

ACCCTGTACTGCAACCACCGGAACAAGCGGGGCCGAAAGAAGCTGCTGT

ACATCTTCAAGCAGCCCTTCATGCGGCCCGTCCAAACTACCCAGGAAGA

GGACGGCTGCTCCTGTCGTTTTCCCGAGGAAGAAGAAGGCGGCTGCGAG

CTGAGAGTGAAGTTCAGCAGAAGCGCCGACGCGCCTGCCTATCAGCAAG

GGCAGAACCAGCTGTATAACGAGTTAAACCTGGGCAGACGGGAAGAGTA

CGATGTGTTGGATAAAAGACGTGGCCGGGATCCTGAGATGGGGGGAAAG

CCGCGCCGAAAAAACCCTCAGGAAGGCCTGTACAATGAACTGCAAAAGG

ATAAGATGGCCGAGGCCTACAGTGAGATTGGGATGAAAGGCGAGCGCCG
```

In an embodiment an anti-BCMA CAR linked to a DN TGF-β Receptor has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 289. EVQLLESGG-GLVQPGGSLRLSCAASGFTFSSYAMSWVRQAPGK-GLEWVSSISGSGDYIY YADSVKGRFTISRDISKNT-LYLQMNSLRAEDTAVYYCAKEGTGANSSLADYRG-QGTLV TVSSFVPVFLPAKPTTTPAPRPPTPAPTIA-SQPLSLRPEACRPAAGGAVHTRGLDFACDIYI WAPLAGTCGVLLLSLVITLYCNHRNKRGRKKLLY-IFKQPFMRPVQTTQEEDGCSCRFPE EEEGGCELRVKFSRSADAPAYQQGQNQLYNELNL-GRREEYDVLDKRRGRDPEMGGKP RRKNPQEGLY-NELQKDKMAEAYSEIGMKGERRRGKGHDGLYQGL-STATKDTYDALH MQALPPRGSGEGRGSLLTCGDVEENPGPMGRGLLR-GLWPLHIVLWTRIASTIPPHVQKS VNNDMIVTDNN-GAVKFPQLCKFCDVRFSTCDNQKSCMSNC-SITSICEKPQEVCVAVWR KNDENITLETVCHDPKLPYHDFILEDAASPKCI-MKEKKKPGETFFMCSCS SDECNDNIIFS EEYNTSNPDLLLVIFQVTGISLLPPLGVAISVIII-FYCYRVNRQ (SEQ ID NO: 291). In embodiments, an anti-BCMA CAR linked to a DN TGF-β Receptor is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                   (SEQ ID NO: 292)
GAGGTGCAGCTGTTGGAGTCCGGGGGAGGCTTGGTACAGCCTGGGGGT

CCCTGAGACTCTCCTGCGCTGCATCTGGATTCACCTTTTCGTCTTATGC

CATGAGCTGGGTCCGCCAGGCTCCAGGGAAGGGGCTGGAGTGGGTCTCA

TCTATTAGTGGTAGTGGTGATTACATATATTACGCAGACTCCGTGAAGG

GCCGGTTCACCATCTCCAGAGACATATCCAAGAACACGCTGTATCTGCA

AATGAACAGTCTGAGAGCCGAGGACACGGCCGTCTATTACTGTGCGAAG

GAAGGAACAGGTGCCAACAGCAGCTTGGCAGACTACAGAGGCCAGGGCA

CCTTGGTAACCGTtTCCTCATTCGTGCCCGTGTTCCTGCCCGCCAAGCC

TACAACAACCCCGCTCCCCGTCCTCCTACGCCTGCACCTACAATCGCC

AGCCAGCCTCTGTCTCTGAGGCCGAAGCTTGTAGACCTGCGGCTGGCG

GAGCCGTGCATACCAGAGGACTGGATTTCGCCTGCGACATCTACATTTG

GGCCCCTTTGGCTGGAACATGTGGCGTTCTGCTGCTGAGCCTCGTGATC

ACCCTGTACTGCAACCACCGGAACAAGCGGGGCCGAAAGAAGCTGCTGT

ACATCTTCAAGCAGCCCTTCATGCGGCCCGTCCAAACTACCCAGGAAGA

GGACGGCTGCTCCTGTCGTTTTCCGAGGAAGAAGAAGGCGGCTGCGAG

CTGAGAGTGAAGTTCAGCAGAAGCGCCGACGCGCCTGCCTATCAGCAAG

GGCAGAACCAGCTGTATAACGAGTTAAACCTGGGCAGACGGGAAGAGTA

CGATGTGTTGGATAAAAGACGTGGCCGGGATCCTGAGATGGGGGGAAAG
```

```
CCGCGCCGAAAAAACCCTCAGGAAGGCCTGTACAATGAACTGCAAAAGG

ATAAGATGGCCGAGGCCTACAGTGAGATTGGGATGAAAGGCGAGCGCCG

GAGGGGCAAGGGGCACGATGGCCTTTACCAGGGTTTGAGTACCGCCACC

AAGGACACCTACGACGCTCTTCACATGCAAGCCCTGCCCCCTCGCGGCT

CTGGAGAAGGCAGGGGCTCTCTGCTGACCTGCGGCGACGTGGAAGAGAA

CCCAGGCCCCATGGGAAGAGGTTTATTGAGAGGACTGTGGCCCTTACAC

ATCGTTCTGTGGACTCGTATCGCCTCTACCATCCCCCCCATGTCCAAA

AGAGCGTAAACAACGACATGATCGTGACCGACAACAATGGCGCTGTCAA

GTTCCCCCAGCTGTGCAAGTTTTGTGACGTGCGCTTCAGCACTTGTGAC

AATCAGAAGAGCTGCATGAGCAACTGCTCCATCACCTCCATCTGTGAGA

AACCCCAAGAAGTGTGCGTCGCCGTCTGGCGTAAGAACGACGAGAACAT

CACTTTAGAGACAGTGTGCCACGATCCCAAACTGCCCTACCATGACTTC

ATTTTAGAAGATGCAGCCTCTCCCAAGTGTATCATGAAGGAAAAGAAAA

AGCCTGGCGAGACCTTCTTCATGTGTTCTTGTTCGTCTGATGAGTGCAA

CGATAACATCATCTTCAGCGAAGAGTACAATACCTCGAACCCCGATTTA

TTACTGGTGATCTTCCAAGTTACCGGCATTTCTCTTCTGCCTCCGTTGG

GTGTGGCTATCAGCGTGATCATCATTTTCTACTGCTATCGTGTTAACCG

TCAGT.
```

In embodiments a dual TACI-BCMA binding CAR linked to a DN TGF-β Receptor is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                   (SEQ ID NO: 295)
GACATCCAGATGACCCAGTCTCCATCCTCCCTGTCTGCAAGCGTTGGAG

AtAGAGTCACtATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCcGGGACAGATTTCACTCTCACCATCAGCAGTCTGCAACCTGAAGA

TTTTGCAACTTACTACTGTCAGCAAAGCCACATCGCCCCTTGGACTTTT

GGCGGAGGGACCAAGGTTGAGATCAAAGGGAGCACtAGCGGCTCTGGCA

AACCTGGATCTGGCGAGGGATCTACCAAGGGCCAGGTGCAGCTGGTGCA

GTCTGGGGCTGAGGTGAAGAAGCCTGGGTCCTCGGTGAAGGTCTCCTGC

AAGGCTTCTGGAGGCACCTTCGCAGACTATGCTATCAGCTGGGTGCGAC

AGGCCCCTGGACAAGGGCTTGAGTGGATGGGAGGGATCATCCCTATATT

GGGCAGAGCAAACTACGCACAGAAGTTCCAGGGCAGAGtACGATTACC

GCGGACGAATCCACGAGCACAGCCTACATGGAGCTGAGCAGCCTGAGAT

CTGAGGACACGGCGGTGTACTACTGCGCCAGAGACAGAGACAGCACAAG

CCTGCCGTACAACCACTACTACATGGACGTATGGGCAAGGGTACAACT

GTCACtGTCTCCTCtggGtctCTAGACAATGAGAAGAGCAATGGAACCA

TTATCCATGTGAAAGGGAAACACCTTTGTCCAAGTCCCCTATTTCCGG
```

```
ACCTTCTAAGCCCTTTTGGGTGCTGGTGGTGGTTGGTGGAGTCCTGGCT

TGCTATAGCTTGCTAGTAACAGTGGCCTTTATTATTTTCTGGGTGAGGA

GTAAGAGGAGCAGGCTCCTGCACAGTGACTACATGAACATGACTCCCCG

CCGCCCCGGGCCCACCCGCAAGCATTACCAGCCCTATGCCCCACCACGC

GACTTCGCAGCCTATCGCTCCCTGAGAGTGAAGTTCAGCAGGAGCGCAG

ACGCCCCGCGTACCAGCAGGGCCAGAACCAGCTCTATAACGAGCTCAA

TCTAGGACGAAGAGAGGAGTACGATGTTTTGGACAAGAGgCGTGGCCGG

GACCCTGAGATGGGGGAAAGCCGAGAAGGAAGAACCCTCAGGAAGGCC

TGTACAATGAACTGCAGAAAGATAAGATGGCGGAGGCCTACAGTGAGAT

TGGGATGAAAGGCGAGCGCCGGAGGGGCAAGGGGCACGATGGCCTTTAC

CAGGGTCTCAGTACAGCCACCAAGGACACCTACGACGCCCTTCACATGC

AGGCCCTGCCCCCTCGCgGCTCTGGAGAAGGCAGGGGCTCTCTGCTGAC

CTGCGGCGACGTGGAAGAGAACCCAGGCCCCATGGGAAGAGGTTTATTG

AGAGGACTGTGGCCCTTACACATCGTTCTGTGGACTCGTATCGCCTCTA

CCATCCCCCCCATGTCCAAAAGAGCGTAAACAACGACATGATCGTGAC

CGACAACAATGGCGCTGTCAAGTTCCCCCAGCTGTGCAAGTTTTGTGAC

GTGCGCTTCAGCACTTGTGACAATCAGAAGAGCTGCATGAGCAACTGCT

CCATCACCTCCATCTGTGAGAAACCCCAAGAAGTGTGCGTCGCCGTCTG

GCGTAAGAACGACGAGAACATCACTTTAGAGACAGTGTGCCACGATCCC

AAACTGCCCTACCATGACTTCATTTTAGAAGATGCAGCCTCTCCCAAGT

GTATCATGAAGGAAAAGAAAAAGCCTGGCGAGACCTTCTTCATGTGTTC

TTGTTCGTCTGATGAGTGCAACGATAACATCATCTTCAGCGAAGAGTAC

AATACCTCGAACCCCGATTTATTACTGGTGATCTTCCAAGTTACCGGCA

TTTCTCTTCTGCCTCCGTTGGGTGTGGCTATCAGCGTGATCATCATTTT

CTACTGCTATCGTGTTAACCGTCAGT.
```

In embodiments a dual TACI-BCMA binding CAR linked to a DN TGF-β Receptor is encoded by a nucleic acid having at least 75% sequence identity (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                        (SEQ ID NO: 296)
GACATCCAGTTGACCCAGTCTCCATCCTCCCTGTCTGCAAGCGTTGGAG

ACAGAGTtACtATCACTTGCCGGGCAAGTCAGAGCATTAGCCTATATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCcGGGACAGATTTCACTCTCACCATCAGCAGTCTGCAACCTGAAGA

TTTTGCAACTTACTACTGTCAGCAAGTGGCCGTCGCCCCTTGGACTTTC

GGCGGAGGGACCAAGGTTGAGATCAAAGGGAGCACAAGCGGCTCTGGCA

AACCTGGATCTGGCGAGGGATCTACCAAGGGCCAGGTGCAGCTGGTGCA

GTCTGGGGCTGAGGTGAAGAAGCCTGGGTCCTCGGTGAAGGTCTCCTGC

AAGGCTTCTGGAGGCACCTTCGAACACTATGCTATCAGCTGGGTGCGAC

AGGCCCCTGGACAGGGGCTTGAGTGGATGGGAGGGATCATCCCcATATT

GGGCCGAGCAAACTACGCACAGAAGTTCCAGGGCAGAGTCACGATTACC

GCGGACGAATCCACGAGCACAGCCTACATGGAGCTGAGCAGCCTGAGAT

CTGAGGACACGGCGGTGTACTACTGCGCCAGAGACAGAAGCTGGGAAGG

ATCTCCCTATATGTACTACGGAATGGACGTTTGGGGCCAAGGGACAATG

GTCACCGTtTCCTCAggGtctCTAGACAATGAGAAGAGCAATGGAACCA

TTATCCATGTGAAAGGGAAACACCTTTGTCCAAGTCCCCTATTTCCCGG

ACCTTCTAAGCCCTTTTGGGTGCTGGTGGTGGTTGGTGGAGTCCTGGCT

TGCTATAGCTTGCTAGTAACAGTGGCCTTTATTATTTTCTGGGTGAGGA

GTAAGAGGAGCAGGCTCCTGCACAGTGACTACATGAACATGACTCCCCG

CCGCCCCGGGCCCACCCGCAAGCATTACCAGCCCTATGCCCCACCACGC

GACTTCGCAGCCTATCGCTCCCTGAGAGTGAAGTTCAGCAGGAGCGCAG

ACGCCCCGCGTACCAGCAGGGCCAGAACCAGCTCTATAACGAGCTCAA

TCTAGGACGAAGAGAGGAGTACGATGTTTTGGACAAGAGgCGTGGCCGG

GACCCTGAGATGGGGGAAAGCCGAGAAGGAAGAACCCTCAGGAAGGCC

TGTACAATGAACTGCAGAAAGATAAGATGGCGGAGGCCTACAGTGAGAT

TGGGATGAAAGGCGAGCGCCGGAGGGGCAAGGGGCACGATGGCCTTTAC

CAGGGTCTCAGTACAGCCACCAAGGACACCTACGACGCCCTTCACATGC

AGGCCCTGCCCCCTCGCgGCTCTGGAGAAGGCAGGGGCTCTCTGCTGAC

CTGCGGCGACGTGGAAGAGAACCCAGGCCCCATGGGAAGAGGTTTATTG

AGAGGACTGTGGCCCTTACACATCGTTCTGTGGACTCGTATCGCCTCTA

CCATCCCCCCCATGTCCAAAAGAGCGTAAACAACGACATGATCGTGAC

CGACAACAATGGCGCTGTCAAGTTCCCCCAGCTGTGCAAGTTTTGTGAC

GTGCGCTTCAGCACTTGTGACAATCAGAAGAGCTGCATGAGCAACTGCT

CCATCACCTCCATCTGTGAGAAACCCCAAGAAGTGTGCGTCGCCGTCTG

GCGTAAGAACGACGAGAACATCACTTTAGAGACAGTGTGCCACGATCCC

AAACTGCCCTACCATGACTTCATTTTAGAAGATGCAGCCTCTCCCAAGT

GTATCATGAAGGAAAAGAAAAAGCCTGGCGAGACCTTCTTCATGTGTTC

TTGTTCGTCTGATGAGTGCAACGATAACATCATCTTCAGCGAAGAGTAC

AATACCTCGAACCCCGATTTATTACTGGTGATCTTCCAAGTTACCGGCA

TTTCTCTTCTGCCTCCGTTGGGTGTGGCTATCAGCGTGATCATCATTTT

CTACTGCTATCGTGTTAACCGTCAGT.
```

Polypeptides of the present disclosure include fusion polypeptides. In some embodiments, fusion polypeptides and polynucleotides encoding fusion polypeptides are provided. Fusion polypeptides and fusion proteins refer to a polypeptide having at least two, three, four, five, six, seven, eight, nine, or ten or more polypeptide segments. Fusion polypeptides are typically linked C-terminus to N-terminus, although they may also be linked C-terminus to C-terminus, N-terminus to N-terminus, or N-terminus to C-terminus. The polypeptides of the fusion protein may be in any order or a specified order. Fusion polypeptides or fusion proteins may also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other common techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site may be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J Gener. Viral.* 78, 699-722; Scymczak et al. (2004) *Nature Biotech.* 5, 589-594). Exemplary protease cleavage sites include, but are not limited to the cleavage sites of potyvirus Nia proteases (e.g., tobacco etch virus protease), potyvirus HC proteases, potyvirus Pl (P35) proteases, byovirus Nia proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites may be used. In other embodiments, self-cleaving peptides may include those polypeptide sequences obtained from potyvirus and cardiovirus 2A peptides, FMDV (foot-and-mouth disease virus), equine rhinitis A virus, Thosea asigna virus and porcine teschovirus. In other embodiments, the self-cleaving polypeptide site comprises a 2A or 2A-like site, sequence or domain (Donnelly et al., 2001. *J Gen. Viral.* 82:1027-1041).

Generally, it is understood that any appropriate viral vector or vectors may be used for transduction of the engineered constructs described herein. In one embodiment described herein, a cell (e.g., T cell or NK cell) is transduced with a retroviral vector, e.g., a lentiviral vector. As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in some embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis encephalitis virus (CAEV); equine infectious anemia virus (EIAV); feline immunodeficiency virus (FIV); bovine immune deficiency virus (BIV); and simian immunodeficiency virus (SIV).

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-retroviral viral sequences. In one embodiment, a hybrid vector refers to a vector or transfer plasmid comprising retroviral e.g., lentiviral, sequences for reverse transcription, replication, integration and/or packaging.

In some embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the disclosure and are present in DNA form in the DNA plasmids of the disclosure. In one embodiment described herein, the expression vector is a lentivirus expression vector.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, Rand U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R, and U5. The U3 region contains the enhancer and promoter elements. The U5 region is the sequence between the primer binding site and the R region and contains the polyadenylation sequence. The R (repeat) region is flanked by the U3 and U5 regions. The LTR is composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. J of Virology, Vol. 69, No. 4; pp. 2101-2109. Several retroviral vectors use the minimal packaging signal (also referred to as the psi ['P] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the disclosure, the 3'LTR is modified such that the U5 region is replaced, for example, with an ideal poly(A) sequence. It should be noted that modifications to the LTRs such as modifications to the 3'LTR, the 5'LTR, or both 3' and 5'LTRs, are also contemplated herein.

An additional safety enhancement is provided by replacing the U3 region of the 5'LTR with a heterologous promoter to drive transcription of the viral genome during production of viral particles. Examples of heterologous promoters which may be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter may be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a includes the central polypurine tract and central termination sequences (cPPT and CTS) of a retrovirus, e.g., HIV-I or HIV-2. Suitable FLAP elements are described in U.S. Pat. No. 6,682,907 and in Zennou, et al., 2000, Cell, 101: 173. During HIV-I reverse transcription, central initiation of the plus-strand DNA at the central polypurine tract (cPPT) and central termination at the central termination sequence (CTS) lead to the formation of a three-stranded DNA structure: the HIV-I central DNA flap. While not wishing to be bound by any theory, the DNA flap may act as a cis-active determinant of lentiviral genome nuclear import and/or may increase the titer of the virus.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J Virol. 65: 1053; and Cullen et al., 1991. Cell 58: 423), and the hepatitis B virus post-transcriptional regulatory element (HPRE). Generally, the RNA export element is placed within the 3' UTR of a gene, and may be inserted as one or multiple copies.

In other embodiments, expression of heterologous sequences in viral vectors is increased by incorporating post-transcriptional regulatory elements, efficient polyadenylation sites, and optionally, transcription termination signals into the vectors. A variety of posttranscriptional regulatory elements may increase expression of a heterologous nucleic acid at the protein, e.g., woodchuck hepatitis virus post-transcriptional regulatory element (WPRE; Zufferey et al., 1999, J Virol., 73:2886); the post-transcriptional regulatory element present in hepatitis B virus (HPRE) (Huang et al., Mol. Cell. Biol., 5:3864); and the like (Liu et al., 1995, Genes Dev., 9:1766).

In some embodiments, vectors may include regulatory oligonucleotides having transcriptional or translational regulatory activity. Such an oligonucleotide can be used in a variety of gene expression configurations for regulating control of expression. A transcriptional regulatory oligonucleotide, can increase (enhance) or decrease (silence) the level of expression of a recombinant expression construct. Regulatory oligonucleotides may selectively regulate expression in a context specific manner, including, for example, for conferring tissue specific, developmental stage specific, or the like expression of the polynucleotide, including constitutive or inducible expression. A regulatory oligonucleotide of the disclosure also can be a component of an expression vector or of a recombinant nucleic acid molecule comprising the regulatory oligonucleotide operatively linked to an expressible polynucleotide. A regulatory element can be of various lengths from a few nucleotides to several hundred nucleotides.

Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences may promote mRNA stability by addition of a poly A tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of poly A signals that may be used in a vector of the disclosure, includes an ideal poly A sequence (e.g., AATAAA, ATTAAA, AGTAAA), a bovine growth hormone poly A sequence (BGHpA), a rabbit β-globin poly A sequence (rβgpA), or another suitable heterologous or endogenous poly A sequence known in the art.

Also described herein are "codon-optimized" nucleic acids. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells) by replacing at least one, more than one, or a significant number, of codons of the native sequence with codons that are more frequently or most frequently used in the genes of that species. Codon optimization does not alter the amino acid sequence of the encoded protein.

The codon-optimized nucleotide sequences can present improved properties related to expression efficacy. In some embodiments, the DNA sequence to be transcribed may be optimized to facilitate more efficient transcription and/or translation. In some embodiments, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability domain, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding.

The vectors may have one or more LTRs, wherein any LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi ('P) packaging signal, RRE), and/or other elements that increase therapeutic gene expression (e.g., poly (A) sequences), and may optionally comprise a WPRE or HPRE. The skilled artisan would appreciate that many other different embodiments may be fashioned from the existing embodiments of the disclosure.

A "host cell" includes cells transfected, infected, or transduced in vivo, ex vivo, or in vitro with a recombinant vector or a polynucleotide of the disclosure. Host cells may include packaging cells, producer cells, and cells infected with viral vectors. In some embodiments, host cells infected with viral vector of the disclosure are administered to a subject in need of therapy. In certain embodiments, the term "target cell" is used interchangeably with host cell and refers to transfected, infected, or transduced cells of a desired cell type. In some embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present disclosure may be introduced into a packaging cell line, via transfection, transduction or infection, to generate a producer cell or cell line. The packaging vectors of the present disclosure may be introduced into human cells or cell lines by common methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene may be linked physically to genes encoding by the packaging vector, e.g., by IRES or self-cleaving viral peptides.

Viral envelope proteins (env) determine the range of host cells which may ultimately be infected and transformed by recombinant retroviruses generated from the cell lines. In the case of lentiviruses, such as HIV-1, HIV-2, SIV, FIV and EIV, the env proteins include gp41 and gp120. In some embodiments, the viral env proteins expressed by packaging cells of the disclosure are encoded on a separate vector from the viral gag and pol genes, as has been previously described.

Illustrative examples of retroviral-derived env genes which may be employed in the embodiments described herein include, but are not limited to: MLV envelopes, 10A1 envelope, BAEV, FeLV-B, RDI 14, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BL V, EBV, CAEV, SNV, ChTL V, STLV, MPMV SMRV, RAV, FuSV, MH2, AEV, AMV, CTIO, and EIAV.

In other embodiments, envelope proteins for pseudotyping a virus of present disclosure include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Barr virus (EBV), human herpesviruses (HHV), human herpesvirus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-Co V), West Nile virus, or any encephalitis causing virus.

The terms "pseudotype" or "pseudotyping" as used herein, refer to a virus whose viral envelope proteins have been substituted with those of another virus possessing other characteristics. For example, HIV may be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line may be employed to prepare packaging cells of the disclosure. Generally, the cells are mammalian cells. In another embodiment, the cells used to produce the packaging cell line are human cells. Suitable cell lines which may be used to produce the packaging cell line include, for example, CHO cells, BHK cells, MDCK cells, C3H 10T1/2 cells, FLY cells, Psi-2 cells, BOSC 23 cells, P A317 cells, WEHI cells, COS cells, BSC 1 cells, BSC 40 cells, BMT 10 cells, VERO cells, W138 cells, MRCS cells, A549 cells, HTIO80 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) Nucl. Acids Res. 23:628-633, and N. R. Landau et al. (1992) J Virol. 66:5110-5113. Infectious virus particles may be collected from the packaging cells using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell or NK cell, is "transduced" if it comprises a gene or other polynucleotide sequence delivered to the cell by infection using a viral or retroviral vector. In some embodiments, a transduced cell comprises one or more genes or other polynucleotide sequences delivered by a retroviral or lentiviral vector in its cellular genome.

Disclosed are host cells expressing one or more of the constructs of the disclosure. The host cells may be transduced with one or more viral vectors comprising nucleic acid sequences encoding one or more polypeptides expressing an engineered TCR and/or a CAR. Other methods relating to the use of viral vectors in gene therapy, which may be utilized according to certain embodiments of the present disclosure, may be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al., (1999) Liver 19:265-74; Oka, K. et al., (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J Hepatol. 23:746-58; Brody, S. L. and Crystal, R. G. (1994) Ann. NY Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al., (2000) Nature 408:483-8.

The compositions described herein may comprise one or more polynucleotides, polypeptides, vectors comprising same, and T cell composition and NK compositions, as contemplated herein. One embodiment described herein is a composition comprising a modified T cell that expresses a dual TACI-BCMA biding TCR and/or CAR. Another embodiment described herein is a composition comprising a modified NK cell that expresses a dual TACI-BCMA biding TCR and/or CAR. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the present disclosure may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In one embodiment described herein, compositions of the present disclosure comprise an amount of modified T cells or NK cells contemplated herein. It may generally be stated that a pharmaceutical composition comprising the T cells or NK cells contemplated herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of cells will depend upon the ultimate use for which the composition is intended as will the type of cells included therein. T cells or NK cells modified to express an engineered TCR or CAR may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised or immunosuppressed. In some, compositions comprising the modified T cells or NK cells contemplated herein are used in the treatment of cancers. The modified T cells or NK cells described herein may be administered either alone, or as a pharmaceutical composition in combination with carriers, diluents, excipients, and/or with other components such as IL-2, IL-7, and/or IL-15 or other cytokines or cell populations. In some embodiments, pharmaceutical compositions contemplated herein comprise an amount of genetically modified T cells or NK cells, in combination with one or more pharmaceutically or physiologically acceptable carriers, diluents or excipients.

Pharmaceutical compositions comprising modified T cells or NK cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for parenteral administration, e.g., intravascular (intravenous or intra-arterial), intraperitoneal or intramuscular administration.

The liquid pharmaceutical compositions, whether they be solutions, suspensions or other like form, may include one or more of the following: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Sterile injectable pharmaceutical composition are also included.

In some embodiments, compositions contemplated herein comprise an effective amount of an expanded modified T cell or NK cell composition, alone or in combination with one or more therapeutic agents. Thus, the T cell or NK cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics and anti-viral agents. Such therapeutic agents may be accepted in the art as a treatment for a disease state as described herein, such as a cancer. In one embodiment the compositions contemplated herein may also be administered with inhibitors of TGF-β, for example the small molecule inhibitor LY55299. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells or NK cells contemplated herein may be administered in conjunction with any number of chemotherapeutic agents. Illustrative examples of chemotherapeutic agents include but are not limited to alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RPS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In some embodiments, NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol or proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary disease-modifying anti-rheumatic drugs (DMARDs) include azathioprine, cyclophosphamide, cyclosporine, methotrexate, penicillamine, leflunomide, sulfasalazine, hydroxychloroquine, Gold (oral (auranofin) and intramuscular) and minocycline.

In other embodiments, the therapeutic antibodies suitable for combination with the CAR or TCR modified T cells or NK cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In some embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha andbeta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-15, a tumor necrosis factor such as TNF-α or TNF-β; and other polypeptide factors including LIF and kit ligand (KL). As used herein, the term cytokine includes proteins from natural sources or from recombinant cell culture, and biologically active equivalents of the native sequence cytokines.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof. Unlike antibody therapies or stand-alone TCR or CAR modified T cells, T cells (or any cells as described above)

Another embodiment described herein is a method of treating a cancer in a subject in need thereof comprising administering an effective amount, e.g., therapeutically effective amount of a composition comprising T cells or NK cells expressing TCR or CAR as described herein. The quantity and frequency of administration will be determined by such factors as the condition of the patient, and the type and severity of the patient's disease, although appropriate dosages may be determined by clinical trials.

In other embodiments, methods comprising administering a therapeutically effective amount of modified T cells contemplated herein or a composition comprising the same, to a patient in need thereof, alone or in combination with one or more therapeutic agents, are provided. In certain embodiments, the cells of the disclosure are used in the treatment of patients at risk for developing a cancer. Thus, the present disclosure provides methods for the treatment or prevention of a cancer comprising administering to a subject in need thereof, a therapeutically effective amount of the modified T cells of the disclosure.

One of ordinary skill in the art would recognize that multiple administrations of the compositions of the disclosure may be required to affect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present disclosure, and reinfuse the patient with these activated and expanded T cells. This process may be carried out multiple times every few weeks. In certain embodiments, T cells may be activated from blood draws of from 10 cc to 400 cc. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In some embodiments, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of proinflammatory cytokines that may induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

In embodiments described herein is a method of treating a subject diagnosed with a cancer, comprising removing T cells from the subject, genetically modifying said T cells with a vector comprising a nucleic acid encoding a dual TACI-BCMA binding CAR as contemplated herein, thereby producing a population of modified T cells, and administering the population of modified T cells to the same subject.

In certain embodiments, the present disclosure also provides methods for stimulating an effector cell mediated immune modulator response to a target cell population in a subject comprising the steps of administering to the subject an immune effector cell population expressing a nucleic acid construct encoding a dual TACI-BCMA binding CAR molecule.

The methods for administering the cell compositions described herein includes any method which is effective to result in reintroduction of ex vivo genetically modified immune effector cells that either directly express an engineered CAR in the subject or on reintroduction of the genetically modified progenitors of immune effector cells that on introduction into a subject differentiate into mature immune effector cells that express the dual TACI-BCMA binding CAR molecule. One method comprises transducing peripheral blood T cells ex vivo with a nucleic acid construct in accordance with the present disclosure and returning the transduced cells into the subject.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those skilled in the art will readily recognize a variety of noncritical parameters that could be changed or modified to yield essentially similar results.

BCMA binding CAR). The CARs were transduced with a multiplicity of infection (MOI) of 5. T cells were de-beaded 3 days after transduction and evaluated for expression and cytotoxicity assays between days 8 and 11 following transduction. All flow cytometry data was collected on BD LSRFortessa™ (BD and Company) with BD FACSDiva™ software (BD and Company and data was analyzed using FlowJo (BD and Company). All antibody staining was performed at 4° C. in PBS containing 1% BSA.

Example 2. Assessment of T Cell Transduction

Seven days after transduction, T cells transduced as described in example 1 were harvested to determine transduction efficiencies. $1.5 \times 10^5$ T cells were plated in 96 well plates in duplicate. The T cells were cultured overnight in hTCM (human T cell media), that included of x-vivo 15 (Lonza (Basel, Switzerland)), 5% human serum (Valley Biomedical (Winchester, Virginia)), and 1% Glutamax (Gibco). After overnight culture, CAR expression was measured using an antibody to the myc tag, which was included on the test constructs solely to aid in detection of expression. The cells were stained with the anti-myc antibody and the stained cells were detected via flow cytometry. The transduction rates of CARs in the T cells, varied from 57-85%. See table 13.

TABLE 13

Percent transduction of T cells.

| CAR | mAb1 | mAb2 | mAb3 | mAb4 | mAb5 | mAb6 | mAb7 | mAb8 | mAb9 |
|---|---|---|---|---|---|---|---|---|---|
| Expression | 84.9% | 80.6% | 82.3% | 83.5% | 69.7% | 77.5% | 77.4% | 57.2% | 69.5% |

EXAMPLES

Example 1. T Cell Transduction

The dual TACI-BCMA binding CARs (mAb1-mAb9) used in the following examples included a CSF2RA signal sequence, a myc tag to detect expression, a dual TACI-BCMA binding scFv, a truncated CD28 hinge, a CD28 transmembrane domain, an CD28 co-stimulatory domain, and a CD3zeta signaling domain. CAR expressing vectors included an EF1a promoter to drive constitutive expression of the dual TACI-BCMA binding CAR.

CD3+ cells obtained from ALLCells® (Alameda, California) were isolated from peripheral blood mononuclear cells obtained from healthy donors and frozen down in CryoStor® cell cryopreservation media (Sigma Aldrich®). Pan CD3+ T cells were isolated from leukopaks containing peripheral blood mononuclear cells (PBMCs) by negative selection using a commercially available kit from STEMCELL Technologies™ (Vancouver, Canada) according to manufacturer's directions and then frozen in liquid nitrogen. Chimeric antigen receptor (CAR) T cells were generated from frozen human Pan CD3+ T cells. Before lentivirus transduction, the CD3+ pan T cells were thawed, and activated ex vivo using anti-CD3/CD28 Dynabeads®, (ThermoFisher Scientific) and 100 IU/ml exogenous interleukin-2 (IL-2) according to manufacturer recommendations. The activated cells were rested overnight. One day after anti-CD3/CD28 bead activation, T cells were plated and transduced with a lentiviral vector (with a dual TACI- Example 3. T Cell-Dependent Cytotoxicity of the CAR T Cells For T cell-dependent cytotoxicity assays, the cytotoxicity of dual TACI-BCMA binding CART cells transduced as described in example 1 was measured at an effector (T cell)-to-target cell ratio of (E:T) of 1-3. T cells were cocultured with target cells for 24 h in X-VIVO 15 without Gentamicin, L-Gln, and Phenol Red (Lonza 04-744Q), and supplemented with 5% Human Serum (Valley Biomedical, HP1022), 10 mL per liter 100× Glutamax (Gibco, 3050-061), 1 mL per liter Gentamicin 50 mg/mL (Lonza, 14-518L). The number of CAR T cells per well in a 96 well plate was normalized for transduction efficiency (see Example 2). To facilitate tracking of T cells in culture, the dual TACI-BCMA binding CAR T cells were labeled with CellTrace™ Violet (CTV) reagent according to the manufacturer's instructions and subsequently washed. To facilitate tracking of cells expressing CAR T target antigens ("target cells"), target cells were engineered to express luciferase. Target cells were added to each well as shown in Table 14.

Luciferase-expressing target cells used for this example comprised K562 cells or K562 cells that were transduced with either TACI or BCMA or with TACI and BCMA. After 24 hours a luciferase assay was performed and the % lysis was calculated by quantifying the target cells that were remaining after 24 h of co-culture. Briefly. D-luciferin substrate was added to the co-culture wells and plates were incubated at 37° C. in the dark. Controls comprised untransduced (UNTR) T cells (i.e., T cells not expressing a CAR) as a negative control. The results are described in Table 14.

TABLE 14

Average % lysis of tumor cells after co-culturing them with Anti-TACI + Anti-BCMA CAR T cells at E:T-1-3 for 24 h

| % Killing | mAb 1 | mAb 2 | mAb 3 | mAb 4 | mAb 5 | mAb 6 | mAb 7 | mAb 8 | mAb 9 | UNTR |
|---|---|---|---|---|---|---|---|---|---|---|
| K562-Parent | 24.5 | 45.7 | 24 | 7.33 | 0.76 | 11.2 | 49.3 | 52.8 | 41.5 | 8.5 |
| K562-BCMA | 53.8 | 73.3 | 61 | 46.9 | 38 | 47.9 | 61.3 | 71.7 | 52.5 | 6.4 |
| K562-TACI | 71.7 | 85 | 76.3 | 66 | 60.37 | 69.6 | 75 | 81.9 | 73.3 | 8.6 |
| K562-TACI + BCMA | 76.9 | 90 | 82 | 74 | 61.8 | 77.5 | 81.7 | 89 | 83 | 13.9 |

Example 4. Cytokine Release of the CAR T Cells

Cytokine release (IL-2) in pg/ml of dual TACI-BCMA binding CAR T cells transduced as described in example 1 was measured at an effector (T cell)-to-target cell ratio of (E:T) of 1-3. T cells were cocultured with target cells for 24 h After 24 h. IL-2 release from CAR T cells was measured after co-culture with either K562 cells or K562 cells that were transduced with either TACI or BCMA or with TACI and BCMA at an E:T-1-3. Supernatants were then harvested and cytokine release (IL-2) was determined via MSD 384-Well Multi-array And Multi-spot Human Cytokine Assay using the manufacturer's directions. Supernatants from the co-cultures of T-cell products plated at the 13 E:T ratio with antigen-expressing target cells were analyzed for levels of IL-2, secretion mediated by antigen engagement. All samples were diluted to be within the range of detection. The level of IL-2 is reported as pg/m. Controls comprised un-transduced (UNTR) T cells (i.e., T cells not expressing a CAR) as a negative control. Shown in table 15 are the average values of IL-2 in pg/ml, released by the CAR T cells after co-culturing them with target cells at an E: T-1-3 for 24h.

TABLE 15

Average IL-2 release

| IL-2 pg/ml | mAb 1 | mAb 2 | mAb 3 | mAb 4 | mAb 5 | mAb 6 | mAb 7 | mAb 8 | mAb 9 | UNTR |
|---|---|---|---|---|---|---|---|---|---|---|
| K562-Parent | 28 | 241 | 32.3 | 54 | 49.2 | 7.5 | 327 | 88 | 225.3 | 80.5 |
| K562-BCMA | 68154 | 77328 | 76091 | 74804 | 67015 | 91081 | 77578 | 87313 | 90700 | 154.9 |
| K562-TACI | 8430 | 15217 | 23201 | 28398 | 20307 | 38930 | 24075 | 20719 | 24840 | 77.68 |
| K562-TACI + BCMA | 49571 | 48890 | 46290 | 60684 | 50541 | 74411 | 50209 | 59339 | 36318 | 89.5 |

Example 5. Tumor Cell Killing by the CAR T Cells

Killing assays were performed with different multiple myeloma cell lines to demonstrate the ability of the dual TACI-BCMA CART cells to kill multiple myeloma cells. The selected cell-lines, Rec-1 (ATCC® Ref No. CRL-3004), MM1.S (ATCC® Ref. No. CRL-2974), RPMI-8226 (ATCC® Ref. No. CCL-155), and JJN3 (DSMZ Ref. No. ACC 541) express one or more of TACI and BCMA. For T cell-dependent cytotoxicity assays, the cytotoxicity of T cells transduced as described in example 1 was measured at an effector (T cell)-to-target cell ratio of (E:T) of 1-3 after 24 h of coculture. Table 16 shows the results of killing assays performed where CAR T cells were co-cultured with either K562 cells, Rec-1, MM1.Sm, RPMI-8226 or JJN3 cells at an E:T-1-3, for 24 h. After 24 hours a luciferase assay was performed and the % lysis was calculated by quantifying the target cells that were remaining after 24 h of co-culture. Briefly. D-luciferin substrate was added to the co-culture wells and plates were incubated at 37° C. in the dark. Luminescent signal was read immediately after in a microplate reader. Controls comprised un-transduced (UNTR) T cells (i.e., T cells not expressing a CAR) as a negative control. The results are described in Table 16.

TABLE 16

Average % lysis of tumor cells after co-culturing with Anti-TACI + Anti-BCMA CAR T cells at E:T-1-3 for 24 h

| % Killing | mAb 1 | mAb 2 | mAb 3 | mAb 4 | mAb 5 | mAb 6 | mAb 7 | mAb 8 | mAb 9 | UNTR |
|---|---|---|---|---|---|---|---|---|---|---|
| K562-Parent | 24.5 | 45.7 | 24 | 7.33 | 0.76 | 11.2 | 49.3 | 52.8 | 41.5 | 8.5 |
| Rec-1 | 62.3 | 74.4 | 66.6 | 62.5 | 45.9 | 63.5 | 72.8 | 74.5 | 70.6 | −4.9 |
| MM1.S | 76.8 | 90 | 78.9 | 69.5 | 50.7 | 78.6 | 90.2 | 96.7 | 95 | 2.9 |
| RPMI-8226 | 83.8 | 89.3 | 82.6 | 79.3 | 76.6 | 87.2 | 92.2 | 90.8 | 91.2 | 33.8 |
| JJN3 | 98.5 | 98.8 | 98.6 | 97.6 | 96.5 | 98.7 | 99 | 99 | 99.5 | 46.4 |

Example 6. Cytokine Release in Coculture with Tumor Cells

Cytokine release (IL-2) in pg/ml of dual TACI-BCMA binding CAR T cells transduced as described in example 1 was measured at an effector (T cell)-to-target cell ratio of (E:T) of 1-3 after coculture with selected multiple myeloma cell lines. Cytokine release was measured as described in Example 4. Table 17 shows results of cytokine release (IL-2) in pg/ml, by each of the CAR T cells after co-culture with either K562 cells or the multiple myeloma cells lines Rec-1, MM1.S, RPMI-8226 and JJN3 cells at an E:T-1-3, for 24 h. Supernatants were harvested and cytokine release (IL-2) was determined via MSD 384-Well Multi-array And Multi-spot Human Cytokine Assay using the manufacturer's directions. Supernatants from the co-cultures of T-cell products plated at the 13 E:T ratio with antigen-expressing target cells were analyzed for levels of IL-2, secretion mediated by antigen engagement. All samples were diluted to be within the range of detection. The level of each cytokine is reported as pg/mL and the lower limit of quantitation and upper limit of quantitation of each assay is reported. Controls comprised un-transduced (UNTR) T cells (i.e., T cells not expressing a CAR) as a negative control. Shown in table 17 are the average values of IL-2 in pg/ml, released by the CAR T cells after co-culturing them with target cells at an E: T-1-3 for 24 h.

TABLE 17

Average IL-2 released by the Anti-TACI + Anti-BCMA CAR T cells after co-culturing them tumor cells E:T-1-3 for 24 h

| IL-2 pg/ml | mAb1 | mAb2 | mAb3 | mAb4 | mAb5 | mAb6 | mAb7 | mAb8 | mAb9 | UNTR |
|---|---|---|---|---|---|---|---|---|---|---|
| K562-Parent | 28 | 241 | 32.3 | 54 | 49.2 | 7.5 | 327 | 88 | 225.3 | 80.5 |
| Rec-1 | 30445 | 52715 | 58756 | 30275 | 13443 | 54032 | 89499 | 86170 | 83976 | 277 |
| MM1.S | 86268 | 75512 | 78572 | 65657 | 67225 | 84258 | 45922 | 48077 | 45724 | 479 |
| RPMI-8226 | 11019 | 12470 | 16356 | 4746 | 7605 | 13119 | 5708 | 6185 | 5280 | 180 |
| JJN3 | 31510 | 31848 | 37325 | 19532 | 31387 | 36307 | 8687 | 8682 | 4144 | 497 |

Example 7. Phenotypes of the CAR T Cells

The phenotype of dual TACI-BCMA binding CAR T cells transduced as described in example 1 was determined. Briefly, 2.0×10⁵ per well were aliquoted to the wells of a 96 well plate. Media was removed and the cells washed with phospho-buffered saline (PBS). The cells were then suspended in a 1:1000 dilution in L/D Near IR and stained in L.D for 15 mins. Cells were washed again with PBS and resuspend with the antibody cocktail shown in Table 19.

TABLE 19

Antibody cocktails

| Fluorochrome | Antibody |
|---|---|
| BV421 | CCR7 |
| BV510 | CD8 |
| BV605 | CD3 |
| BV786 | CD4 |
| FITC | CD45RO |
| PE | aMyc |
| PE-Cy7 | CD107a |
| APC-Cy7 | Live Dead |
|  | N/R |
| DL650 | rBCMA |

All antibodies were used at 1:100 dilution and cells were stained for 30 mins on ice. Cells were washed PBS or FACS buffer, and read on a flowcytometer. Table 20 Shows quantification of expression of CD4 and CD8 positive CAR T cells. A transduction check was done using day 9 cells, by staining with anti-Myc antibody and rBCMA protein. No significant difference in the CD4:CD8 ratio and the phenotype observed between CARs. Controls comprised un-transduced (UNTR) T cells (i.e., T cells not expressing a CAR) as a negative control.

TABLE 20

Quantification of CD4:CD8 ratio and the phenotype of Anti-TACI + Anti-BCMA CAR T cells

|  | CAR+/CD4+ | CAR+/CD8+ |
|---|---|---|
| mAb1 | 59.7% | 36.3% |
| mAb5 | 55.2% | 40.6% |
| mAb6 | 59.7% | 35.9% |
| mAb7 | 52.3% | 44.1% |
| UNTR | 3.01% | 53.1% |

TABLE 21

Quantification of expression of markers of phenotype for CAR T cells

| | CCR7−, CD45RO+ Effector Memory Cells | CCR7+, CD45RO+ Central Memory Cells | CCR7+, CD45RO− Naïve Cells | CCR7−, CD45RO− Effector Cells |
|---|---|---|---|---|
| mAb1 | 59.6% | 2.00% | 0.059% | 38.3% |
| mAb5 | 37.8% | 1.95% | 0.59% | 59.7% |
| mAb6 | 47.1% | 1.89% | 0.28% | 50.7% |
| mAb7 | 47.5% | 2.21% | 0.31% | 50.0% |
| UNTR | 43.5% | 9.00% | 4.84% | 42.7% |

Example 8. In Vivo Anti-Tumor Efficacy

The anti-tumor efficacy of CAR T cells comprising a dual TACI-BCMA binding CAR was tested against RPMI-8226 cell that express both BCMA and TACI. Dual TACI-BCMA binding CAR T cells were tested against disseminated luciferase-expressing RPMI-8226 multiple myeloma tumors in NSG mice. Response was evaluated based on bioluminescence imaging (BLI). BLI was performed on days 7, 9, 12, 14, 16, 19, 21, 23, 26, 28, 30, 33, 35, 37, 40, 42, 44, 47, 49, and 51 to monitor tumor reduction. The study was terminated on day 51. CAR T cells were administered at a dose, and to a number of mice, shown in Table 22. All CAR T cells were administered intravenously (QDx1).

TABLE 22

CAR T cell dosing schedule

| Group | # of mice | # RPMI-8226 | Staging/ Dosing Day | CAR scFv | Dose |
|---|---|---|---|---|---|
| 1 | 6 | 1e7, s.c. | | Vehicle | N/A |
| 2 | 6 | 1e7, s.c. | D7 | Un-transduced | 1.5e6 |
| 3 | 6 | 1e7, s.c. | D7 | Un-transduced | 3e5 |
| 4 | 6 | 1e7, s.c. | D7 | mAb1 | 1.5e6 |
| 5 | 6 | 1e7, s.c. | D7 | mAb1 | 3e5 |
| 6 | 6 | 1e7, s.c. | D7 | mAb5 | 1.5e6 |
| 7 | 6 | 1e7, s.c. | D7 | mAb5 | 3e5 |
| 8 | 6 | 1e7, s.c. | D7 | mAb6 | 1.5e6 |
| 9 | 6 | 1e7, s.c. | D7 | mAb6 | 3e5 |
| 10 | 6 | 1e7, s.c. | D7 | mAb7 | 1.5e6 |
| 11 | 6 | 1e7, s.c. | D7 | mAb7 | 3e5 |
| 12 | 6 | 1e7, s.c. | D7 | mAb9 | 1.5e6 |
| 13 | 6 | 1e7, s.c. | D7 | mAb9 | 3e5 |

Results are shown in Table 23 below. Anti-tumor efficacy was observed for Dual TACI-BCMA binding CAR T cells.

TABLE 23

In vivo anti-tumor efficacy

| Day | Group 1 Mean tumor volume (mm³) +/− Standard error | Group 2 Mean tumor volume (mm³) +/− Standard error | Group 3 Mean tumor volume (mm³) +/− Standard error | Group 4 Mean tumor volume (mm³) +/− Standard error | Group 5 Mean tumor volume (mm³) +/− Standard error | Group 6 Mean tumor volume (mm³) +/− Standard error | Group 7 Mean tumor volume (mm³) +/− Standard error |
|---|---|---|---|---|---|---|---|
| 7 | 100 +/− 6 | 96 +/− 6 | 101 +/− 5 | 99 +/− 5 | 94 +/− 7 | 100+/6 | 98 +/− 9 |
| 9 | 122 +/− 11 | 119 +/− 11 | 120 +/− 9 | 122 +/− 5 | 112 +/− 6 | 115 +/− 7 | 107 +/− 11 |
| 12 | 166 +/− 17 | 173 +/− 12 | 155 +/− 13 | 227 +/− 23 | 207 +/− 13 | 191 +/− 17 | 203 +/− 17 |
| 14 | 220 +/− 22 | 212 +/− 18 | 179 +/− 15 | 241 +/− 26 | 279 +/− 25 | 266 +/− 29 | 252 +/− 24 |
| 16 | 308 +/− 24 | 265 +/− 20 | 231 +/− 24 | 245 +/− 24 | 330 +/− 34 | 268 +/− 29 | 311 +/− 18 |
| 19 | 430 +/− 23 | 374 +/− 29 | 340 +/− 40 | 99 +/− 15 | 175 +/− 20 | 175 +/− 23 | 383 +/− 21 |
| 21 | 451 +/− 28 | 404 +/− 25 | 365 +/− 41 | 46 +/− 21 | 155 +/− 14 | 157 +/− 23 | 407 +/− 21 |
| 23 | 503 +/− 31 | 356 +/− 29 | 380 +/− 44 | 25 +/− 16 | 66 +/− 22 | 111 +/− 23 | 417 +/− 25 |
| 26 | 582 +/− 34 | 417 +/− 58 | 490 +/− 73 | | 28 +/− 18 | 81 +/− 18 | 497 +/− 40 |
| 28 | 663 +/− 42 | 466 +/− 74 | 539 +/− 70 | | 24 +/− 15 | 50 +/− 23 | 566 +/− 66 |
| 30 | 859 +/− 58 | 593+/115 | 697 +/− 96 | | | 27 +/− 17 | 720 +/− 88 |
| 33 | 1193 +/− 77 | 776 +/− 196 | 877 +/− 134 | | | 11 +/− 11 | 884 +/− 124 |
| 35 | | 888 +/− 227 | 1060 +/− 181 | | | | 1125 +/− 203 |
| 37 | | 1032 +/− 268 | 1310 +/− 197 | | | | 1358 +/− 260 |
| 40 | | 1315 +/− 392 | 1840 +/− 297 | | | | 1698 +/− 358 |
| 42 | | 1021 +/− 394 | | | | | |
| 44 | | 1056 +/− 408 | | | | | |
| 47 | | 1302 +/− 544 | | | | | |
| 49 | | | | | | | |
| 51 | | | | | | | |

TABLE 23-continued

In vivo anti-tumor efficacy

| Day | Group 8 Mean tumor volume (mm$^3$) +/− Standard error | Group 9 Mean tumor volume (mm$^3$) +/− Standard error | Group 10 Mean tumor volume (mm$^3$) +/− Standard error | Group 11 Mean tumor volume (mm$^3$) +/− Standard error | Group 12 Mean tumor volume (mm$^3$) +/− Standard error | Group 13 Mean tumor volume (mm$^3$) +/− Standard error |
|---|---|---|---|---|---|---|
| 7  | 99 +/− 6   | 97 +/− 5   | 97 +/− 7   | 97 +/− 5   | 96 +/− 4   | 96 +/− 7   |
| 9  | 113 +/− 10 | 112 +/− 6  | 114 +/− 9  | 112 +/− 6  | 110 +/− 6  | 109 +/− 8  |
| 12 | 135 +/− 17 | 178 +/− 18 | 163 +/− 13 | 145 +/− 13 | 152 +/− 11 | 120 +/− 11 |
| 14 | 148 +/− 18 | 248 +/− 21 | 201 +/− 21 | 249 +/− 19 | 209 +/− 28 | 181 +/− 12 |
| 16 | 170 +/− 15 | 304 +/− 19 | 206 +/− 23 | 348 +/− 23 | 238 +/− 28 | 239 +/− 28 |
| 19 | 115 +/− 13 | 144 +/− 19 | 118 +/− 18 | 289 +/− 15 |            | 289 +/− 31 |
| 21 | 85 +/− 20  | 91 +/− 19  | 72 +/− 26  | 262 +/− 17 |            | 248 +/− 36 |
| 23 | 50 +/− 23  | 62 +/− 20  | 14 +/− 14  | 286 +/− 26 |            | 196 +/− 35 |
| 26 | 15 +/− 15  | 29 +/− 19  |            | 271 +/− 41 |            | 134 +/− 23 |
| 28 |            | 25 +/− 16  |            | 290 +/− 67 |            |            |
| 30 |            | 12 +/− 12  |            | 356 +/− 112 |           |            |
| 33 |            |            |            | 394 +/− 150 |           |            |
| 35 |            |            |            | 464 +/− 191 |           |            |
| 37 |            |            |            | 588 +/− 241 |           |            |
| 40 |            |            |            | 695 +/− 284 |           |            |
| 42 |            |            |            | 850 +/− 363 |           |            |
| 44 |            |            |            | 679 +/− 336 |           |            |
| 47 |            |            |            | 802 +/− 403 |           |            |
| 49 |            |            |            | 518 +/− 315 |           |            |
| 51 |            |            |            | 735 +/− 459 |           |            |

Example 9. TGFβRII DNR Enhancement in BCMA/TACI Dual Binder CARs In Vivo

This example tested the use of a dominant negative (DN) TGF-β receptor in combination with the CAR T in a myeloma mouse model with RPMI8226 cells.

Each test group included 6 animals, and received T cells transduced with a corresponding CAR. The numbers of animals and their received treatments are listed in Table 24. The volume of each tumor in the animal was about 150-250 mm$^3$. A BCMA scFv and two dual binders were used, each tested with or without expression of the dominant negative (DN) TGF-β receptor (DNR). Dual Binder #1 includes the scFv sequence (SEQ ID NO:23) of Table 4. Dual Binder #3 includes the scFv sequence (SEQ ID NO:143) of Table 9. The DNR includes the sequence of SEQ ID NO: 297.

TABLE 24

Test groups and treatments

| Group | # of mice | scFv | Dose |
|---|---|---|---|
| 1  | 6 | Vehicle           | N/A            |
| 3  | 6 | NTD (untransduced)| Low Dose Match |
| 9  | 6 | BCMA CAR          | 2 × 10$^5$ cells |
| 11 | 6 | BCMA CAR + DNR    | 2 × 10$^5$ cells |
| 13 | 6 | Dual Binder #1    | 2 × 10$^5$ cells |
| 15 | 6 | Dual Binder #1 + DNR | 2 × 10$^5$ cells |
| 17 | 6 | Dual Binder #3    | 2 × 10$^5$ cells |
| 19 | 6 | Dual Binder #3 + DNR | 2 × 10$^5$ cells |

The tumor volumes were measured after the treatments, and the results are presented in FIG. 1. Without the DNR, the single BCMA-targeting CAR T cells did not exhibit observable efficacy; in combination with the DNR, by contrast, tumor growth slowed down on about day 24 and the tumor started to shrink on day 55 (FIG. 1A). Both dual CARs, with Binders #1 and #3, exhibited significant antitumor effects starting on day 40 (FIGS. 1B and 1C, middle curves). When used in combination with DNR, the efficacy was remarkably enhanced. For dual Binder #1, the tumors started to shrink on day 20, and essentially disappeared on day 50 (FIG. 1B). For dual Binder #3, the tumors were gone even on day 30 (FIG. 1C).

This example, therefore, demonstrates significantly enhanced efficacy for low dose CAR-T cell treatments with TGFβRII dominant-negative receptors.

Example 10. TGFβRII DNR Enhancement in Codon Optimized BCMA/TACI Dual Binder CARs In Vivo This example tested the expression of codon optimized BCMA/TACI dual binder CARs with co-expression of a dominant negative (DN) TGF-β receptor. Further tested were in vitro cytotoxicity as well as cytokine assays. Also, tested was in vivo efficacy using a model of disseminated the OPM2 multiple myeloma cell line labeled with luciferase. BCMA/TACI dual binders were tested with or without expression of the dominant negative (DN) TGF-β receptor (DNR). Dual Binder #1 includes the scFv sequence (SEQ ID NO:23) of Table 4. Dual Binder #3 includes the scFv sequence (SEQ ID NO:143) of Table 9. The DNR includes the sequence of SEQ ID NO: 297. The codon optimized sequence for Dual Binder #1 Version 2 (CAR only) is SEQ ID NO: 302. The codon optimized sequence for Dual Binder #3 Version 2 (CAR only) is SEQ ID NO: 303.

Figure 2A:
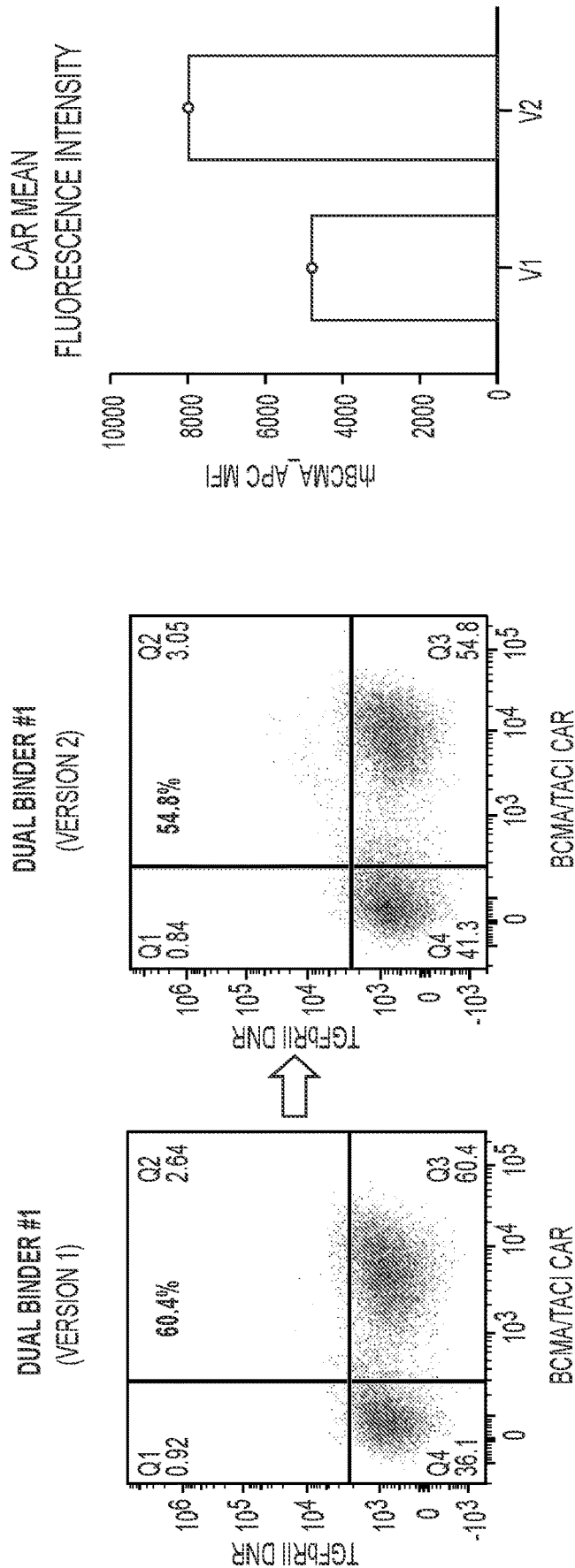
FIGS. 2A and 2B show increased mean fluorescence intensity (MFI) for codon-optimized BCMA/TACI dual binders, indicating relatively increased expression of the codon-optimized CARs.
Figure 2B:
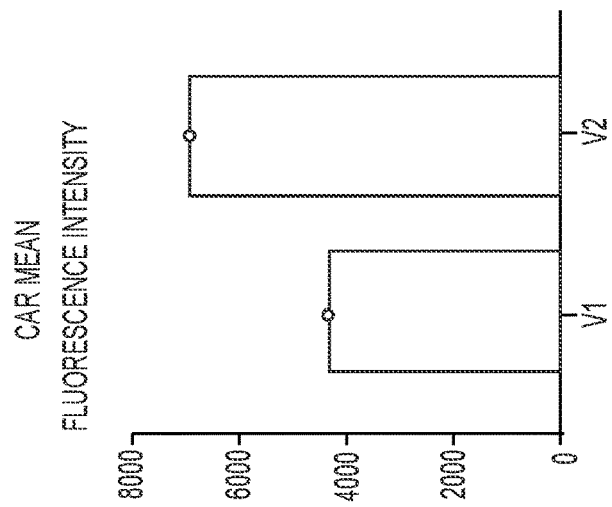
Figure 2B:
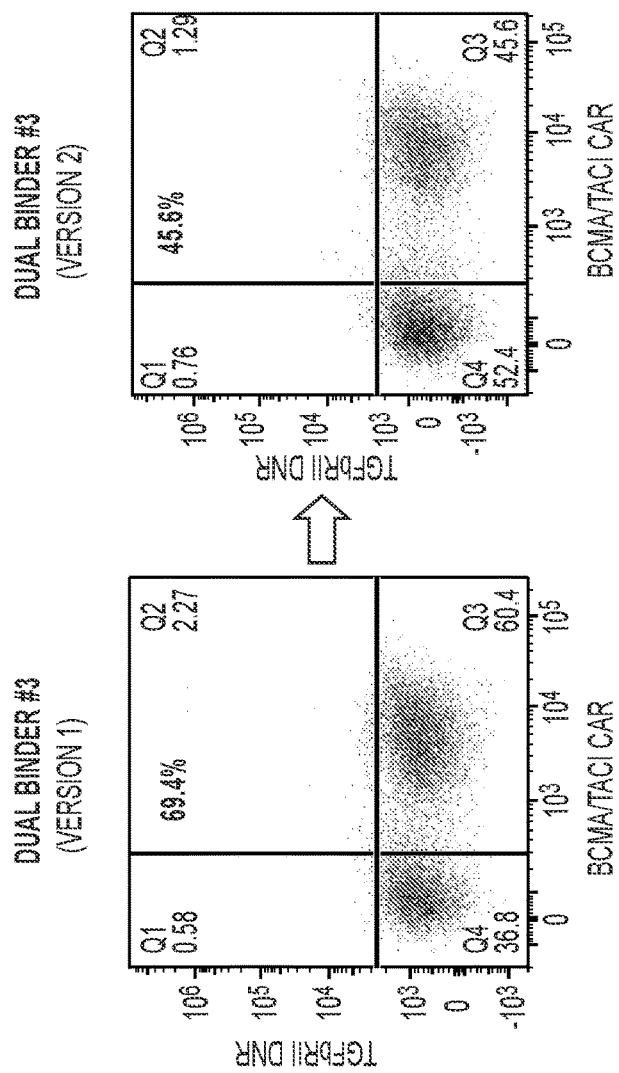

As shown in FIGS. 2A and 2B, CART cells were manufactured and stained with Dylight-650 labelled recombinant BCMA to detect CAR. Codon optimization of dual binder #1 (indicated as dual binder #1 version 2) as well as codon optimization of dual binder #3 (indicated as dual binder #3 version 2) improved expression (as indicated by mean fluorescence intensity (MFI)) of both CARs.

Figure 3A:
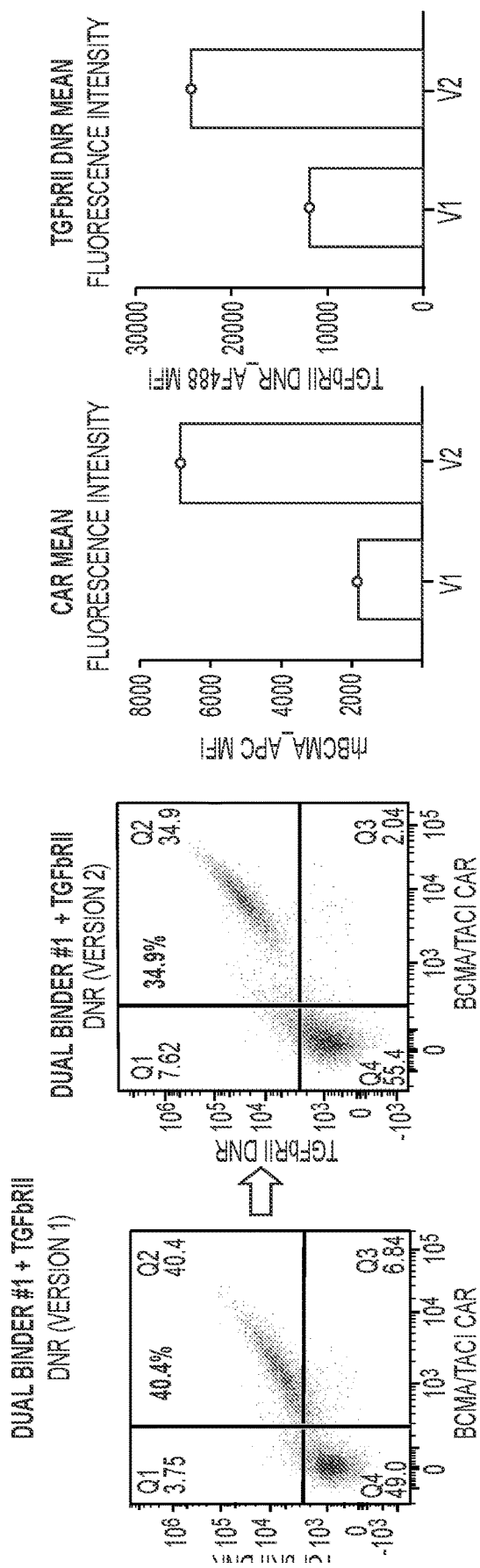
FIGS. 3A and 3B show increased MFI for codon-optimized BCMA/TACI dual binders linked to TGFβII DNR, indicating relatively increased expression of both the codon-optimized CARs and DNR.
Figure 3B:
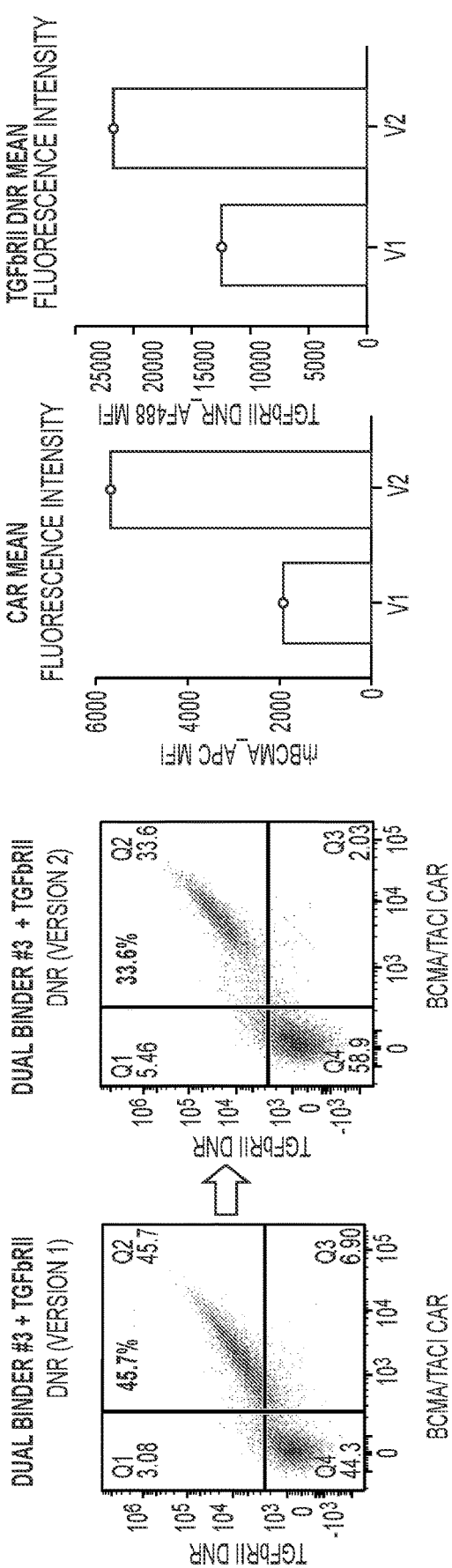

As shown in FIGS. 3A and 3B, CAR T cells were manufactured to express both CAR and TGFβRII DNR and stained with Dylight-650 labelled recombinant BCMA to detect CAR and anti-TGFβRII-FITC to detect TGFβRII DNR. Codon optimization of dual binder #1 (indicated as dual binder #1 version 2) as well as codon optimization of dual binder #3 (indicated as dual binder #3 version 2) improved expression (as indicated by MFI) of both CARs and the TGFβRII DNR.

Figure 4A:
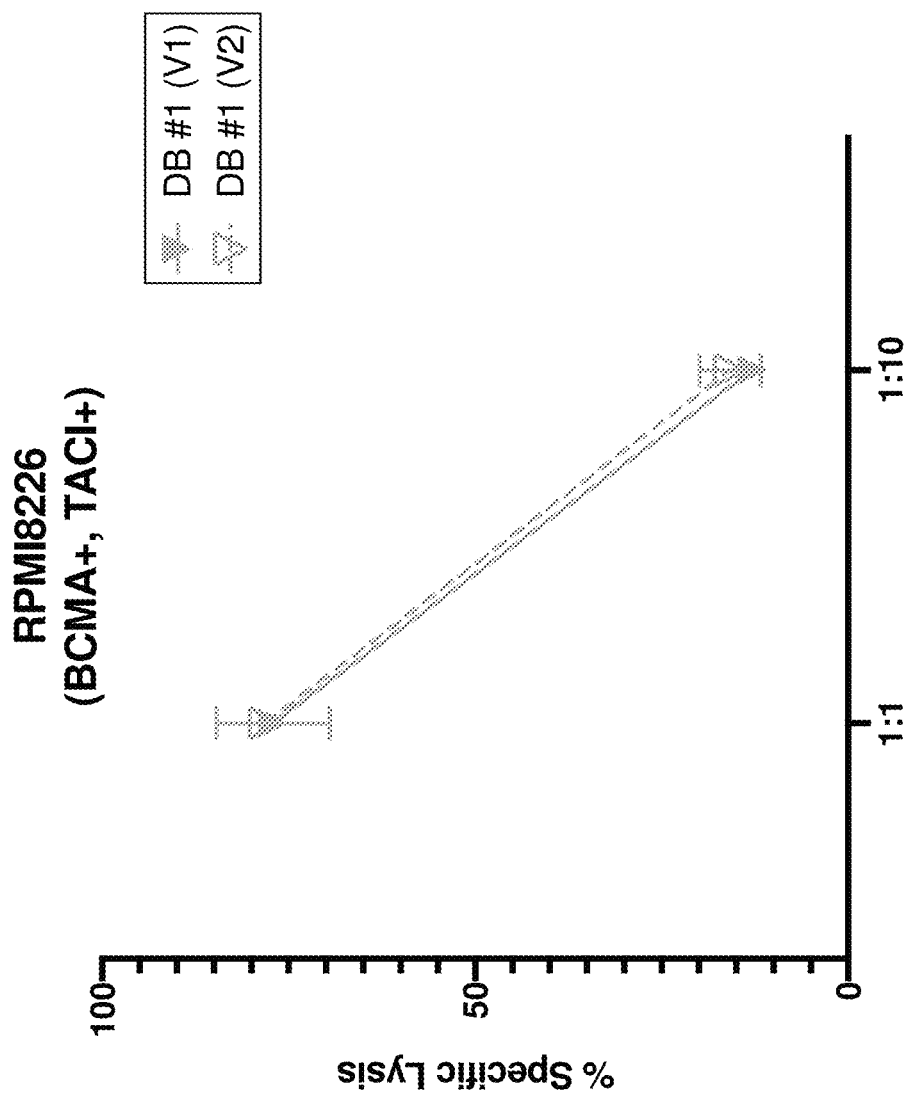
Figure 4B:
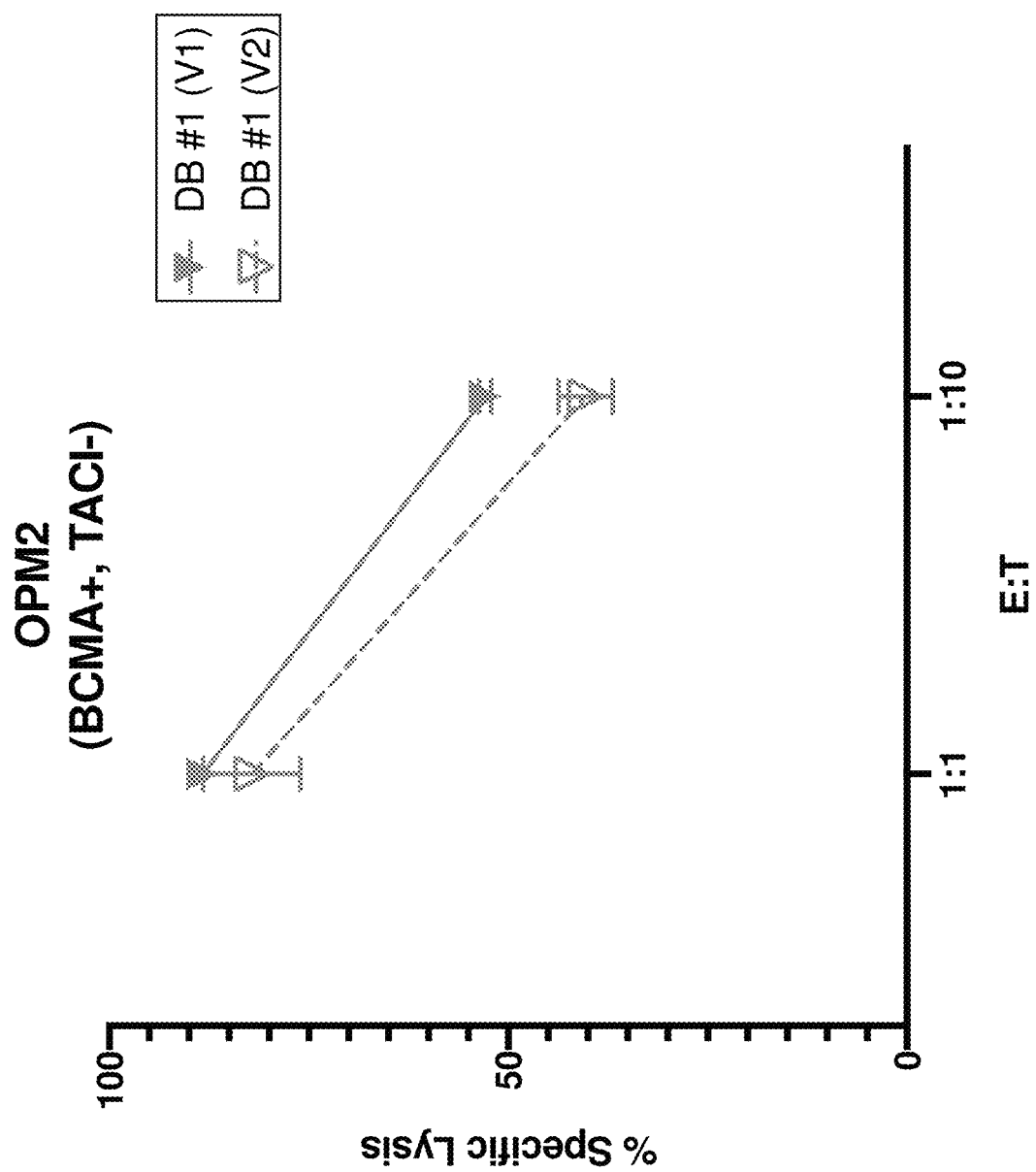
Figure 4D:
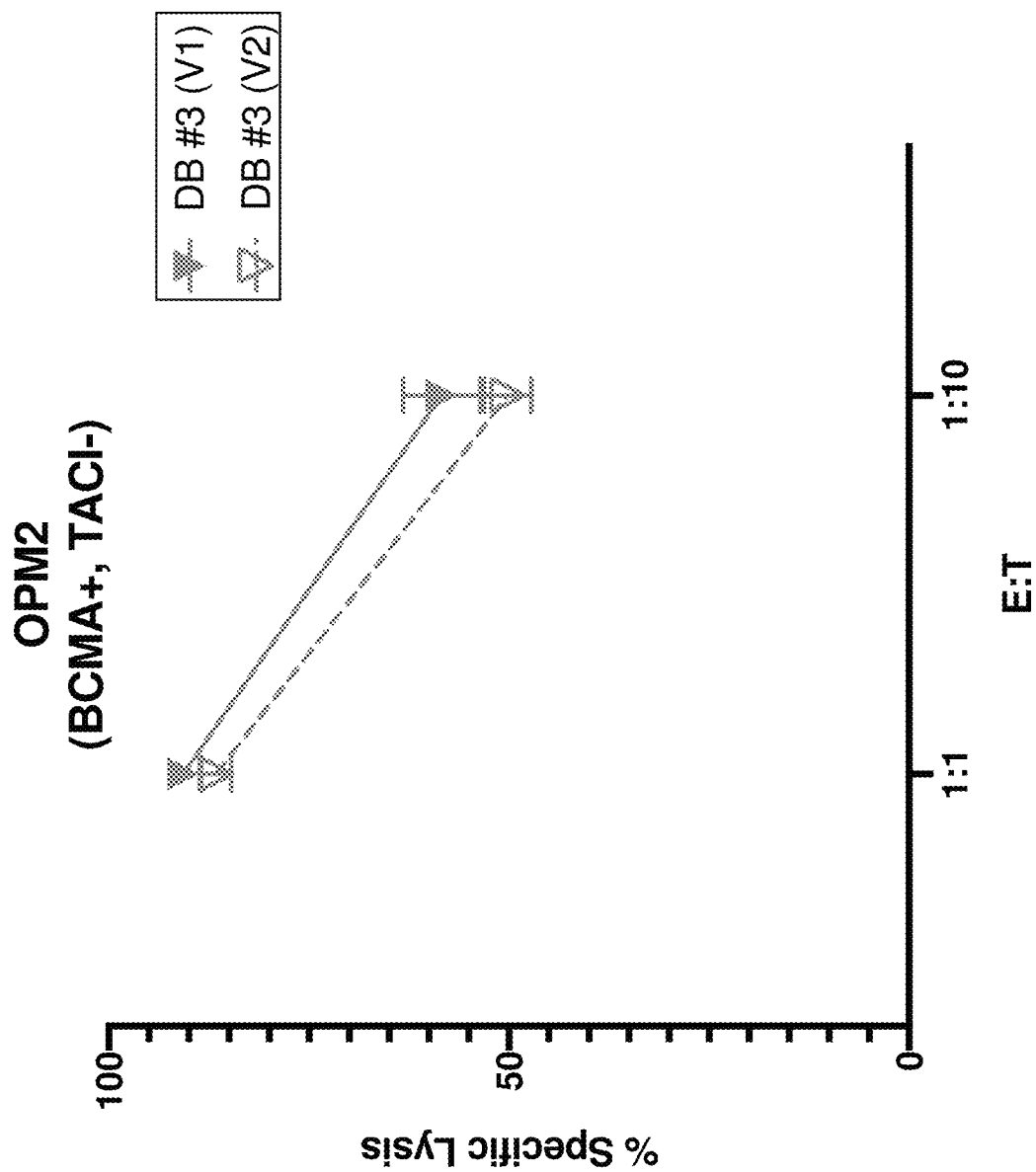
Figure 4E:
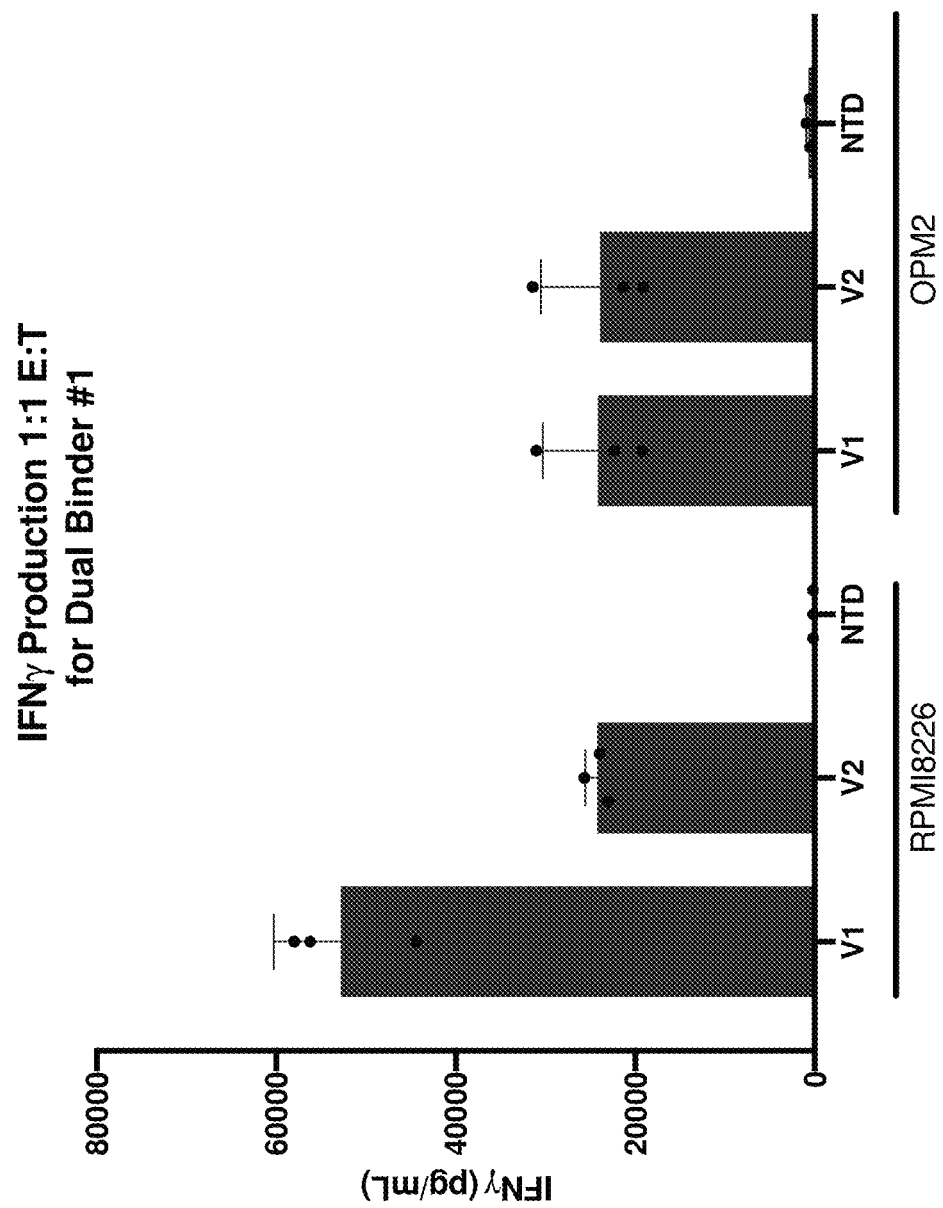
FIGS. 4E-4H show results of cytokine assays of codon-optimized and noncodon-optimized CARs linked to TGFβII DNR.
Figure 4F:
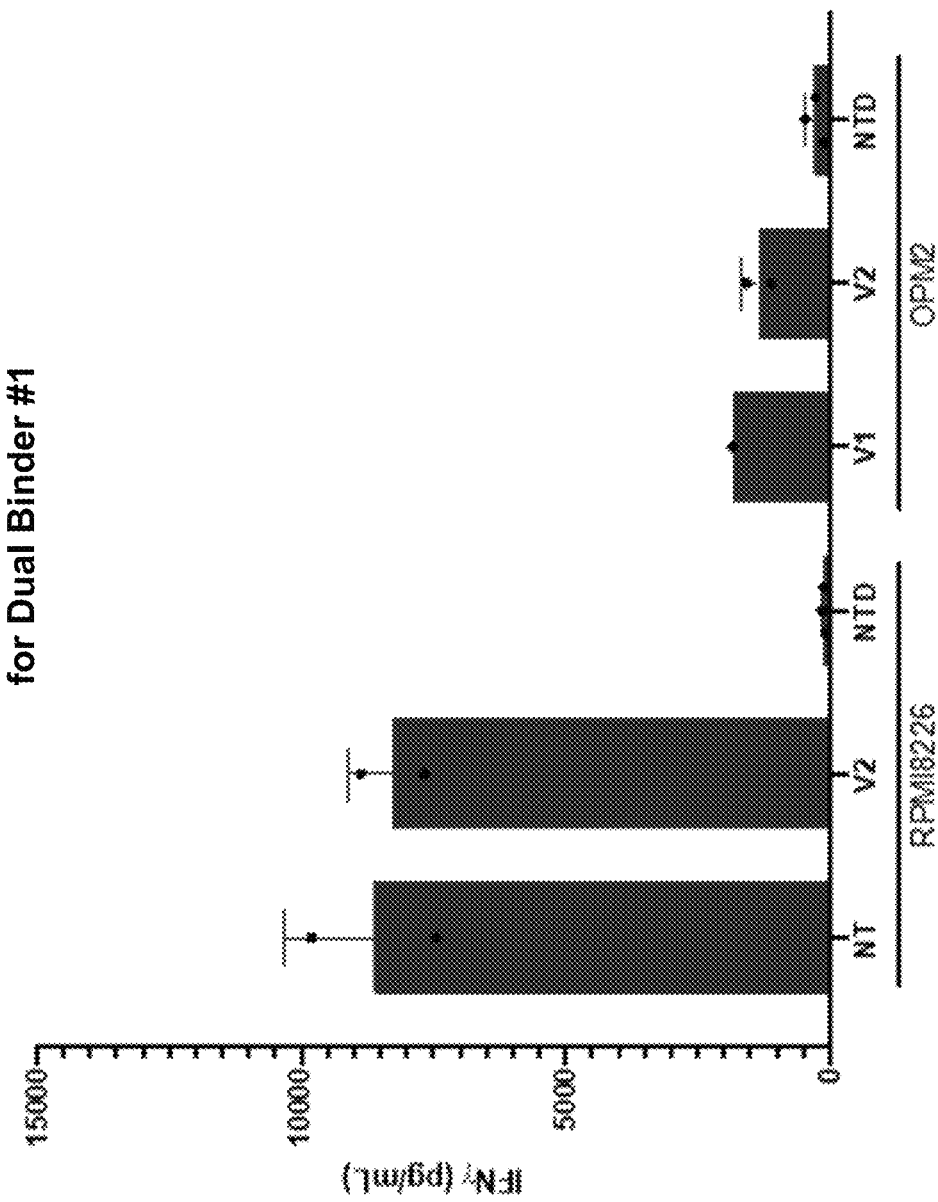
Figure 4G:
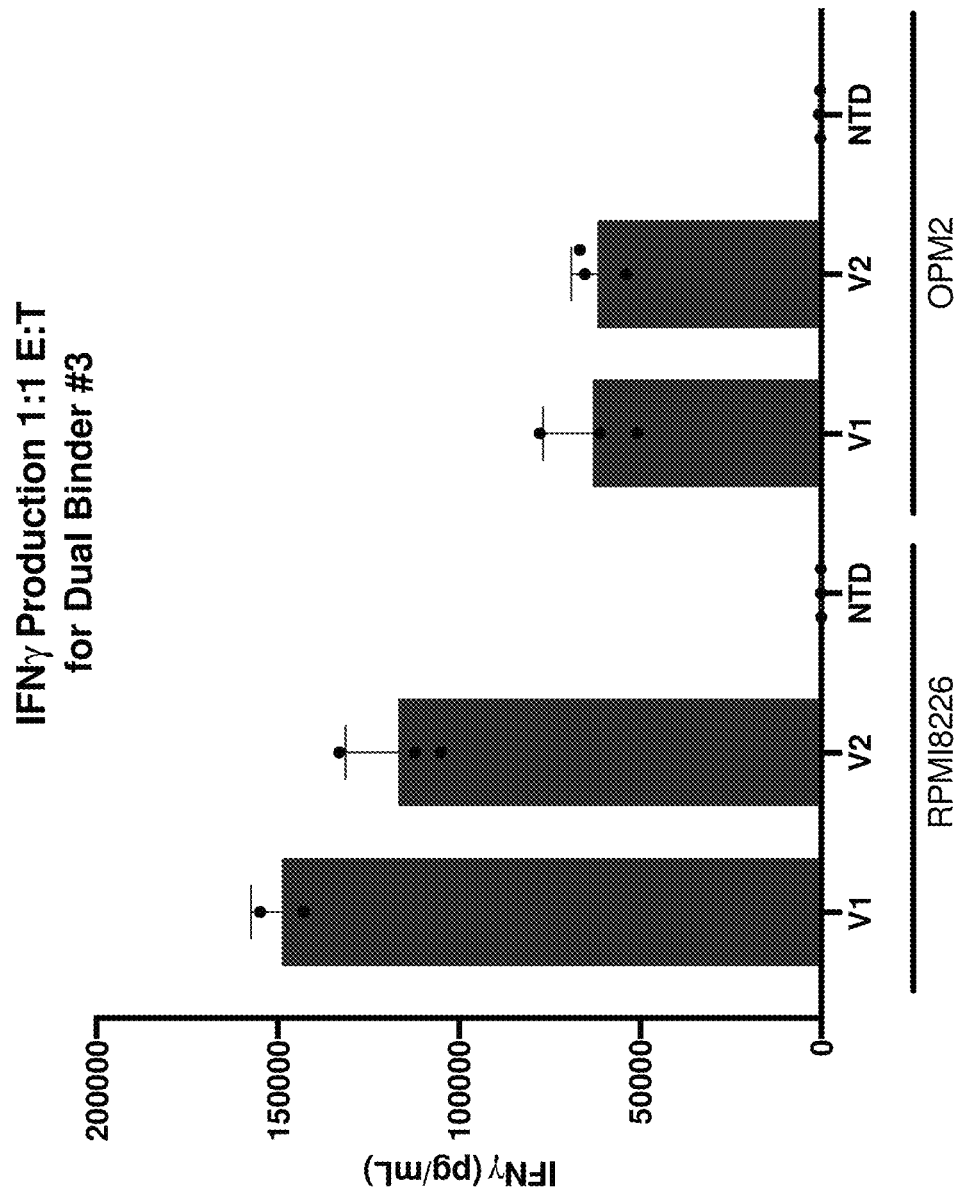
Figure 4H:
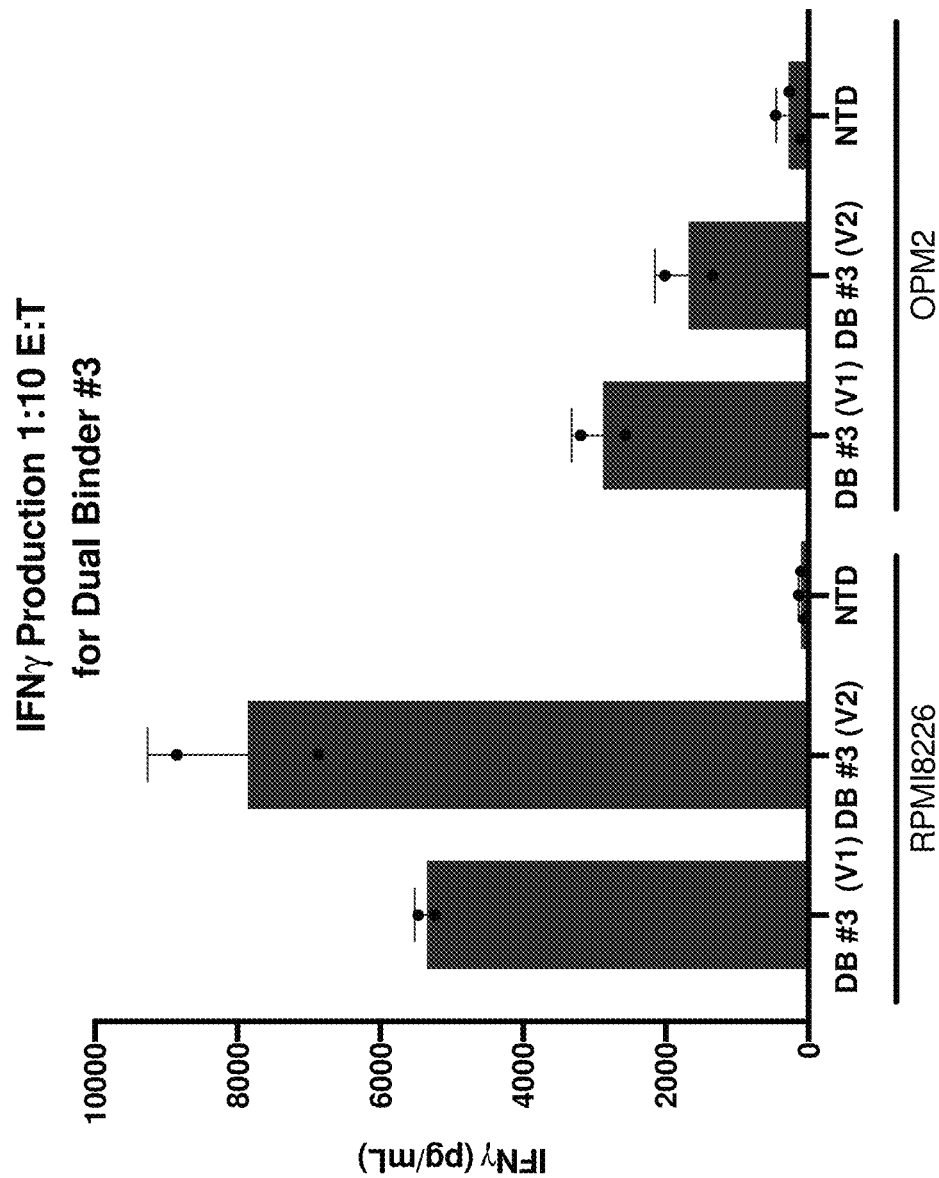

As shown in FIGS. 4A and 4B, similar cytotoxicity and cytokine secretion is seen in coculture assays of the CAR and TGFβRII DNR (with and without codon optimization) with OPM2 and RPMI 8226 multiple myeloma target cells.

CAR-T cell in vivo efficacy was assessed using a model of disseminated OPM2 multiple myeloma cell line labeled with luciferase. The OPM2 in vivo study was designed to compare version 1 and codon optimized, version 2 dual binders+TGFβRII DNR as shown in Table 25.

TABLE 25

Test groups and treatments

| Group | # of mice | CAR construct | CAR+ Dose |
|---|---|---|---|
| 1 | 5 | Vehicle | N/A |
| 2 | 5 | NTD (untransduced) | $2 \times 10^6$ cells match |
| 3 | 5 | DB#1 + DNR Version 1 | $2 \times 10^6$ cells |

TABLE 25-continued

Test groups and treatments

| Group | # of mice | CAR construct | CAR+ Dose |
|---|---|---|---|
| 5 | 5 | DB#1 + DNR Version 2 | $2 \times 10^6$ cells |
| 7 | 5 | DB#3 + DNR Version 1 | $2 \times 10^6$ cells |
| 9 | 5 | DB#3 + DNR Version 2 | $2 \times 10^6$ cells |

Figure 5A:
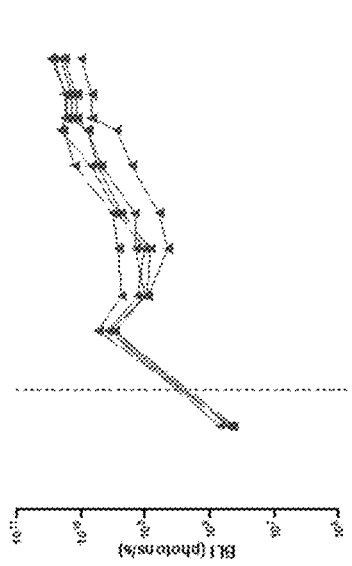
FIGS. 5A and 5B show in vivo data of codon-optimized and noncodon-optimized CARs linked to TGFβII DNR.
Figure 5A:
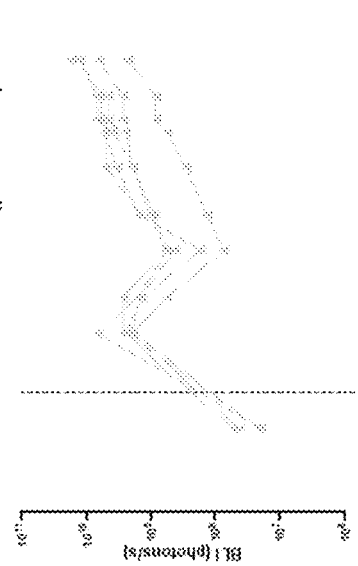
Figure 5A:
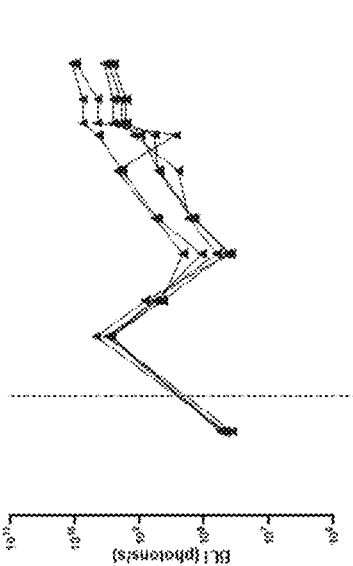
Figure 5A:
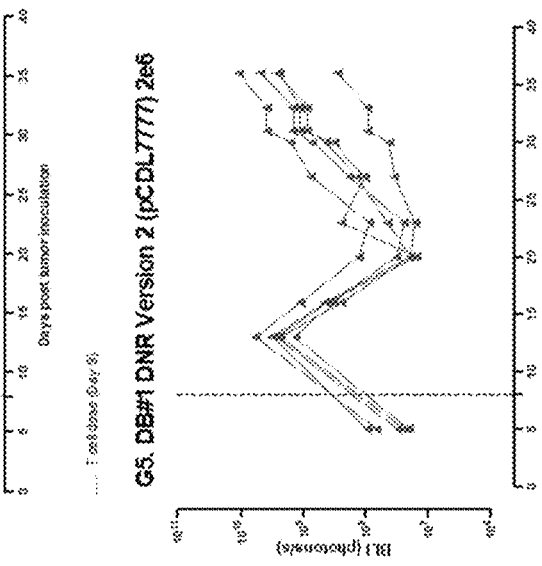
Figure 5B:
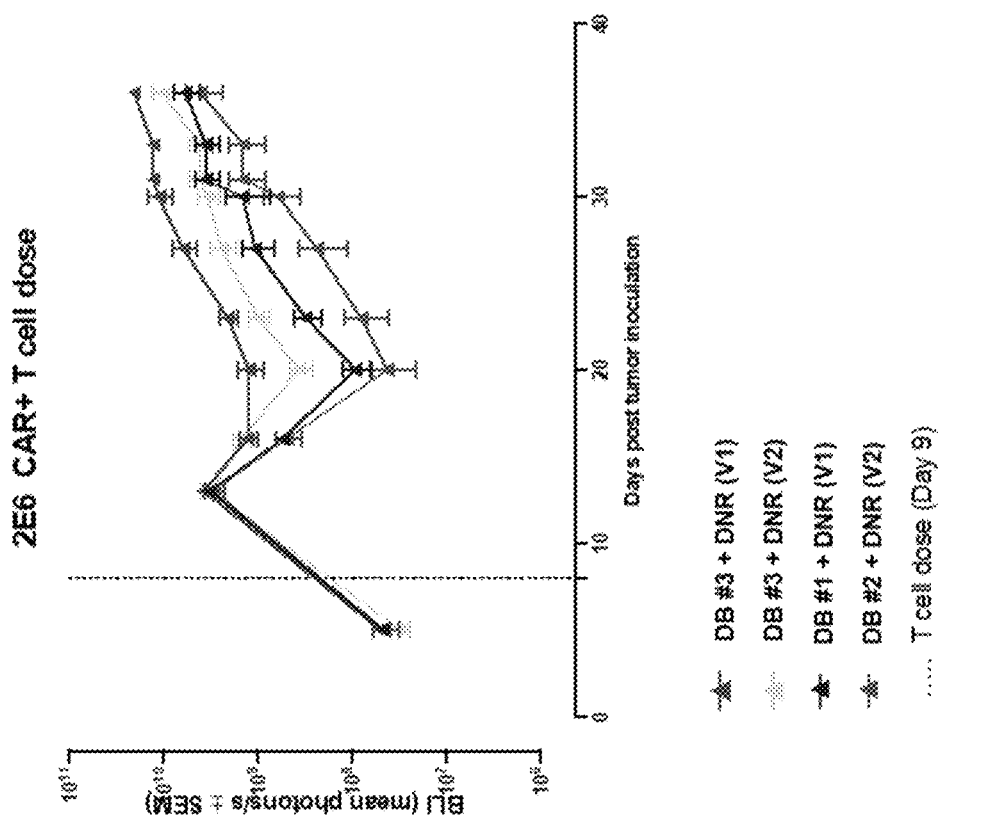

Mice were treated with 2E6 CAR-T cells on Day 9, and tumor growth was monitored by bioluminescent imaging to detect luciferase-labeled tumor cells. As shown in FIGS. 5A and 5B, the codon optimized versions (version 2) of the dual binders were better able to control tumors than their non-codon optimized variants as seen by the lower BLI signal in mice treated with the codon optimized (version 2) CARs compared to the non-codon optimized (version 1) counterparts.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An antibody, or antigen binding fragment thereof having specificity to TACI (transmembrane activator and CAML interactor) and BCMA (B-cell maturation antigen), wherein the antibody or antigen binding fragment thereof comprises a heavy chain variable domain (VH) comprising heavy chain complementarity determining regions (HCDRs) HCDR1, HCDR2 and HCDR3, and a light chain variable domain (VL) comprising light chain complementarity determining regions (LCDRs) LCDR1, LCDR2 and LCDR3, and wherein the HCDR1, HCDR2, HCDR3, LCDR1, LCDR2 and LCDR3 comprise, respectively, the amino acid sequences of:
(i) SEQ ID NO:4, 7, 10, 15, 18, and 20;
(ii) SEQ ID NO:28, 31, 34, 39, 18, and 44;
(iii) SEQ ID NO:28, 31, 58, 15, 66, and 68;
(iv) SEQ ID NO: 76, 31, 82, 87, 18, and 92;
(v) SEQ ID NO:28, 31, 106, 111, 18, and 116;
(vi) SEQ ID NO:76, 31, 130, 135, 18, and 140;
(vii) SEQ ID NO:148, 151, 154, 15, 162, and 164;
(viii) SEQ ID NO: 148, 151, 178, 15, 186, and 164; or
(ix) SEQ ID NO: 196, 199, 202, 15, 210, and 212.

2. The antibody, or antigen binding fragment thereof of claim 1, wherein the three HCDRs and the three LCDRs are comprised by a single polypeptide.

3. The antibody, or antigen binding fragment thereof of claim 1, wherein the antigen binding fragment thereof comprises an scFv.

4. The antibody, or antigen binding fragment thereof of claim 3, wherein the scFv comprises an amino acid sequence selected from the group consisting of SEQ ID NO: 23, 47, 71, 95, 119, 143, 167, 191, and 215.

5. A nucleic acid encoding the antibody, or antigen binding fragment thereof of claim 1.

6. A recombinant vector comprising the nucleic acid of claim 5.

7. The recombinant vector of claim 6, wherein the recombinant vector further comprises a nucleic acid encoding a dominant negative TGFβ receptor (DN TGFβR), comprising:
an extracellular domain (ECD) from a TGF-β receptor and
a transmembrane domain (TMD), wherein the recombinant polypeptide lacks amino acid residues responsible for signaling and phosphorylation present in a wild-type TGF-β receptor.

8. The recombinant vector according to claim 7, wherein the ECD is selected from TGF-βRI or TGF-βRII.

9. The recombinant vector according to claim 7, wherein the TMD is selected from TGF-βRI, TGF-βRII, PDGFR, CD4, CD8, CD28, CD127, CD132, CD3ζ, 4-IBB, OX40, ICOS, CTLA-4, PD-1, LAG-3, 2B4, IL-5, IL-7, IL-7Rα, BTLA or mutants of any of the foregoing.

10. The recombinant vector according to claim 7, wherein the DN TGFβR further comprises a heterologous intracellular domain (ICD) which lacks amino acid residues responsible for signaling and phosphorylation present in wild-type TGF-β receptor.

11. A host cell transformed with the nucleic acid of claim 5.

12. The host cell of claim 11, where the host cell comprises an iPSC, a T cell or a NK cell.

13. A pharmaceutical composition comprising the T cell and/or an NK cell of claim 12.

14. A method of treating cancer in a patient in need of thereof, comprising administering the T cell and/or an NK cell of claim 12 to the patient, wherein the patient comprises a cancer cell expressing TACI or BCMA.

15. The method of claim 14, where the cancer is multiple myeloma.

16. The method of claim 14, wherein the T cell and/or NK cell is allogeneic to the patient.

17. A method of inducing an immune response in a subject or immunizing a subject against a multiple myeloma, the method comprising administering to the subject the T cell and/or an NK cell of claim 12.

18. A host cell transformed with:
the nucleic acid of claim 5, and
a nucleic acid encoding a dominant negative TGFβ receptor (DN TGFβR).

19. The host cell of claim 18, wherein the host cell is transformed with a nucleic acid encoding a membrane bound IL-15-IL-15Rα sushi domain chimeric receptor.

20. A chimeric antigen receptor, comprising the antibody, or antigen binding fragment thereof of claim 1.

21. The chimeric antigen receptor of claim 20, further comprising a transmembrane domain of 4-1BB/CD137, an alpha chain of a T cell receptor, a beta chain of a T cell receptor, 2B4, CD3 epsilon, CD4, CD5, CD8 alpha, CD9, CD16, CD19, CD22, CD28, CD33, CD37, CD45, CD64, CD80, CD86, CD134, CD137, CD154, NKG2D, or a zeta chain of a T cell receptor, or any combination thereof.

22. A nucleic acid encoding the chimeric antigen receptor of claim 20.

23. The chimeric antigen receptor of claim 20, which comprises an amino acid sequence selected from the group consisting of SEQ ID NO: 246, 248, 250, 252, 254, 256, 258, 260, and 262.

24. The antibody, or antigen binding fragment thereof of claim 1, wherein the VH and VL, respectfully, comprise the amino acid sequences of:
(i) SEQ ID NO:1 and 12;
(ii) SEQ ID NO:25 and 36;
(iii) SEQ ID NO:49 and 60;
(iv) SEQ ID NO:73 and 84;
(v) SEQ ID NO:97 and 108;
(vi) SEQ ID NO:121 and 132;
(vii) SEQ ID NO:145 and 156;
(viii) SEQ ID NO:169 and 180; or
(ix) SEQ ID NO:193 and 204.

* * * * *